(12) United States Patent
Takahashi et al.

US008912180B2

(10) Patent No.: US 8,912,180 B2
(45) Date of Patent: Dec. 16, 2014

(54) HETEROCYCLIC COMPOUND

(71) Applicant: Astellas Pharma Inc., Chuo-ku (JP)

(72) Inventors: Fumie Takahashi, Tokyo (JP); Sunao Imada, Tokyo (JP); Toru Asano, Tokyo (JP); Yoshihiro Kozuki, Tokyo (JP); Junko Maeda, Tokyo (JP); Koji Kato, Tokyo (JP); Hidehiko Fukahori, Tokyo (JP); Masahiko Shiwaku,deceased, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 13/762,906

(22) Filed: Feb. 8, 2013

(65) Prior Publication Data

US 2013/0150364 A1    Jun. 13, 2013

Related U.S. Application Data

(63) Continuation-in-part of application No. PCT/JP2011/068169, filed on Aug. 9, 2011.

(30) Foreign Application Priority Data

Aug. 10, 2010  (JP) ................................ 2010-179418

(51) Int. Cl.
| | |
|---|---|
| *A61K 31/5377* | (2006.01) |
| *A61K 31/497* | (2006.01) |
| *C07D 413/14* | (2006.01) |
| *C07D 403/14* | (2006.01) |
| *C07D 403/04* | (2006.01) |
| *C07D 401/14* | (2006.01) |
| *C07D 405/14* | (2006.01) |
| *C07D 409/14* | (2006.01) |
| *C07D 417/14* | (2006.01) |
| *C07D 471/04* | (2006.01) |
| *C07D 471/10* | (2006.01) |
| *C07D 487/04* | (2006.01) |

(52) U.S. Cl.
CPC ............ *C07D 403/04* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 471/10* (2013.01); *C07D 487/04* (2013.01); *A61K 31/5377* (2013.01); *A61K 31/497* (2013.01)
USPC ....................... 514/234.5; 544/113

(58) Field of Classification Search
CPC ............. A61K 31/5377; A61K 31/497; C07D 413/14; C07D 403/14
USPC ....................... 514/234.5; 544/113
See application file for complete search history.

(56) References Cited

U.S. PATENT DOCUMENTS

| | | | |
|---|---|---|---|
| 2007/0244110 | A1 | 10/2007 | Yaguchi et al. |
| 2008/0113987 | A1 | 5/2008 | Haruta et al. |
| 2010/0249063 | A1 | 9/2010 | Sugama et al. |
| 2012/0165309 | A1 | 6/2012 | Takahashi et al. |

FOREIGN PATENT DOCUMENTS

| | | |
|---|---|---|
| EP | 1 020 462 | 7/2000 |
| EP | 1 389 617 | 2/2004 |
| EP | 1 557 415 | 7/2005 |
| EP | 1 741 714 | 1/2007 |
| EP | 1 864 665 | 12/2007 |
| WO | 00/43385 | 7/2000 |
| WO | 01/81346 | 11/2001 |
| WO | 02/088112 | 11/2002 |
| WO | 03/035075 | 5/2003 |
| WO | 2004/037812 | 5/2004 |
| WO | 2005/095389 | 10/2005 |
| WO | 2005/113556 | 12/2005 |
| WO | 2006/095906 | 9/2006 |
| WO | 2007/042810 | 4/2007 |
| WO | 2008/000421 | 1/2008 |
| WO | 2008/032027 | 3/2008 |
| WO | 2008/032028 | 3/2008 |
| WO | 2008/032033 | 3/2008 |
| WO | 2008/032036 | 3/2008 |
| WO | 2008/032041 | 3/2008 |
| WO | 2008/032060 | 3/2008 |
| WO | 2008/032064 | 3/2008 |
| WO | 2008/032072 | 3/2008 |
| WO | 2008/032077 | 3/2008 |
| WO | 2008/032086 | 3/2008 |
| WO | 2008/032089 | 3/2008 |
| WO | 2008/032091 | 3/2008 |
| WO | 2008/125839 | 10/2008 |
| WO | 2009/007751 | 1/2009 |

(Continued)

OTHER PUBLICATIONS

Cancer and Metastasis Reviews (1998), 17(1), 91-106.*

(Continued)

*Primary Examiner* — Rebecca Anderson
(74) *Attorney, Agent, or Firm* — Oblon, Spivak, McClelland, Maier & Neustadt, L.L.P.

(57) ABSTRACT

Provided is a novel compound which is an agent for treating rejection reactions in various organ transplantations, allergy diseases, autoimmune diseases, and hematologic tumor, and based on a PI3Kδ selective inhibitory action and/or an IL-2 production inhibitory action and/or a B cell proliferation inhibitory action (including an activation inhibitory action). The provided compound has a PI3Kδ selective inhibitory action, an IL-2 production inhibitory action, and/or a B cell proliferation inhibitory action, including an activation inhibitory action.

9 Claims, No Drawings

(56) References Cited

FOREIGN PATENT DOCUMENTS

| WO | 2009/066775 | 5/2009 |
|---|---|---|
| WO | 2009/093981 | 7/2009 |
| WO | 2009/120094 | 10/2009 |
| WO | 2010/092962 | 8/2010 |

OTHER PUBLICATIONS

Science (1999), vol. 286, 531-537.*
Extended Search Report issued Oct. 25, 2013 in European Application No. 11816426.8.
Mark Sabat, et al., The development of 2-benzimidazole substituted pyrimidine based inhibitors of lymphocyte specific kinase (Lck), Bioorganic & Medicinal Chemistry Letters, 16 (2006) 5973-5977.
Shin-ichi Yaguchi, et al., "Antitumor Activity of ZSTK474, a New Phosphatidylinositol 3-Kinase Inhibitor", Journal of the National Cancer Institute, vol. 98, No. 8, Apr. 19, 2006.
International Search Report dated Sep. 6, 2011 as received in International Application No. PCT/JP2011/068169.
Office Action issued Jul. 22, 2014, in Eurasian patent application No. 201390198/28 (w/English translation).
Office Action issued Jul. 18, 2014, in European patent application No. 11816426.8.

* cited by examiner

HETEROCYCLIC COMPOUND

TECHNICAL FIELD

The present invention relates to a heterocyclic compound which is useful as an active ingredient of a pharmaceutical composition, for example, a pharmaceutical composition for preventing and/or treating phosphatidylinositol-3-kinase δ (PI3Kδ)-related diseases.

BACKGROUND ART

Phosphatidylinositol-3-kinase (PI3K) is a lipid signaling kinase, which is present universally throughout species, ranging from plants or yeasts to mammals including humans. PI3K is an enzyme for phosphorylating the hydroxyl group at the 3-position of phosphatidylinositol, phosphatidylinositol-4-phosphate, and phosphatidylinositol-4,5-diphosphate, which are cell membrane phospholipids, and from each of these substrates, phosphatidylinositol-3-phosphate, phosphatidylinositol-3,4-diphosphate, and phosphatidylinositol-3,4,5-triphosphate (PIP3) are produced. These phosphorylated phosphatidylinositols thus produced act as an intracellular second messenger. Particularly, PIP3 causes migration of various molecules having pleckstrin homology (PH) domains to a position near the cell membrane to induce activation of the molecules, and thus it is considered to be the most important phosphorylated phosphatidylinositol ("The Journal of Biological Chemistry", 1999, Vol. 274, p. 8347-8350).

PI3K is divided into three classes, Classes I, II, and III, according to various characteristics, and from the viewpoints that the only enzyme producing PIP3 in vivo is Class I PI3K, the Class I PI3K is considered to be the most important class ("Biochimica et Biophysica Acta", 2008, Vol. 1784, p. 159-185). The Class I PI3K is subdivided into IA and IB. The Class IA PI3K consists of heterodimers including a combination of a 110-kDa catalytic subunit (p110α, β, or δ) and a 50- to 85-kDa regulatory subunit (p85α, p85β, p55α, p55γ, or p50α), and the Class IB PI3K is a heterodimer of a 110-kDa catalytic subunit (p110γ) and a 101-kDa regulatory subunit (p101) ("Nature Immunology", 2003, No. 4, p. 313-319). Hereinafter, the respective names of PI3K are referred to as PI3Kα, β, δ, and γ, corresponding to catalytic subunits included therein.

PI3Kα and β are widely present in a biological body and deficiency of PI3Kα and β in mice has been reported to be fetally lethal in both cases ("The Journal of Biological Chemistry", 1999, Vol. 274, p. 10963-10968; and "Mammalian Genome", 2002, Vol. 13, p. 169-172). As a result of studies using subtype selective compounds, it has been reported that PI3Kα plays an important role in insulin signaling and a PI3Kα inhibitor causes insulin resistance ("Cell", 2006, Vol. 125, p. 733-747). Further, it has been reported that PI3Kβ is involved in platelet aggregation and a PI3Kβ inhibitor has an antithrombotic effect ("Nature Medicine", 2005, Vol. 11, p. 507-514). On the other hand, mice deficient in PI3Kβ or γ are all born normally, and no problems concerning growth, life span, reproduction, or the like have been found ("Science", 2000, Vol. 287, p. 1040-1046; and "Molecular and Cellular Biology", 2002, Vol. 22, p. 8580-8591). In particular, expression of PI3Kδ is significantly limited to hemocytes and lymphoid tissues, and mice deficient in PI3Kδ have been found to have significant damage in activation of lymphocytes. A close relationship between the activation of lymphocytes and immunity/inflammation is well known, and compounds selectively inhibiting PI3Kδ have a potential to be immunity/inflammatory inhibitors having both a potent inhibitory action on the activation of lymphocytes and safety.

Interleukin-2 (IL-2) is a kind of cytokine which is mainly produced from activated T cells. IL-2 induces proliferation and activation of lymphocytes via an IL-2 receptor which is a receptor for IL-2. IL-2 is a very important molecule in signaling the activation of an immune system, and its production inhibitors (for example, Tacrolimus and Cyclosporin A) have been used clinically as immunosuppressing agents. In addition, anti-IL-2 receptor monoclonal antibodies such as Basiliximab and Daclizumab have been used clinically as immunosuppressing agent.

B cells are one of the main subsets of lymphocytes, along with T cells, and are cells which is a main actor of humoral immunity. It is known that humoral immunity plays an extremely important role in preventing infection from pathogens or the like, but in autoimmune diseases such as rheumatoid arthritis and the like, abnormal activation of humoral immunity occurs, which is deeply involved in the pathogenesis. In fact, an anti-CD20 antibody, Rituximab, has been used clinically as a drug for treating rheumatoid arthritis.

As the compound having a PI3K inhibitory action, for example, the compounds of the formula (A-1) (Patent Document 1), the formula (A-2) (Patent Document 2), the formula (A-3) (Patent Document 3), the formula (B-1) (Patent Document 4), the formula (B-2) (Patent Document 5), the formula (B-3) (Patent Document 6), the formula (C) (Patent Document 7), the formula (D-1) (Patent Document 8), the formula (D-2) (Patent Document 9), the formula (E-1) (Patent Document 10), the formula (E-2) (Patent Document 11), the formula (E-3) (Patent Document 12), the formula (F) (Patent Document 13), the formula (G) (Patent Document 14), the formula (H) (Patent Document 15 and Non-Patent Document 1), the formula (J) (Patent Document 16), and the formula (K) (Patent Document 17) described below have been reported. However, the compound of the formula (I) of the present application as described later is different in the structure of the group $R^1$ of the formula (I) from the compounds of the formulae (A-1) to (E-3), (H), and (K). It is different in structure from the compounds of the formulae (F) and (G), in that it has a benzimidazolyl-1-yl group. As the group $R^2$ of the formula (J), a heteroaryl group has been disclosed, but there is no specific disclosure of the benzimidazolyl-1-yl group, and there is no disclosure of the compound of the formula (I) of the present invention in Patent Document 16. Further, there is no description of a PI3Kδ selective inhibitory action in any documents.

[Chem. 1]

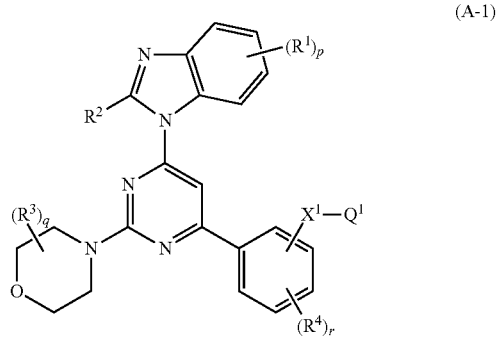

(A-1)

-continued
(A-2)
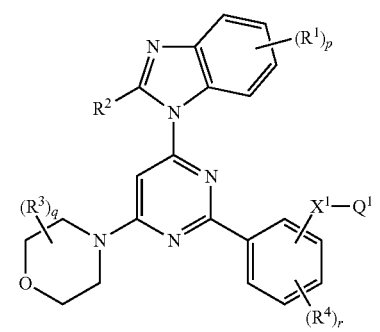
(A-3)
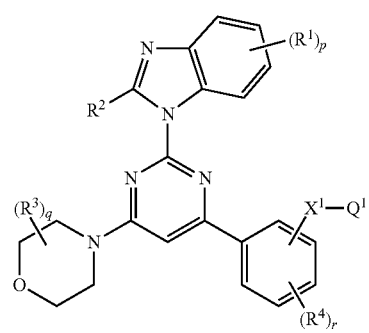
(B-1)
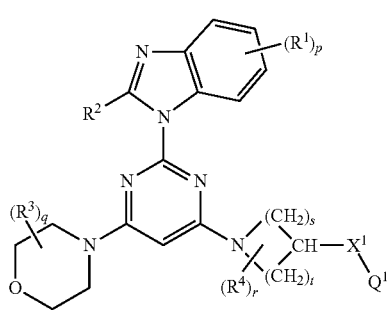
(B-2)
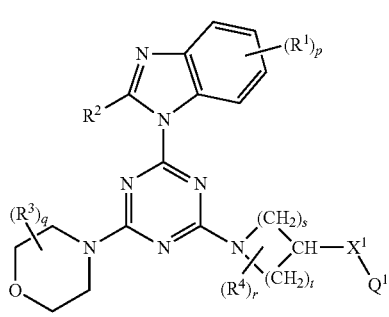
(B-3)
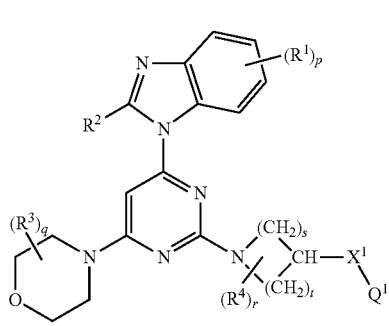
-continued
(C)
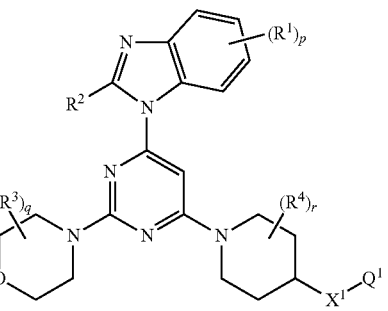
(D-1)
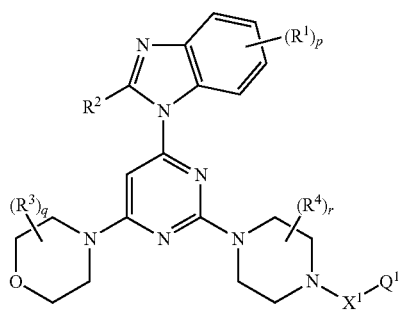
(D-2)
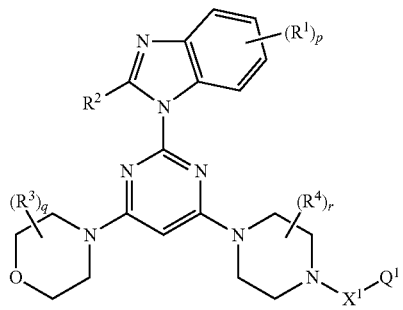
(E-1)
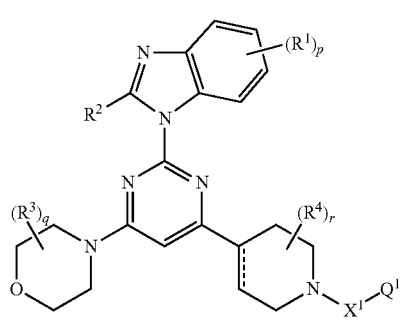
(E-2)
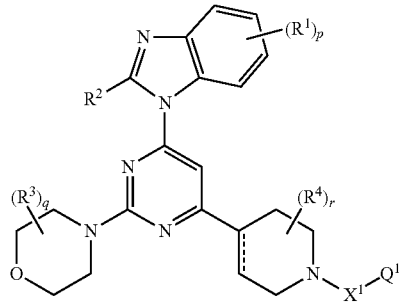

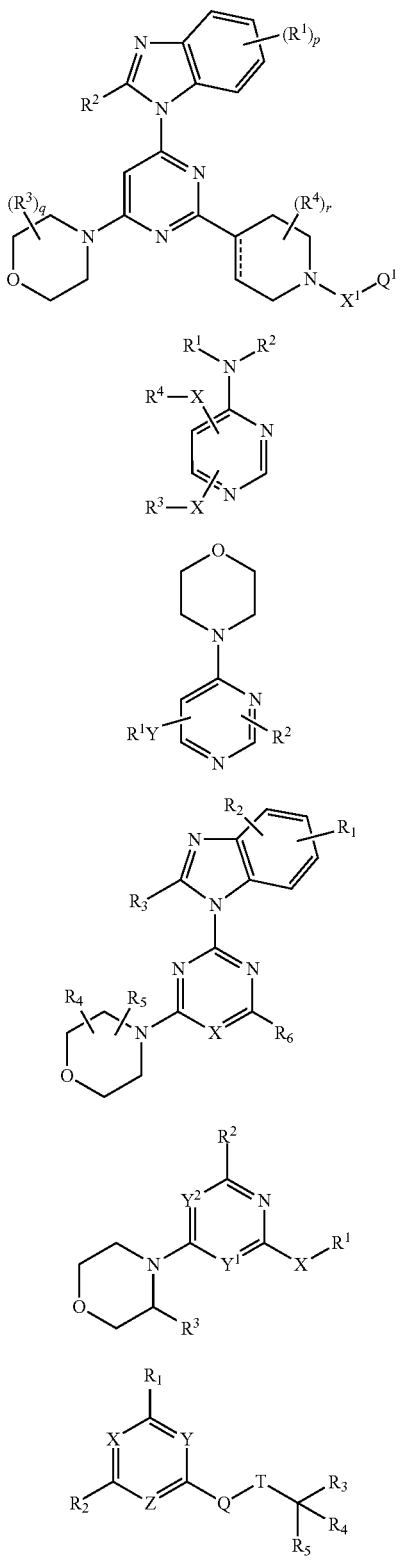

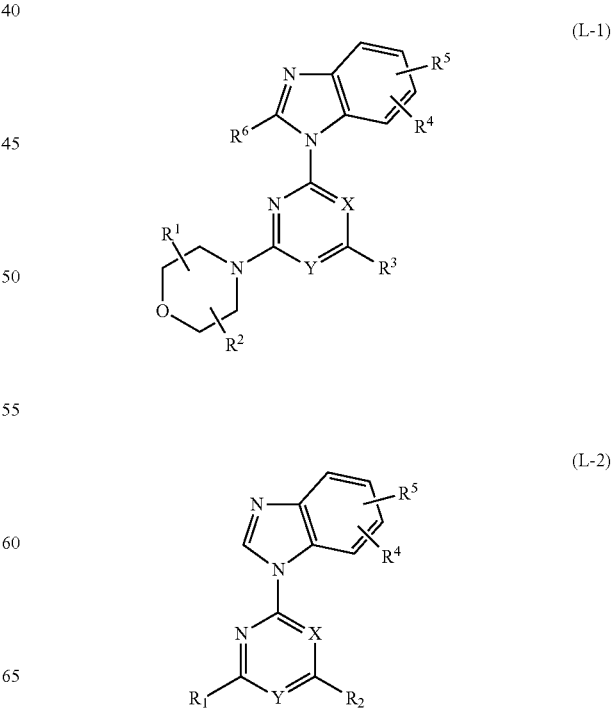

(wherein $R^2$ in the formulae (A-1) to (E-3) represents a difluoromethyl group or the like. $R^1$ and $R^2$ in the formula (F) are combined with each other to form an unsubstituted or substituted morpholino group, together with N to which they are bonded, X represents a bond or the like, and $R^3$ represents an unsubstituted or substituted indolyl group. $R^2$ in the formula (G) represents a substituted indol-4-yl group at the position 5 or 6. $R^3$ in the formula (H) represents a difluoromethyl group or the like, and $R^6$ represents a morpholino group which may be substituted, or the like. In the formula (J), $Y^1$ and $Y^2$ represent N, CH, or the like, X represents $NR^4CR^6R^7$ or the like, $R^1$ represents a heterocyclic group or the like, and $R^2$ represents a heteroaryl group or the like. In the formula (K), X, Y, and Z represent N or CH, provided that at least two of X, Y, and Z represent N, $R^1$ represents heteroaryl or the like, $R^2$ represents a heterocycle or the like, Q represents a bond, azetidinylen-4-amino, or the like, T represents —C(O)—, —C(=S)—, or —S(O)$_2$—, and $R^5$ represents halogen or —O—S(O)$_2$—$R^7$. For the other symbols, reference may be made to the publication.)

It has been reported that the compounds of the formula (L-1) (Patent Document 18), the formula (L-2) (Patent Document 19), the formula (L-3) (Patent Document 20), the formula (L-4) (Patent Document 21), and the formula (L-5) (Patent Document 22) described below have an anti-tumor activity. Further, in Non-Patent Document 2, it has been suggested that a secondary amine compound of the formula (M) has an Lck inhibitory action and an IL-2 production inhibitory action, and is applied for autoimmune diseases and rejection reaction in organ transplantation. However, the compound of the formula (I) of the present invention essentially has a difluoromethyl group, which is different in the structure from the compounds of the formulae (L-1), (L-2), and (M). It is also different in the structure of the group of $R^1$ of the formula (I) from the compounds of the formulae (L-3) and (L-5). In addition, it is different in the structure of the substituent on a benzimidazole ring from the compound of the formulae (L-4). Further, there is no description of a PI3Kδ selective inhibitory action in any literature.

[Chem. 2]

-continued

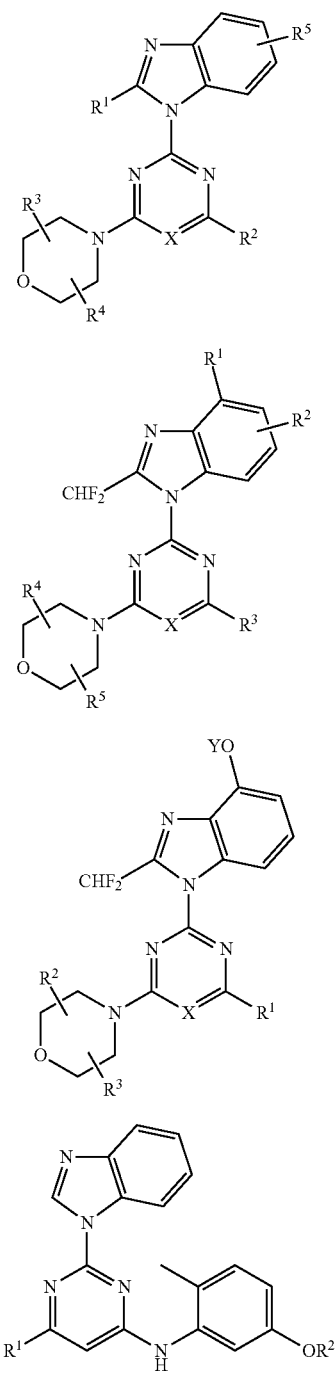

(in the formula (L-1), both of X and Y represent N, or one of X and Y represents N and the other represents $CR^7$, and $R^6$ represents H or $C_{1-6}$ alkyl; in the formula (L-2), both of X and Y represent N, or one of X and Y represents N and the other represents $CR^3$, and $R^1$ represents a morpholino group or the like; in the formula (L-3), X represents N or CH, $R^1$ represents $CH_nF_{3-n}$ (n is 1 or 2), and $R^2$ represents morpholino which may be substituted, or the like; in the formula (L-4), X represents N or CH, and $R^1$ represents halogen or a hydroxyl group; in the formula (L-5), X represents N or CH, $R^1$ represents a morpholino group which may be substituted with 1 to 4 $C_{1-6}$ alkyl groups, and Y represents $C_{1-6}$ alkyl; and in the formula (M), $R^1$ represents a morpholino group or the like. For the other symbols, reference may be made to the publication.)

Furthermore, a quinazolin-4-one derivative (Patent Documents 23 to 25) has been reported as a PI3Kδ selective inhibitor, and its usability in inflammation, immune diseases, or hematologic tumors (leukemia and the like) is indicated. As other PI3Kδ selective inhibitors, a thiazolylurea derivative (Patent Document 26) has been reported together with its usability in inflammation, immune diseases, or the like.

Furthermore, the invention relating to a triazine or pyrimidine derivative having a PI3Kδ selective inhibitory action, which is an invention in the prior art by the present inventors, has been disclosed after the priority date of the present application (Patent Document 27). The compound of the present invention is different in the structure of the group $R^1$ in the formula (I) from the compound disclosed in the prior application.

RELATED ART

Patent Documents

[Patent Document 1] Pamphlet of International Publication WO 2008/032027
[Patent Document 2] Pamphlet of International Publication WO 2008/032077
[Patent Document 3] Pamphlet of International Publication WO 2008/032086
[Patent Document 4] Pamphlet of International Publication WO 2008/032028
[Patent Document 5] Pamphlet of International Publication WO 2008/032036
[Patent Document 6] Pamphlet of International Publication WO 2008/032041
[Patent Document 7] Pamphlet of International Publication WO 2008/032033
[Patent Document 8] Pamphlet of International Publication WO 2008/032060
[Patent Document 9] Pamphlet of International Publication WO 2008/032064
[Patent Document 10] Pamphlet of International Publication WO 2008/032072
[Patent Document 11] Pamphlet of International Publication WO 2008/032089
[Patent Document 12] Pamphlet of International Publication WO 2008/032091
[Patent Document 13] Pamphlet of International Publication WO 2007/042810
[Patent Document 14] Pamphlet of International Publication WO 2008/125839
[Patent Document 15] Specification of European Patent Application Publication No. 1864665
[Patent Document 16] Pamphlet of International Publication WO 2009/007751
[Patent Document 17] Pamphlet of International Publication WO 2009/120094
[Patent Document 18] Specification of European Patent Application Publication No. 1020462
[Patent Document 19] International Publication WO 00/43385
[Patent Document 20] Pamphlet of European Patent Application Publication No. 1389617
[Patent Document 21] Pamphlet of European Patent Application Publication No. 1557415
[Patent Document 22] Pamphlet of European Patent Application Publication No. 1741714

[Patent Document 23] Pamphlet of International Publication WO 01/81346

[Patent Document 24] Pamphlet of International Publication WO 03/035075

[Patent Document 25] Pamphlet of International Publication WO 2005/113556

[Patent Document 26] Pamphlet of International Publication WO 2008/000421

[Patent Document 27] Pamphlet of International Publication WO 2010/092962

Non-Patent Documents

[Non-Patent Document 1] Journal of the National Cancer Institute, 2006, Vol. 98, p. 545-556

[Non-Patent Document 2] Bioorganic & Medicinal Chemistry Letters, 2006, Vol. 16, p. 5973-5977

DISCLOSURE OF INVENTION

Problems to be Solved by the Invention

A pharmaceutical composition, for example, a pharmaceutical composition having a PI3Kδ inhibitory action, in particular, a pharmaceutical composition for preventing and/or treating rejection reactions in various organ transplantations, allergy diseases, autoimmune diseases, and hematologic tumors, and a heterocyclic compound which is useful as an active ingredient of the pharmaceutical composition, are provided.

Means for Solving the Problems

The present inventors have extensively studied a PI3Kδ selective inhibitory action and/or an IL-2 production inhibitory action and/or a B cell proliferation inhibitory action (including an activation inhibitory action), and as a result, they have found that a novel triazine or pyrimidine derivative has an excellent PI3Kδ selective inhibitory action and/or IL-2 production inhibitory action and/or B cell proliferation inhibitory action (including an activation inhibitory action), and can be an agent for preventing and/or treating rejection reactions in various organ transplantations, allergy diseases, autoimmune diseases, and hematologic tumor, thereby completing the present invention.

That is, the present invention relates to a compound of the formula (I) or a salt thereof, and a pharmaceutical composition comprising the compound or a salt thereof and an excipient.

[Chem. 3]

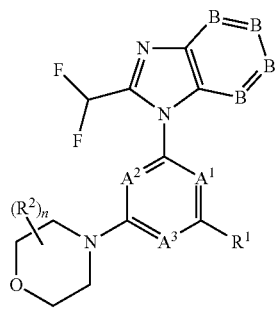

(I)

(wherein
$A^1$, $A^2$, and $A^3$ are the same as or different from each other and are CH or N, provided that at least two of $A^1$ to $A^3$ are N, B's are the same as or different from each other and are $CR^3$ or N, provided that at least three of four B's are $CR^3$, $R^1$ is —NH-lower alkylene-C(O)—OH or -$L^1$-$L^2$-Y, $R^2$'s are the same as or different from each other and are halogen, —OH, —O-lower alkyl, —CN, or lower alkyl which may be substituted with one or more substituents selected from the group consisting of halogen, —OH, —O-lower alkyl, and —CN, n is an integer of 0 to 8, $R^3$'s are the same as or different from each other and are H, —O-lower alkyl, cyano, —N($R^4$)$_2$, —C(O)—OH, —C(O)—O-lower alkyl, —C(O)—N($R^4$)$_2$, or lower alkyl which may be substituted with one or more substituents selected from the group consisting of —OH, —O-lower alkyl, —N($R^4$)$_2$, —C(O)—OH, —C(O)—O-lower alkyl, —C(O)—N($R^4$)$_2$, and halogen, $R^4$'s are the same as or different from each other and are H, or lower alkyl which may be substituted with one or more substituents selected from the group consisting of —OH, —O-lower alkyl, —CN, halogen, cycloalkyl, and phenyl, $L^1$ is -lower alkynylene-, —$NR^5$—, —$NR^5$—S(O)$_2$—, —$NR^5$—C(O)—, —O—, —S—, or —S(O)$_m$—, m's are the same as or different from each other and are 1 or 2, $L^2$ is a bond, -ALK-$X^2$—, -ALK-$NR^6$—C(O)—, -ALK-$NR^6$—C(O)—O-ALK-, -ALK-S(O)$_m$—$X^1$—, or -ALK-C(O)—$X^2$—, ALK's are the same as or different from each other and are lower alkylene which may be substituted with one or more substituents selected from the group consisting of —OH, —O-lower alkyl, —CN, halogen, cycloalkyl, and phenyl, $X^1$ is a bond, —$NR^6$—, or —$NR^6$-ALK-, $X^2$'s are the same as or different from each other and are a bond, —$NR^6$—, —$NR^6$-ALK-, —O—, —S—, —$NR^6$-ALK-O—, —$NR^6$-ALK-C(O)—$NR^6$—, or —$NR^6$-ALK-C(O)—, $R^5$'s are the same as or different from each other and are —$R^4$, lower alkenyl, or cycloalkyl, $R^6$'s are the same as or different from each other and are H, cycloalkyl, phenyl, a non-aromatic heterocycle which may be substituted with lower alkyl, or lower alkyl which may be substituted with one or more substituents selected from the group consisting of —OH, —O-lower alkyl, —CN, halogen, —N($R^4$)$_2$, cycloalkyl, phenyl, and a non-aromatic heterocycle, Y is lower alkyl which may be substituted with one or more substituents selected from the group consisting of —OH, —O-lower alkyl, —N(lower alkyl)$_2$ and —C(O)—N(lower alkyl)$_2$, cycloalkyl which may be substituted with one or more substituents selected from a Group D1, aryl which may be substituted with one or more substituents selected from the Group D1, an aromatic heterocycle which may be substituted with one or more substituents selected from the Group D1, or a non-aromatic heterocycle which may be substituted with one or more substituents selected from the Group D1, the Group D1 consists of:
(1) halogen,
(2) —O—$R^8$,
(3) —S—$R^8$,
(4) —CN,
(5) —NO$_2$,
(6) —$NR^4R^7$, in which $R^7$ is —$R^8$, —C(O)—$R^8$, —C(O)—C(O)—N($R^8$)$_2$, —C(O)—O—$R^8$, and —S(O)$_2$—$R^8$,
(7) —C(O)—$R^8$, (8) —S(O)$_2$—R$^8$ and —S(O)$_2$—N(R$^8$)$_2$,
(9) —C(O)—O—R$^8$,
(10) —C(O)—N(R$^8$)$_2$,
(11) —C(O)—C(O)—N(R$^8$)$_2$,
(12) —O—C(O)—R$^8$, —O—C(O)—NH—C(=NH)—NH$_2$, and —O—C(O)—N(R$^8$)$_2$,
(13) -L$^3$-cycloalkyl, -L$^3$-aryl, -L$^3$-aromatic heterocycle, and -L$^3$-non-aromatic heterocycle, in which the cycloalkyl, aryl, aromatic heterocycle, and non-aromatic heterocycle may be each substituted with one or more substituents selected from the group consisting of lower alkyl which may be substituted with one or more substituents selected from the group consisting of —O—R$^6$, —CN, halogen, —N(R$^6$)$_2$, —C(O)—R$^6$, —C(O)—O—R$^6$, —C(O)—N(R$^6$)$_2$, —N(R$^6$)—C(O)—O—R$^6$, —S(O)$_2$-lower alkyl, cycloalkyl, phenyl, and a non-aromatic heterocycle; oxo; cycloalkyl, aryl, aromatic heterocycle, and a non-aromatic heterocycle, each of which may be substituted with one or more substituents selected from the group consisting of lower alkyl, —OH, —O-lower alkyl, —CN, and halogen; and the substituents of (1) to (12),
(14) oxo, and
(15) lower alkyl, —O-lower alkyl, and lower alkenyl, each of which may be substituted with one or more substituents selected from the substituents described in (1) to (14), L$^3$'s are the same as or different from each other and are -a bond, —O—, —S—, —NR$^5$—, —NR$^5$—S(O)$_2$—, —NR$^5$—C(O)—, —C(O)—NR$^5$—, —S(O)$_m$—, -ALK-, —O-ALK-, -ALK-O—, —O-ALK-O—, —S-ALK-, -ALK-S—, -ALK-S(O)$_m$—, —S(O)$_m$-ALK-, —NR$^5$-ALK-, -ALK-NR$^5$—, —C(O)—NR$^5$-ALK-, —C(O)—NR$^5$-ALK-C(O)—, —C(O)—NR$^5$-ALK-O-ALK-, —NR$^5$—C(O)-ALK-, —NR$^5$—C(O)-ALK-C(O)—, —NR$^5$—C(O)-ALK-O-ALK-, -ALK-C(O)—NR$^5$—, -ALK-NR$^5$—C(O)—, —C(O)—O—, -ALK-C(O)—O—, —C(O)—O-ALK-, —C(O)-ALK-, -ALK-C(O)—, —NR$^5$—C(O)-ALK-NR$^5$—, or —C(O)—, R$^8$'s are the same as or different from each other and are H; cycloalkyl, phenyl, pyridyl, or a non-aromatic heterocycle, each of which may be substituted with one or more substituents selected from the group consisting of lower alkyl, —OH, —O-lower alkyl, —CN, and halogen; —R$^9$ or -ALK-L$^4$-R$^9$, in which R$^9$ is lower alkyl which may be substituted with one or more substituents selected from the group consisting of —O—R$^6$, —S—R$^6$, —CN, —N(R$^6$)$_2$, —C(O)—R$^6$, —C(O)—O—R$^6$, —C(O)—N(R$^6$)$_2$, —N(R$^6$)—C(O)—O—R$^6$, -cycloalkyl, phenyl, and a non-aromatic heterocycle, and L$^4$ is —C(O)—, —C(O)—NR$^5$—, —NR$^5$—, —NR$^5$—S(O)$_2$—, —NR$^5$—C(O)—, —NR$^5$—C(O)—O—, —O—, —S—, or —S(O)$_m$—, provided that in a case where R$^1$ has the following formula (II), all of B's are CH, W is NH or O, B$^1$ is a bond or lower alkylene, and B$^2$ is a bond or lower alkylene,

[Chem. 4]

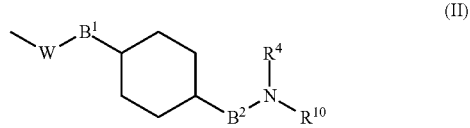

(II)

R$^{10}$ is —C(O)-(lower alkylene substituted with —NH—C(O)—O-lower alkyl)-S-lower alkyl, —C(O)-non-aromatic heterocycle, —C(O)-lower alkylene-NH-lower alkylene-(cycloalkyl which may be substituted with —OH), —C(O)-lower alkylene-NH-(cycloalkyl which may be substituted with a group selected from the group consisting of lower alkyl and —OH), —C(O)-lower alkylene-NH-non-aromatic heterocycle, —C(O)-lower alkylene-NH-(lower alkyl substituted with —OH), or —C(O)-(cycloalkyl substituted with one or more substituents selected from the group consisting of —NH$_2$, —N(lower alkyl)$_2$, and —NH—C(O)—O-lower alkyl), or R$^4$ and R$^{10}$ form a 4- to 8-membered monocyclic heterocyclic group containing 1 to 4 hetero atoms selected from O, S, and N, together with N to which they are bonded, and are further substituted with at least one substituent selected from a Group D2, in which the Group D2 consists of:
(a) —O-(lower alkyl substituted with one or more substituents selected from the group consisting of —O—R$^6$, —S—R$^6$, —CN, —N(R$^6$)$_2$, —C(O)—R$^6$, —C(O)—O—R$^6$, —C(O)—N(R$^6$)$_2$, —N(R$^6$)—C(O)—O—R$^6$, cycloalkyl, and a non-aromatic heterocycle), —O-(cycloalkyl, phenyl, pyridyl, or a non-aromatic heterocycle, each of which may be substituted with one or more substituents selected from the group consisting of lower alkyl, —OH, —O-lower alkyl, —CN, and halogen), and —O-ALK-L$^4$—R$^9$,
(b) —SR$^8$,
(c) —NO$_2$,
(d) —NR$^{11}$R$^7$, in which R$^7$ is —R$^8$, —C(O)—R$^8$, —C(O)—C(O)—N(R$^8$)$_2$, —C(O)—O—R$^8$, and —S(O)$_2$—R$^8$, and R$^{11}$ is lower alkyl substituted with one or more substituents selected from the group consisting of —OH, —O-lower alkyl, —CN, halogen, cycloalkyl, and phenyl,
(e) —C(O)—R$^8$,
(f) —S(O)$_2$—R$^8$ and —S(O)$_2$—N(R$^8$)$_2$,
(g) —C(O)—O-(lower alkyl substituted with one or more substituents selected from the group consisting of —O—R$^6$, —S—R$^6$, —CN, —N(R$^6$)$_2$, —C(O)—R$^6$, —C(O)—O—R$^6$, —C(O)—N(R$^6$)$_2$, —N(R$^6$)—C(O)—O—R$^6$, cycloalkyl, phenyl, and a non-aromatic heterocycle), —C(O)—O-(cycloalkyl, phenyl, pyridyl, or a non-aromatic heterocycle, each of which may be substituted with one or more substituents selected from the group consisting of lower alkyl, —OH, —O-lower alkyl, —CN, and halogen), and —C(O)O-ALK-L$^4$-R$^9$,
(h) —C(O)—N(R$^8$)$_2$,
(i) —C(O)—C(O)—N(R$^8$)$_2$,
(j) —O—C(O)-(lower alkyl substituted with one or more substituents selected from the group consisting of —O—R$^6$, —S—R$^6$, —CN, —N(R$^6$)$_2$, —C(O)—R$^6$, —C(O)—O—R$^6$, —C(O)—N(R$^6$)$_2$, —N(R$^6$)—C(O)—O—R$^6$, cycloalkyl, phenyl, and a non-aromatic heterocycle), —O—C(O)-(cycloalkyl, phenyl, pyridyl, or a non-aromatic heterocycle, each of which may be substituted with one or more substituents selected from the group consisting of lower alkyl, —OH, —O-lower alkyl, —CN, and halogen), —O—C(O)-ALK-L$^4$-R$^9$, —O—C(O)—NH—C(=NH)—NH$_2$, and —O—C(O)—N(R$^8$)$_2$,
(k) lower alkyl substituted with one or more substituents selected from the group consisting of —CN, —N(R$^6$)$_2$, —C(O)—R$^6$, —C(O)—O—R$^6$, —C(O)—N(R$^6$)$_2$, —N(R$^6$)—C(O)—O—R$^6$, —S(O)$_2$-lower alkyl, cycloalkyl, and phenyl,
(l) cycloalkyl which may be substituted with one or more substituents selected from the group consisting of lower alkyl, —OH, —O-lower alkyl, —CN, and halogen,
(m) aryl which may be substituted with one or more substituents selected from the group consisting of lower alkyl, —OH, —O-lower alkyl, —CN, and halogen, (n) an aromatic heterocycle substituted with one or more substituents selected from the group consisting of lower alkyl, —OH, —O-lower alkyl, —CN, and halogen, and (o) a non-aromatic heterocycle substituted with one or more substituents selected from the group consisting of lower alkyl, —OH, —O-lower alkyl, —CN, and halogen.)

Unless specified otherwise, in the case where the symbols of the chemical formulae in the present specification are also used in other chemical formulae, the same symbols denote the same meanings.

Furthermore, the present invention relates to a pharmaceutical composition for preventing and/or treating rejection reactions in various organ transplantations, allergy diseases, autoimmune diseases, and hematologic tumor, which comprises the compound of the formula (I) or a salt thereof as an active ingredient. Further, the pharmaceutical composition includes an agent for preventing and/or treating rejection reactions in various organ transplantations, allergy diseases, autoimmune diseases, and hematologic tumor, which comprises the compound of the formula (I) or a salt thereof. In a certain embodiment, the present invention relates to an agent for preventing and/or treating rejection reactions in kidney, liver, and heart transplantations, in another embodiment, an agent for preventing and/or treating chronic rejection and acute rejection, and in still another embodiment, an agent for preventing and/or treating antibody-related rejection.

Furthermore, the present invention relates to use of the compound of the formula (I) or a salt thereof in the manufacture of a pharmaceutical composition for preventing and/or treating rejection reactions in various organ transplantations, allergy diseases, autoimmune diseases, and hematologic tumor, and use of the compound of the formula (I) or a salt thereof in preventing and/or treating rejection reactions in various organ transplantations, allergy diseases, autoimmune diseases, and hematologic tumor, the compound of the formula (I) or a salt thereof for preventing and/or treating rejection reactions in various organ transplantations, allergy diseases, auto immune diseases, and hematologic tumor, and a method for preventing or treating rejection reactions in various organ transplantations, allergy diseases, autoimmune diseases, and hematologic tumor, including administering to a subject an effective amount of the compound of the formula (I) or a salt thereof. Here, the "subject" is a human or any of other animals in need of prevention or treatment thereof, and in a certain embodiment, a human in need of prevention or treatment thereof.

Furthermore, the present invention relates to a PI3Kδ selective inhibitor and/or an IL-2 production inhibitor and/or a B cell proliferation inhibitor, each of which contains the compound of the formula (I) or a salt thereof.

Effects of the Invention

The compound of the formula (I) has a PI3Kδ selective inhibitory action and/or an IL-2 production inhibitory action and/or a B cell proliferation inhibitory action (including an activation inhibitory action), and can therefore be used as an agent for preventing or treating rejection reactions in various organ transplantations, allergy diseases, autoimmune diseases, and hematologic tumor.

EMBODIMENTS FOR CARRYING OUT THE INVENTION

Hereinbelow, the present invention will be described in detail.

The "lower alkyl" is linear or branched alkyl having 1 to 6 carbon atoms (which is hereinafter simply referred to as $C_{1-6}$), and examples thereof include methyl, ethyl, n-propyl, isopropyl, n-butyl, isobutyl, sec-butyl, tert-butyl, n-pentyl, n-hexyl, and the like. In another embodiment, the lower alkyl is $C_{1-4}$ alkyl, in still another embodiment, methyl, ethyl, or tert-butyl, and in a further still other embodiment, methyl.

The "lower alkenyl" is linear or branched $C_{2-6}$ alkenyl, and examples thereof include vinyl, propenyl, butenyl, pentenyl, 1-methylvinyl, 1-methyl-2-propenyl, 1,3-butadienyl, pentadienyl, and the like. In another embodiment, the lower alkenyl is $C_{2-4}$ alkenyl, and in still another embodiment, propenyl.

The "lower alkylene" is a divalent group formed by the removal of any hydrogen atom of the "lower alkyl". Accordingly, the "$C_{1-6}$ alkylene" is linear or branched alkylene having 1 to 6 carbon atoms, and examples thereof include methylene, ethylene, trimethylene, tetramethylene, pentamethylene, hexamethylene, methylmethylene, dimethylmethylene, ethylmethylene, methylethylene, dimethylethylene, ethylethylene, and the like. In another embodiment, the lower alkylene is methylene, ethylene, and in still another embodiment, methylene.

The "lower alkenylene" is linear or branched $C_{2-6}$ alkenylene, and examples thereof include vinylene, ethylidene, propenylene, butenylene, pentenylene, hexenylene, 1,3-butadienylene, 1,3-pentadienylene, and the like. In another embodiment, the lower alkenylene is $C_{2-4}$ alkenylene, and in still another embodiment, propenylene.

The "lower alkynylene" is linear or branched $C_{2-6}$ alkynylene, and examples thereof include ethynylene, propynylene, butynylene, pentynylene, hexynylene, 1,3-butadiynylene, 1,3-pentadiynylene, and the like. In another embodiment, the lower alkynylene is $C_{2-4}$ alkynylene, and in still another embodiment, propynylene.

The "halogen" is F, Cl, Br, or I, in another embodiment, F, and in still another embodiment, Cl.

The "cycloalkyl" is $C_{3-10}$ saturated hydrocarbon ring group, which may have a bridge and may be combined with a non-aromatic heterocyclic group to form a spiro ring. Specific examples thereof include cyclopropyl, cyclobutyl, cyclopentyl, cyclohexyl, cycloheptyl, cyclohexenyl, cyclooctyl, bicyclo[3.3.0]octane, hexahydro-1'H-spiro-1,3-dioxane-2,2'-pentalene, 1,4-dioxaspiro[4.5]decane, bicyclo[2.2.2]octyl, adamantyl, azaspiro[5.5]undecanyl, octahydrocyclopenta[c]pyrrole, indanyl, and the like. In another embodiment, the cycloalkyl is cyclopropyl, cyclobutyl, cyclopentyl, cyclohexyl, octahydropentalene, bicyclo[2.2.2]octyl, or adamantyl, in still another embodiment, $C_{3-8}$ cycloalkyl, in further still another embodiment, $C_{3-6}$ cycloalkyl, in further still another embodiment, cyclohexyl, in further still another embodiment, octahydropentalene, and in further still another embodiment, adamantyl.

The "aryl" is $C_{6-14}$ monocyclic to tricyclic aromatic hydrocarbon ring group, and examples thereof include phenyl, naphthyl, and the like. In another embodiment, the aryl is phenyl.

The "aromatic heterocycle" is an aromatic heterocycle having 5 to 6 ring members, containing at least one hetero atom selected from O, N, and S as a ring-constituting atom, and may be fused with a benzene ring or an aromatic heterocycle. Examples thereof include pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isooxazolyl, thiadiazolyl, oxadiazolyl, thienyl, furyl, indolyl, isoindolyl, benzoimidazolyl, indazolyl, quinolyl, isoquinolyl, quinazolinyl, quinoxalinyl, phthalazinyl, benzothiazolyl, benzoisothiazolyl, benzothiadiazolyl, benzoxazolyl, benzoisoxazolyl, benzofuranyl, benzothienyl, carbazolyl, dibenzo[b,d]furanyl, dibenzo[b,d]thienyl, thienopyridyl, thienopyrimidinyl, thienopyrazyl, 1,4-benzodioxin-2-yl, [1,2,4]triazolo[4,3-a]pyridyl, imidazo[1,2-a]pyridyl, and the like. In another embodiment, the aromatic heterocycle is imidazolyl, pyridyl, pyrazinyl, indolyl, indazolyl, benzoimidazolyl, or benzothiazolyl.

The "non-aromatic heterocycle" is a non-aromatic heterocycle having 4 to 8 ring members, containing at least one hetero atom selected from O, N, and S as a ring-constituting atom, which may have unsaturated bonds in a part of the ring and may be bridged. The non-aromatic heterocycle may be fused with a benzene ring or an aromatic heterocycle. Further, the sulfur atom that is a ring-constituting atom may be oxidized. Examples of the non-aromatic heterocycle include azetidinyl, pyrrolidinyl, piperidinyl, piperazinyl, azepanyl, diazepanyl, morpholinyl, thiomorpholinyl, quinuclidinyl, 1,1-dioxidethiomorpholinyl, tetrahydropyridinyl, oxetanyl, tetrahydrofuranyl, tetrahydropyranyl, tetrahydrothienyl, 4,5-dihydrothiazolyl, dioxolanyl, dioxanyl, tetrahydrothiopyranyl, tetrahydroisoquinolyl, oxazolidinyl, tropane, 3,9-diazaspiro[5.5]undecanyl, 2,8-diazaspiro[4.5]decanyl, octahydropyrrolo[1,2-a]pyrazyl, 5,6,7,8-tetrahydro-1,7-naphthalinyl, 3,4-dihydro-2H-1,4-benzoxazinyl, 1,3-benzodioxolyl, chromenyl, 1,4-benzothiazinyl, 4,5-dihydro-1,3-thiazolyl, and the like. In another embodiment, the non-aromatic heterocycle is azetidinyl, pyrrolidinyl, piperidinyl, piperazinyl, morpholinyl, tetrahydrofuranyl, tetrahydropyranyl, or azepanyl, in still another embodiment, pyrrolidinyl, piperidinyl, tetrahydropyranyl, or azepanyl, in further still another embodiment, piperidinyl, and in further still another embodiment, pyrrolidinyl.

The "cyclic amino" is a non-aromatic heterocyclic group having a nitrogen atom-containing group and has a bonding position on the nitrogen atom, among the above "non-aromatic heterocycles" and may form a spiro ring, and specific examples thereof include pyrrolidin-1-yl, piperidin-1-yl, azepan-1-yl, piperazin-1-yl, 1,3-oxazolidin-2-one, morpholin-4-yl, thiomorpholin-4-yl, 1,1-dioxidethiomorpholin-4-yl, 2-oxa-6-azaspiro[3.3]hept-6-yl, 1-oxa-3-azaspiro[4.5]decan-2-one, 2,5-diazabicyclo[2.2.1]heptane, 2-oxa-5-azaspiro[3.4]octane, 2-oxa-5-azabicyclo[2.2.1]heptane, and the like. In another embodiment, the cyclic amino is pyrrolidin-1-yl.

Furthermore, the monocyclic heterocyclic group in the expression "$R^{10}$ and $R^4$ form a 4- to 8-membered monocyclic heterocyclic group containing 1 to 4 hetero atoms selected from O, S, and N, together with N to which they are bonded" is a 4- to 8-membered monocyclic group containing 1 to 4 hetero atoms selected from O, S, and N in the "aromatic heterocycle" and the "cyclic amino" above.

In the present specification, the expression "which may be substituted" means non-substitution or substitution with 1 to 5 substituents. In a certain embodiment, it is unsubstitution or substitutions with 1 to 3 substituents, in another embodiment, unsubstitution or substitution with 1 substituent, and in still another embodiment, unsubstitution. Further, in a case of having a plurality of substituents, the substituents may be the same as or different from each other.

In a certain embodiment, the Group D1 consists of:
(1) halogen,
(2) —OH,
(3) —O-lower alkyl,
(4) —CN,
(5) —NO$_2$,
(6) —NR$^{4a}$R$^7$, in which R$^{4a}$ is H or lower alkyl, R$^7$ is lower alkyl which may be substituted with one or more substituents selected from the group consisting of halogen, —OH, —O-lower alkyl, and aryl, —C(O)-lower alkyl, —C(O)-lower alkylene-N(lower alkyl)$_2$, lower alkenyl, —C(O)-lower alkylene-NH-(lower alkyl substituted with cycloalkyl), —C(O)-lower alkylene-NH-(cycloalkyl which may be substituted with lower alkyl), —C(O)O-lower alkyl or H,
(7) —C(O)-lower alkyl,
(8) —C(O)-lower alkylene-N(R$^4$)$_2$,
(9) —C(O)O-lower alkyl,
(10) —C(O)OH,
(11) —C(O)—N(R$^4$)$_2$,
(12) —O—C(O)—NH—C(=NH)—NH$_2$,
(13) -L$^5$-cycloalkyl, -L$^5$-aromatic heterocycle, and -L$^5$-non-aromatic heterocycle, in which the cycloalkyl, aryl, aromatic heterocycle, and non-aromatic heterocycle may be each substituted with one or more substituents selected from the group consisting of lower alkyl which may be substituted with one or more substituents selected from the group consisting of —OH, halogen, —O-lower alkyl, and a non-aromatic heterocycle, —OH, —O-lower alkyl, —NH$_2$, halogen, —C(O)O-lower alkyl, —C(O)-lower alkyl, oxo, —NH—S(O)$_2$-lower alkyl, —NH—S(O)$_2$-cycloalkyl, —NH—C(O)-lower alkyl, —NR$^4$—C(O)—O-(lower alkyl which may be substituted with —OH), —S(O)$_2$-lower alkyl, —NH-(lower alkyl which may be substituted with —OH), cycloalkyl which may be substituted with —OH, and a non-aromatic heterocycle, in which L$^5$'s are the same as or different from each other and are a bond, —O—, -lower alkylene, —O-lower alkylene, —O-lower alkylene-O—, —C(O)—NH—, —NH—C(O)—, —C(O)-lower alkylene-, or —C(O)—;

in another embodiment, the cycloalkyl may be substituted with one or more substituents selected from the group consisting of lower alkyl which may be substituted with one or more substituents selected from the group consisting of halogen, —OH, and —O-lower alkyl, halogen, —OH, —O-lower alkyl, —NH-lower alkylene-OH, —NH$_2$, —NH—C(O)—O-lower alkyl, —NH-lower alkyl, and —C(O)—O-lower alkyl; the aryl may be substituted with one or more substituents selected from the group consisting of lower alkyl, halogen, —O-lower alkyl, and —C(O)—O-lower alkyl; the aromatic heterocycle may be substituted with one or more substituents selected from the group consisting of lower alkyl and —NH$_2$; and the non-aromatic heterocycle may be substituted with one or more substituents selected from the group consisting of lower alkyl which may be substituted with one or more substituents selected from the group consisting of —OH, halogen, —O-lower alkyl, and a non-aromatic heterocycle, —NH$_2$, halogen, —C(O)—O-lower alkyl, —C(O)-lower alkyl, oxo, —NH—S(O)$_2$-lower alkyl, —NH—S(O)$_2$-cycloalkyl, —NH—C(O)-lower alkyl, —NR$^4$—C(O)—O-(lower alkyl which may be substituted with —OH), —S(O)$_2$-lower alkyl, —NH-(lower alkyl substituted with —OH), cycloalkyl which may be substituted with —OH, and a non-aromatic heterocycle,
(14) oxo, and
(15) lower alkyl, —O-lower alkyl, and lower alkenyl, each of which may be substituted with one or more substituents selected from the substituents described in (1) to (14) above.

In another embodiment, the Group D1 consists of:
(1) halogen,
(2) —OH,
(3) —O-lower alkyl,
(4) —NR$^{4a}$R$^7$, in which R$^{4a}$ represents H or lower alkyl, R$^7$ represents lower alkyl which may be substituted with —OH, —C(O)-lower alkylene-N(lower alkyl)$_2$, —C(O)-lower alkylene-NH-(lower alkyl substituted with cycloalkyl), —C(O)-(cycloalkyl substituted with —NH$_2$—C(O)-lower alkylene-NH-tetrahydropyran, —C(O)-lower alkylene-N(lower alkyl)-(cycloalkyl which may be substituted with lower alkyl) or —C(O)-lower alkylene-NH-(cycloalkyl which may be substituted with lower alkyl), (5) —C(O)-lower alkylene-N(R$^4$)$_2$, (6) —C(O)O-lower alkyl, (7) -L$^5$-(aryl which may be substituted with one or more substituents selected from the group consisting of lower alkyl, halogen, and —O-lower alkyl), (8) -L$^5$-(non-aromatic heterocycle which may be substituted with one or more substituents selected from the group consisting of lower alkyl, —NH—C(O)—O-lower alkyl, —NH—C(O)-lower alkyl, —C(O)—O-lower alkyl, —C(O)-lower alkyl, —S(O)$_2$-lower alkyl, oxo, and —NH-lower alkyl), (9) -L$^5$-(cycloalkyl which may be substituted with one or more substituents selected from the group consisting of lower alkyl which may be substituted with one or more groups selected from the group consisting of halogen and —OH, halogen, —OH, —O-lower alkyl, and —C(O)O-lower alkyl), and

(10) lower alkyl which may be each substituted with one or more substituents selected from the substituents described in (1) to (9) above.

In still another embodiment, the Group D1 consists of:
(1) —OH,
(2) —O-lower alkyl,
(3) —NR$^{4a}$R$^7$, in which R$^{4a}$ represents H or lower alkyl, R$^7$ represents lower alkyl which may be substituted with —OH, —C(O)-(cycloalkyl substituted with —NH$_2$), —C(O)-lower alkylene-NH-tetrahydropyran, —C(O)-lower alkylene-N(lower alkyl)-(cycloalkyl which may be substituted with lower alkyl), or —C(O)-lower alkylene-NH-(cycloalkyl which may be substituted with lower alkyl),
(4) -L$^{5a}$-(non-aromatic heterocycle which may be substituted with one or more substituents selected from the group consisting of lower alkyl, —NH—C(O)—O-lower alkyl, —NH—C(O)-lower alkyl, —C(O)—O-lower alkyl, —C(O)-lower alkyl, and oxo), in which L$^{5a}$ represents a bond, —C(O)-lower alkylene-, or —C(O)—, and
(5) -L$^{5b}$-(cycloalkyl which may be substituted with one or more substituents selected from the group consisting of lower alkyl which may be substituted with —OH, halogen, —OH, and —O-lower alkyl), in which L$^{5b}$ represents a bond or —C(O)—.

In further still another embodiment, the Group D1 consists of:
(1) -L$^{5a}$-(non-aromatic heterocycle which may be substituted with one or more substituents selected from the group consisting of lower alkyl, —NH—C(O)—O-lower alkyl, —C(O)O-lower alkyl, —C(O)-lower alkyl, and oxo), in which L$^{5a}$ represents a bond, —C(O)-lower alkylene-, or —C(O)—, and
(2) —C(O)-(cycloalkyl which may be substituted with one or more substituents selected from the group consisting of lower alkyl which may be substituted with —OH, —OH, and —O-lower alkyl).

Certain embodiments of the compound of the formula (I) of the present invention are shown below.

(1) In a certain embodiment of A$^1$, A$^2$ and A$^3$, any one of A$^1$, A$^2$ and A$^3$ is CH, in another embodiment, A$^1$ and A$^3$ are N and A$^2$ is CH, and in still another embodiment, A$^2$ and A$^3$ are N and A$^1$ is CH.

(2) In a certain embodiment of B, all of B's are CR$^3$, in which R$^3$ is H, lower alkyl which may be substituted with halogen, or —O-lower alkyl, in another embodiment, R$^3$ is H or lower alkyl, in still another embodiment, R$^3$ is lower alkyl, in further still another embodiment, R$^3$ is H, in further still another embodiment, one of B's is N and the others are CH, and in further still another embodiment, all of B's are CH.

(3) In a certain embodiment of R$^1$, R$^1$ is -L$^1$-L$^2$-Y.

(4) In a certain embodiment of L$^1$, L$^1$ is —NR$^5$—, —NR$^5$—S(O)$_2$—, —NR$^5$—C(O)—, or —O—, in another embodiment, L$^1$ is —NH—, —N(lower alkyl)-, or —O—, in still another embodiment, —NH— or —O—, in further still another embodiment, —NH—, and in further still another embodiment, —O—.

(5) In a certain embodiment, L$^2$ is a bond, -ALK-, -ALK-S—, -ALK-S(O)$_m$—X$^1$—, or -ALK-C(O)—X$^2$—, in which X$^1$ is a bond or —NR$^6$—, X$^2$ is a bond, —NR$^6$—, —NR$^6$-ALK-, or —O—, ALK is lower alkylene, and R$^6$ is H or lower alkyl, in another embodiment, L$^2$ is a bond, lower alkylene, or -lower alkylene-C(O)NH—, in still another embodiment, a bond or lower alkylene, in further still another embodiment, a bond, in further still another embodiment, lower alkylene, and in further still another embodiment, methylene.

(6) In a certain embodiment, Y is cycloalkyl which may be substituted with one or more substituents selected from the Group D1, aryl which may be substituted with one or more substituents selected from the Group D1, an aromatic heterocycle which may be substituted with one or more substituents selected from the Group D1, or a non-aromatic heterocycle which may be substituted with one or more substituents selected from the Group D1, in another embodiment, cycloalkyl which may be substituted with one or more substituents selected from the Group D1 or a non-aromatic heterocycle which may be substituted with one or more substituents selected from the Group D1, in still another embodiment, cycloalkyl which may be substituted with one or more substituents selected from the Group D1, in further still another embodiment, a non-aromatic heterocycle which may be substituted with one or more substituents selected from the Group D1, in further still another embodiment, cyclohexyl or cyclic amino, in further still another embodiment, cyclohexyl, cyclic amino, in further still another embodiment, piperidinyl, pyrrolidinyl, or azetidinyl, and in further still another embodiment, pyrrolidinyl or azetidinyl.

(7) In a certain embodiment, n is an integer of 0 or 1 to 2, and in another embodiment, 0.

(8) In a certain embodiment, R$^2$'s are the same as or different from each other and are lower alkyl which may be substituted with halogen.

(9) The compound or a salt thereof, which is a combination of any two or more of the embodiments of (1) to (8) as described above.

The compound or a salt thereof, which is a combination of any two or more of the embodiments of (1) to (8) as described above, is also included in the present invention, as described in (9) above, and the specific examples thereof also include the following embodiments.

(10) The compound or a salt thereof, wherein R$^1$ is —NH-lower alkylene-C(O)—OH or -L$^1$-L$^2$-Y, L$^1$ is -lower alkylene-, —NR$^5$—, —NR$^5$—S(O)$_2$—, —NR$^5$—C(O)—, —O—, —S—, or —S(O)$_m$—, m is 1 or 2, L$^2$ is a bond, -ALK-X$^2$—, -ALK-NR$^6$—C(O)—, -ALK-NR$^6$—C(O)—O-ALK-, -ALK-S(O)$_m$—X$^1$—, or -ALK-C(O)—X$^2$—, ALK's are the same as or different from each other and are lower alkylene which may be substituted with one or more substituents selected from the group consisting of —OH, —O-lower alkyl, —CN, halogen, and cycloalkyl, X$^1$ is a bond, —NR$^6$—, or —NR$^6$-ALK-, X$^2$'s are the same as or different from each other and are a bond, —NR$^6$—, —NR$^6$-ALK-, —O—, —S—, —NR$^6$-ALK-O—, —NR$^6$-ALK-C(O)—NR$^6$—, or —NR$^6$-ALK-C(O)—, R$^4$'s are the same as or different from each other and are H, or lower alkyl which may be substituted with one or more substituents selected from the group consisting of —OH, —O-lower alkyl, —CN, halogen, and cycloalkyl, $R^5$'s are the same as or different from each other and are —$R^4$, lower alkenyl, or cycloalkyl, $R^6$'s are the same as or different from each other and are H, cycloalkyl, a non-aromatic heterocycle which may be substituted with lower alkyl, or lower alkyl which may be substituted with one or more substituents selected from the group consisting of —OH, —O-lower alkyl, —CN, halogen, —N($R^4$)$_2$, cycloalkyl, and a non-aromatic heterocycle, Y is lower alkyl which may be substituted with one or more substituents selected from the group consisting of —OH, —O-lower alkyl, —N(lower alkyl)$_2$ and —C(O)—N(lower alkyl)$_2$, cycloalkyl which may be substituted with one or more substituents selected from the Group D1, or a non-aromatic heterocycle which may be substituted with one or more substituents selected from the Group D1, provided that $L^2$ is -ALK-$X^{2a}$—, -ALK-$NR^6$—C(O)—, -ALK-$NR^6$—C(O)—O-ALK-, -ALK-S(O)$_m$—$X^1$—, or -ALK-C(O)—$X^2$—, in which in a case where $X^{2a}$ is —$NR^6$—, —$NR^6$-ALK-, —O—, —S—, —$NR^6$-ALK-O—, —$NR^6$-ALK-C(O)—$NR^6$—, or —$NR^6$-ALK-C(O)—, Y is aryl which may be substituted with one or more substituents selected from the Group D1 or an aromatic heterocycle which may be substituted with one or more substituents selected from the Group D1.

(11) The compound or a salt thereof as described in (10), wherein $R^1$ is -$L^1$-$L^2$-Y, $L^1$ is —$NR^5$—, —$NR^5$—S(O)$_2$—, —$NR^5$—C(O)—, or —O—, in which $R^5$ is H or lower alkyl, $L^2$ is a bond, -ALK-, -ALK-S—, -ALK-S(O)$_m$—$X^1$—, or -ALK-C(O)—$X^2$—, in which $X^1$ is a bond or —$NR^6$—, $X^2$ is a bond, —$NR^6$—, —$NR^6$-ALK-, or —O—, ALK is lower alkylene, $R^6$ is H or lower alkyl, and Y is cycloalkyl which may be substituted with one or more substituents selected from the Group D1, or a non-aromatic heterocycle which may be substituted with one or more substituents selected from the Group D1.

(12) The compound or a salt thereof as described in (11), wherein -$L^1$-$L^2$- is —NH— or —O—.

(13) The compound or a salt thereof as described in (12), wherein B's are all CH and n is 0.

(14) The compound or a salt thereof as described in (13), wherein $A^1$ and $A^3$ are N and $A^2$ is CH.

(15) The compound or a salt thereof as described in (13), wherein $A^2$ and $A^3$ are N and $A^1$ is CH.

Examples of the specific compounds included in the compound of the formula (I) or a salt thereof include the following compounds:

methyl {(3S)-1-[trans-4-({6-[2-(difluoromethyl)-1H-benzimidazol-1-yl]-2-(morpholin-4-yl)pyrimidin-4-yl}oxy)cyclohexyl]-2-oxopyrrolidin-3-yl}carbamate,
methyl {(3R)-1-[trans-4-({6-[2-(difluoromethyl)-1H-benzimidazol-1-yl]-2-(morpholin-4-yl)pyrimidin-4-yl}oxy)cyclohexyl]-2-oxopyrrolidin-3-yl}carbamate,
ethyl {(3R)-1-[trans-4-({6-[2-(difluoromethyl)-1H-benzimidazol-1-yl]-2-(morpholin-4-yl)pyrimidin-4-yl}oxy)cyclohexyl]-2-oxopyrrolidin-3-yl}carbamate,
[(3S)-3-({6-[2-(difluoromethyl)-1H-benzimidazol-1-yl]-2-(morpholin-4-yl)pyrimidin-4-yl}amino)pyrrolidin-1-yl][(2R)-tetrahydrofuran-2-yl]methanone,
[(3S)-3-({6-[2-(difluoromethyl)-1H-benzimidazol-1-yl]-2-(morpholin-4-yl)pyrimidin-4-yl}amino)pyrrolidin-1-yl](tetrahydro-2H-pyran-4-yl)methanone,
methyl {(3S)-1-[trans-4-({4-[2-(difluoromethyl)-1H-benzimidazol-1-yl]-6-(morpholin-4-yl)pyrimidin-2-yl}amino)cyclohexyl]-2-oxopyrrolidin-3-yl}carbamate,
methyl {(3R)-1-[trans-4-({4-[2-(difluoromethyl)-1H-benzimidazol-1-yl]-6-(morpholin-4-yl)pyrimidin-2-yl}amino)cyclohexyl]-2-oxopyrrolidin-3-yl}carbamate,
methyl {(3R)-1-[trans-4-({6-[2-(difluoromethyl)-1H-benzimidazol-1-yl]-2-(morpholin-4-yl)pyrimidin-4-yl}amino)cyclohexyl]-2-oxopyrrolidin-3-yl}carbamate,
1-[(3S)-3-({6-[2-(difluoromethyl)-1H-benzimidazol-1-yl]-2-(morpholin-4-yl)pyrimidin-4-yl}amino)pyrrolidin-1-yl]-2-(tetrahydrofuran-2-yl)ethanone,
1-[(3S)-3-({6-[2-(difluoromethyl)-1H-benzimidazol-1-yl]-2-(morpholin-4-yl)pyrimidin-4-yl}amino)pyrrolidin-1-yl]-2-(tetrahydro-2H-pyran-4-yl)ethanone,
1-[3-({6-[2-(difluoromethyl)-1H-benzimidazol-1-yl]-2-(morpholin-4-yl)pyrimidin-4-yl}oxy)azetidin-1-yl]-2-(tetrahydrofuran-2-yl)ethanone,
methyl 4-{[(3S)-3-({6-[2-(difluoromethyl)-1H-benzimidazol-1-yl]-2-(morpholin-4-yl)pyrimidin-4-yl}amino)pyrrolidin-1-yl]carbonyl}piperidine-1-carboxylate,
[(3S)-3-({6-[2-(difluoromethyl)-1H-benzimidazol-1-yl]-2-(morpholin-4-yl)pyrimidin-4-yl}oxy)pyrrolidin-1-yl](tetrahydrofuran-3-yl)methanone,
4-{[(3S)-3-({6-[2-(difluoromethyl)-1H-benzimidazol-1-yl]-2-(morpholin-4-yl)pyrimidin-4-yl}oxy)pyrrolidin-1-yl]carbonyl}-1-methylpyrrolidin-2-one,
2-(1-acetylpiperidin-4-yl)-1-[(3S)-3-({6-[2-(difluoromethyl)-1H-benzimidazol-1-yl]-2-(morpholin-4-yl)pyrimidin-4-yl}amino)pyrrolidin-1-yl]ethanone,
[(3S)-3-({6-[2-(difluoromethyl)-1H-benzimidazol-1-yl]-2-(morpholin-4-yl)pyrimidin-4-yl}amino)pyrrolidin-1-yl](tetrahydrofuran-3-yl)methanone,
4-{[(3S)-3-({6-[2-(difluoromethyl)-1H-benzimidazol-1-yl]-2-(morpholin-4-yl)pyrimidin-4-yl}amino)pyrrolidin-1-yl]carbonyl}-1-methylpyrrolidin-2-one,
1-[(3S)-3-({6-[2-(difluoromethyl)-1H-benzimidazol-1-yl]-2-(morpholin-4-yl)pyrimidin-4-yl}amino)pyrrolidin-1-yl]-2-(piperidin-1-yl)ethanone,
(5S)-5-{[3-({6-[2-(difluoromethyl)-1H-benzimidazol-1-yl]-2-(morpholin-4-yl)pyrimidin-4-yl}oxy)azetidin-1-yl]carbonyl}pyrrolidin-2-one,
(5S)-5-{[3-({6-[2-(difluoromethyl)-1H-benzimidazol-1-yl]-2-(morpholin-4-yl)pyrimidin-4-yl}amino)azetidin-1-yl]carbonyl}pyrrolidin-2-one,
2-(1-acetylpiperidin-4-yl)-1-[3-({6-[2-(difluoromethyl)-1H-benzimidazol-1-yl]-2-(morpholin-4-yl)pyrimidin-4-yl}amino)azetidin-1-yl]ethanone,
[3-({6-[2-(difluoromethyl)-1H-benzimidazol-1-yl]-2-(morpholin-4-yl)pyrimidin-4-yl}amino)azetidin-1-yl](tetrahydrofuran-3-yl)methanone,
4-{[3-({6-[2-(difluoromethyl)-1H-benzimidazol-1-yl]-2-(morpholin-4-yl)pyrimidin-4-yl}amino)azetidin-1-yl]carbonyl}-1-methylpyrrolidin-2-one,
[(3S)-3-({6-[2-(difluoromethyl)-1H-benzimidazol-1-yl]-2-(morpholin-4-yl)pyrimidin-4-yl}amino)pyrrolidin-1-yl][cis-4-(hydroxymethyl)cyclohexyl]methanone, and
[(3S)-3-({6-[2-(difluoromethyl)-1H-benzimidazol-1-yl]-2-(morpholin-4-yl)pyrimidin-4-yl}amino)pyrrolidin-1-yl][trans-4-(hydroxymethyl)cyclohexyl]methanone, and salts thereof.

The compound of the formula (I) may exist in the form of tautomers or geometrical isomers depending on the kind of substituents. In the present specification, the compound of the formula (I) shall be described in only one form of isomer, yet the present invention includes other isomers, isolated forms of the isomers, or a mixture thereof.

In addition, the compound of the formula (I) may have asymmetric carbon atoms or axial asymmetry in some cases, and correspondingly, it may exist in the form of optical isomers based thereon. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Molecular Design, 163-198.

Furthermore, the salt of the compound of the formula (I) may form an acid addition salt or a salt with a base depending on the kind of substituents, and such salts are included in the present invention as long as they are pharmaceutically acceptable salts. Specific examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid, and salts with inorganic bases such as sodium, potassium, magnesium, calcium, and aluminum, or organic bases such as methylamine, ethylamine, ethanolamine, lysine, and ornithine, salts with various amino acids such as acetylleucine, and amino acid derivatives, as well as ammonium salts.

In addition, the present invention also includes various hydrates or solvates, and polymorphic crystalline substances of the compound of the formula (I) and pharmaceutically acceptable salts thereof. In addition, the present invention also includes compounds labeled with various radioactive or non-radioactive isotopes.

The "PI3Kδ selective inhibitor" means an inhibitor exhibiting a potent activity, in which the inhibitory activity of PI3Kδ is 10-times or more, in another embodiment, 30-times or more, and in still another embodiment, 100-times or more than the inhibitory activity of PI3Kα in terms of the $IC_{50}$ value.

(Preparation Methods)

The compound of the formula (I) and a pharmaceutically acceptable salt thereof can be prepared by applying various known synthesis methods on the basis of characteristics derived from their skeletal structure or the type of their substituents. During the preparation, replacement of the relevant functional group with a suitable protective group (a group that can be easily converted into the relevant functional group) at the stage from starting material to an intermediate may be effective depending on the type of the functional group in the production technology in some cases. Examples of such the functional group include an amino group, a hydroxyl group, and a carboxyl group, and such the protective group for such a functional group may include, for example, the protective groups described in Greene and Wuts, "Protective Groups in Organic Synthesis ($3^{rd}$ edition, 1999)", which may be selected and used as appropriate, depending on reaction conditions. In such a method, after introduction of the protective group and a subsequent reaction, the protective group may be removed, if necessary to obtain a desired compound.

In addition, the prodrug of the compound of the formula (I) can be prepared by introducing a specific group at the stage from a starting material to an intermediate, or by carrying out the reaction using the obtained compound of the formula (I), as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

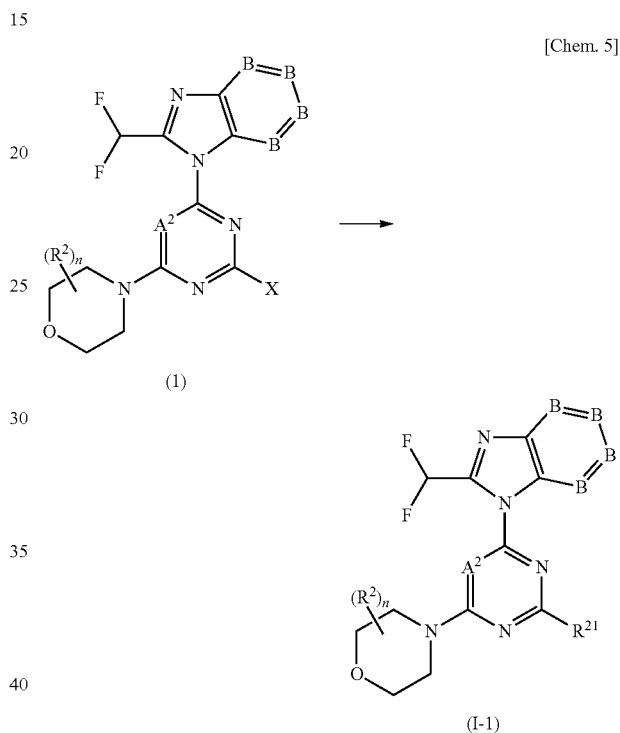

[Chem. 5]

(wherein X represents a leaving group, $R^{21}$ represents —NH-lower alkylene-C(O)—OH or -$L^1$-$L^2$-Y, and $L^1$ represents —$NR^5$—, —$NR^5$—S(O)$_2$—, —$NR^5$—C(O)—, —O—, —S—, or —S(O)$_m$—. The same shall apply hereinafter.)

The compound (I-1) of the present invention can be obtained by the ipso substitution reaction of the compound (1) with, for example, -$L^1$-$L^2$-Y.

Examples of the leaving group X include halogen, methylsulfinyl, methylsulfonyl groups, and the like.

The present reaction is carried out by using the compound (1) and, for example, a compound -$L^1$-$L^2$-Y in equivalent amounts, or either thereof in an excess amount, and stirring a mixture thereof in a solvent which is inert to the reaction, or in the absence of a solvent, in a range of from cooling to heating and refluxing, preferably at 0° C. to 100° C., usually for 0.1 hours to 5 days. Examples of the solvent used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, N,N-dimethylacetamide, dimethylsulfoxide, ethyl acetate, acetonitrile, and a mixture thereof. It is preferable in some cases for the smooth progress of the reaction to use organic bases such as triethylamine, N,N-diisopropylethylamine, N-methylmorpholine, and the like, or inorganic bases such as potassium carbonate, sodium carbonate, cesium carbonate, potassium hydroxide, and the like. It may be advantageous in some cases for the smooth progress of the reaction to carry out the reaction by heating the reaction mixture by microwave irradiation.

[Documents]

S. R. Sandler and W. Karo, "Organic Functional Group Preparations", 2$^{nd}$ edition, Vol. 1, Academic Press Inc., 1991

"Jikken Kagaku Koza (Courses in Experimental Chemistry) (5$^{th}$ Edition) (Vol. 14)", edited by The Chemical Society of Japan, Maruzen, 2005

(Production Process 2)

[Chem. 6]

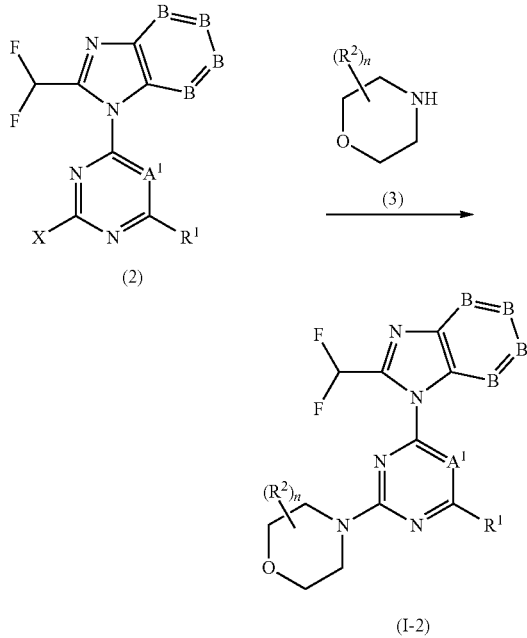

The compound of the formula (I-2) can be obtained by the reaction of a compound (2) and a compound (3). The reaction conditions are the same as in the Production Process 1.

(Production Process 3)

[Chem. 7]

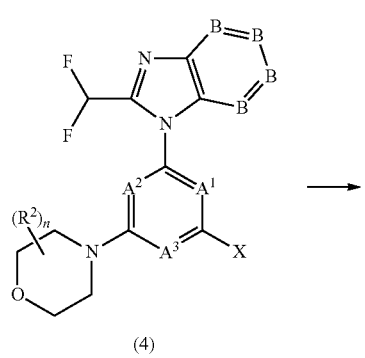

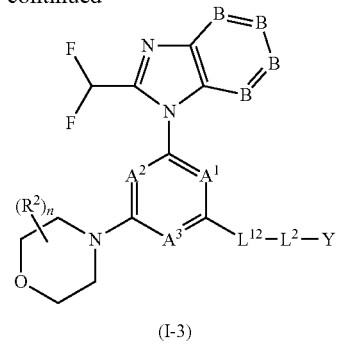

(wherein $L^{12}$ represents -lower alkynylene.)

The compound (I-3) of the present invention can be obtained by a Sonogashira coupling reaction of a compound (4) and a terminal alkyne derivative.

Examples of the leaving group X include halogen, and the like.

The present reaction is carried out by using the compound (4) and the terminal alkyne derivative in equivalent amounts, or either thereof in an excess amount, and stirring a mixture thereof in a solvent which is inert to the reaction, under the temperature condition ranging from room temperature to heating and refluxing, usually for 0.1 hours to 5 days, in the presence of a base and a palladium catalyst. The present reaction is preferably carried out under inert gas atmosphere. Examples of the solvent used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, dimethylsulfoxide, and a mixed solvent thereof. As the base, inorganic bases such as potassium carbonate, sodium carbonate, cesium carbonate, potassium hydroxide, and the like are preferable. As the palladium catalyst, tetrakis(triphenylphosphine)palladium, dichlorobis(triphenylphosphine)palladium, palladium-1,1'-bis(diphenylphosphino)ferrocene chloride, and the like are preferred. Further, it may be advantageous in some cases for the smooth progress of the reaction to heat the reaction mixture by microwave irradiation.

[Documents]

"Metal-Catalyzed Cross-Coupling Reactions", edited by A. d. Meijere and F. Diederich, Vol. 1, VCH Publishers Inc., 1997

"Jikken Kagaku Koza (Courses in Experimental Chemistry) (5$^{th}$ Edition)", edited by The Chemical Society of Japan, Vol. 13 (2005) (Maruzen)

Various substituents on $R^1$ in the compound of the formula (I) can be easily converted into other functional groups by using the compound of the formula (I) as a starting material by means of the reactions described in Examples as described later, the reactions apparent to a person skilled in the art, or modified methods thereof. For example, the steps that can be usually employed by a person skilled in the art, such as O-alkylation, N-alkylation, oxidation, reduction, reductive alkylation, ring formation, hydrolysis, amidation, acylation, deprotection, epoxylation, and the like can be arbitrarily combined and performed.

(Preparation of Starting Compound)

In the preparation method above, the starting compound can be prepared by using any of, for example, the methods below, the methods described in Preparation Examples as described later, known methods, or modified methods thereof.

(Starting Material Synthesis 1)

[Chem. 8]

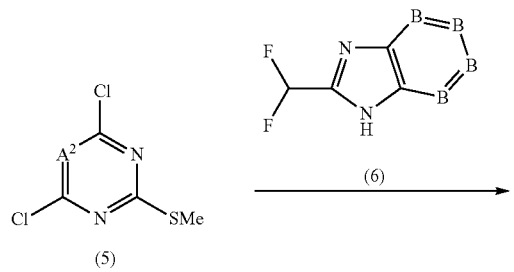

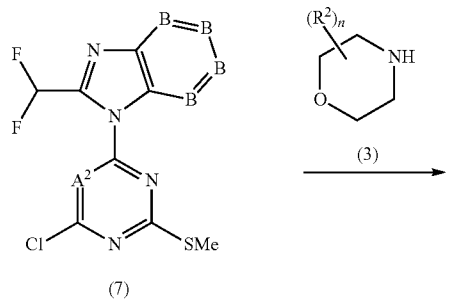

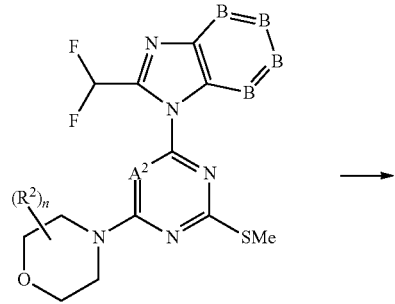

The present production process is a method for preparing a compound (9), in which X is —S(O)$_m$-methyl in (1) which is the starting compound in Production Process 1.

A compound (7) can be obtained by the reaction of a compound (5) with a compound (6).

The reaction condition is the same as in Production Process 1.

A compound (8) can be obtained by the reaction of the compound (7) with the compound (3).

The reaction condition is the same as in Production Process 1.

A compound (9) can be obtained by the oxidation reaction of the compound (8).

The present reaction can be carried out by using the compound (9) in an equivalent amount or an excess amount, in a range of from cooling to heating. As the solvent, solvents such as aromatic hydrocarbons and halogenated hydrocarbons may be used singly or in a mixture of two or more kinds thereof. Examples of the oxidant include m-chloroperbenzoic acid, peracetic acid, and a hydrogen peroxide solution.

(Starting Material Synthesis 2)

[Chem. 9]

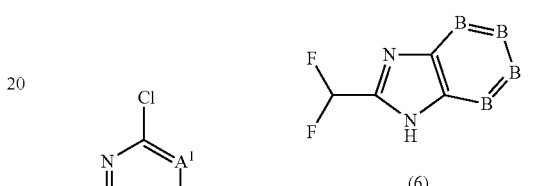

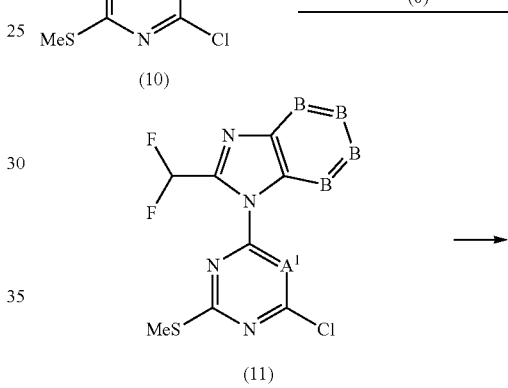

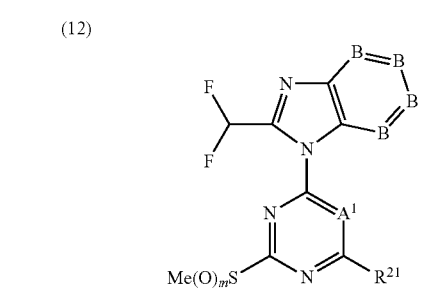

The present production process is a method for preparing a compound (13), in which X is —S(O)$_m$-methyl and R$^1$ is R$^{21}$, in (2) which is the starting compound in Production Process 2.

A compound (11) can be obtained by the reaction of the compound (10) with the compound (6).

The reaction conditions are the same as in Production Process 1.

A compound (12) can be obtained by the ipso substitution reaction of the compound (11) with, for example, $-L^1-L^2-Y$.

The reaction conditions are the same as in Production Process 1.

A compound (13) can be obtained by the oxidation reaction of the compound (12).

The reaction conditions are the same as in the oxidation reaction described in Starting Material Synthesis 1.

Other starting compounds (1), (2), and (4) can be prepared by, for example, the methods described in the following documents: WO2002/088112, EP1389617, WO2008/032033, WO2008/032036, WO2008/032041, or WO2008/032060.

The compounds of the formula (I) can be isolated and purified as their free compounds, pharmaceutically acceptable salts, hydrates, solvates, or polymorphic crystalline substances thereof. The pharmaceutically acceptable salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemates (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

1. PI3Kδ Enzyme Inhibitory Activity

For the experiment, a PI3-Kinase HTRF Assay kit (Millipore Corporation, Catalogue No. 33-016) and a human PI3Kδ enzyme (Millipore Corporation, Catalogue No. 14-604) were used. The measurement method was in accordance with the appended instructions. The overview thereof is as follows.

PI3Kδ (10 ng/well), phosphatidylinositol-4,5-bisphosphate (10 μM), ATP (30 μM), and the test compound were mixed in a 384-well plate (total 20 μL), and incubated at room temperature for 30 minutes. EDTA and biotinylated phosphatidylinositol-3,4,5-triphosphate were added thereto to stop the reaction. Thereafter, a Europium labeled anti-GST antibody, a GST bond GRP1 PH domain, and streptavidin-APC were added thereto, followed by incubation overnight. An HTRF ratio was measured using an HTRF plate reader. The $IC_{50}$ value of the compound was calculated, taking the inhibition rate without addition of the enzyme as 100% and the inhibition rate without addition of the test compound and with addition of an enzyme as 0%, by means of a logistic method.

2. PI3Kα Enzyme Inhibitory Activity

Human PI3Kα (12 ng/well, Millipore Corporation, Catalogue No. 14-602), phosphatidylinositol (0.2 μg/well), and the test compound were mixed in a 384-well plate in a reaction buffer (50 mM Hepes, 10 mM NaCl, 10 mM $MgCl_2$, 2 mM EGTA, 2 mM DTT, pH 7.3) (total 10 μl), and incubated at 37° C. for 3 hours. After the reaction, 10 μL of a Kinase-Glo Plus reagent (Promega, Catalogue No. V3772) was added thereto, and a luminescence was measured with a luminometer. The $IC_{50}$ value of the compound was calculated, taking the inhibition rate without addition of the enzyme as 100% and the inhibition rate without addition of the test compound as 0%, by a logistic method.

The results of the $IC_{50}$ values (nM) of several representative compounds are shown in Table 1. In the Table, Ex represents Example Compound No. as described later of the test compounds.

TABLE 1

| Ex | PI3Kδ | PI3Kα |
|---|---|---|
| 1 | 29 | 2800 |
| 4 | 60 | >3000 |
| 10 | 5.8 | >3000 |
| 13 | 36 | 980 |
| 16 | 69 | >10000 |
| 18 | 50 | 7700 |
| 20 | 19 | 1800 |
| 25 | 69 | 6200 |
| 28 | 35 | >3000 |
| 29 | 45 | >3000 |
| 30 | 12 | >3000 |
| 33 | 11 | >3000 |
| 34 | 14 | >3000 |
| 35 | 18 | 4200 |
| 36 | 17 | 6700 |
| 37 | 20 | 1900 |
| 38 | 23 | 2200 |
| 39 | 27 | 3900 |
| 40 | 20 | >10000 |
| 43-1 | 8 | 13000 |
| 43-2 | 8.6 | 8000 |
| 44 | 14 | 5000 |
| 45 | 56 | 6800 |
| 67 | 47 | 990 |
| 69 | 22 | 10000 |
| 75 | 25 | 5400 |
| 77 | 18 | 5400 |
| 78 | 8.5 | 2900 |
| 85 | 21 | 5500 |
| 87 | 4.9 | >10000 |
| 99 | 16 | >10000 |
| 100 | 5.7 | >3000 |
| 120 | 27 | 6400 |
| 121 | 13 | 4900 |
| 123 | 4.5 | >3000 |
| 132 | 12 | >10000 |
| 133 | 5.2 | 5900 |
| 134 | 4.7 | 6600 |
| 135 | 3.0 | 8000 |
| 136 | 4.0 | >10000 |
| 137 | 5.2 | >10000 |
| 158 | 11 | 6700 |
| 193 | 4.9 | 8200 |
| 194 | 5.8 | 3300 |
| 195 | 4.1 | >10000 |
| 196 | 4.8 | >10000 |
| 215 | 13 | >10000 |
| 216 | 13 | >10000 |
| 224 | 3.3 | 7300 |
| 248 | 34 | 720 |
| 371 | 35 | 5000 |
| 389 | 11 | >10000 |
| 423 | 24 | >10000 |
| 441 | 48 | 1400 |
| A4 | 31 | 730 |
| A290 | 7.4 | 3800 |
| A293 | 19 | 3200 |
| A298 | 28 | 3500 |
| A299 | 25 | 4900 |
| A300 | 26 | 6500 |
| A449 | 20 | 1400 |
| A451 | 35 | 2200 |
| A463 | 27 | 3100 |
| A464 | 10 | 2200 |
| A466 | 15 | 2000 |
| A475 | 25 | 1400 |

TABLE 1-continued

| Ex | PI3Kδ | PI3Kα |
|---|---|---|
| A562 | 14 | 2900 |
| A564 | 19 | 3000 |
| A567 | 11 | 1600 |

3. Rat In Vivo IL-2 Production Inhibition Test

For the experiment, male LEW/CrlCrlj rats (Charles River Laboratories, Japan, Inc.) (6-week old, body weight 130 to 180 g) were used. The test compound was suspended in a 0.5% methyl cellulose solution and orally administered at 5 mL/kg. IL-2 production was induced by tail vein injection of Concanavalin A (Funakoshi Corporation, Catalogue No. L-1000) at a dose of 15 mg/kg.

The test was carried out according to the protocol shown below. At 2 hours or 16 hours before administration of Concanavalin A, the test compound was orally administered to rats. At 3 hours after administration of Concanavalin A, blood was collected. The IL-2 concentration in blood was quantified using an ELISA kit (R&D Systems, Inc., Catalogue No. DY502E). An inhibition rate was calculated from the amount of IL-2 produced in a group administered with the test compound with respect to the amount of the IL-2 produced in a control group administered with a vehicle.

As a result, it was confirmed that when the test compounds (10 mg/kg) were administered, for example, 2 hours before the administration of Concanavalin A, the several representative compounds of Examples 10, 29, 33, 34, 37, 43-1, and A4 exhibited inhibitory activities of 77%, 51%, 75%, 72%, 81%, 73%, and 58%, respectively, and had excellent IL-2 production inhibitory activities.

4. Rat B Cell Proliferation Inhibition Test

Spleen cells ($1.0 \times 10^5$ cells/well) prepared from male LEW/CrlCrlj rats (Charles River Laboratories, Japan, Inc.), mouse F(ab')$_2$ fragment anti-rat IgM (3 μg/well, Southern-Biotech Associates, Inc., Catalogue No. 3082-14) and the test compound dissolved in DMSO (final DMSO concentration 0.1%) were mixed in a 96-well plate using a 10% FCS-containing RPMI-1640 culture medium (total 200 μL). They were cultured in a $CO_2$ incubator for 48 hours and [$^3$H]thymidine (925 GBq/mmol, Moravek Biochemicals, Inc., Catalogue No. MT6038) was added thereto at 0.037 MBq/well at 4 hours before completion of culture. Cells were harvested in a GF/C glass filter using a cell harvester, and a radioactivity on the filter was measured using a liquid scintillation counter. The $IC_{50}$ value of the compound was calculated, taking the dpm (disintegration per minute) without addition of IgM as an inhibition rate of 100% and the dpm without addition of the test compound as an inhibition rate of 0%, by a logistic method.

The results of several representative compounds are shown in Table 2.

TABLE 2

| Ex | $IC_{50}$(nM) |
|---|---|
| 10 | 2.9 |
| 36 | 6.8 |
| 37 | 1.52 |
| 38 | 2.9 |
| 40 | 9.0 |
| 43-1 | 2.1 |
| 43-2 | 3.1 |
| 85 | 2.6 |
| 87 | 3.5 |
| 99 | 2.5 |
| 121 | 2.0 |
| 132 | 1.5 |
| 134 | 3.4 |
| 135 | 2.5 |
| 136 | 1.7 |
| 137 | 4.6 |
| 158 | 10 |
| 193 | 4.1 |
| 195 | 3.0 |
| 196 | 3.6 |
| 215 | 6.7 |
| 216 | 5.7 |
| 224 | 1.5 |
| 248 | 1.4 |
| 389 | 4.4 |
| 423 | 3.1 |
| 441 | 1.8 |
| A290 | 2.2 |
| A293 | 2.6 |
| A298 | 1.2 |
| A299 | 2.5 |
| A300 | 2.6 |
| A449 | 0.4 |
| A451 | 1.2 |
| A463 | 1.4 |
| A466 | 1.8 |
| A475 | 1.1 |
| A562 | 3.9 |
| A564 | 2.2 |
| A567 | 1.8 |

As shown in the tests above, it was confirmed that several representative compounds have excellent PI3Kδ selective inhibitory action, and/or IL-2 production inhibitory action, and/or B cell proliferation inhibitory action (including an activation inhibitory action). Accordingly, the compound of the formula (I) can be used as an agent for preventing or treating rejection reactions in various organ transplantations, allergy diseases, autoimmune diseases, and/or hematologic tumor.

Furthermore, since the compound of the formula (I) is a PI3Kδ inhibitor having a significantly potent PI3Kδ inhibitory action than a PI3Kα inhibitory action, it can be an excellent immunosuppressing agent which does not cause insulin resistance based on the PI3Kα inhibitory action.

The various types of organs include the kidney, liver, and heart. The rejection reaction in organ transplantation involves chronic rejection and acute rejection, and its mechanism is largely classified into antibody-related rejection and T cell-related rejection. The compound of the formula (I) or a salt thereof is useful particularly as an agent for preventing and/or treating antibody-related rejection.

A pharmaceutical composition containing one or two or more kinds of the compound of the formula (I) or a salt thereof as an active ingredient can be prepared using excipients that are usually used in the art, that is, excipients for pharmaceutical preparations, carriers for pharmaceutical preparations, and the like according to the methods usually used.

Administration can be accomplished either by oral administration via tablets, pills, capsules, granules, powders, solutions, or the like, or parenteral administration, such as use of injections such as intraarticular, intravenous, and intramuscular injections, suppositories, eye drops, eye ointments, transdermal liquid preparations, ointments, transdermal patches, transmucosal liquid preparations, transmucosal patches, inhalers, and the like.

The solid composition for use in the oral administration is used in the form of tablets, powders, granules, or the like. In such a solid composition, one or more active ingredient(s) are mixed with at least one inactive excipient such as lactose, mannitol, glucose, hydroxypropyl cellulose, microcrystalline cellulose, starch, polyvinylpyrrolidone, and/or magnesium aluminometasilicate. In an ordinary method, the composition may contain inactive additives, such as a lubricant such as magnesium stearate, a disintegrating agent such as sodium carboxymethyl starch, a stabilizer, or a solubilization assisting agent. If necessary, tablets or pills may be coated with sugar or a film of a gastric-soluble or enteric coating substance.

The liquid composition for oral administration contains pharmaceutically acceptable emulsions, solutions, suspensions, syrups, elixirs, or the like, and also contains generally used inert diluents, for example, purified water and ethanol. In addition to the inert diluent, the liquid composition may also contain auxiliary agents such as a solubilization assisting agent, a moistening agent, and a suspending agent, sweeteners, flavors, aromatics, or antiseptics.

The injections for parenteral administration include sterile aqueous or non-aqueous solutions, suspensions and emulsions. The aqueous solvent includes, for example, distilled water for injection and physiological saline. Examples of the non-aqueous solvent include propylene glycol, polyethylene glycol, plant oils such as olive oil, alcohols such as ethanol, Polysorbate 80 (Japanese Pharmacopeia), and the like. Such a composition may further contain a tonicity agent, an antiseptic, a moistening agent, an emulsifying agent, a dispersing agent, a stabilizer, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, poultices, sprays, lotions, eye drops, and eye ointments. The agents contain generally used ointment bases, lotion bases, aqueous or non-aqueous liquid preparations, suspensions, and emulsions. Examples of the ointment bases or the lotion bases include polyethylene glycol, propylene glycol, white vaseline, bleached beeswax, polyoxyethylene hydrogenated castor oil, glyceryl monostearate, stearyl alcohol, cetyl alcohol, lauromacrogol, and sorbitan sesquioleate.

As the transmucosal agents such as an inhaler and a transnasal agent, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device. A dry powder inhaler or the like may be for single or multiple administration use, and a dry powder or a powder-containing capsule may be used. Alternatively, this may be in a form such as a pressurized aerosol spray which uses an appropriate propellant, for example, a suitable gas such as chlorofluoroalkane, hydrofluoroalkane, and carbon dioxide.

Typically, in oral administration, the daily dose is appropriately from about 0.001 to 100 mg/kg, preferably from 0.1 to 30 mg/kg, and more preferably 0.1 to 10 mg/kg, per body weight, administered in one portion or in 2 to 4 separate portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) can be used in combination with various agents for treating or preventing the diseases, in which the compound of the formula (I) is considered effective. In such use in combination, drugs may be administered simultaneously or separately in succession or at desired time intervals. Formulations for simultaneous administration may be in either mixed or have separate forms.

EXAMPLES

Hereinbelow, the preparation methods for the compound of the formula (I) and the starting compounds thereof will be described in more detail with reference to Examples, but the present invention is not limited to the compounds described in the Examples below. Further, the production processes for the starting compounds will be each described in Preparation Examples. In addition, the preparation methods for the compound of the formula (I) are not limited to the preparation methods of the specific Examples shown below, but the compound of the formula (I) can be prepared by a combination of the preparation methods or a method that is apparent to a person skilled in the art.

Furthermore, the following abbreviations may be used in some cases in Preparation Examples, Examples, and Tables below.

PEx: Preparation Example No., Ex: Example No., Syn: Example No. prepared by the same method, PSyn: Preparation Example No. prepared by the same method, Str: Structural formula, DAT: Physicochemical data, ESI+: m/z values in mass spectroscopy (Ionization ESI, representing (M+H)$^+$ unless otherwise specified), ESI−: m/z values (Ionization ESI, representing (M−H)$^-$ unless otherwise specified), NMR1: δ (ppm) in $^1$H NMR in DMSO-$d_6$, NMR2: δ (ppm) in $^1$H NMR in CDCl$_3$, s: singlet (spectrum), d: doublet (spectrum), t: triplet (spectrum), q: quartet (spectrum), br: broad line (spectrum) (e.g.: br-s), RT: retention time (min) in HPLC, [M] in Preparation Examples and Examples: [mol/L], SFC preparative: preparative supercritical fluid chromatography, DEA: diethylamine.

Furthermore, for example, a description of "26+44" in Syn of Example Tables indicates that preparation is performed by the same method as in Example 26, and subsequently the product is prepared by the same method as in Example 44 as a starting material. Further, in Preparation Example Tables, there is, for example, a description of Syn. 87 in the PSyn column of Preparation Example 148, indicating that Preparation Example 148 is prepared by the same method as in Example 87. In Example Tables, there is, for example, a description of PSyn. 8 in the Syn column of Example 295, indicating that Example 295 is prepared by the same method as in Preparation Example 8. HCl in the structural formula denotes hydrochloride and the numeral before HCl denotes a molar ratio. For example, 2HCl means dihydrochloride. Further, Me in the structural formula denotes a methyl group, Et denotes an ethyl group, Ph denotes a phenyl group, iBu denotes an isobutyl group, tBu denotes a tert-butyl group, and Boc denotes a tert-butoxycarbonyl group. The compound having "*" in the structure indicates that the compound is an optically active substance.

Preparation Example 1

To a solution of 4,6-dichloro-2-(methylsulfanyl)pyrimidine (5 g) in N,N-dimethylformamide (50 mL) were added potassium carbonate (5.3 g) and 2-(difluoromethyl)-1H-benzimidazole (3.9 g), and the mixture was stirred at room temperature for 5 hours. To the reaction mixture was added water, followed by extraction with ethyl acetate. The organic layer was washed with saturated brine and dried over anhydrous magnesium sulfate. The solvent was evaporated under reduced pressure and then the residue was purified by silica gel column chromatography (hexane:ethyl acetate) to obtain 1-[6-chloro-2-(methylsulfanyl)pyrimidin-4-yl]-2-(difluoromethyl)-1H-benzimidazole (5.49 g) as a white powder.

Preparation Example 2

To a solution of 1-[6-chloro-2-(methylsulfanyl)pyrimidin-4-yl]-2-(difluoromethyl)-1H-benzimidazole (2.2 g) in N,N-dimethylformamide (11 mL) were added potassium carbonate (1.4 g) and morpholine (0.88 mL), and the mixture was stirred at room temperature for 1 hour. To the reaction solution was added water, followed by extraction with ethyl acetate. The organic layer was washed with saturated brine and dried over anhydrous magnesium sulfate. The solvent was evaporated under reduced pressure and then the residue was purified by silica gel column chromatography (hexane:ethyl acetate) to obtain 2-(difluoromethyl)-1-[2-(methylsulfanyl)-6-morpholin-4-ylpyrimidin-4-yl]-1H-benzimidazole (2.1 g) as a white powder.

Preparation Example 3

To a solution of 2-(difluoromethyl)-1-[2-(methylsulfanyl)-6-morpholin-4-ylpyrimidin-4-yl]-1H-benzimidazole (3 g) in dichloromethane (60 mL) was added m-chloroperbenzoic acid (75% wet) (1.9 g) under ice-cooling, and the mixture was stirred at 0° C. for 15 minutes. To the reaction mixture was added a saturated aqueous sodium bicarbonate solution, followed by extraction with dichloromethane. The organic layer was washed with water and saturated brine, and dried over anhydrous magnesium sulfate. The solvent was evaporated under reduced pressure and then the residue was purified by silica gel column chromatography (chloroform:methanol) to obtain 2-(difluoromethyl)-1-[2-(methylsulfinyl)-6-morpholin-4-ylpyrimidin-4-yl]-1H-benzimidazole (2.8 g) as a white amorphous substance.

Preparation Example 4

To a solution of 2-(difluoromethyl)-1-[2-(methylsulfanyl)-6-morpholin-4-ylpyrimidin-4-yl]-1H-benzimidazole (2.1 g) in dichloromethane (42 mL) was added m-chloroperbenzoic acid (75% wet) (2.7 g) under ice-cooling and the mixture was stirred at 0° C. for 15 minutes. To the reaction mixture was added a saturated aqueous sodium bicarbonate solution, followed by extraction with dichloromethane. The organic layer was washed with water and saturated brine, and dried over anhydrous magnesium sulfate. The solvent was evaporated under reduced pressure and then the residue was purified by silica gel column chromatography (chloroform:methanol) to obtain 2-(difluoromethyl)-1-[2-(methylsulfonyl)-6-morpholin-4-ylpyrimidin-4-yl]-1H-benzimidazole (2.27 g) as a pale yellow amorphous substance.

Preparation Example 5

To a mixture of 1-[6-chloro-2-(methylsulfanyl)pyrimidin-4-yl]-2-(difluoromethyl)-1H-benzimidazole (1 g) and N,N-dimethylacetamide (10 mL) were added tert-butyl 4-(hydroxymethyl)piperidine-1-carbamate (1 g) and cesium carbonate (3 g), and the mixture was stirred at 120° C. for 3 hours. The reaction mixture was poured into water, followed by extraction with hexane-ethyl acetate (1:1). The organic layer was washed with water and saturated brine, and dried over anhydrous magnesium sulfate. The solvent was evaporated under reduced pressure and then the residue was purified by silica gel column chromatography (hexane:ethyl acetate) to obtain tert-butyl 4-[({6-[2-(difluoromethyl)-1H-benzimidazol-1-yl]-2-(methylsulfanyl)pyrimidin-4-yl}oxy)methyl]piperidine-1-carbamate (680 mg) as a white amorphous substance.

Preparation Example 6

N-(2-{[6-Chloro-2-(methylsulfanyl)pyrimidin-4-yl]amino}-5-methylphenyl)acetamide (270 mg) was dissolved in a mixed solvent of ethanol (2.8 mL) and 1,4-dioxane (2.8 mL), and 6 M hydrochloric acid (9.6 mL) was added thereto, followed by heating and refluxing for 3 hours. After air-cooling to room temperature, the pH was adjusted to 6 to 7 using saturated aqueous sodium bicarbonate, followed by extraction with ethyl acetate. The organic layer was dried over anhydrous magnesium sulfate and the solvent was evaporated under reduced pressure to obtain $N^1$-[6-chloro-2-(methylsulfanyl)pyrimidin-4-yl]-4-methylbenzene-1,2-diamine (230 mg).

Preparation Example 7

A mixture of 2-(methylsulfanyl)-6-(morpholin-4-yl)pyrimidin-4-amine (500 mg), 2-bromo-1-methyl-3-nitrobenzene (1 g), tris(dibenzylideneacetone)dipalladium (0) (202 mg), (9,9-dimethyl-9H-xanthen-4,5-diyl)bis(diphenylphosphine) (192 mg), and cesium carbonate (1.0 g) in toluene was stirred in a microwave reactor at 140° C. for 1 hour. The reaction mixture was filtered through celite and concentrated under reduced pressure. The residue was purified by silica gel column chromatography (hexane:ethyl acetate) to obtain N-(2-methyl-6-nitrophenyl)-2-(methylsulfanyl)-6-(morpholin-4-yl)pyrimidin-4-amine (756 mg) as a yellow powder.

Preparation Example 8

N-(2-Methyl-6-nitrophenyl)-2-(methylsulfanyl)-6-(morpholin-4-yl)pyrimidin-4-amine (750 mg) was dissolved in ethanol (22.5 mL), and iron chloride (III) hexahydrate (56 mg) and activated carbon (75 mg) were added thereto, followed by stirring at 80° C. Hydrazine monohydrate (0.3 mL) was added dropwise thereto, followed by heating and refluxing overnight. The reaction mixture was cooled to room temperature and filtered through celite. The mother liquid was concentrated and the residue was purified using silica gel column chromatography (hexane:ethyl acetate) to obtain 3-methyl-$N^2$-[2-(methylsulfanyl)-6-(morpholin-4-yl)pyrimidin-4-yl]benzene-1,2-diamine (544 mg) as a pale yellow powder.

Preparation Example 9

To tert-butyl [(2S)-1-{[trans-4-({6-[2-(difluoromethyl)-1H-benzimidazol-1-yl]-2-(morpholin-4-yl)pyrimidin-4-yl}oxy)cyclohexyl]amino}-4-(methylsulfanyl)-1-oxobutan-2-yl]carbamate (760 mg) was added methyl iodide (3.5 mL), followed by stirring at room temperature overnight. Methyl iodide was evaporated under reduced pressure to obtain a desired compound [(3S)-3-[(tert-butoxycarbonyl)amino]-4-{[trans-4-({6-[2-(difluoromethyl)-1H-benzimidazol-1-yl]-2-(morpholin-4-yl)pyrimidin-4-yl}oxy)cyclohexyl]amino}-4-oxobutyl](dimethyl)sulfonium iodide (919 mg).

Preparation Example 10

4,6-Dichloro-2-(methylsulfanyl)pyrimidine (50 mg) and tert-butyl (2-amino-4-methylphenyl)carbamate (57 mg) were dissolved in dimethylacetamide (250 μL), and N,N-diisopropyl ethylamine (69 μL) was added thereto, followed by stirring at 100° C. for 7 hours. After the completion of the reaction, the mixture was cooled to room temperature, and water was added thereto, followed by extraction with ethyl acetate. The extracts were washed with saturated brine, the organic layer was dried over anhydrous magnesium sulfate, and the solvent was evaporated under reduced pressure. The residue was purified by silica gel column chromatography (ethyl acetate:hexane) to obtain a desired compound tert-butyl (2-{[6-chloro-2-(methylsulfanyl)pyrimidin-4-yl]amino}-4-methylphenyl)carbamate (50 mg) as a white powder.

Preparation Example 11 tert-Butyl (2-{[6-chloro-2-(methylsulfanyl)pyrimidin-4-yl]amino}-4-methylphenyl)carbamate (8.5 g) was dissolved in 1,4-dioxane (85 mL), and a 4 M solution (56 mL) of hydrogen chloride in 1,4-dioxane was added thereto, followed by stirring at room temperature for 8 hours. After the completion of the reaction, a saturated aqueous sodium bicarbonate solution and a 4 M aqueous sodium hydroxide solution were added thereto. The mixture was quenched, made free, and extracted with ethyl acetate. The organic layer was dried over anhydrous magnesium sulfate and the solvent was evaporated under reduced pressure to obtain $N^2$-[6-chloro-2-(methylsulfanyl)pyrimidin-4-yl]-4-methylbenzene-1,2-diamine (6 g) as a yellow powder.

Preparation Example 12

$N^2$-[6-Chloro-2-(methylsulfanyl)pyrimidin-4-yl]-4-methylbenzene-1,2-diamine (6 g) and difluoroacetic anhydride (7.4 g) were dissolved in acetonitrile (60 mL), followed by stirring at room temperature for 1 hour. After confirming that the starting material had been disappeared, a 4 M solution (53 mL) of hydrogen chloride in 1,4-dioxane was added thereto, followed by stirring at 100° C. for 10 hours. After the completion of the reaction, the mixture was cooled to room temperature, and water was added thereto, followed by extraction with ethyl acetate. The organic layer was washed with saturated brine. The obtained organic layer was dried over anhydrous magnesium sulfate and the solvent was evaporated under reduced pressure. The residue was purified by silica gel column chromatography (ethyl acetate:hexane) to obtain 1-[6-chloro-2-(methylsulfanyl)pyrimidin-4-yl]-2-(difluoromethyl)-6-methyl-1H-benzimidazole (2.9 g) as a pale yellow powder.

Preparation Example 13

(3a'R,5's,6a'S)-5,5-Dimethylhexahydro-1'H-spiro[1,3-dioxane-2,2'-pentalen]-5'-ol (1.0 g) and 1H-isoindole-1,3(2H)-dione (780 mg) and triphenylphosphine (1.39 g) were dissolved in tetrahydrofuran (17 mL), and a 2.2 M solution (2.41 mL) of ethyl azodicarbonate in tetrahydrofuran was added dropwise thereto at 0° C., followed by stirring at 0° C. for 1 hour and at room temperature for 4 hours. To the reaction solution was added silica gel, followed by concentrating and purifying using silica gel column chromatography (hexane:ethyl acetate) to obtain 2-[(3a'R,5'r,6a'S)-5,5-dimethylhexahydro-1'H-spiro[1,3-dioxane-2,2'-pentalen]-5'-yl]-1H-isoindole-1,3(2H)-dione (1.1 g) as a white powder.

Preparation Example 14

To a mixture of ethyl-4-(4-cyanophenyl)-1-piperazine carboxylate (10 g), sodium borohydride (3.4 g), and tetrahydrofuran (50 mL) was added a mixture of iodine (9.8 g) and tetrahydrofuran (50 mL) under a nitrogen gas flow while ice-cooling, followed by stirring at the same temperature for 1 hour, and then further heating and refluxing for 3 hours. The reaction solution was ice-cooled and a 6 M hydrochloric acid solution was added thereto to adjust the pH to 1. The reaction solution was stirred at 70° C. for 30 minutes. After leaving to be cooled, sodium hydroxide was added thereto to adjust the pH to 10, followed by extraction with ethyl acetate. The extracts were washed with saturated brine, the organic layer was dried over anhydrous sodium sulfate, and the solvent was evaporated under reduced pressure. The residue was made into powder using tetrahydrofuran, ethyl acetate, and diisopropyl ether, to obtain ethyl-4-[4-(aminomethyl)phenyl]-1-piperazine carboxylate (5.2 g).

Preparation Example 15

2-(Difluoromethyl)-1-[2-(methylsulfanyl)-6-morpholin-4-ylpyrimidin-4-yl]-1H-benzimidazole (2.1 g) was dissolved in methylene chloride (42 mL), and m-chloroperbenzoic acid (75% wet) (2.7 g) was added thereto under ice-cooling, followed by stirring at 0° C. for 1 hour. Saturated aqueous sodium bicarbonate was added thereto, followed by extraction with methylene chloride. The extracts were washed with water and saturated brine, the organic layer was dried over anhydrous magnesium sulfate, and the solvent was evaporated under reduced pressure. The residue was purified using silica gel column chromatography (chloroform:methanol) to obtain 2-(difluoromethyl)-1-[2-(methylsulfonyl)-6-morpholin-4-ylpyrimidin-4-yl]-1H-benzimidazole (2.27 g) as a pale yellow amorphous substance.

Preparation Example 16

To a mixture of 2-[(3a'R,5'r,6a'S)-5,5-Dimethylhexahydro-1'H-spiro[1,3-dioxane-2,2'-pentalen]-5'-yl]-1H-isoindole-1,3(2H)-dione (1.1 g), tetrahydrofuran (22 mL) and ethanol (22 mL) was added hydrazine monohydrate (0.75 mL), followed by heating and refluxing for 2 hours. The insoluble matter was removed by filtration through celite and concentrated under reduced pressure. To the residue was added chloroform, followed by drying over sodium sulfate, and then the solvent was evaporated under reduced pressure to obtain (3a'R,5'r,6a'S)-5,5-dimethylhexahydro-1'H-spiro[1,3-dioxane-2,2'-pentalen]-5'-amine (0.74 g) as a white powder.

Preparation Example 17

Benzyl 9-oxo-3-azaspiro[5.5]undecane-3-carboxylate (230 mg) was dissolved in methanol (4.5 mL) and methylene chloride (1.5 mL), and ammonium acetate (1.47 g) was added thereto, followed by stirring at room temperature for 10 minutes. Subsequently, sodium triacetoxyborohydride (323 mg) was added thereto, followed by stirring at room temperature overnight. To the reaction solution was added saturated aqueous sodium bicarbonate, followed by extraction with chloroform. The organic layer was washed with saturated brine and dried over anhydrous sodium sulfate. The solvent was evaporated under reduced pressure to obtain benzyl 9-amino-3-azaspiro[5.5]undecane-3-carboxylate (255 mg).

Preparation Example 80 trans-4-(Dibenzylamino)cyclohexanol (200 mg), 2-(3-bromopropoxy)tetrahydro-2H-pyran (604 mg), powder potassium hydroxide (179 mg), and tetrabutylammonium bromide (44 mg) were suspended in xylene (2 mL), followed by stirring at room temperature for 2 hours. To the reaction mixture were added ethyl acetate and water, and the organic layer was extracted and washed with saturated brine and dried over anhydrous magnesium sulfate. The solvent was evaporated under reduced pressure. The residue was purified by amino silica gel column chromatography (hexane:ethyl acetate=100:0-80:20) to obtain trans-N,N-dibenzyl-4-[3-(tetrahydro-2H-pyran-2-yloxy)propoxy]cyclohexanamine (174 mg).

Preparation Example 81 trans-N,N-Dibenzyl-4-[3-(tetrahydro-2H-pyran-2-yloxy)propoxy]cyclohexanamine (170 ml) was dissolved in methanol (1 mL), and a 4 M solution (972 µL) of hydrogen chloride in 1,4-dioxane was added thereto, followed by stirring at room temperature for 2 hours. The reaction solution was neutralized with a saturated aqueous sodium bicarbonate solution and extracted with ethyl acetate. The organic layer was washed with saturated brine and then dried over anhydrous magnesium sulfate, and the solvent was evaporated under reduced pressure to obtain 3-{[trans-4-(dibenzylamino)cyclohexyl]oxy}propan-1-ol (110 mg).

Preparation Example 82

To 3-{[trans-4-(dibenzylamino)cyclohexyl]oxy}propan-1-ol (110 mg) were added tosyl chloride (60 mg) and pyridine (51 µL) under ice-cooling, followed by stirring at room temperature for 1 hour. To the reaction mixture were added N,N-dimethylformamide (1.1 mL), potassium carbonate (43 mg), and pyrrolidine (26 µL), followed by stirring at room temperature overnight. The reaction mixture were added ethyl acetate and water, and the organic layer was extracted, washed with saturated brine, and then dried over anhydrous magnesium sulfate. Then, the solvent was evaporated under reduced pressure. The residue was purified by amino silica gel column chromatography (hexane:ethyl acetate-90:10-70:30) to obtain trans-N,N-dibenzyl-4-[3-(pyrrolidin-1-yl)propoxy]cyclohexanamine (70 mg).

Preparation Example 83 trans-N,N-Dibenzyl-4-[3-(pyrrolidin-1-yl)propoxy]cyclohexanamine (115 mg) was dissolved in ethanol (2.3 ml), and 20% palladium hydroxide/carbon 50% wet (20 mg) was added thereto, followed by catalytic reduction at room temperature for 4 hours at 3 atm under a hydrogen atmosphere. The catalyst was removed by filtration after nitrogen substitution, and then concentrated under reduced pressure to obtain trans-4-[3-(pyrrolidin-1-yl)propoxy]cyclohexanamine (48 mg).

Preparation Example 84

Triethyl phosphonoacetate (107 mg) was dissolved in tetrahydrofuran (1 mL), and 60% sodium hydride (19 mg) was added thereto, followed by stirring at room temperature for 30 minutes. A solution of tert-butyl (trans-4-formylcyclohexyl) carbamate (90 mg) in tetrahydrofuran (1 mL) was added dropwise thereto, followed by stirring at room temperature for 2 hours. Ethyl acetate and water were added thereto, followed by extraction with ethyl acetate. The extracts were washed with saturated brine and then dried over anhydrous magnesium sulfate, and the solvent was evaporated under reduced pressure. The residue was purified by silica gel column chromatography (hexane:ethyl acetate=95:5-50:50) to obtain ethyl (2E)-3-{trans-4-[(tert-butoxycarbonyl)amino] cyclohexyl}acrylate (100 mg).

Preparation Example 85

60% Sodium hydride (394 mg) was suspended in 1,2-dimethoxyethane (20 mL), and tert-butyl 4-hydroxybenzylcarbamate (1 g) and 15-crown-5-ether (1.09 g) were added thereto, followed by stirring at room temperature for 30 minutes. 4,6-Dichloro-2-(methylsulfonyl)pyrimidine was added thereto, followed by stirring at 80° C. overnight. The reaction solution was cooled to room temperature and then an aqueous ammonium chloride solution (50 mL) was added thereto, followed by extraction with ethyl acetate. The extracts were washed with water and saturated brine, and the organic layer was dried over anhydrous magnesium sulfate. The desiccant was removed by filtration and the solvent was evaporated under reduced pressure. The residue was purified using silica gel column chromatography (hexane:ethyl acetate=95:5-85:15) to obtain tert-butyl{-4-[(4,6-dichloropyrimidin-2-yl) oxy]benzyl}carbamate (762 mg).

Preparation Example 86

A mixture of 4,6-dichloro-2-(methylsulfanyl)pyrimidine (700 mg), 2-(difluoromethyl)-4-ethoxy-1H-benzimidazole (761 mg), potassium carbonate (744 mg), and N,N-dimethylformamide (7 mL) was stirred at room temperature overnight. To the mixture was added water, followed by extraction with ethyl acetate. The organic layer was washed with saturated brine and dried over anhydrous sodium sulfate. The desiccant was removed by filtration and then the solvent was evaporated under reduced pressure. The residue was purified by silica gel column chromatography (chloroform:methanol=100:0-80:20) to obtain 1-[6-chloro-2-(methylsulfanyl) pyrimidin-4-yl]-2-(difluoromethyl)-4-ethoxy-1H-benzimidazole (464 mg) (Preparation Example 86-1) and 1,1'-[2-(methylsulfanyl)pyrimidine-4,6-diyl]bis[2-(difluoromethyl)-4-ethoxy-1H-benzimidazole]. 1,1'-[2-(Methylsulfanyl)pyrimidine-4,6-diyl]bis[2-(difluoromethyl)-4-ethoxy-1H-benzimidazole] was suspended in ethyl acetate and warmed. After leaving to be cooled, the insoluble matter was collected by filtration to obtain 1,1'-[2-(methylsulfanyl)pyrimidine-4,6-diyl]bis[2-(difluoromethyl)-4-ethoxy-1H-benzimidazole] (275 mg) (Preparation Example 86-2).

Preparation Example 87

To a mixture of trans-4-({6-[2-(difluoromethyl)-1H-benzimidazol-1-yl]-2-(morpholin-4-yl)pyrimidin-4-yl}oxy)cyclohexanamine (700 mg) and N,N-dimethylformamide (7.0 mL) were added N-(tert-butoxycarbonyl)-N-methyl-L-methionine (622 mg), 1H-benzotriazol-1-ol (319 mg), and N-[3-(dimethylamino)propyl]-N'-ethylcarbodiimide hydrochloride (452 mg), followed by stirring at room temperature overnight. After the completion of the reaction, water was added thereto, followed by extraction with ethyl acetate. The organic layer was washed with saturated brine and then dried over anhydrous magnesium sulfate. The desiccant was removed by filtration and then the solvent was evaporated under reduced pressure. The residue was purified by silica gel chromatography (hexane:ethyl acetate=90:10-40:60) to obtain tert-butyl [(2S)-1-{[trans-4-({6-[2-(difluoromethyl)-1H-benzimidazol-1-yl]-2-(morpholin-4-yl)pyrimidin-4-yl}oxy)cyclohexyl]amino}-4-(methylsulfanyl)-1-oxobutan-2-yl]methylcarbamate (859 mg).

Preparation Example 88

To a mixture of methyl[(2S)-1-({trans-4-[(tert-butoxycarbonyl)amino]cyclohexyl}amino)-4-(methylsulfanyl)-1-oxobutan-2-yl]carbamate (2.0 g), methylene chloride (20 mL) and methanol (20 mL) was added methyl iodide (15.5 mL), followed by stirring at room temperature overnight. The solvent was evaporated under reduced pressure, and to a mixture of the residue and dimethylformamide (10 mL) was added cesium carbonate (4.8 g), followed by stirring overnight. To the reaction solution was added water, followed by extraction with ethyl acetate. The organic layer was washed with saturated brine. The organic layer was dried over anhydrous sodium sulfate, the desiccant was removed by filtration, and then the solvent was evaporated under reduced pressure. To the residue was added ethanol, and the resulting solid was collected by filtration and dried under reduced pressure to obtain methyl[(3S)-1-{trans-4-[(tert-butoxycarbonyl)amino]cyclohexyl}-2-oxopyrrolidin-3-yl]carbamate (0.65 g).

Preparation Example 89

To a solution of 1,1'-[2-(methylsulfanyl)pyrimidine-4,6-diyl]bis[2-(difluoromethyl)-1H-benzimidazole] (2 g) in N,N-dimethylacetamide (10 mL) were added tert-butyl (3S)-3-(hydroxymethyl)pyrrolidine-1-carboxylate (965 mg) and cesium carbonate (2.1 g), followed by stirring at 60° C. for 5 hours. After the completion of the reaction, to the reaction solution was added ice water and the precipitated solid was collected by filtration. After drying, the resultant was dissolved in dichloromethane and purified by silica gel column chromatography (hexane:ethyl acetate=90:10-65:35) to obtain tert-butyl (3S)-3-[({6-[2-(difluoromethyl)-1H-benzimidazol-1-yl]-2-(methylsulfanyl)pyrimidin-4-yl}oxy)methyl]pyrrolidine-1-carboxylate (2.01 g).

Preparation Example 90

A mixture of 1-[6-chloro-2-(methylsulfanyl)pyrimidin-4-yl]-2-(difluoromethyl)-1H-benzimidazole (350 mg), methyl [(3R)-1-(trans-4-aminocyclohexyl)-2-oxopyrrolidin-3-yl]carbamate hydrochloride (344 mg), potassium carbonate (178 mg), N-ethyl-N-isopropylpropan-2-amine (1.1 mL), and N,N-dimethylacetamide (1.75 mL) was stirred at 60° C. overnight. To the reaction solution were added water and ethyl acetate. The insoluble matter was collected by filtration, followed by extraction with ethyl acetate. The solvent was evaporated under reduced pressure, and then the residue and the insoluble matter were combined. Ethyl acetate was added thereto, and the mixture was suspended, stirred, and then collected by filtration. The resultant was washed with water and dried to obtain methyl{(3R)-1-[trans-4-({6-[2-(difluoromethyl)-1H-benzimidazol-1-yl]-2-(methylsulfanyl)pyrimidin-4-yl}amino)cyclohexyl]-2-oxopyrrolidin-3-yl}carbamate (446 mg).

Preparation Example 183

60% Sodium hydride (110 mg) was suspended in N,N-dimethylformamide (20 mL), and tert-butyl[trans-4-({6-[2-(difluoromethyl)-1H-benzimidazol-1-yl]-2-(morpholin-4-yl)pyrimidin-4-yl}amino)cyclohexyl]carbamate (1 g) was added thereto at 0° C., followed by stirring at room temperature for 30 minutes. To the reaction mixture was added a 1-bromo-2-methylpropan (807 mg), followed by stirring at room temperature for 12 hours. After the completion of the reaction, to the reaction solution was added ice water, followed by extraction with ethyl acetate. The organic layer was washed with water and saturated brine and dried over anhydrous magnesium sulfate. The solvent was evaporated under reduced pressure. The residue was purified using silica gel chromatography to obtain tert-butyl{trans-4-[{6-[2-(difluoromethyl)-1H-benzimidazol-1-yl]-2-(morpholin-4-yl)pyrimidin-4-yl}(isobutyl)amino]cyclohexyl}carbamate (163 mg).

Preparation Example 185

A mixture of 4-[2-(difluoromethyl)-1H-benzimidazol-1-yl]-N-(3,4-dimethoxy benzyl)-6-(morpholin-4-yl)pyrimidin-2-amine (5.3 g) and trifluoroacetic acid (0.82 mL) was stirred at 10 for 1 hour. The reaction mixture was neutralized by the addition of saturated aqueous sodium hydrogen carbonate solution, and extracted with ethyl acetate. The organic layer was washed with saturated brine and dried over anhydrous magnesium sulfate. The solvent was evaporated under reduced pressure. The resulting solid was collected by filtration and washed with diisopropyl ether to obtain 4-[2-(difluoromethyl)-1H-benzimidazol-1-yl]-6-(morpholin-4-yl)pyrimidin-2-amine (1.36 g).

Example 1

A mixture of 2-difluoromethyl-1-[2-(methylsulfonyl)-6-morpholin-4-ylpyrimidin-4-yl]-1H-benzimidazole (770 mg), tert-butyl (3S)-3-aminopyrrolidine-1-carboxylate (525 mg), potassium carbonate (390 mg), and N,N-dimethylacetamide (19 mL) was stirred in a microwave reactor at 100° C. for 1 hour. The reaction mixture was cooled to room temperature and then poured into water, followed by extraction with ethyl acetate. The organic layer was washed with saturated brine and dried over anhydrous magnesium sulfate. The solvent was evaporated under reduced pressure and then the residue was purified by amino silica gel column chromatography (hexane:ethyl acetate=80:20-50:50) to obtain tert-butyl (3S)-3-({4-[2-(difluoromethyl)-1H-benzimidazol-1-yl]-6-morpholin-4-ylpyrimidin-2-yl}amino)pyrrolidine-1-carboxylate (310 mg) as a pale yellow amorphous substance.

Example 22

A mixture of 2-(difluoromethyl)-1-[2-(methylsulfonyl)-6-morpholin-4-ylpyrimidin-4-yl]-1H-benzimidazole (100 mg), 1-benzyl-3-(methylamino)pyrrolidine (93 mg), potassium carbonate (50 mg), and N,N-dimethylacetamide (2.5 mL) was stirred in a microwave reactor at 100° C. for 1 hour. The reaction mixture was cooled to room temperature and then poured into water, followed by extraction with ethyl acetate. The organic layer was washed with saturated brine and dried over anhydrous magnesium sulfate. The solvent was evaporated under reduced pressure and then the residue was purified by amino silica gel column chromatography (hexane:ethyl acetate=80:20-50:50). Desired fractions were combined and concentrated under reduced pressure. The residue was dissolved in 1,4-dioxane, and a 4 M solution (61 μL) of hydrogen chloride in 1,4-dioxane was added thereto. Further, diisopropyl ether (10 mL) was added thereto. The resulting powder was collected by filtration, washed with diisopropyl ether, and dried under reduced pressure to obtain N-(1-benzylpyrrolidin-3-yl)-4-[2-(difluoromethyl)-1H-benzimidazol-1-yl]-N-methyl-6-morpholin-4-ylpyrimidin-2-amine hydrochloride (28 mg) as a pale yellow powder.

Example 26

To a mixture of 4-[2-(difluoromethyl)-1H-benzimidazol-1-yl]-6-morpholin-4-yl-N-[(3S)-pyrrolidin-3-yl]pyrimidin-2-amine dihydrochloride (58 mg) and N,N-dimethylformamide (1.2 mL) were added phenylacetaldehyde (21 mg), sodium triacetoxyborohydride (75 mg), and acetic acid (0.29 mL), and the mixture was stirred at room temperature overnight. To the reaction mixture was added a saturated aqueous sodium bicarbonate solution, followed by extraction with ethyl acetate. The organic layer was washed with saturated brine and dried over anhydrous magnesium sulfate. The solvent was evaporated under reduced pressure and then the residue was purified by amino silica gel column chromatography (chloroform:methanol=100:0-90:10) to obtain 4-[2-(difluoromethyl)-1H-benzimidazol-1-yl]-6-morpholin-4-yl-N-[(3S)-1-(2-phenylethyl)pyrrolidin-3-yl]pyrimidin-2-amine (30 mg) as a white powder.

Example 43

To a solution of 4-[2-(difluoromethyl)-1H-benzimidazol-1-yl]-6-morpholin-4-yl-N-(piperidin-4-ylmethyl)pyrimidin-2-amine (400 mg) in 1,2-dichloroethane (8 mL) was added 4-fluorocyclohexanone (210 mg), and the mixture was stirred at room temperature for 10 minutes. Subsequently sodium triacetoxyborohydride (382 mg) was added thereto, followed by stirring at room temperature overnight. To the reaction mixture was added a saturated aqueous sodium bicarbonate solution, followed by extraction with chloroform. The organic layer was washed with saturated brine and dried over anhydrous sodium sulfate. The solvent was evaporated under reduced pressure and then the residue was purified by amino silica gel column chromatography (hexane:ethyl acetate=70: 30-40:60) to obtain two types of compounds below, each as a white powder.

4-[2-(Difluoromethyl)-1H-benzimidazol-1-yl]-N-{[1-(trans-4-fluorocyclohexyl)piperidin-4-yl]methyl}-6-(morpholin-4-yl)pyrimidin-2-amine (109 mg)

The Rf value in amino silica gel TLC (hexane:ethyl acetate=50:50) of the present compound was 0.35.

4-[2-(Difluoromethyl)-1H-benzimidazol-1-yl]-N-{[1-(cis-4-fluorocyclohexyl)piperidin-4-yl]methyl}-6-(morpholin-4-yl)pyrimidin-2-amine (87 mg)

The Rf value in amino silica gel TLC (hexane:ethyl acetate=50:50) of the present compound was 0.28.

The 4-[2-(difluoromethyl)-1H-benzimidazol-1-yl]-N-{[1-(trans-4-fluorocyclohexyl)piperidin-4-yl]methyl}-6-(morpholin-4-yl)pyrimidin-2-amine (80 mg) obtained above was dissolved in a mixed solvent of methylene chloride (1.7 mL) and methanol (0.3 mL), and a 4 M solution (0.37 mL) of hydrogen chloride in 1,4-dioxane was added thereto. The mixture was stirred at room temperature for 10 minutes. The reaction mixture was concentrated to obtain 4-[2-(difluoromethyl)-1H-benzimidazol-1-yl]-N-{[1-(trans-4-fluorocyclohexyl)piperidin-4-yl]methyl}-6-(morpholin-4-yl)pyrimidin-2-amine dihydrochloride (Example 43-1, 87 mg) as a white powder.

In the similar manner, 4-[2-(difluoromethyl)-1H-benzimidazol-1-yl]-N-{[1-(cis-4-fluorocyclohexyl)piperidin-4-yl]methyl}-6-(morpholin-4-yl)pyrimidin-2-amine dihydrochloride (Example 43-2, 70 mg) was obtained as a white powder from the 4-[2-(difluoromethyl)-1H-benzimidazol-1-yl]-N-{[1-(cis-4-fluorocyclohexyl)piperidin-4-yl]methyl}-6-(morpholin-4-yl)pyrimidin-2-amine (62 mg) obtained above.

Example 44

To a mixture of 4-[2-(difluoromethyl)-1H-benzimidazol-1-yl]-6-(morpholin-4-yl)-N-[(1-phenylpiperidin-4-yl)methyl]pyrimidin-2-amine (38 mg), chloroform (0.75 mL), and methanol (0.35 mL) was added a 4 M solution (0.2 mL) of hydrogen chloride in 1,4-dioxane, and the mixture was stirred at room temperature for 10 minutes. The reaction mixture was concentrated under reduced pressure to obtain 4-[2-(difluoromethyl)-1H-benzimidazol-1-yl]-6-(morpholin-4-yl)-N-[(1-phenylpiperidin-4-yl)methyl]pyrimidin-2-amine dihydrochloride (43 mg) as a white powder.

Example 45

To a mixture of 4-[2-(difluoromethyl)-1H-benzimidazol-1-yl]-6-morpholin-4-yl-N-[(3S)-pyrrolidin-3-yl]pyrimidin-2-amine dihydrochloride (75 mg) and N,N-dimethylformamide (1.5 mL) were added 2-(dimethylamino)ethyl bromide (26 mg) and potassium carbonate (85 mg), and the mixture was stirred at room temperature overnight. To the reaction mixture was added water, followed by extraction with ethyl acetate. The organic layer was washed with saturated brine and dried over anhydrous magnesium sulfate. The solvent was evaporated under reduced pressure and then the residue was purified by amino silica gel column chromatography (hexane:ethyl acetate=50:50-0:100, and subsequently chloroform:methanol=100:0-80:20). Desired fractions are combined and concentrated under reduced pressure. The residue was dissolved in 1,4-dioxane (0.5 mL) and a 4 M solution (80 μL) of hydrogen chloride in 1,4-dioxane was added thereto. Diisopropyl ether (10 mL) was further added thereto. The resulting powder was collected by filtration, washed with diisopropyl ether, and dried under reduced pressure to obtain 4-[2-(difluoromethyl)-1H-benzimidazol-1-yl]-N-{(3S)-1-[2-(dimethylamino)ethyl]pyrrolidin-3-yl}-6-morpholin-4-ylpyrimidin-2-amine dihydrochloride (10 mg) as a white powder.

Example 52

To a mixture of 4-[2-(difluoromethyl)-1H-benzimidazol-1-yl]-6-morpholin-4-yl-N-(piperidin-4-ylmethyl)pyrimidin-2-amine (100 mg) and ethanol (2 mL) were added 2-(fluoromethyl)oxirane (19 μL) and N,N-diisopropyl ethylamine (79 μL), and the mixture was stirred in a microwave reactor at 120° C. for 1 hour. To the reaction mixture was added water, followed by extraction with ethyl acetate. The organic layer was washed with saturated brine and dried over anhydrous magnesium sulfate. The solvent was evaporated under reduced pressure and then the residue was purified by amino silica gel column chromatography (ethyl acetate:hexane) to obtain 1-{4-[({4-[2-(difluoromethyl)-1H-benzimidazol-1-yl]-6-(morpholin-4-yl)pyrimidin-2-yl}amino)methyl]piperidin-1-yl}-3-fluoropropan-2-ol (81 mg) as a white powder.

Example 53

To a mixture of tert-butyl (3S)-3-({4-[2-(difluoromethyl)-1H-benzimidazol-1-yl]-6-morpholin-4-ylpyrimidin-2-yl}amino)pyrrolidine-1-carboxylate (300 mg) and 1,4-dioxane (3 mL) was added a 4 M solution (1.5 mL) of hydrogen chloride in 1,4-dioxane, and the mixture was stirred at room temperature for 2 hours. To the reaction mixture was added diisopropyl ether (10 mL). The resulting powder was collected by filtration, washed with diisopropyl ether, and dried under reduced pressure to obtain 4-[2-(difluoromethyl)-1H-benzimidazol-1-yl]-6-morpholin-4-yl-N-[(3S)-pyrrolidin-3-yl]pyrimidin-2-amine dihydrochloride (354 mg) as a pale yellow powder.

Example 54

To a mixture of tert-butyl 4-({4-[2-(difluoromethyl)-1H-benzimidazol-1-yl]-6-morpholin-4-ylpyrimidin-2-yl}amino)piperidine-1-carboxylate (63 mg) and methanol (1.3 mL) were added a 4 M solution of hydrogen chloride in 1,4-dioxane (0.15 mL), and the mixture was stirred at room temperature for 4 hours. The reaction mixture was neutralized by the addition of saturated aqueous sodium bicarbonate solution, and extracted with chloroform. The organic layer was dried over anhydrous magnesium sulfate and the solvent was evaporated under reduced pressure. The residue was purified by amino silica gel column chromatography (hexane:ethyl acetate=50:50) to obtain 4-[2-(difluoromethyl)-1H-benzimidazol-1-yl]-6-morpholin-4-yl-N-piperidin-4-ylpyrimidin-2-amine (27 mg) as a pale yellow powder.

Example 66

To a mixture of 4-[2-(difluoromethyl)-1H-benzimidazol-1-yl]-6-morpholin-4-yl-N-piperidin-4-ylpyrimidin-2-amine (18 mg) and N,N-dimethylformamide (0.36 mL) were added N,N-dimethylglycine (4.8 mg), 1-hydroxybenzotriazole (6.2 mg), and N-[3-(dimethylamino)propyl]-N'-ethylcarbodiimide hydrochloride (8.8 mg), and the mixture was stirred at room temperature for 6 hours. To the reaction mixture was added water, followed by extraction with chloroform. The organic layer was dried over anhydrous magnesium sulfate. The solvent was evaporated under reduced pressure and then the residue was purified by amino silica gel column chromatography (ethyl acetate, and subsequently chloroform:methanol=96:4). Desired fractions were combined and concentrated under reduced pressure. The residue was solidified by the addition of a small amount of diisopropyl ether to obtain 4-[2-(difluoromethyl)-1H-benzimidazol-1-yl]-N-{1-[(dimethylamino)acetyl]piperidin-4-yl}-6-morpholin-4-ylpyrimidin-2-amine (9 mg) as a white powder.

Example 71

To a mixture of 4-[2-(difluoromethyl)-1H-benzimidazol-1-yl]-6-morpholin-4-yl-N-(piperidin-4-ylmethyl)-1,3,5-triazin-2-amine (50 mg) and pyridine (2 mL) was added acetic anhydride (14 μL), and the mixture was stirred at room temperature overnight. To the reaction mixture was added toluene, followed by concentrating under reduced pressure. The residue was dissolved in dichloromethane, and silica gel was added thereto, followed by concentrating under reduced pressure. The residue was purified by silica gel column chromatography (hexane:ethyl acetate, and subsequently chloroform:methanol) to obtain N-[(1-acetylpiperidin-4-yl)methyl]-4-[2-(difluoromethyl)-1H-benzimidazol-1-yl]-6-morpholin-4-yl-1,3,5-triazine-2-amine (44 mg) as a white powder.

Example 74

To a mixture of 4-[2-(difluoromethyl)-1H-benzimidazol-1-yl]-6-morpholin-4-yl-N-(piperidin-4-ylmethyl)pyrimidin-2-amine (50 mg) and 1,2-dimethoxyethane (1 mL) were added bromobenzene (24 μL), tris(dibenzylideneacetone)dipalladium (0) (6.5 mg), dicyclohexyl(2',4',6'-triisopropylbiphenyl-2-yl)phosphine (11 mg), and potassium phosphate (96 mg), and the mixture was stirred in a microwave reactor at 130° C. for 1 hour. The reaction mixture was filtered through celite, and to the filtrate was added silica gel, followed by concentrating under reduced pressure. The residue was purified by silica gel column chromatography (hexane:ethyl acetate) to obtain 4-[2-(difluoromethyl)-1H-benzimidazol-1-yl]-6-(morpholin-4-yl)-N-[(1-phenylpiperidin-4-yl)methyl]pyrimidin-2-amine (39 mg) as a white powder.

Example 80

A mixture of tert-butyl 4-[({6-[2-(difluoromethyl)-1H-benzimidazol-1-yl]-2-(methylsulfinyl)pyrimidin-4-yl}oxy)methyl]piperidine-1-carbamate (240 mg), morpholine (0.3 mL), and N,N-dimethylacetamide (2 mL) was stirred at room temperature for 1 hour. To the reaction mixture was added water, followed by extraction with ethyl acetate. The organic layer was washed with water and saturated brine, and then dried over anhydrous magnesium sulfate. The solvent was evaporated under reduced pressure and then the residue was purified by silica gel column chromatography (hexane:ethyl acetate=70:30-50:50) to obtain tert-butyl 4-[({6-[2-(difluoromethyl)-1H-benzimidazol-1-yl]-2-(morpholin-4-yl)pyrimidin-4-yl}oxy)methyl]piperidine-1-carbamate (246 mg) as a white powder.

Example 82

1-[4-Chloro-6-(morpholin-4-yl)pyrimidin-2-yl]-2-(difluoromethyl)-1H-benzimidazole (100 mg) was dissolved in dimethylformamide (1 mL), and 3-methoxyprop-1-yne (45 μL), tetrakistriphenylphosphine palladium (0) (16 mg), copper (I) iodide (1.3 mg), and potassium carbonate (227 mg) were added thereto, followed by stirring in a microwave reactor at 80° C. for 1 hour. An aqueous ammonium chloride solution and chloroform were added thereto, and the organic layer was extracted, washed with saturated brine, and then dried over anhydrous magnesium sulfate. Then, the solvent was evaporated under reduced pressure. The residue was purified by silica gel column chromatography (hexane:ethyl acetate=60:40). A mixed solvent of diisopropyl ether and hexane was added thereto, and the resulting solid was collected by filtration and further washed with hexane to obtain 2-(difluoromethyl)-1-[4-(3-methoxyprop-1-yn-1-yl)-6-(morpholin-4-yl)pyrimidin-2-yl]-1H-benzimidazole (10 mg) as a yellow powder.

Example 83

Methyl trans-4-[({4-[2-(difluoromethyl)-1H-benzimidazol-1-yl]-6-(morpholin-4-yl)pyrimidin-2-yl}amino)methyl] cyclohexane carboxylate (150 mg) was dissolved in a mixed solvent of methanol (750 µL) and tetrahydrofuran (750 µL), and a 1 M aqueous sodium hydroxide solution (899 mL) was added thereto, followed by stirring at room temperature for 2 hours. After the completion of the reaction, 1 M hydrochloric acid was added thereto under ice-cooling until the reaction solution became weakly acidic, followed by stirring at 0° C. for 1 hour. The resulting solid was collected by filtration and washed with hexane to obtain trans-4-[({4-[2-(difluoromethyl)-1H-benzimidazol-1-yl]-6-(morpholin-4-yl)pyrimidin-2-yl}amino)methyl]cyclohexanecarboxylic acid (74 mg) as a white powder.

Example 84

[(3S)-3-[(tert-Butoxycarbonyl)amino]-4-{[trans-4-({6-[2-(difluoromethyl)-1H-benzimidazol-1-yl]-2-(morpholin-4-yl)pyrimidin-4-yl}oxy)cyclohexyl]amino}-4-oxobutyl] (dimethyl)sulfonium iodide (919 mg) was dissolved in tetrahydrofuran (9.2 mL), and cooled to 0° C. under a nitrogen air flow, and a 1.6 M solution (0.7 mL) of hexamethyldisilazanelithium in tetrahydrofuran was added dropwise thereto, followed by stirring at 0° C. for 2 hours. A 1.6 M solution (0.7 mL) of hexamethyldisilazanelithium in tetrahydrofuran was further added dropwise thereto, followed by stirring at 0° C. for 1 hour. A saturated aqueous ammonium chloride solution was added thereto, followed by extraction with ethyl acetate. The organic layer was washed with saturated brine and dried over anhydrous magnesium sulfate. The solvent was evaporated under reduced pressure and the residue was purified by silica gel column chromatography (hexane:ethyl acetate=70:30-0:100) to obtain tert-butyl{(3S)-1-[trans-4-({6-[2-(difluoromethyl)-1H-benzimidazol-1-yl]-2-(morpholin-4-yl)pyrimidin-4-yl}oxy)cyclohexyl]-2-oxopyrrolidin-3-yl}carbamate (154 mg).

Example 85

N-[(4-Aminobicyclo[2.2.2]oct-1-yl)methyl]-4-[2-(difluoromethyl)-1H-benzimidazol-1-yl]-6-(morpholin-4-yl)pyrimidin-2-amine (150 mg) was dissolved in ethanol (3 mL), and N,N-diisopropyl ethylamine (81 µL) and 2,2-dimethyloxirane (36 µL) were added thereto, followed by stirring at 120° C. for 1 hour and at 140° C. for 1 hour using a microwave reactor. The reaction solution was concentrated and the residue was purified by amino silica gel column chromatography (hexane:ethyl acetate=20:80, and subsequently chloroform:methanol=98:2) to obtain 1-({4-[({4-[2-(difluoromethyl)-1H-benzimidazol-1-yl]-6-(morpholin-4-yl)pyrimidin-2-yl}amino)methyl]bicyclo[2.2.2]oct-1-yl}amino)-2-methylpropan-2-ol (148 mg) as a white amorphous substance.

Example 86

1-({trans-4-[({4-[2-(Difluoromethyl)-6-methyl-1H-benzimidazol-1-yl]-6-[(3S)-3-methylmorpholin-4-yl]pyrimidin-2-yl}amino)methyl]cyclohexyl}amino)-2-methylpropan-2-ol (100 mg) was dissolved in tetrahydrofuran (2 mL), and di-1H-imidazol-1-ylmethanone (131 mg) and triethylamine (50 µL) were added thereto, followed by stirring for 3 hours while heating and refluxing. After the completion of the reaction, water was added thereto, followed by extraction with ethyl acetate. The extracts were washed with saturated brine and dried over anhydrous magnesium sulfate, and then the solvent was evaporated under reduced pressure. The residue was purified by amino silica gel column chromatography (hexane:ethyl acetate=60:40) to obtain 3-{trans-4-[({4-[2-(difluoromethyl)-6-methyl-1H-benzimidazol-1-yl]-6-[(3S)-3-methylmorpholin-4-yl]pyrimidin-2-yl}amino)methyl]cyclohexyl}-5,5-dimethyl-1,3-oxazolidin-2-one (100 mg) as a white powder.

Example 87

To (3S)-3-amino-1-[trans-4-({6-[2-(difluoromethyl)-1H-benzimidazol-1-yl]-2-(morpholin-4-yl)pyrimidin-4-yl}oxy)cyclohexyl]pyrrolidin-2-one (75 mg), triethylamine (22 µL), and dichloromethane (750 µL) was added methylchlorocarbonate (12 µL), followed by stirring at room temperature for 1 hour. After the completion of the reaction, a saturated aqueous sodium bicarbonate solution was added thereto, followed by extraction with chloroform. The organic layer was washed with saturated brine and then dried over anhydrous magnesium sulfate, and the solvent was evaporated under reduced pressure. The residue was purified by silica gel column chromatography (chloroform:methanol) to obtain methyl{(3S)-1-[trans-4-({6-[2-(difluoromethyl)-1H-benzimidazol-1-yl]-2-(morpholin-4-yl)pyrimidin-4-yl}oxy)cyclohexyl]-2-oxopyrrolidin-3-yl}carbamate (55 mg) as a white powder.

Example 88

To (3S)-3-amino-1-[trans-4-({6-[2-(difluoromethyl)-1H-benzimidazol-1-yl]-2-(morpholin-4-yl)pyrimidin-4-yl}oxy)cyclohexyl]pyrrolidin-2-one (75 mg), N-ethyl-N-isopropyl-propan-2-amine (73 µL), and 1,2-dichloroethane (750 µL) was added methanesulfonyl chloride (17 µL), followed by stirring at room temperature for 1 hour. After the completion of the reaction, a saturated aqueous sodium bicarbonate solution was added thereto, followed by extraction with chloroform. The organic layer was washed with saturated brine and then dried over anhydrous magnesium sulfate, and the solvent was evaporated under reduced pressure. The residue was purified by silica gel column chromatography (chloroform:methanol) to obtain N-{(3S)-1-[trans-4-({6-[2-(difluoromethyl)-1H-benzimidazol-1-yl]-2-(morpholin-4-yl)pyrimidin-4-yl}oxy)cyclohexyl]-2-oxopyrrolidin-3-yl}methanesulfonamide (82 mg) as a pale yellow powder.

Example 89

2-Bromo-N-[trans-4-({6-[2-(difluoromethyl)-1H-benzimidazol-1-yl]-2-(morpholin-4-yl)pyrimidin-4-yl}oxy)cyclohexyl]acetamide (100 mg) was suspended in dimethylformamide (2 mL), and potassium carbonate (30 mg) and cyclobutylamine (60 µL) were added thereto, followed by stirring at room temperature overnight. To the reaction solution was added water, followed by extraction with ethyl acetate. The extracts were washed with water and saturated brine, the organic layer was dried over anhydrous sodium sulfate, and the solvent was evaporated under reduced pressure. The residue was purified by amino silica gel chromatography (hexane:ethyl acetate=40:60-10:90) to obtain $N^2$-cyclobutyl-N-[trans-4-({6-[2-(difluoromethyl)-1H-benzimidazol-1-yl]-2-(morpholin-4-yl)pyrimidin-4-yl}oxy)cyclohexyl]glycinamide (79 mg).

Example 91

N-[2-(Cyclopentylsulfanyl)ethyl]-4-[2-(difluoromethyl)-1H-benzimidazol-1-yl]-6-(morpholin-4-yl)-1,3,5-triazin-2-amine (60 mg) was dissolved in methylene chloride (1.2 mL), and m-chloroperbenzoic acid (75% wet) (32 mg) was added thereto at 0° C., followed by stirring for 10 minutes. Water was added thereto, followed by extraction with chloroform. The organic layer was dried over anhydrous magnesium sulfate and the solvent was evaporated under reduced pressure. The residue was purified by silica gel column chromatography (hexane:ethyl acetate=20:80, and subsequently chloroform:methanol=98:2-90:10) to obtain N-[2-(cyclopentyl sulfinyl)ethyl]-4-[2-(difluoromethyl)-1H-benzimidazol-1-yl]-6-(morpholin-4-yl)-1,3,5-triazin-2-amine (53 mg) as a white powder.

Example 92

2-(Difluoromethyl)-1-[6-(1,4-dioxaspiro[4.5]deca-8-yl-methoxy)-2-(methylsulfanyl)pyrimidin-4-yl]-1H-benzimidazole (1.3 g) was dissolved in dichloromethane (20 mL), and m-chloroperbenzoic acid (75% wet) (712 mg) was added thereto at 0° C., followed by stirring for 30 minutes. To the reaction solution was added a saturated aqueous sodium bicarbonate, followed by extraction with chloroform. The extracts were washed with water and saturated brine, the organic layer was dried over anhydrous magnesium sulfate, and the solvent was evaporated under reduced pressure. The residue was dissolved in dimethylformamide (10 mL), and morpholine (1.22 mL) was added thereto, followed by stirring at room temperature for 2 hours. The reaction solution was poured into water, followed by extraction with ethyl acetate. The extracts were washed with water and saturated brine, the organic layer was dried over anhydrous magnesium sulfate, and the solvent was evaporated under reduced pressure. The residue was purified by silica gel column chromatography (hexane:ethyl acetate=95:5-80:20) to obtain 2-(difluoromethyl)-1-[6-(1,4-dioxaspiro[4.5]deca-8-ylmethoxy)-2-(morpholin-4-yl)pyrimidin-4-yl]-1H-benzimidazole (1.21 g) as a white powder.

Example 93

2-(Difluoro methyl)-1-[6-(1,4-dioxaspiro[4.5]deca-8-yl-methoxy)-2-(morpholin-4-yl)pyrimidin-4-yl]-1H-benzimidazole (1.2 g) was dissolved in a mixed solvent of tetrahydrofuran (12 mL) and water (12 mL), and 4-methylbenzene sulfonic acid monohydrate (2.27 g) was added thereto, followed by stirring at room temperature for 3 hours. To the reaction solution was added saturated aqueous sodium bicarbonate, followed by extraction with ethyl acetate. The extracts were washed with water and saturated brine, the organic layer was dried over anhydrous magnesium sulfate, and the solvent was evaporated under reduced pressure. The residue was purified by silica gel column chromatography (hexane:ethyl acetate=80:20-40:60) to obtain 4-[({6-[2-(difluoromethyl)-1H-benzimidazol-1-yl]-2-(morpholin-4-yl)pyrimidin-4-yl}oxy)methyl]cyclohexanone (941 mg) as a white powder.

Example 94

N-[2-(Cyclopentylsulfanyl)ethyl]-4-[2-(difluoromethyl)-1H-benzimidazol-1-yl]-6-(morpholin-4-yl)-1,3,5-triazin-2-amine (60 mg) was dissolved in methylene chloride (1.2 ml), and m-chloroperbenzoic acid (75% wet) (73 mg) was added thereto at 0° C., followed by stirring for 10 minutes. Water was added thereto, followed by extraction with chloroform. The organic layer was dried over anhydrous magnesium sulfate and the solvent was evaporated under reduced pressure. The residue was purified by amino silica gel column chromatography (hexane:ethyl acetate=50:50-0:100) to obtain N4-[2-(cyclopentylsulfonyl)ethyl]-4-[2-(difluoromethyl)-1H-benzimidazol-1-yl]-6-(morpholin-4-yl)-1,3,5-triazin-2-amine (58 mg) as a white powder.

Example 237

To a solution of [3-({6-[2-(difluoromethyl)-1H-benzimidazol-1-yl]-2-(morpholin-4-yl)pyrimidin-4-yl}oxy)azetidin-1-yl](cis-4-hydroxycyclohexyl)methanone (60 mg) in methylene chloride (1.2 mL) was added a Dess-Martin reagent (53 mg) under ice-cooling, followed by stirring at room temperature overnight. To the reaction mixture were added ethyl acetate and a saturated aqueous sodium bicarbonate solution, the organic layer was extracted, washed with saturated brine, and then dried over anhydrous magnesium sulfate, and the solvent was evaporated under reduced pressure. The residue was purified by silica gel column chromatography (chloroform:methanol=100:0-90:10) to obtain 4-{[3-({6-[2-(difluoromethyl)-1H-benzimidazol-1-yl]-2-(morpholin-4-yl)pyrimidin-4-yl}oxy)azetidin-1-yl]carbonyl}cyclohexanone (20 mg).

Example 238

4-(Morpholin-4-ylmethyl)benzenesulfonamide (35 mg) was dissolved in N,N-dimethylacetamide (1.25 mL), and 60% sodium hydride (4 mg) was added thereto, followed by stirring at room temperature for 30 minutes. To the reaction mixture was added 1-[6-chloro-2-(morpholin-4-yl)pyrimidin-4-yl]-2-(difluoromethyl)-1H-benzimidazole (50 mg), followed by stirring at 120° C. for 1 hour. The mixture was cooled to room temperature, and then a saturated aqueous sodium chloride solution, ethyl acetate, and tetrahydrofuran were added thereto, followed by neutralization with a 10% aqueous potassium hydrogen sulfate solution, and then the organic layer was extracted. The organic layer was washed with a saturated aqueous sodium chloride solution, and dried over anhydrous magnesium sulfate. The desiccant was removed by filtration and then the solvent was evaporated under reduced pressure. The residue was purified by silica gel column chromatography (hexane:ethyl acetate=20:80-0:100 and subsequently chloroform:methanol=100:0-80:20) to obtain N-{6-[2-(difluoromethyl)-1H-benzimidazol-1-yl]-2-(morpholin-4-yl)pyrimidin-4-yl}-4-(morpholin-4-ylmethyl)benzenesulfonamide (13 mg).

Example 239 trans-4-({6-[2-(Difluoromethyl)-1H-benzimidazol-1-yl]-2-(morpholin-4-yl)pyrimidin-4-yl}amino)cyclohexanecarboxylic acid (232 mg) was dissolved in tetrahydrofuran (2.3 mL), and isobutyl chloroformate (70 μL) and 4-methylmorpholine (60 μL) were added thereto at 0° C., followed by stirring at 0° C. for 30 minutes and at room temperature for 2 hours. Subsequently, 28% aqueous ammonia (300 μL) was added thereto at 0° C., followed by stirring for 2 hours. The solvent was evaporated under reduced pressure and purified by silica gel chromatography (hexane:ethyl acetate=40:60-0:100 and chloroform:methanol-100:0-95:5) to obtain trans-4-({6-[2-(difluoromethyl)-1H-benzimidazol-1-yl]-2-(morpholin-4-yl)pyrimidin-4-yl}amino)cyclohexanecarboxamide (230 mg).

Example 240

To a solution of N-{4-[2-(difluoromethyl)-1H-benzimidazol-1-yl]-6-(morpholin-4-yl)pyrimidin-2-yl}cyclohexane-1, 3-diamine (70 mg) in dimethylacetamide (1.4 mL) were added triethylamine (56 µL) and bis(2-bromomethyl)ether (31 µL), followed by stirring at 120° C. for 2 hours using a microwave reactor. To the reaction solution was added water, followed by extraction with ethyl acetate. The extracts were washed with water and saturated brine. The organic layer was dried over anhydrous magnesium sulfate, the desiccant was removed by filtration, and then the solvent was evaporated under reduced pressure. The residue was purified by amino silica gel column chromatography (hexane:ethyl acetate=60: 40-20:80) to obtain 4-[2-(difluoromethyl)-1H-benzimidazol-1-yl]-6-(morpholin-4-yl)-N-[3-(morpholin-4-yl)cyclohexyl]pyrimidin-2-amine (42 mg).

Example 241

To a mixture of 4-[2-(difluoromethyl)-1H-benzimidazol-1-yl]-6-morpholin-4-yl)-N-[(3S)-pyrrolidin-3-yl]pyrimidin-2-amine dihydrochloride (100 mg) and methylene chloride (1 mL) were added triethylamine (0.1 mL) and benzoyl chloride (28.5 µL) under a nitrogen air flow while ice-cooling, followed by stirring at the same temperature for 4 hours. To the reaction mixture was added water (30 mL), followed by extraction with ethyl acetate (100 mL). The organic layer was washed with saturated brine (50 mL) and dried over anhydrous sodium sulfate. The desiccant was removed by filtration and the solvent was evaporated under reduced pressure. The residue was purified by silica gel column chromatography (chloroform:methanol=100:0-90:10). This was solidified with ethyl acetate and diisopropyl ether, then collected by filtration, and dried to obtain [(3S)-3-({4-[2-(difluoromethyl)-1H-benzimidazol-1-yl]-6-(morpholin-4-yl)pyrimidin-2-yl}amino)pyrrolidin-1-yl](phenyl)methanone (66 mg) as a white powder.

Example 242

To a solution of trans-N-{4-[2-(difluoromethyl)-6-methyl-1H-benzimidazol-1-yl]-6-(morpholin-4-yl)pyrimidin-2-yl}cyclohexane-1,4-diamine (150 mg) in ethanol (3 mL) was added 1H-1,2,3-benzotriazol-1-ylmethanol (59 mg), followed by stirring at room temperature for 5 hours. To this mixture was added sodium borohydride (25 mg), followed by further stirring at room temperature for 1 hour. To the reaction mixture was added water, followed by extraction with ethyl acetate. The organic layer was washed with a saturated aqueous sodium chloride solution and dried over anhydrous magnesium sulfate. The desiccant was removed by filtration and then the solvent was evaporated under reduced pressure. The residue was separated and purified by amino silica gel column chromatography (hexane:ethyl acetate=50:50-0:100 and chloroform:methanol=100:0-98:2) to obtain trans-N'-{4-[2-(difluoromethyl)-6-methyl-1H-benzimidazol-1-yl]-6-(morpholin-4-yl)pyrimidin-2-yl}-N,N-dimethylcyclohexane-1,4-diamine (50 mg) (free compound of Example 242-2) and trans-N-{4-[2-(difluoromethyl)-6-methyl-1H-benzimidazol-1-yl]-6-(morpholin-4-yl)pyrimidin-2-yl}-N'-methylcyclohexane-1,4-diamine (100 mg) (free compound of Example 242-1).

Example 243

To a solution of trans-N-{4-[2-(difluoromethyl)-6-methyl-1H-benzimidazol-1-yl]-6-(morpholin-4-yl)pyrimidin-2-yl}cyclohexane-1,4-diamine (50 mg) in methylene chloride (1 mL) were added triethylamine (46 µL) and 4-chlorobutyryl chloride (16 mg), followed by stirring for 1 hour in a water bath. The reaction solution was concentrated under reduced pressure and to the residue were added tetrahydrofuran (5 mL) and 60% sodium hydride (13 mg), followed by stirring at 0° C. for 30 minutes and at room temperature for 1 hour. To the reaction solution was added water, followed by extraction with ethyl acetate, and the extracts were washed with water and saturated brine, and dried over anhydrous magnesium sulfate. The desiccant was removed by filtration and then the solvent was evaporated under reduced pressure. The residue was purified by amino silica gel column chromatography (hexane:ethyl acetate=50:50-0:100 and chloroform:methanol=100:0-90:10) to obtain 1-[trans-4-({4-[2-(difluoromethyl)-6-methyl-1H-benzimidazol-1-yl]-6-(morpholin-4-yl)pyrimidin-2-yl}amino)cyclohexyl]pyrrolidin-2-one (40 mg).

Example 244

To a mixture of tert-butyl N-{4-[2-(difluoromethyl)-1H-benzimidazo-1-yl]-6-(morpholin-4-yl)pyrimidin-2-yl}-L-alaninate (80 mg) and methylene chloride (3 mL) were added a 4 M solution of hydrogen chloride in 1,4-dioxane (0.84 mL), followed by stirring for 4 hours. After the completion of the reaction, the solvent was evaporated under reduced pressure and then dried to obtain N-{4-[2-(difluoromethyl)-1H-benzimidazo-1-yl]-6-(morpholin-4-yl)pyrimidin-2-yl}-L-alanine hydrochloride (83 mg).

Example 245

To a solution of 2-(benzyloxy)ethyl {(3S)-1-[trans-4-({6-[2-(difluoromethyl)-1H-benzimidazol-1-yl]-2-(morpholin-4-yl)pyrimidin-4-yl}oxy)cyclohexyl]-2-oxopyrrolidin-3-yl}carbamate (84 mg) in methanol (1 mL) was added 10% palladium-carbon (50% wet) (84 mg), followed by stirring at room temperature overnight at 3 atm under a hydrogen atmosphere. The catalyst was removed and the filtrate was concentrated under reduced pressure. The residue was purified by silica gel chromatography (chloroform:methanol=100:0-92:8) to obtain 2-hydroxyethyl {(3S)-1-[trans-4-({6-[2-(difluoromethyl)-1H-benzimidazol-1-yl]-2-(morpholin-4-yl)pyrimidin-4-yl}oxy)cyclohexyl]-2-oxopyrrolidin-3-yl}carbamate (30 mg).

Example 246

To a mixture of methyl 2-{4-[({4-[2-(difluoromethyl)-1H-benzimidazol-1-yl]-6-(morpholin-4-yl)pyrimidin-2-yl}amino)methyl]piperidin-1-yl}cyclopentane carboxylate (50 mg) and tetrahydrofuran (1 mL) were added a 1.06 M solution of methyllithium in diethyl ether (0.33 mL) at 0° C., followed by stirring at the same temperature for 4 hours. To the reaction mixture was added a saturated aqueous ammonium chloride solution, followed by extraction with ethyl acetate. The organic layer was washed with saturated brine, dried over anhydrous magnesium sulfate, and then concentrated under reduced pressure. The residue was purified by amino silica gel column chromatography (hexane:ethyl acetate) to obtain 2-(2-{4-[({4-[2-(difluoromethyl)-1H-benzimidazol-1-yl]-6-(morpholin-4-yl)pyrimidin-2-yl}amino)methyl]piperidin-1-yl}cyclopentyl)propan-2-ol (11.1 mg).

Example 247 trans-4-({6-[2-(Difluoromethyl)-1H-benzimidazol-1-yl]-2-(morpholin-4-yl)pyrimidin-4-yl}oxy)cyclohexanol (100 mg) was suspended in N,N-dimethylformamide (4 mL), and 1,1'-carbonyldiimidazole (73 mg) was added thereto, followed by stirring at 60° C. for 2 hours. Further, 1,1'-carbonyldiimidazole (182 mg) was added thereto, followed by stirring at 60° C. for 2 hours. To this mixture was added guanidine carbonate (405 mg) at room temperature, followed by stirring at room temperature overnight. Water was added thereto, followed by extraction with ethyl acetate, the organic layer was washed with water and saturated brine, and dried over anhydrous sodium sulfate, and then the solvent was evaporated under reduced pressure. The residue was purified by silica gel column chromatography (10% MeOH/chloroform: chloroform=10:90-90:10) to obtain trans-4-({6-[2-(difluoromethyl)-1H-benzimidazol-1-yl]-2-(morpholin-4-yl)pyrimidin-4-yl}oxy)cyclohexylcarbamimidylcarbamate (103 mg).

Example 248

A mixture of 2-(difluoromethyl)-1-[2-(methylsulfonyl)-6-(morpholin-4-yl)pyrimidin-4-yl]-1H-benzimidazole (200 mg) and methyl[(3S)-1-(trans-4-aminocyclohexyl)-2-oxopyrrolidin-3-yl]carbamate hydrochloride (214 mg), potassium carbonate (135 mg), N-ethyl-N-diisopropylpropan-2-amine (0.38 mL) and N,N-dimethylacetamide (3 mL) was stirred at 100° C. for 6 hours. After leaving to be cooled, to the reaction solution was added water, followed by extraction with ethyl acetate. The organic layer was washed with saturated brine and dried over anhydrous sodium sulfate. The desiccant was removed by filtration and the solvent was evaporated under reduced pressure. The residue was purified by silica gel column chromatography (chloroform/methanol-100:0-80:20) to obtain methyl{(3S)-1-[trans-4-({4-[2-(difluoromethyl)-1H-benzimidazol-1-yl]-6-(morpholin-4-yl)pyrimidin-2-yl}amino)cyclohexyl]-2-oxopyrrolidin-3-yl}carbamate (102 mg) as a white powder.

Example 249

N-(Azetidin-3-yl)-6-[2-(difluoromethyl)-1H-benzimidazol-1-yl]-2-(morpholin-4-yl)pyrimidin-4-amine (100 mg) was dissolved in N,N-dimethylformamide (1 ml), and 4-methoxycyclohexanecarboxylic acid (43 mg), O-(7-azabenzotriazol-1-yl)-N,N,N',N'-tetramethyluronium hexafluorophosphate (HATU) (142 mg), and N,N-diisopropyl ethylamine (213 µL) were added thereto, followed by stirring at room temperature for 3 hours. The reaction mixture was added water (100 ml), followed by extraction with ethyl acetate (100 ml). The extracts were washed with water and saturated brine, and then dried over anhydrous magnesium sulfate. The desiccant was removed by filtration and then the solvent was evaporated under reduced pressure. The residue was separated/purified by silica gel column chromatography (from hexane:ethyl acetate=50:50-0:100 to chloroform:methanol=100:0-80:20) to obtain [3-({6-[2-(difluoromethyl)-1H-benzimidazol-1-yl]-2-(morpholin-4-yl)pyrimidin-4-yl}amino)azetidin-1-yl](cis-4-methoxycyclohexyl)methanone (26 mg) (Example 249-1) and [3-({6-[2-(difluoromethyl)-1H-benzimidazol-1-yl]-2-(morpholin-4-yl)pyrimidin-4-yl}amino)azetidin-1-yl](trans-4-methoxycyclohexyl)methanone (7.1 mg) (Example 249-2).

Example 422

To a mixture of methyl 2-{-4-[({4-[2-(difluoromethyl)-1H-benzimidazol-1-yl]-6-(morpholin-4-yl)pyrimidin-2-yl}amino)methyl]piperidin-1-yl}cyclopentane carboxylate (50 mg) and tetrahydrofuran (1 mL) were added a 1.01 M solution of (240 µL) diisobutylaluminum in toluene at 0° C., followed by stirring at the same temperature for 6 hours. To the reaction mixture were added methanol and sodium sulfate decahydrate, followed by stirring at room temperature for 1 hour. The insoluble matter was removed by filtration and then concentrated under reduced pressure, and the residue was purified by silica gel column chromatography (hexane:ethyl acetate=50:50-0:100) to obtain desired (2-{4-[({4-[2-(difluoromethyl)-1H-benzimidazol-1-yl]-6-(morpholin-4-yl)pyrimidin-2-yl}amino)methyl]piperidin-1-yl}cyclopentyl) methanol (33 mg).

Example 432

Racemic N-{6-[2-(Difluoromethyl)-1H-benzimidazol-1-yl]-2-(morpholin-4-yl)pyrimidin-4-yl}-1-(tetrahydro-2H-pyran-4-yl)azepan-4-amine (300 mg) was optically resolved using supercritical fluid chromatography to obtain optically active substance, N-{6-[2-(difluoromethyl)-1H-benzimidazol-1-yl]-2-(morpholin-4-yl)pyrimidin-4-yl}-1-(tetrahydro-2H-pyran-4-yl)azepan-4-amines (135 mg (RT 6.76 min) and 137 mg (RT 8.03 min)) as white amorphous substances, respectively.

SFC fractionation: AD-H/4.6×250 mm/$CO_2$ 75%, MeOH (0.1% DEA) 25%/Flow 3 ml/min/Conc. 2 mg/mL/rt=6.76 min, 8.03 min

Example A1

To a solution of 1-methylpiperidin-4-amine (4.6 mg) in N,N-dimethylformamide (200 µL) were added a solution of N,N-diisopropyl ethylamine (8.7 µL) in N,N-dimethylformamide (50 µL) and a solution of 1-[4-chloro-6-(morpholin-4-yl)-1,3,5-triazin-2-yl]-2-(difluoromethyl)-1H-benzimidazole (9.2 mg) in N,N-dimethylformamide (300 µL), followed by stirring at 80° C. overnight. To the reaction mixture were added a saturated aqueous sodium bicarbonate solution and chloroform at room temperature, followed by liquid-liquid phase separation, and the organic layer was concentrated under reduced pressure. The residue was purified by preparative HPLC to obtain 4-[2-(difluoromethyl)-1H-benzimidazolyl]-N-(1-methylpiperidin-4-yl)-6-(morpholin-4-yl)-1,3,5-triazin-2-amine (11.1 mg).

Example B1

To a solution of 1-(4-hydroxyphenyl)ethanone (5.4 mg) in N,N-dimethylformamide (200 µL) were added potassium carbonate (6.9 mg) and a solution of 1-[4-chloro-6-(morpholin-4-yl)-1,3,5-triazin-2-yl]-2-(difluoromethyl)-1H-benzimidazole (9.2 mg) in N,N-dimethylformamide (300 µL), followed by stirring at 80° C. overnight. To the reaction solution were added water and chloroform at room temperature, followed by liquid-liquid phase separation, and the organic layer was evaporated under reduced pressure. The residue was purified by preparative HPLC to obtain 1-[4-({4-[2-(difluoromethyl)-1H-benzimidazol-1-yl]-6-(morpholin-4-yl)-1,3,5-triazin-2-yl}oxy)phenyl]ethanone (1.4 mg).

The conditions for HPLC carried out to determine RT in Examples A1 and B1 are shown below.

Columns: Wakosil-II 5 C18AR (Wako Pure Chemical Industries, Ltd.) (particle diameter: 5 µM, internal diameter: 2.0 mm, length: 30 mm)

Mobile phase: A Solution 5 mM aqueous trifluoroacetic acid solution, B Solution methanol Flow rate: 1.2 mL/min; detection wavelength: 254 nm; column temperature: 35.0° C.; injection amount: 5 µL

TABLE 3

| Time (min) | A sol (%) | B sol (%) | Elution |
|---|---|---|---|
| 0-4 | 95→0 | 5→100 | Gradient |
| 4-4.5 | 0 | 100 | Isocratic |

Example A245

To a solution of rel-(1R,3R)-3-({6-[2-(difluoromethyl)-1H-benzimidazol-1-yl]-2-(morpholin-4-yl)pyrimidin-4-yl}oxy)cyclopentanamine (10.8 mg), glycolic acid (1.9 mg), and 1-hydroxybenzotriazole (3.4 mg) in N,N-dimethylformamide (1.0 mL) was added a PS-Carbodiimide (Biotage Inc.) (100 mg), followed by stirring at room temperature overnight. To the reaction solution were added a PS-Isocyanate (Biotage Inc.) (50 mg) and a MP-Carbonate (Biotage Inc.) (50 mg), followed by stirring for four hours, and the insoluble matter was removed by filtration. The filtrate was concentrated under reduced pressure to obtain rel-N-[(1R,3R)-3-({6-[2-(difluoromethyl)-1H-benzimidazol-1-yl]-2-(morpholin-4-yl)pyrimidin-4-yl}oxy)cyclopentyl]-2-hydroxyacetamide (7.2 mg).

Example B59

To a 2-methoxyethanamine (1.9 mg) were added a solution of trans-4-({6-[2-(difluoromethyl)-1H-benzimidazol-1-yl]-2-(morpholin-4-yl)pyrimidin-4-yl}oxy)cyclohexanecarboxylic acid (11.8 mg) and N,N-diisopropylethylamine (10.5 μL) in N,N-dimethylformamide (400 μL), and were added a solution of N-[(dimethylamino)(3H-[1,2,3]triazolo[4,5-b]pyridin-3-yloxy)methylene]-N-methylMethanaminium hexafluorophosphoric acid (11.4 mg) in N,N-dimethylformamide (100 μL), followed by stirring at room temperature overnight. To the reaction solution were added water and chloroform, followed by liquid separation, and the organic layer was concentrated under reduced pressure. The residue was subjected to preparative purification with HPLC to obtain trans-4-({6-[2-(difluoromethyl)-1H-benzimidazol-1-yl]-2-(morpholin-4-yl)pyrimidin-4-yl}oxy)-N-(2-methoxyethyl)cyclohexanecarboxamide (5.9 mg).

The condition for HPLC carried out to determine RT in Examples A245 and B59 are shown below.

columns: ACQUITY UPLC HSS T3 (particle diameter: 1.8 μm, internal diameter: 2.1 mm, length: 50 mm)

Mobile phase: A Solution 0.1% aqueous formic acid solution, B Solution 0.1% formic acid-methanol solution Flow rate: 0.70 mL/min; detection wavelength: 254 nm; column temperature: 40.0° C.; injection amount: 1 μL

TABLE 4

| Time (min) | A sol (%) | B sol (%) | Elution |
|---|---|---|---|
| 0-3 | 95→10 | 5→90 | Gradient |
| 3-4 | 10 | 90 | Isocratic |

The compounds of Preparation Examples and Examples shown in Tables below were prepared in the same manner as in Preparation Examples and Examples as described above.

The chemical structural formulae, the preparation methods, and the physicochemical data of the compounds of Preparation Examples are shown in Tables 5 to 40. Further, the chemical structural formulae of the compounds of Examples are shown in Tables 41 to 145, and the preparation methods and the physicochemical data of the compounds of Examples are shown in Tables 146 to 167.

Furthermore, the structures and the physicochemical data of the compounds of Examples A1 to A60 prepared in the same manner as the method of Example A1 are shown in Tables 169 to 180, and the structures and the physicochemical data of the compounds of Examples A61 to A693 prepared in the same manner as the method of Example A245 are shown in Tables 181 to 312, and the structures and the physicochemical data of the compounds of Examples B1 to B56 prepared in the same manner as the method of Example B1 are shown in Tables 313 to 324, and the structures and the physicochemical data of the compounds of Examples B57 to B151 prepared in the same manner as the method of Example B59 are shown in Tables 324 to 343.

TABLE 5

| PEx | PSyn | Str | DAT |
|---|---|---|---|
| 1 | 1 | 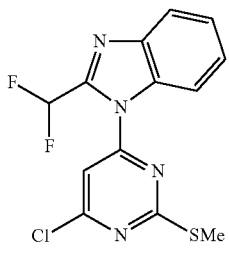 [SMILES: CSc1nc(Cl)cc(-n2c(C(F)F)nc3ccccc32)n1] | ESI+: 327 |
| 2 | 2 | 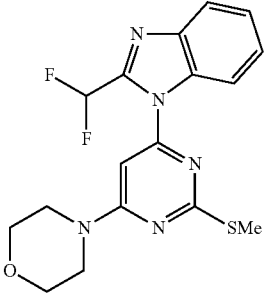 | ESI+: 378 |
| 3 | 3 | 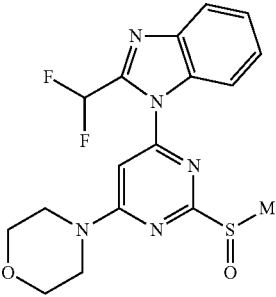 | ESI+: 394 |

TABLE 5-continued
| PEx | PSyn | Str | DAT |
|---|---|---|---|
| 4 | 4 | 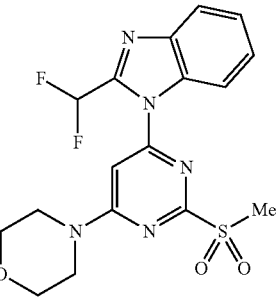 | ESI+: 410 |
| 5 | 5 | 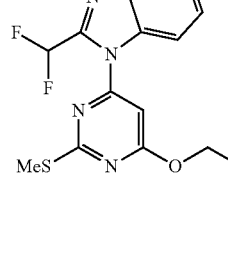 | ESI+: 506 |
TABLE 6
| PEx | PSyn | Str | DAT |
|---|---|---|---|
| 6 | 6 | 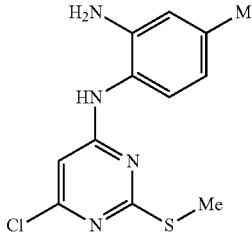 | ESI+: 281 |
| 7 | 7 | 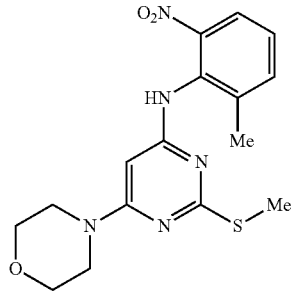 | ESI+: 362 |
| 8 | 8 | 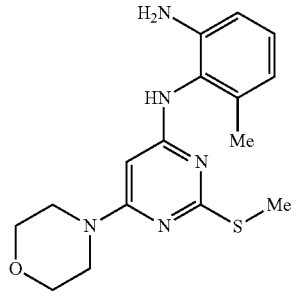 [SMILES: CSc1nc(Nc2c(C)cccc2N)cc(N2CCOCC2)n1] | ESI+: 332 |
| 9 | 9 | 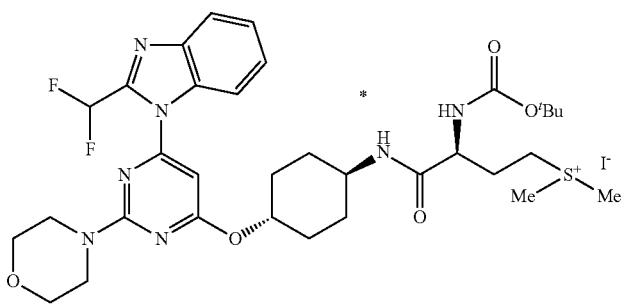 [SMILES: C[S+](C)CC[C@H](NC(=O)OC(C)(C)C)C(=O)N[C@H]1CC[C@H](Oc2cc(-n3c(C(F)F)nc4ccccc43)nc(N3CCOCC3)n2)CC1 ; [I-]] | ESI+: 690(M+) |

TABLE 6-continued
| PEx | PSyn | Str | DAT |
|---|---|---|---|
| 10 | 10 | 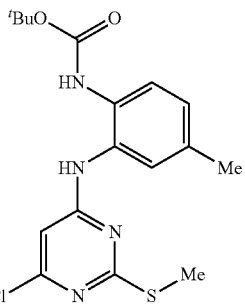 | ESI+: 381 |
TABLE 7
| PEx | PSyn | Str | DAT |
|---|---|---|---|
| 11 | 11 | 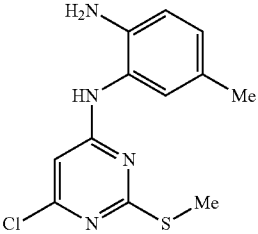 [SMILES: CSc1nc(Cl)cc(Nc2cc(C)ccc2N)n1] | ESI+: 281 |
| 12 | 12 | 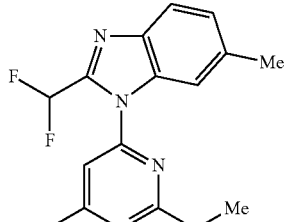 | ESI+: 341 |
| 13 | 13 | 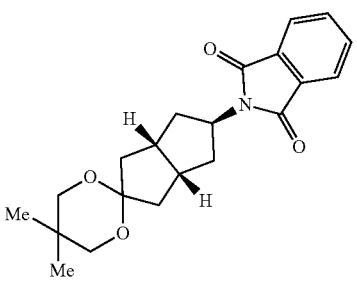 [SMILES: CC1(C)COC2(C[C@H]3C[C@H](N4C(=O)c5ccccc5C4=O)C[C@H]3C2)OC1] | ESI+: 356 |
| 14 | 14 | 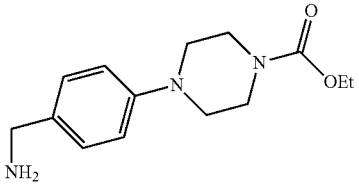 [SMILES: CCOC(=O)N1CCN(c2ccc(CN)cc2)CC1] | ESI+: 264 |
TABLE 7-continued
| PEx | PSyn | Str | DAT |
|---|---|---|---|
| 15 | 15 | 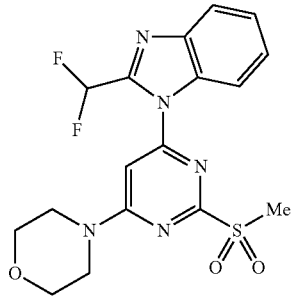 [SMILES: CS(=O)(=O)c1nc(N2CCOCC2)cc(-n2c(C(F)F)nc3ccccc32)n1] | ESI+: 410 |
TABLE 8
| PEx | PSyn | Str | DAT |
|---|---|---|---|
| 16 | 16 | 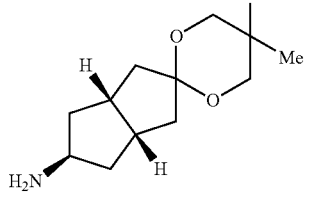 | ESI+: 226 |
| 17 | 17 | 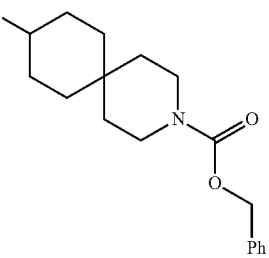 | ESI+: 303 |

TABLE 8-continued

| PEx | PSyn | Str | DAT |
|---|---|---|---|
| 18 | 2 | | ESI+: 392 |
| 19 | 2 | | ESI+: 392 |
| 20 | 2 | | ESI+: 406 |

TABLE 9

| PEx | PSyn | Str | DAT |
|---|---|---|---|
| 21 | 2 | | ESI+: 410 |

TABLE 9-continued

| PEx | PSyn | Str | DAT |
|---|---|---|---|
| 22 | 2 | | ESI+: 408 |
| 23 | 3 | | ESI+: 522 |
| 24 | 3 | | ESI+: 408 |
| 25 | 3 | | ESI+: 408 |

TABLE 10
| PEx | PSyn | Str | DAT |
|---|---|---|---|
| 26 | 3 | | ESI+: 424 |
| 27 | 3 | | ESI+: 426 |
| 28 | 3 | | ESI+: 422 |
TABLE 10-continued
| PEx | PSyn | Str | DAT |
|---|---|---|---|
| 29 | 1 | | ESI+: 459 |
| 30 | 1 | | ESI+: 459 |
TABLE 11
| PEx | PSyn | Str | DAT |
|---|---|---|---|
| 31 | 1 | 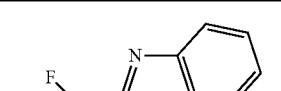 | ESI+: 378 |

TABLE 11-continued
| PEx | PSyn | Str | DAT |
|---|---|---|---|
| 32 | 3 | 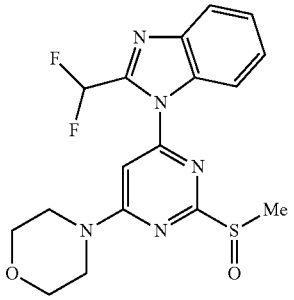 [SMILES: CS(=O)c1nc(N2CCOCC2)cc(-n2c(C(F)F)nc3ccccc32)n1] | ESI+: 394 |
| 33 | 1 | 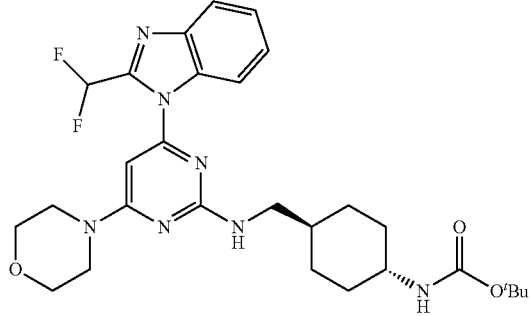 [SMILES: CC(C)(C)OC(=O)N[C@H]1CC[C@H](CNc2nc(N3CCOCC3)cc(-n3c(C(F)F)nc4ccccc43)n2)CC1] | ESI+: 580(M + Na) |
| 34 | 1 | 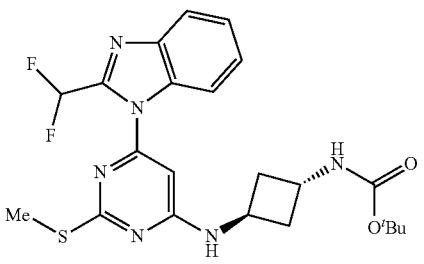 [SMILES: CSc1nc(N[C@H]2C[C@H](NC(=O)OC(C)(C)C)C2)cc(-n2c(C(F)F)nc3ccccc32)n1] | ESI+: 477 |
| 35 | 1 | 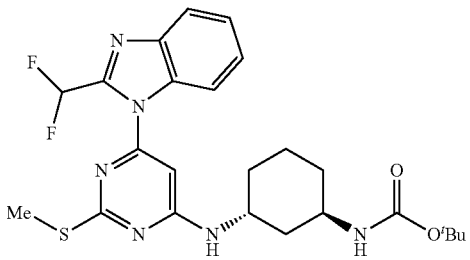 [SMILES: CSc1nc(N[C@@H]2CCC[C@@H](NC(=O)OC(C)(C)C)C2)cc(-n2c(C(F)F)nc3ccccc32)n1] | ESI+: 505 |

TABLE 12

| PEx | PSyn | Str | DAT |
|---|---|---|---|
| 36 | 3 | (5-methylbenzimidazole with CHF2, linked to pyrimidine with morpholine and S(O)Me) | ESI+: 408 |
| 37 | 1 | (5-methylbenzimidazole with CHF2, linked to pyrimidine with morpholine and SMe) | ESI+: 392 |
| 38 | 12 | (5-methylbenzimidazole with CHF2, linked to pyrimidine with Cl and SMe) | ESI+: 341 |
| 39 | 1 | (N-acetyl methylphenyl linked via NH to chloropyrimidine with SMe) | ESI+: 323 |
| 40 | 3 | (6-methylbenzimidazole with CHF2, linked to pyrimidine with morpholine and S(O)Me) | ESI+: 408 |

TABLE 13

| PEx | PSyn | Str | DAT |
|---|---|---|---|
| 41 | 1 | (6-methylbenzimidazole with CHF2, linked to pyrimidine with morpholine and SMe) | ESI+: 392 |
| 42 | 3 | (6-methylbenzimidazole with CHF2, linked to pyrimidine with (3-methyl)morpholine and S(O)Me) | ESI+: 422 |
| 43 | 1 | (6-methylbenzimidazole with CHF2, linked to pyrimidine with (3-methyl)morpholine and SMe) | ESI+: 406 |
| 44 | 10 | (2-methyl-6-aminoaniline linked via NH to chloropyrimidine with SMe) | ESI+: 281 |
| 45 | 12 | (4-methylbenzimidazole with CHF2, linked to chloropyrimidine with SMe) | ESI+: 341 |

TABLE 14
| PEx | PSyn | Str | DAT |
|---|---|---|---|
| 46 | 1 | 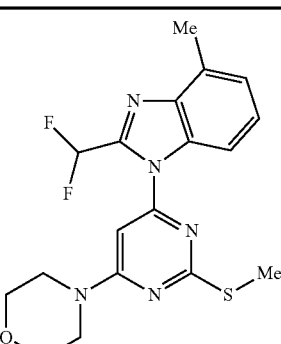 | ESI+: 392 |
| 47 | 3 | 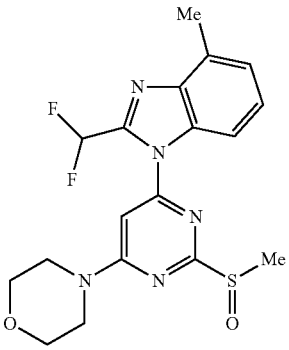 [SMILES: Cc1cccc2c1nc(C(F)F)n2-c1cc(N2CCOCC2)nc(S(C)=O)n1] | ESI+: 408 |
| 48 | 12 | 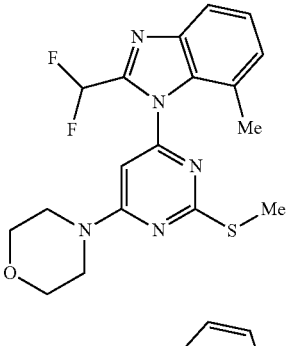 | ESI+: 392 |
| 49 | 15 | 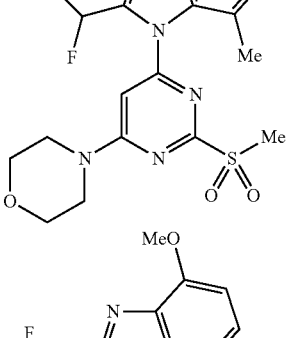 | ESI+: 424 |
| 50 | 1 | 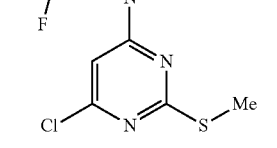 | ESI+: 357 |
TABLE 15
| PEx | PSyn | Str | DAT |
|---|---|---|---|
| 51 | 1 | 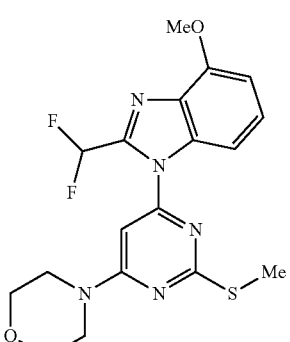 | ESI+: 408 |
| 52 | 3 | 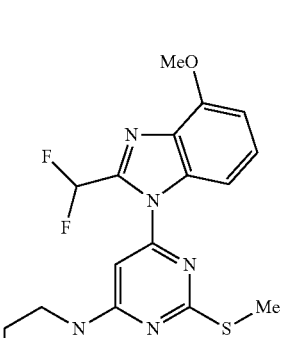 | ESI+: 424 |
| 53 | 1 | 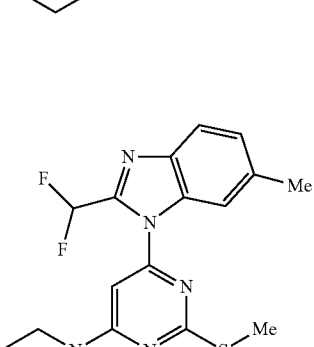 | ESI+: 406 |
| 54 | 3 | 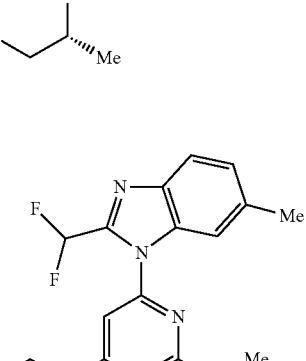 | ESI+: 422 |

TABLE 15-continued
| PEx | PSyn | Str | DAT |
|---|---|---|---|
|  | 10 | 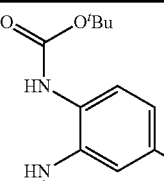 | ESI+: 401/403 |
TABLE 16
| PEx | PSyn | Str | DAT |
|---|---|---|---|
| 56 | 10 | 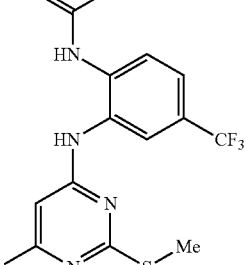 | ESI+: 435 |
| 57 | 11 | 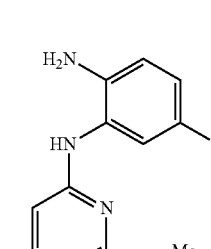 | ESI+: 301 |
| 58 | 5 | 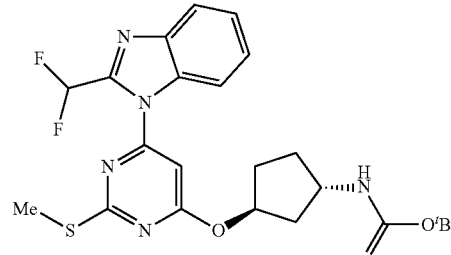 | ESI+: 492 |

TABLE 16-continued
| PEx | PSyn | Str | DAT |
|---|---|---|---|
| 59 | 5 | | ESI+: 492 |
| 60 | 1 | | ESI+: 279 |
| 61 | 12 | | ESI+: 361/363 |
TABLE 17
| PEx | PSyn | Str | DAT |
|---|---|---|---|
| 62 | 11 | | ESI+: 335 |
| 63 | 12 | | ESI+: 395 |
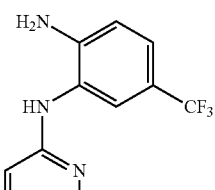
TABLE 17-continued
| PEx | PSyn | Str | DAT |
|---|---|---|---|
| 64 | 1 | | ESI+: 412 |
| 65 | 1 | | ESI+: 446 |
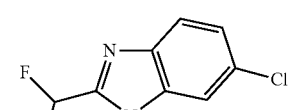

TABLE 17-continued

| PEx | PSyn | Str | DAT |
|---|---|---|---|
| | 3 | 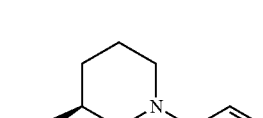 | ESI+: 428 |

TABLE 17-continued

| PEx | PSyn | Str | DAT |
|---|---|---|---|
| 67 | Syn.53 | (structure: 3-amino-1-(pyrazin-2-yl)piperidine, 2HCl) | ESI+: 179 |

TABLE 18

| PEx | PSyn | Str | DAT |
|---|---|---|---|
| 68 | 3 | (structure with difluoromethyl benzimidazole, CF3, morpholine, methylsulfinyl pyrimidine) | ESI+: 462 |
| 69 | 89 | (structure with difluoromethyl benzimidazole, methylthio pyrimidine, cyclohexanediol ether) | ESI+: 407 |
| 70 | 3 | (structure with difluoromethyl benzimidazole, methylsulfinyl pyrimidine, cyclohexanediol ether) | ESI+: 423 |
| 71 | 3 | (structure with difluoromethyl benzimidazole, methylsulfinyl pyrimidine, trans-cyclohexanediol ether) | ESI+: 423 |

TABLE 18-continued
| PEx | PSyn | Str | DAT |
|---|---|---|---|
| 72 | 1 | | ESI+: 516 |
TABLE 19
| PEx | PSyn | Str | DAT |
|---|---|---|---|
| 73 | 3 | | ESI+: 423 |
| 74 | 89 | 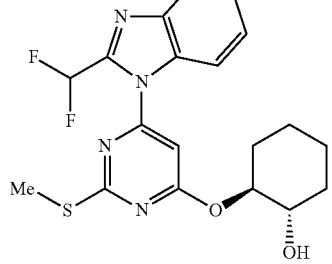 | ESI+: 407 |
| 75 | 89 | 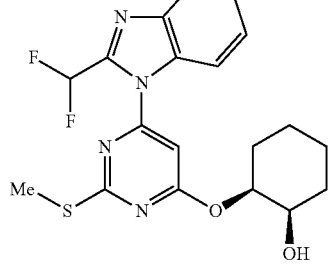 | ESI+: 407 |
TABLE 19-continued
| PEx | PSyn | Str | DAT |
|---|---|---|---|
| 76 | 3 | 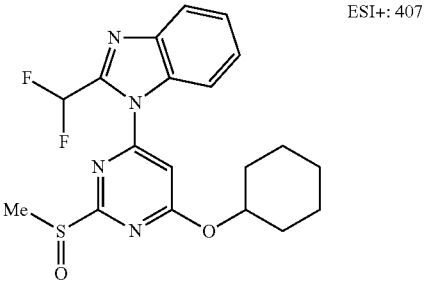 | ESI+: 407 |
| 77 | 5 | | ESI+: 391 |
TABLE 20
| PEx | PSyn | Str | DAT |
|---|---|---|---|
| 78 | 1 | | ESI+: 505 |

TABLE 20-continued

| PEx | PSyn | Str | DAT |
|---|---|---|---|
| 79 | 11 | | ESI+: 458<br>NMR1: 0.82-1.03(4H, m), 1.35-1.60(2H, m), 1.65-1.82(4H, m), 2.36-2.52(2H, m), 2.99-3.03(2H, m), 3.56-3.75(8H, m), 6.23-6.37(1H, m), 7.09-7.17(1H, m), 7.37-7.73(3H, m), 7.75-7.79(1H, m), 7.82-7.88(1H, m) |
| 80 | 80 | | ESI+: 438 |
| 81 | 81 | | ESI+: 354 |
| 82 | 82 | | ESI+: 407 |
| 83 | 83 | | ESI+: 227 |

TABLE 21

| PEx | PSyn | Str | DAT |
|---|---|---|---|
| 84 | 84 | | ESI+: 320(M + Na)+ |
| 85 | 85 | | NMR1: 1.40(9H, s), 4.08-4.19(2H, m), 7.09-7.34(4H, m), 7.37-7.47(1H, m) |

TABLE 21-continued

| PEx | PSyn | Str | DAT |
|---|---|---|---|
| 86-1 | 86 | | ESI+: 371 |
| 86-2 | 86 | | ESI+: 547 |
| 87 | 87 | | ESI+: 690 |

TABLE 22

| PEx | PSyn | Str | DAT |
|---|---|---|---|
| 88 | 88 | | ESI+: 356 |

TABLE 22-continued

| PEx | PSyn | Str | DAT |
|---|---|---|---|
| 89 | 89 | | ESI+: 492 * |
| 90 | 90 | | ESI+: 546 * |
| 91 | 5 | | NMR2: 1.83-1.95 (2H, m), 2.04-2.14 (2H, m), 3.58-3.67 (2H, m), 3.95-4.03 (2H, m), 5.32-5.40 (1H, m) |
| 92 | Syn. 422 | | ESI+: 256 |
| 93 | 80 | | ESI+: 424 |

TABLE 23

| PEx | PSyn | Str | DAT |
|---|---|---|---|
| 94 | 5 | | not found |

TABLE 23-continued

| PEx | PSyn | Str | DAT |
|---|---|---|---|
| 95 | 89 | | ESI+: 506 |
| 96 | 89 | | ESI+: 449 |
| 97 | 89 | | ESI+: 550 |
| 98 | 89 | | ESI+: 407 |
| 99 | 89 | | ESI+: 506 |

TABLE 24
| PEx | PSyn | Str | DAT |
|---|---|---|---|
| 100 | 89 | 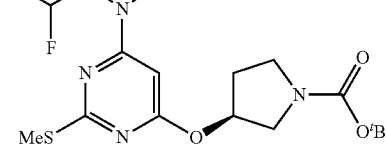 | ESI+: 478 |
| 101 | 89 | 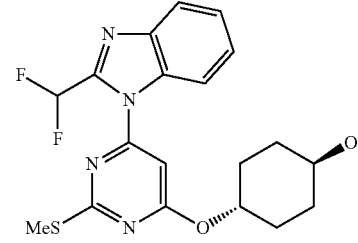 | ESI+: 407 |
| 102 | 9 | 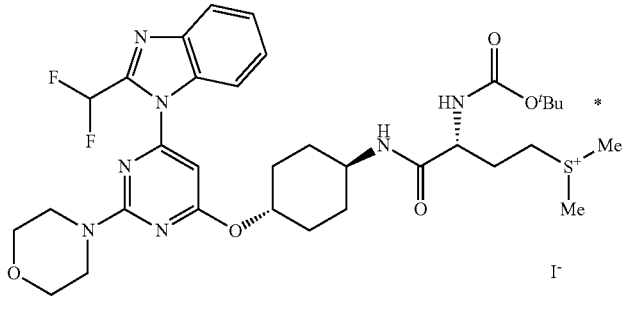 [SMILES: C[S+](C)CC[C@@H](NC(=O)OC(C)(C)C)C(=O)N[C@H]1CC[C@H](Oc2cc(-n3c(C(F)F)nc4ccccc43)nc(N3CCOCC3)n2)CC1 ; [I-]] | ESI+: 690 |
| 103 | 9 | 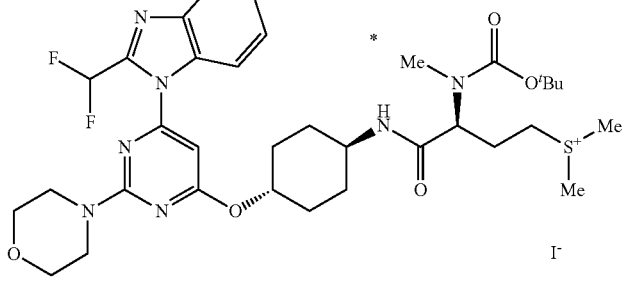 | ESI+: 704 |
| 104 | 3 | 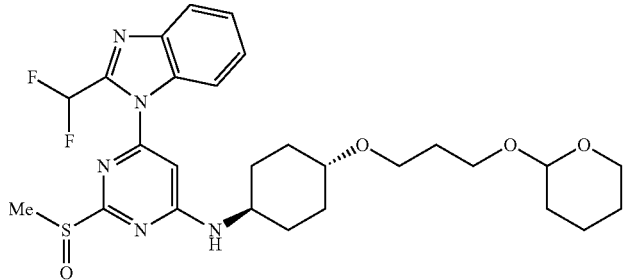 [SMILES: CS(=O)c1nc(N[C@H]2CC[C@H](OCCCOC3CCCCO3)CC2)cc(-n2c(C(F)F)nc3ccccc32)n1] | ESI+: 564 |

TABLE 25

| PEx | PSyn | Str | DAT |
|---|---|---|---|
| 105 | 3 | | ESI+: 550 |
| 106 | 3 | | ESI+: 423 |
| 107 | 3 | | ESI+: 566 |
| 108 | 4 | | ESI+: 454 |
| 109 | 4 | | ESI+: 537 |

TABLE 26
| PEx | PSyn | Str | DAT |
|---|---|---|---|
| 110 | 4 | 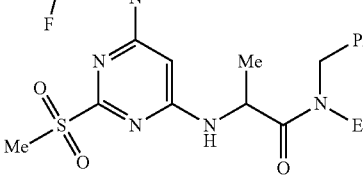 | ESI+: 529 |
| 111 | 4 | 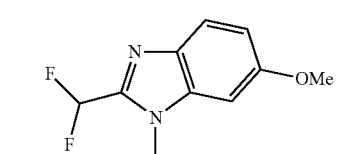 | ESI+: 440 |
| 112 | 4 | 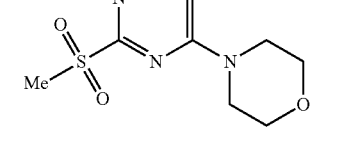 | ESI+: 577 |
| 113 | 4 | 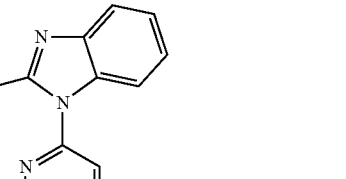 | ESI+: 538 |
| 114 | 4 | 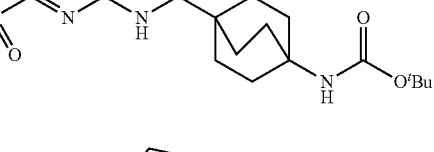 | ESI+: 510 |

TABLE 27
| PEx | PSyn | Str | DAT |
|---|---|---|---|
| 115 | 4 | 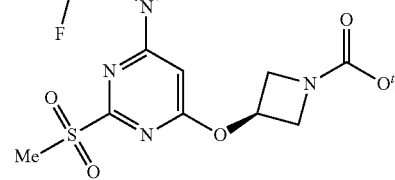 | ESI+: 496 |
| 116 | 87 | 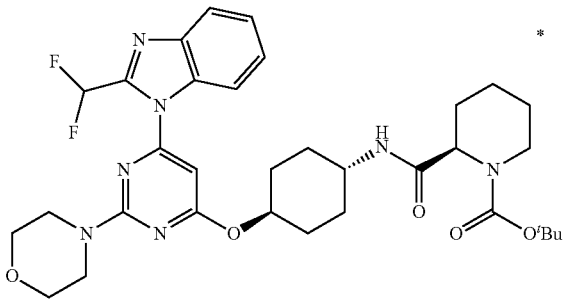 [SMILES: CC(C)(C)OC(=O)N1CCCC[C@@H]1C(=O)N[C@H]1CC[C@H](Oc2cc(-n3c(C(F)F)nc4ccccc43)nc(N3CCOCC3)n2)CC1] | ESI+: 656 * |
| 117 | 87 | 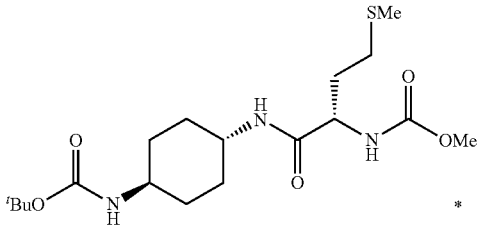 [SMILES: COC(=O)N[C@@H](CCSC)C(=O)N[C@H]1CC[C@H](NC(=O)OC(C)(C)C)CC1] | ESI+: 404 * |
| 118 | 87 | 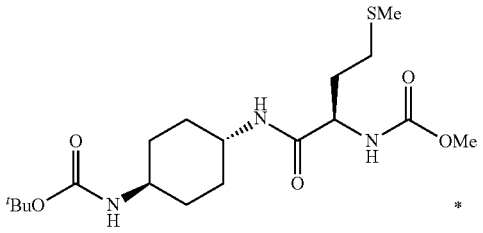 [SMILES: COC(=O)N[C@H](CCSC)C(=O)N[C@H]1CC[C@H](NC(=O)OC(C)(C)C)CC1] | ESI+: 404 * |
| 119 | 1 | 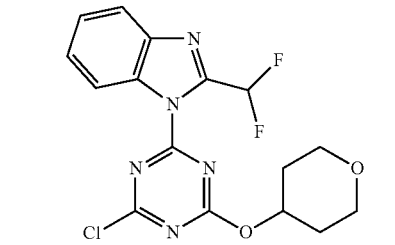 [SMILES: FC(F)c1nc2ccccc2n1-c1nc(Cl)nc(OC2CCOCC2)n1] | ESI+: 382 |

TABLE 28

| PEx | PSyn | Str | DAT |
|---|---|---|---|
| 120 | 1 | 2-(difluoromethyl)benzimidazol-1-yl / 4-chloro-6-morpholino-1,3,5-triazine | ESI+: 367 |
| 121 | 1 | 1-[2-(difluoromethyl)benzimidazol-1-yl]-4-chloro-2-morpholinopyrimidine | NMRI: 3.66-3.79 (8H, m), 7.19 (1H, s), 7.40-7.69 (3H, m), 7.80-7.85 (1H, d), 7.87-7.92 (1H, d) |
| 122 | 1 | 2,4-dichloro-6-morpholinopyrimidine | ESI+: 234 |

TABLE 28-continued

| PEx | PSyn | Str | DAT |
|---|---|---|---|
| 123 | 1 | 2,4-dichloro-6-morpholino-1,3,5-triazine | ESI+: 236 |
| 124 | 1 | 2-(difluoromethyl)benzimidazol-1-yl / 4-chloro-6-morpholino-1,3,5-triazine isomer | ESI+: 366 |

TABLE 29

| PEx | PSyn | Str | DAT |
|---|---|---|---|
| 125 | 1 | triazine with difluoromethylbenzimidazole, morpholino, and 2-(methylthio)ethylamino substituents | ESI+: 422 |
| 126 | 1 | pyrimidine with difluoromethylbenzimidazole, methylthio, and cyclohexyl-NH-Boc carbamate substituents | ESI+: 527(M + Na)+ |

TABLE 29-continued
| PEx | PSyn | Str | DAT |
|---|---|---|---|
| 127 | 1 | 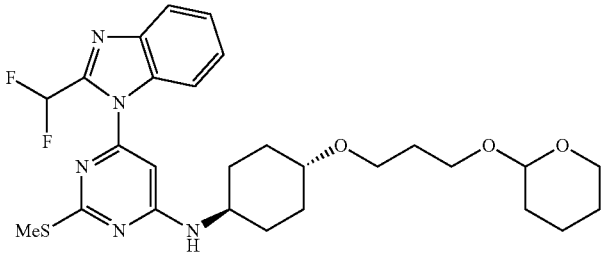 [SMILES: CSc1nc(N[C@H]2CC[C@H](OCCCOC3CCCCO3)CC2)cc(-n2c(C(F)F)nc3ccccc32)n1] | ESI+: 548 |
| 128 | 1 | 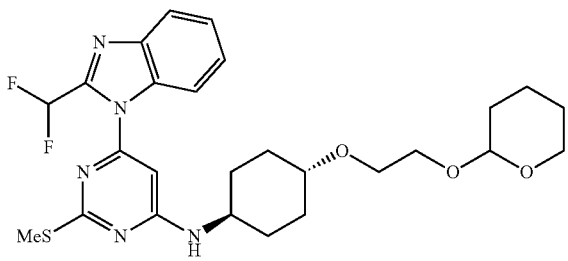 [SMILES: CSc1nc(N[C@H]2CC[C@H](OCCOC3CCCCO3)CC2)cc(-n2c(C(F)F)nc3ccccc32)n1] | ESI+: 534 |
| 129 | 1 | 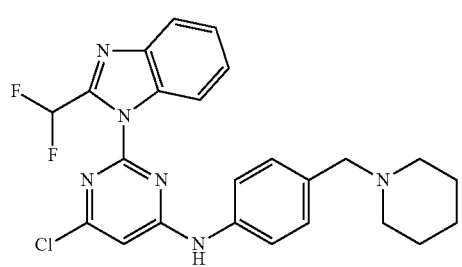 [SMILES: FC(F)c1nc2ccccc2n1-c1nc(Cl)cc(Nc2ccc(CN3CCCCC3)cc2)n1] | ESI+: 469 |
TABLE 30
| PEx | PSyn | Str | DAT |
|---|---|---|---|
| 130 | 1 | 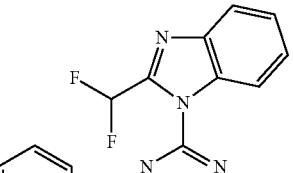 | not found |
| 131 | 1 | 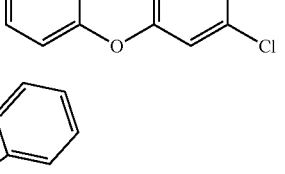 | ESI+: 462 |

TABLE 30-continued

| PEx | PSyn | Str | DAT |
|---|---|---|---|
| 132 | 1 | (structure) | ESI+: 476 |
| 133 | 1 | (structure) | ESI+: 476 |
| 134 | 1 | (structure) | Not found |

TABLE 31

| PEx | PSyn | Str | DAT |
|---|---|---|---|
| 135 | 1 | (structure) | ESI+: 490 |
| 136 | 1 | (structure) | ESI+: 516 |

TABLE 31-continued

| PEx | PSyn | Str | DAT |
|---|---|---|---|
| 137 | 1 | (structure) | ESI+: 422 |
| 138 | 1 | (structure) | ESI+: 505 |
| 139 | 1 | (structure) | ESI+: 505 |

TABLE 32

| PEx | PSyn | Str | DAT |
|---|---|---|---|
| 140 | 1 | (structure) | ESI+: 497 |

TABLE 32-continued

| PEx | PSyn | Str | DAT |
|-----|------|-----|-----|
| 141 | 1 | | ESI+: 544 |
| 142 | 1 | | ESI+: 545 |
| 143 | 1 | | ESI+: 517 |
| 144 | 1 | | ESI+: 477 |

TABLE 33

| PEx | PSyn | Str | DAT |
|---|---|---|---|
| 145 | 1 | | ESI+: 491 |
| 146 | 1 | | ESI+: 477 |
| 147 | 90 | | ESI+: 546 |
| 148 | Syn. 87 | | ESI+: 706 |
| 149 | 82 | | ESI+: 393 |

TABLE 34

| PEx | PSyn | Str | DAT |
|---|---|---|---|
| 150 | 83 | (structure: trans-4-aminocyclohexyl 2-(pyrrolidin-1-yl)ethyl ether) | ESI+: 213 |
| 151 | 83 | (structure: trans-4-aminocyclohexyl 3-(tetrahydropyran-2-yloxy)propyl ether) | ESI+: 258 |
| 152 | 83 | (structure: trans-4-aminocyclohexyl 2-(tetrahydropyran-2-yloxy)ethyl ether) | ESI+: 244 |
| 153 | Syn53 | (structure: trans-4-aminocyclohexyl propenol, HCl) | ESI+: 156 |
| 154 | Syn53 | (structure: methyl carbamate pyrrolidinone cyclohexylamine, HCl) * | ESI+: 256 |
| 155 | 81 | (structure: N,N-dibenzyl trans-4-aminocyclohexyl 2-hydroxyethyl ether) | ESI+: 340 |
| 156 | Syn. 54 | (structure: difluoromethyl benzimidazole pyrimidine morpholine cyclohexyl pyrrolidinone amine) * | ESI+: 528 |
| 157 | Syn. 54 | (structure: difluoromethyl benzimidazole pyrimidine morpholine cyclohexyl pyrrolidinone amine) * | ESI+: 528 |

TABLE 35

| PEx | PSyn | Str | DAT |
|---|---|---|---|
| 158 | Syn. 54 | | ESI+: 445 |
| 159 | 2 | | ESI+: 567[M + Na] |
| 160 | 5 | | ESI+: 528[M + Na] |
| 161 | Syn. 53 | | ESI+: 256 |
| 162 | 90 | | ESI+: 546 |

TABLE 36
| PEx | PSyn | Str | DAT |
|---|---|---|---|
| 163 | 5 | 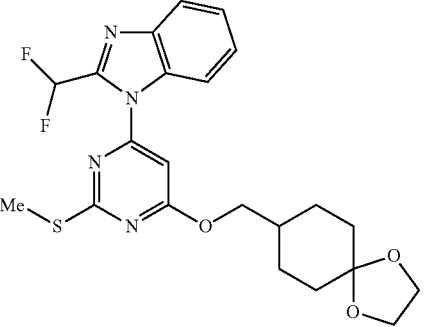 [SMILES: CSc1nc(OCC2CCC3(CC2)OCCO3)cc(-n2c(C(F)F)nc3ccccc32)n1] | ESI+: 463 |
| 164 | 88 | 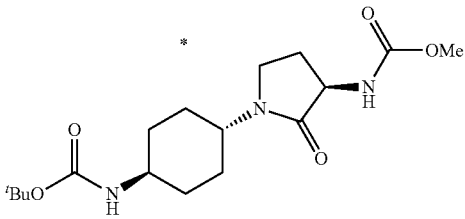 [SMILES: COC(=O)N[C@@H]1CCN([C@H]2CC[C@H](NC(=O)OC(C)(C)C)CC2)C1=O] | ESI+: 356 |
| 165 | 2 | 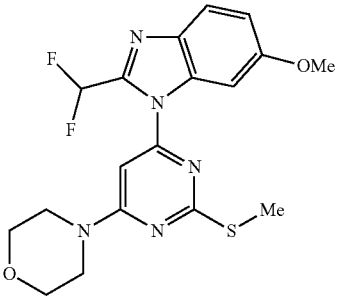 [SMILES: COc1ccc2nc(C(F)F)n(-c3cc(N4CCOCC4)nc(SC)n3)c2c1] | ESI+: 408 |
| 166 | 12 | 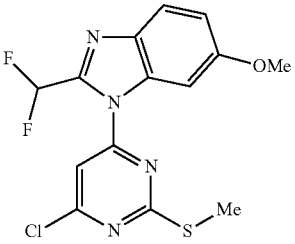 [SMILES: COc1ccc2nc(C(F)F)n(-c3cc(Cl)nc(SC)n3)c2c1] | ESI+: 357 |
| 167 | 11 | 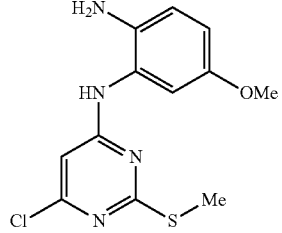 [SMILES: COc1ccc(N)c(Nc2cc(Cl)nc(SC)n2)c1] | ESI+: 297 |

TABLE 37
| PEx | PSyn | Str | DAT |
|---|---|---|---|
| 168 | 10 | 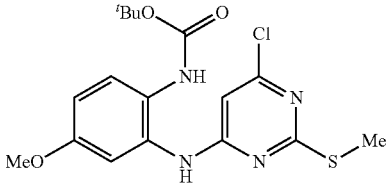 | ESI+: 397 |
| 169 | 89 | 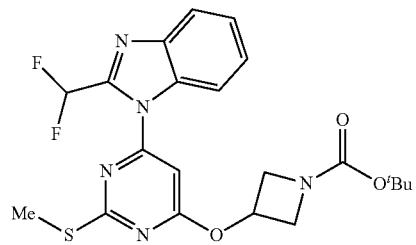 [SMILES: CSc1nc(OC2CN(C(=O)OC(C)(C)C)C2)cc(-n2c(C(F)F)nc3ccccc32)n1] | ESI+: 464 |
| 170 | Syn. 54 | 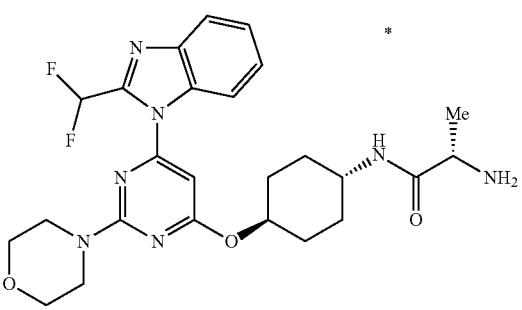 [SMILES: C[C@H](N)C(=O)N[C@H]1CC[C@H](Oc2cc(-n3c(C(F)F)nc4ccccc43)nc(N3CCOCC3)n2)CC1] | ESI+: 516 |
| 171 | 87 | 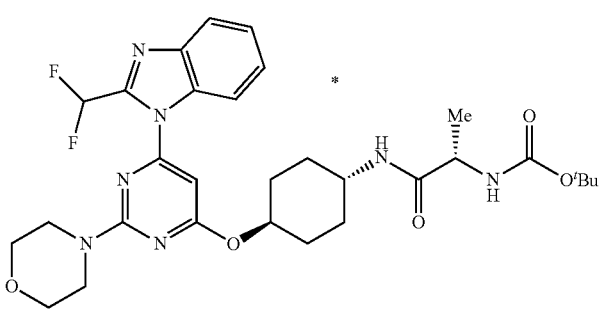 [SMILES: C[C@H](NC(=O)OC(C)(C)C)C(=O)N[C@H]1CC[C@H](Oc2cc(-n3c(C(F)F)nc4ccccc43)nc(N3CCOCC3)n2)CC1] | ESI+: 616 |
| 172 | Syn. 1 | 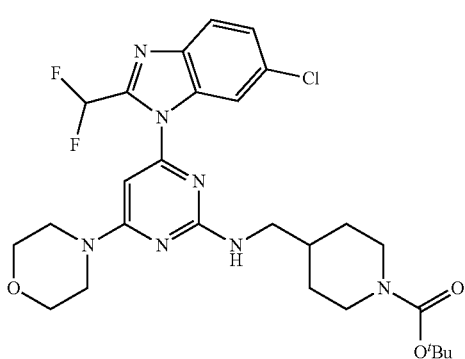 [SMILES: CC(C)(C)OC(=O)N1CCC(CNc2nc(N3CCOCC3)cc(-n3c(C(F)F)nc4ccc(Cl)cc43)n2)CC1] | ESI+: 578 |

TABLE 38
| PEx | PSyn | Str | DAT |
|---|---|---|---|
| 173 | Syn. 54 | 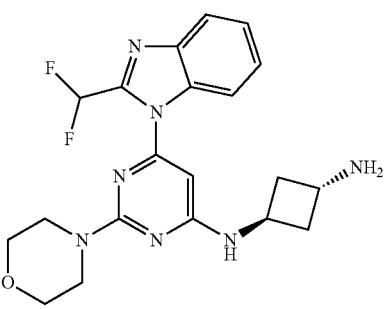 [SMILES: N[C@H]1C[C@H](Nc2cc(-n3c(C(F)F)nc4ccccc43)nc(N3CCOCC3)n2)C1] | ESI+: 416 |
| 174 | Syn. 92 | 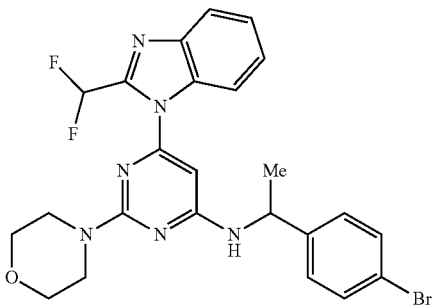 [SMILES: CC(Nc1cc(-n2c(C(F)F)nc3ccccc32)nc(N2CCOCC2)n1)c1ccc(Br)cc1] | ESI+: 529/531 |
| 175 | Syn. 92 | 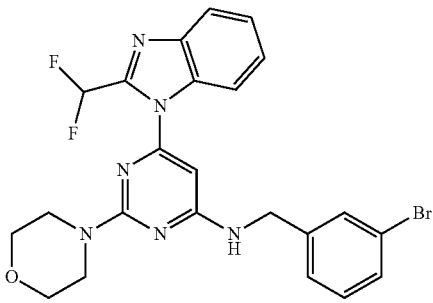 [SMILES: FC(F)c1nc2ccccc2n1-c1cc(NCc2cccc(Br)c2)nc(N2CCOCC2)n1] | ESI+: 515/517 |
| 176 | 4 | 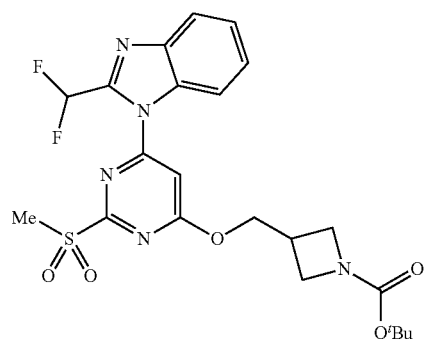 [SMILES: CC(C)(C)OC(=O)N1CC(COc2cc(-n3c(C(F)F)nc4ccccc43)nc(S(C)(=O)=O)n2)C1] | ESI+: 510 |
| 177 | 89 | 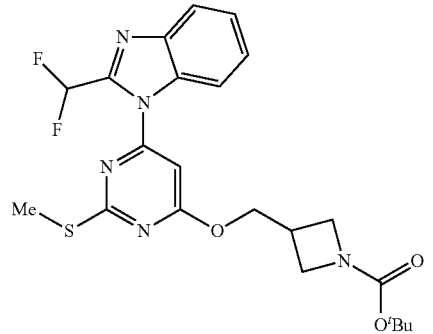 [SMILES: CSc1nc(OCC2CN(C(=O)OC(C)(C)C)C2)cc(-n2c(C(F)F)nc3ccccc32)n1] | ESI+: 478 |

TABLE 39

| PEx | PSyn | Str | DAT |
|---|---|---|---|
| 178 | Syn. 54 | | ESI+: 459 |
| 179 | Syn. 92 | | not found |
| 180 | Syn. 54 | | ESI+: 542 |
| 181 | Syn. 241 | | ESI+: 565/567 |
| 182 | 2 | | ESI+: 527 (M + Na)+ |

TABLE 40

| PEx | PSyn | Str | DAT |
|-----|------|-----|-----|
| 183 | 183 | | ESI+: 600 |
| 184 | Syn. 92 | | ESI+: 544 |
| 185 | 185 | | ESI+: 347 |
| 186 | Syn. 92 | | ESI+: 488 |
| 187 | 89 | | ESI+: 449 |

TABLE 41
| Ex | Str |
|---|---|
| 1 | 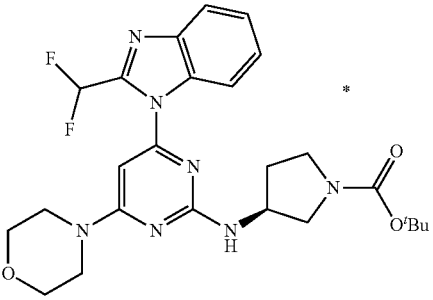 [SMILES: CC(C)(C)OC(=O)N1CC[C@H](Nc2nc(N3CCOCC3)cc(-n3c(C(F)F)nc4ccccc43)n2)C1] |
| 2 | 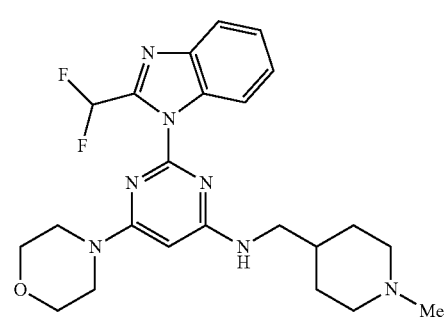 [SMILES: CN1CCC(CNc2cc(N3CCOCC3)nc(-n3c(C(F)F)nc4ccccc43)n2)CC1] |
| 3 | 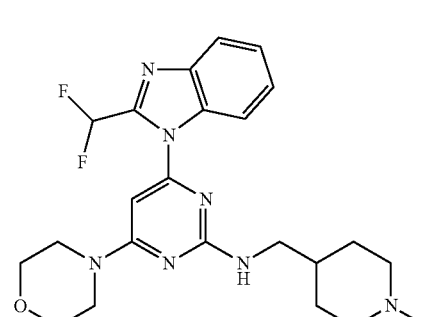 |
| 4 | 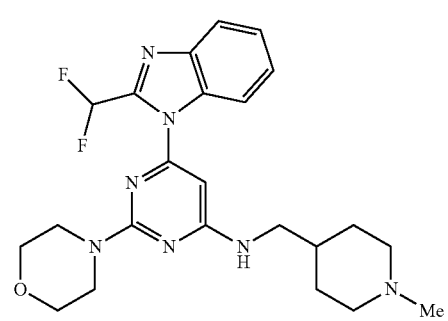 [SMILES: CN1CCC(CNc2cc(-n3c(C(F)F)nc4ccccc43)nc(N3CCOCC3)n2)CC1] |
TABLE 42
| Ex | Str |
|---|---|
| 5 | 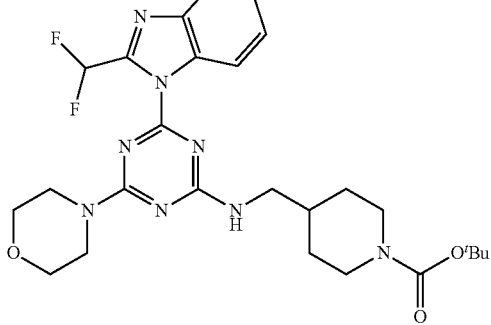 |
| 6 | 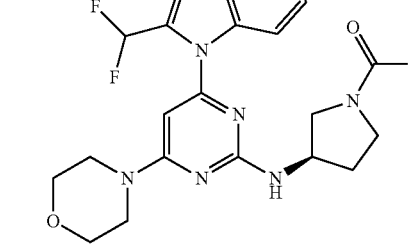 |
| 7 | 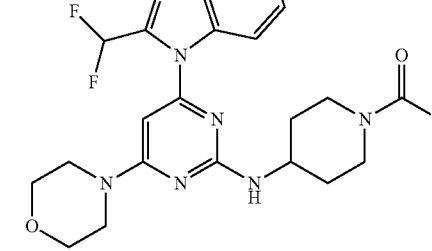 |
| 8 | 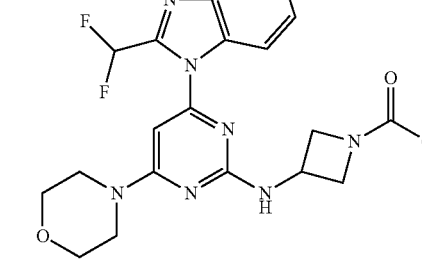 |
| 9 | 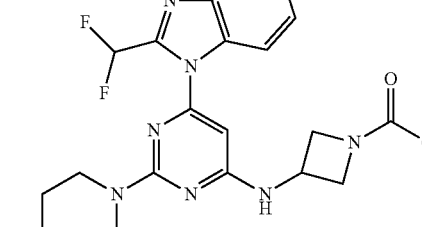 |

TABLE 43
| Ex | Str |
|---|---|
| 10 | 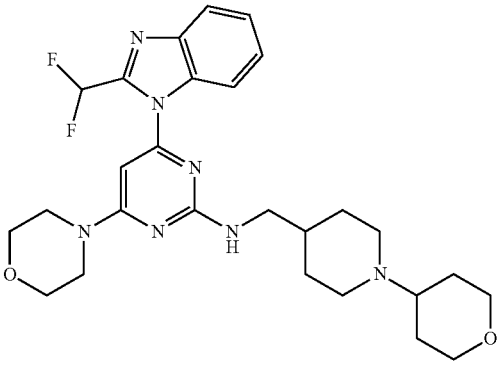 [SMILES: FC(F)c1nc2ccccc2n1-c1cc(N2CCOCC2)nc(NCC2CCN(C3CCOCC3)CC2)n1] |
| 11 | 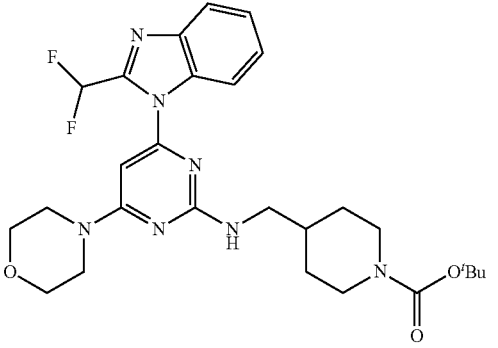 [SMILES: CC(C)(C)OC(=O)N1CCC(CNc2nc(N3CCOCC3)cc(-n3c(C(F)F)nc4ccccc43)n2)CC1] |
| 12 | 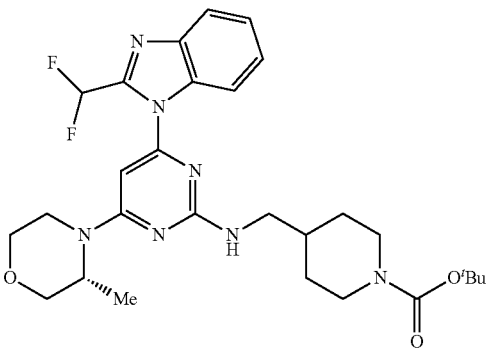 [SMILES: C[C@@H]1COCCN1c1cc(-n2c(C(F)F)nc3ccccc32)nc(NCC2CCN(C(=O)OC(C)(C)C)CC2)n1] |
| 13 | 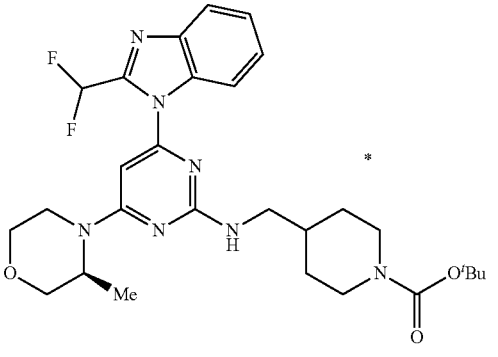 [SMILES: C[C@H]1COCCN1c1cc(-n2c(C(F)F)nc3ccccc32)nc(NCC2CCN(C(=O)OC(C)(C)C)CC2)n1] |
TABLE 44
| Ex | Str |
|---|---|
| 14 | 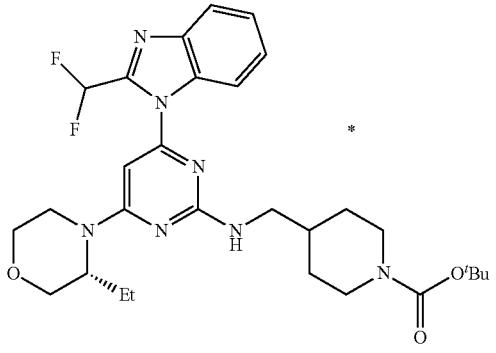 [SMILES: CC[C@@H]1COCCN1c1cc(-n2c(C(F)F)nc3ccccc32)nc(NCC2CCN(C(=O)OC(C)(C)C)CC2)n1] |
| 15 | 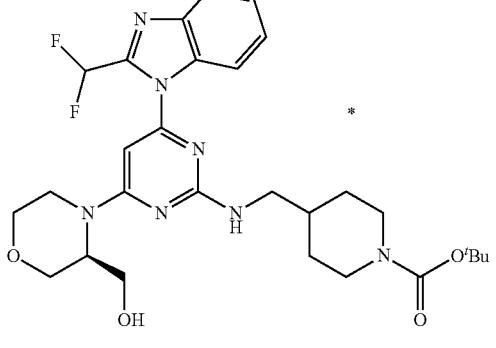 |
| 16 | 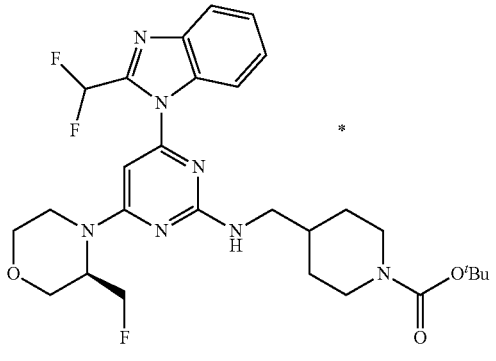 [SMILES: CC(C)(C)OC(=O)N1CCC(CNc2nc(N3CCOC[C@@H]3CF)cc(-n3c(C(F)F)nc4ccccc43)n2)CC1] |
| 17 | 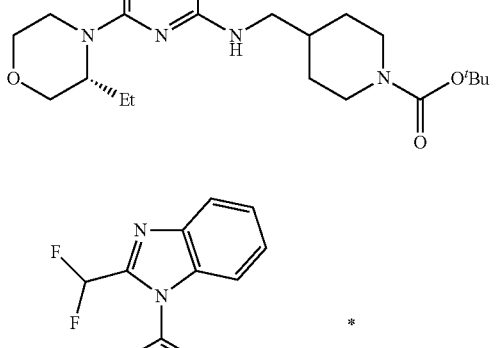 |

TABLE 45
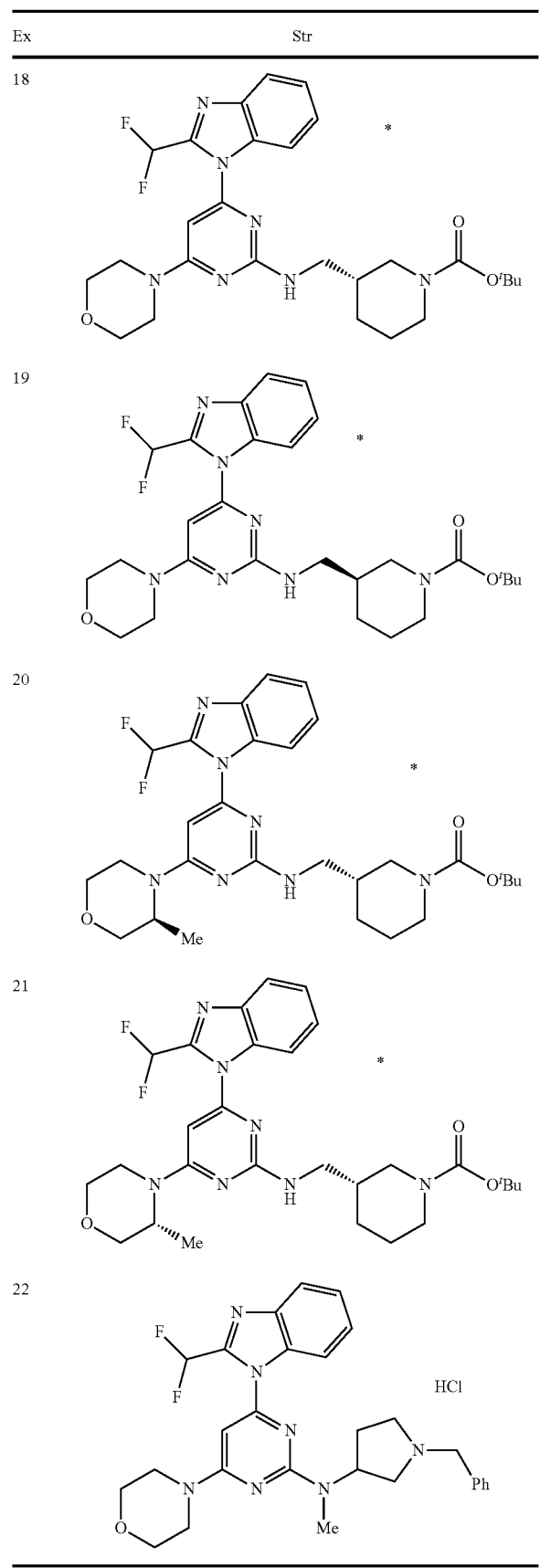
TABLE 46
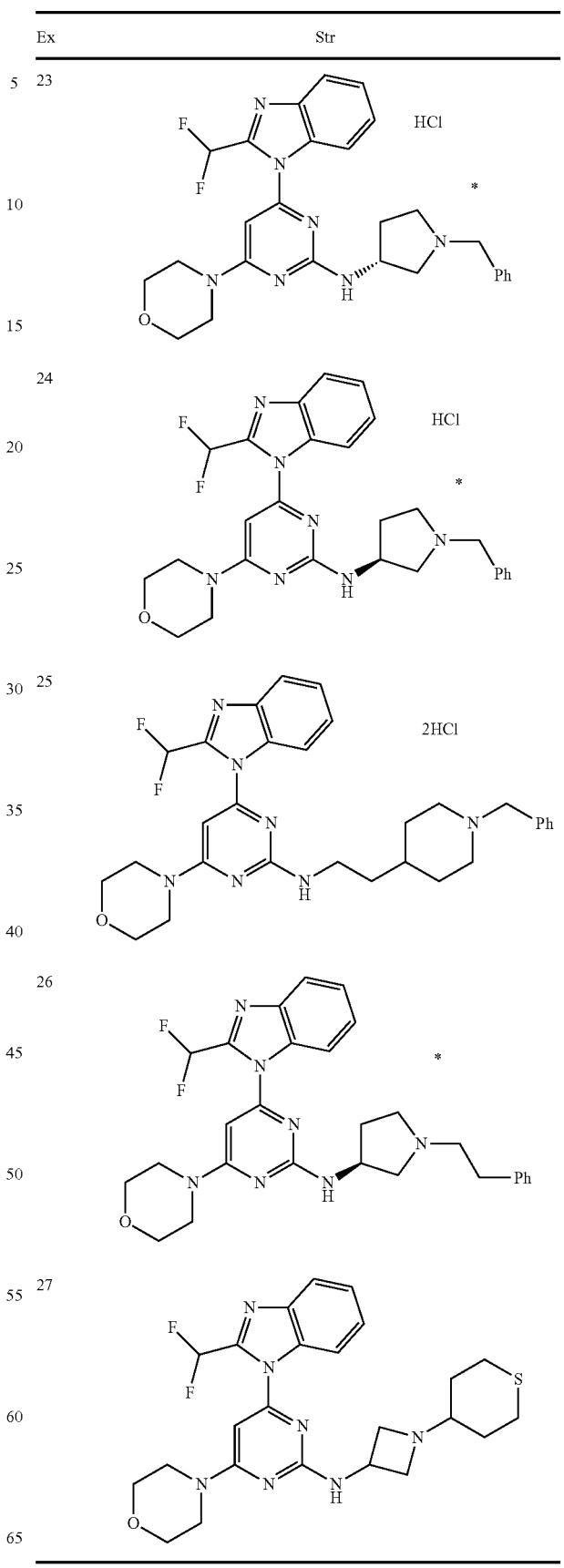

TABLE 47
| Ex | Str |
|---|---|
| 28 | |
| 29 | |
| 30 | |
| 31 | |
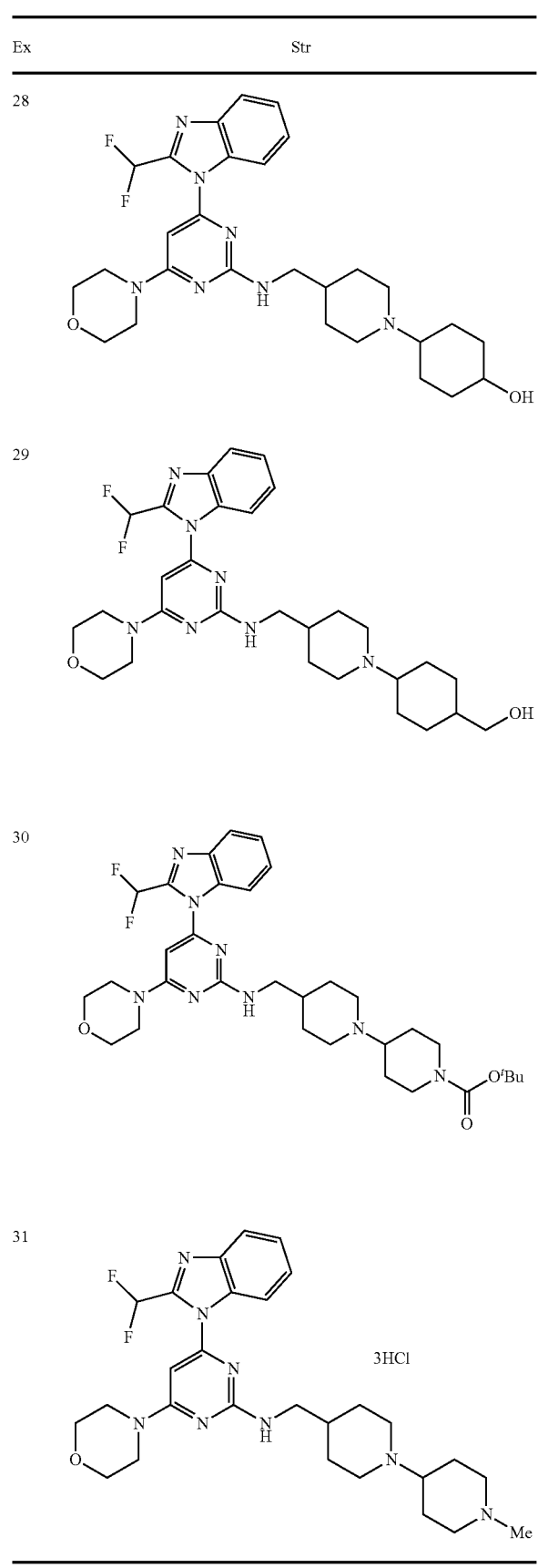
TABLE 48
| Ex | Str |
|---|---|
| 32 | |
| 33 | |
| 34 | |
| 35 | |
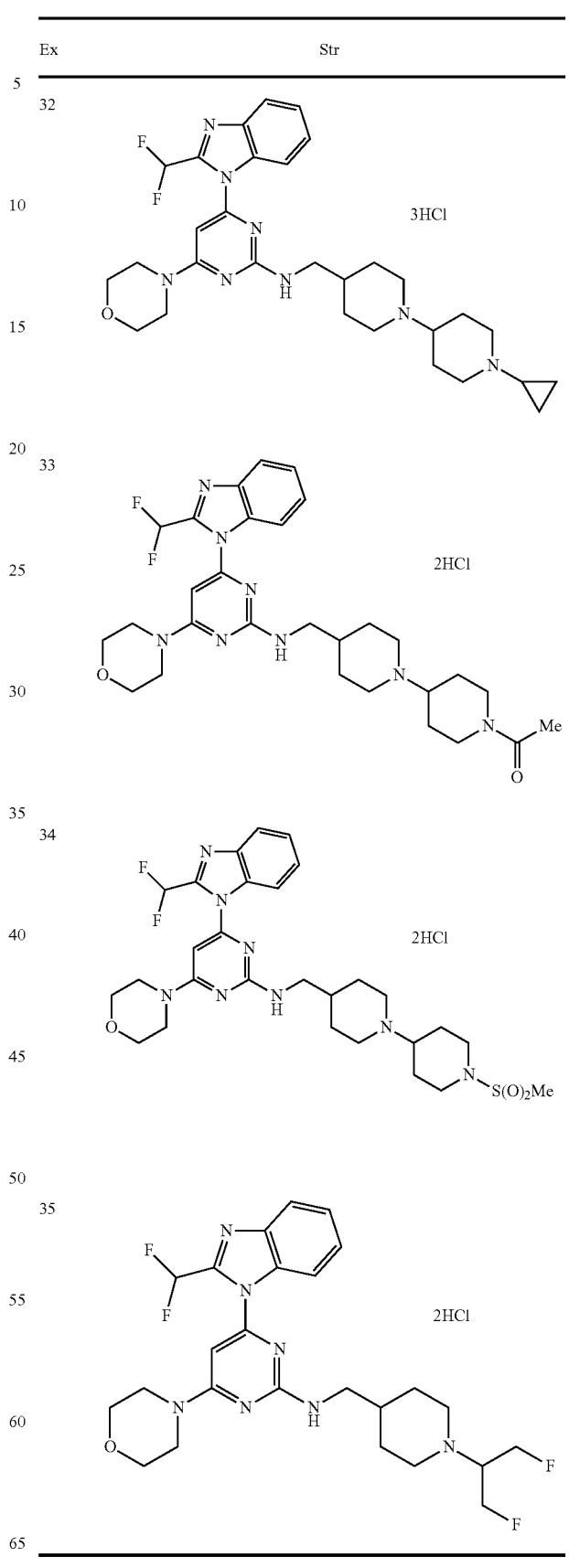

TABLE 49
| Ex | Str |
|---|---|
| 36 | 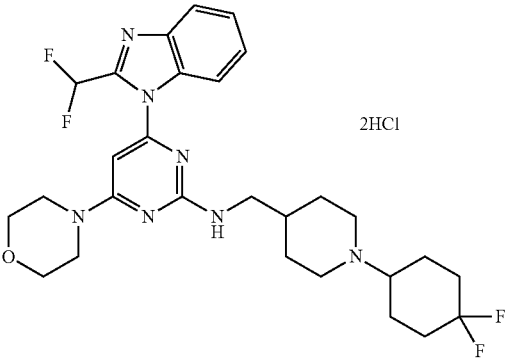 [SMILES: FC(F)c1nc2ccccc2n1-c1cc(N2CCOCC2)nc(NCC2CCN(C3CCC(F)(F)CC3)CC2)n1] 2HCl |
| 37 | 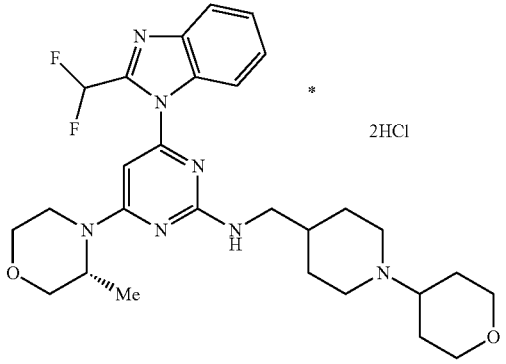 [SMILES: C[C@@H]1COCCN1c1cc(-n2c(C(F)F)nc3ccccc32)nc(NCC2CCN(C3CCOCC3)CC2)n1] * 2HCl |
| 38 | 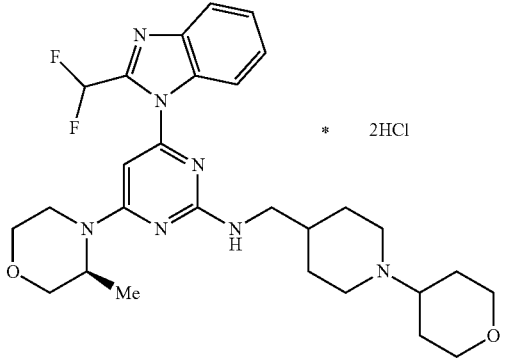 [SMILES: C[C@H]1COCCN1c1cc(-n2c(C(F)F)nc3ccccc32)nc(NCC2CCN(C3CCOCC3)CC2)n1] * 2HCl |
| 39 | 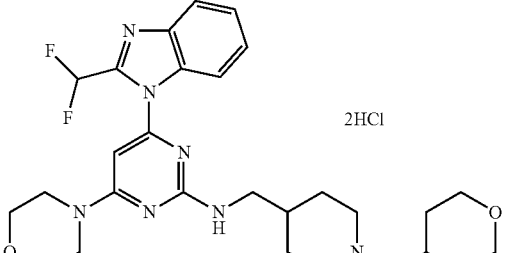 2HCl |
TABLE 50
| Ex | Str |
|---|---|
| 40 | 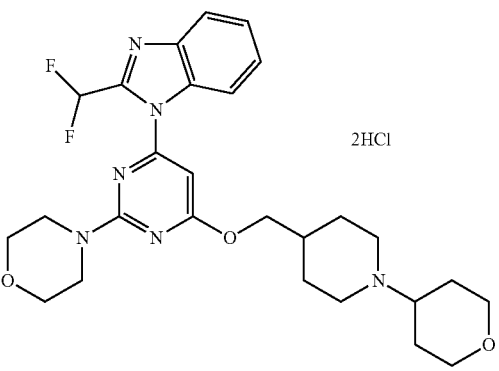 [SMILES: FC(F)c1nc2ccccc2n1-c1cc(OCC2CCN(C3CCOCC3)CC2)nc(N2CCOCC2)n1] 2HCl |
| 41 | 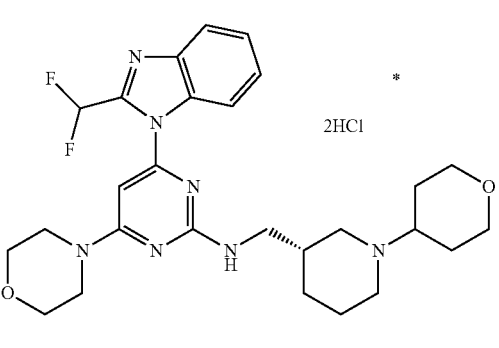 [SMILES: FC(F)c1nc2ccccc2n1-c1cc(N2CCOCC2)nc(NC[C@H]2CCCN(C3CCOCC3)C2)n1] * 2HCl |
| 42 | 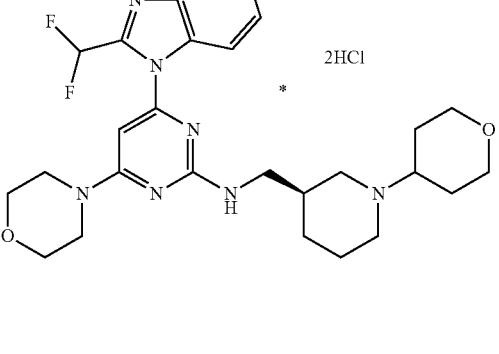 * 2HCl |
| 43-1 | 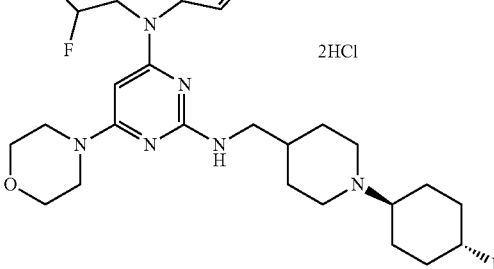 2HCl |

TABLE 51
| Ex | Str |
|---|---|
| 43-2 | 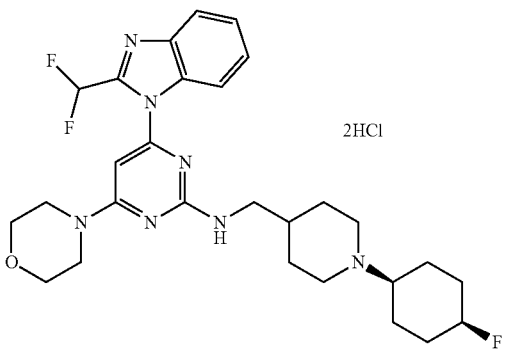 [SMILES: FC(F)c1nc2ccccc2n1-c1cc(N2CCOCC2)nc(NCC2CCN([C@H]3CC[C@@H](F)CC3)CC2)n1] 2HCl |
| 44 | 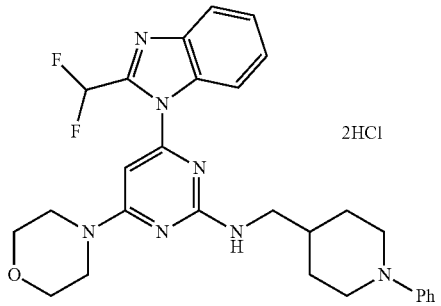 [SMILES: FC(F)c1nc2ccccc2n1-c1cc(N2CCOCC2)nc(NCC2CCN(c3ccccc3)CC2)n1] 2HCl |
| 45 | 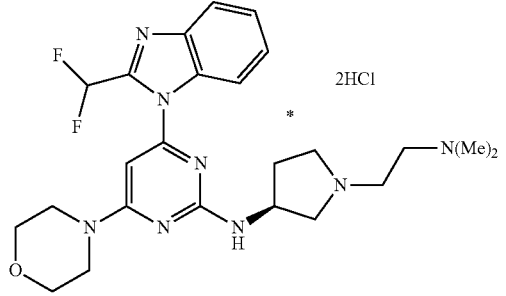 2HCl |
| 46 | 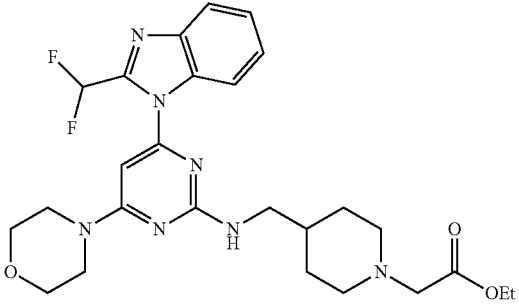 [SMILES: CCOC(=O)CN1CCC(CNc2nc(N3CCOCC3)cc(-n3c(C(F)F)nc4ccccc43)n2)CC1] 2HCl |
TABLE 52
| Ex | Str |
|---|---|
| 47 | 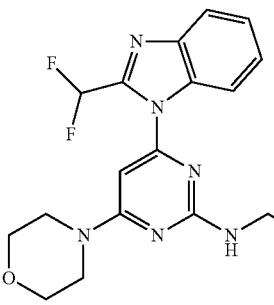 2HCl |
| 48 | 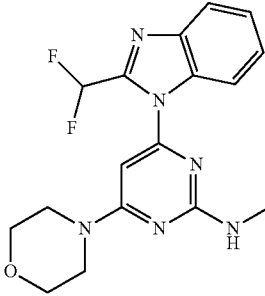 2HCl |
| 49 | 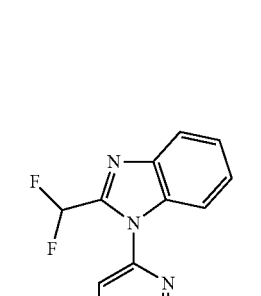 2HCl |
| 50 | 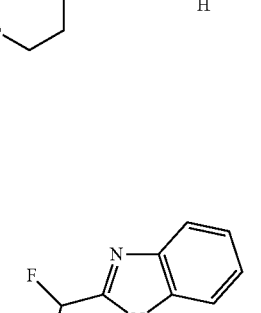 2HCl |

TABLE 53
| Ex | Str |
|---|---|
| 51 | |
| 52 | |
| 53 | |
| 54 | |
| 55 | |
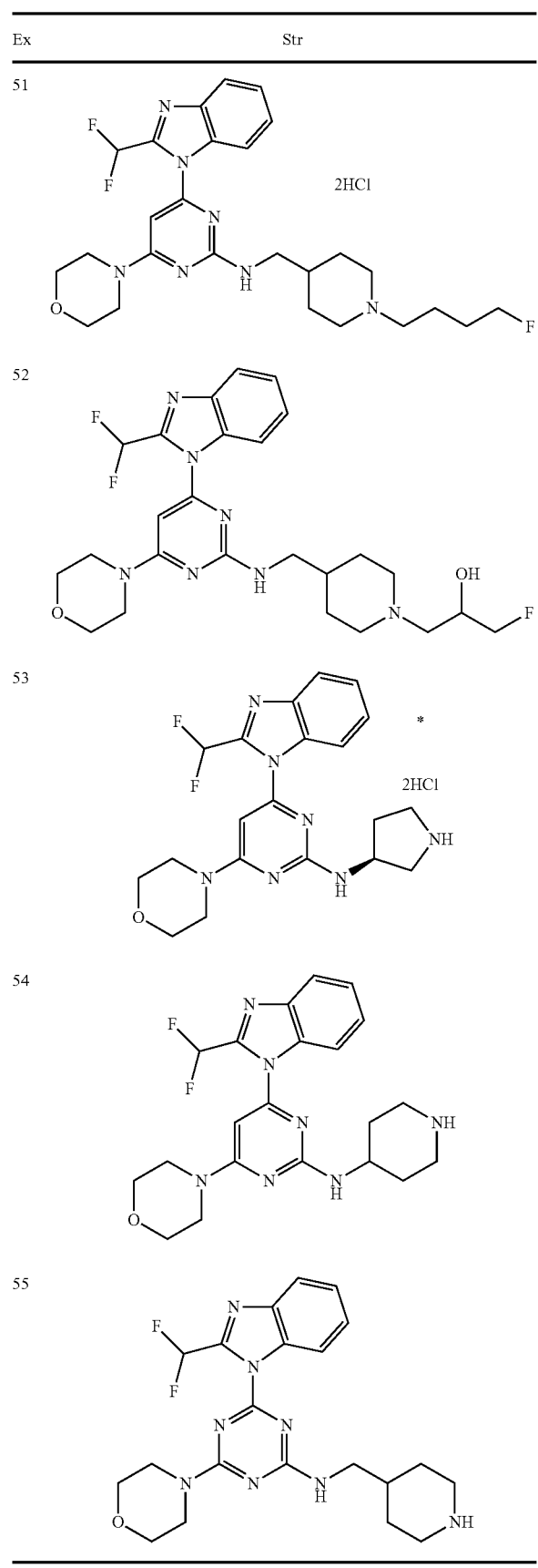
TABLE 54
| Ex | Str |
|---|---|
| 56 | |
| 57 | |
| 58 | |
| 59 | |
| 60 | |
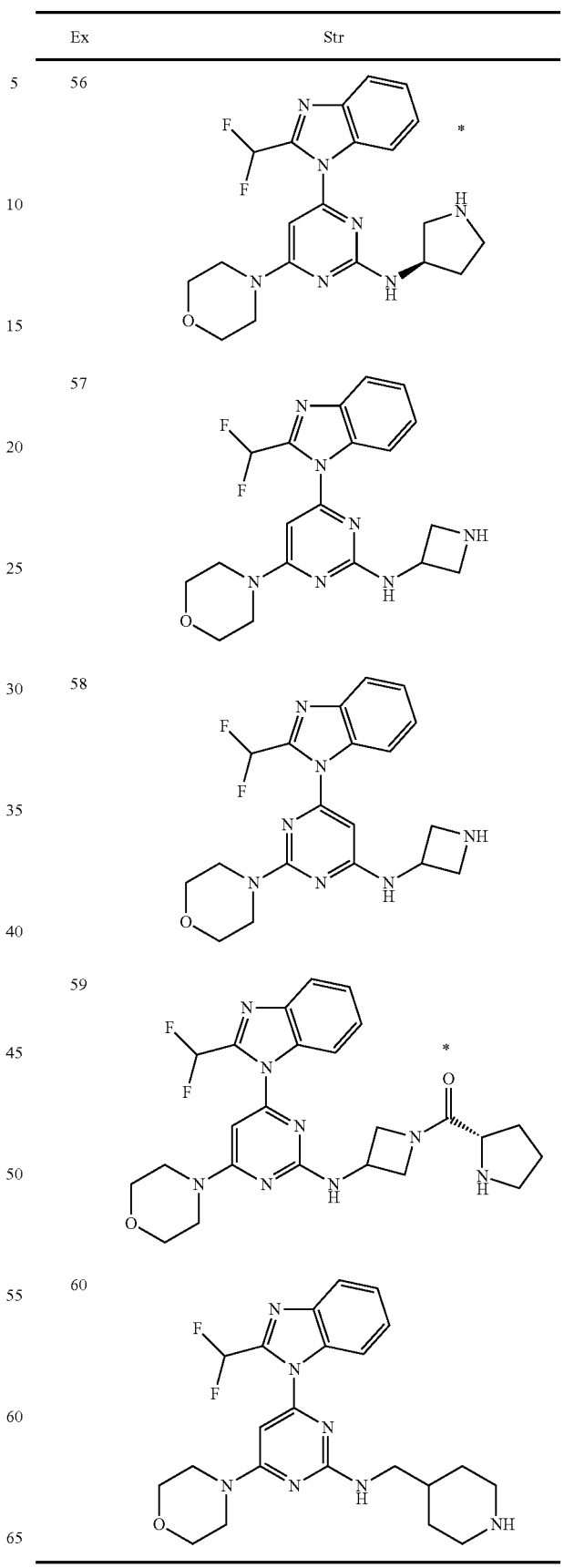

TABLE 55

| Ex | Str |
|---|---|
| 61 | (structure) |
| 62 | (structure) |
| 63 | (structure) |
| 64 | (structure) |
| 65 | (structure) |

TABLE 56

| Ex | Str |
|---|---|
| 66 | (structure) |
| 67 | (structure) |
| 68 | (structure) |
| 69 | (structure) |
| 70 | (structure) |

TABLE 57

| Ex | Str |
|---|---|
| 71 | (structure) |
| 72 | (structure) 2HCl |
| 73 | (structure) 2HCl |
| 74 | (structure) |

TABLE 58

| Ex | Str |
|---|---|
| 75 | (structure) 2HCl |
| 76 | (structure) 2HCl |
| 77 | (structure) 2HCl |
| 78 | (structure) 2HCl |

TABLE 59
| Ex | Str |
|---|---|
| 79 | 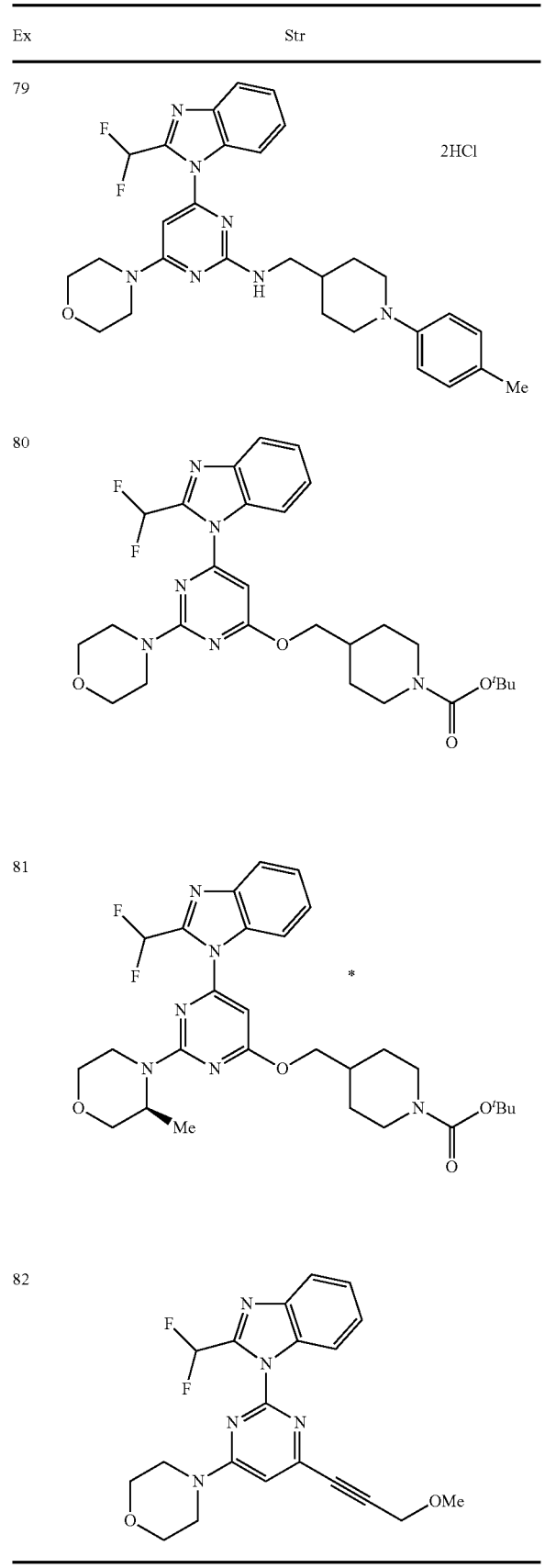 |
| 80 | |
| 81 | |
| 82 | |
TABLE 60
| Ex | Str |
|---|---|
| 83 | 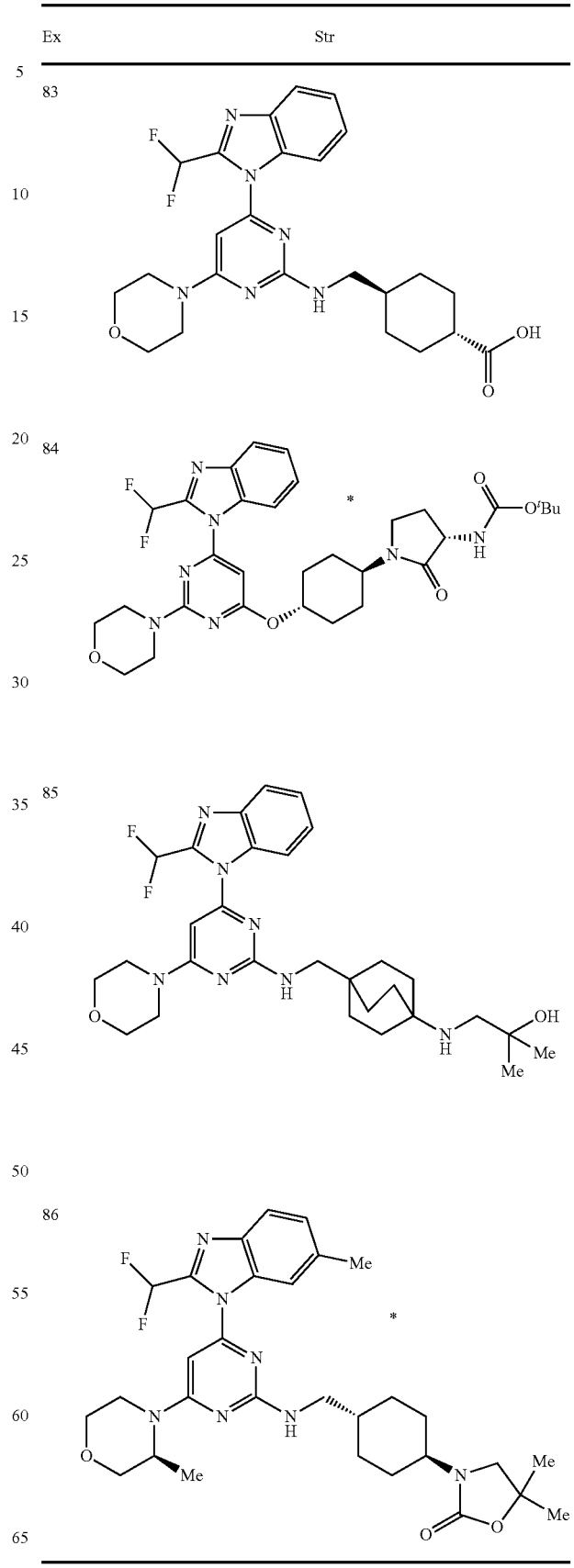 |
| 84 | |
| 85 | |
| 86 | |

TABLE 61
| Ex | Str |
|---|---|
| 87 | 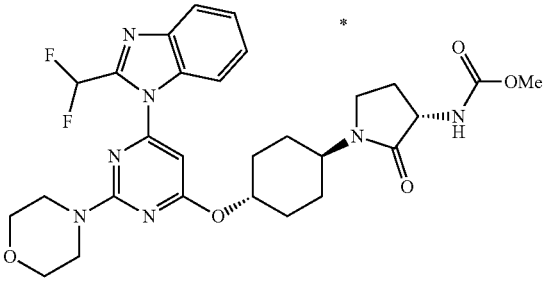 [SMILES: COC(=O)N[C@H]1CCN([C@H]2CC[C@H](Oc3cc(-n4c(C(F)F)nc5ccccc54)nc(N4CCOCC4)n3)CC2)C1=O] |
| 88 | 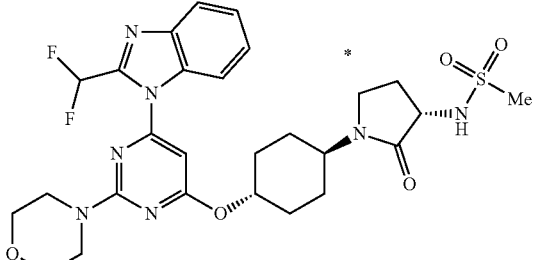 |
| 89 | 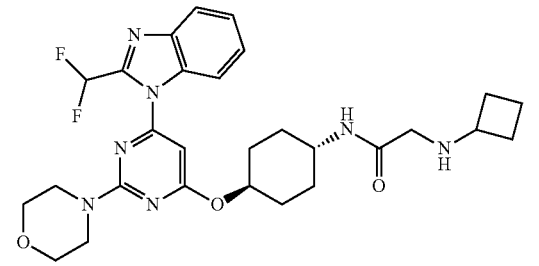 [SMILES: O=C(CNC1CCC1)N[C@H]1CC[C@H](Oc2cc(-n3c(C(F)F)nc4ccccc43)nc(N3CCOCC3)n2)CC1] |
| 90 | 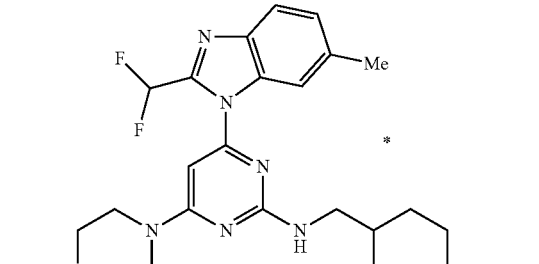 |
| 91 | 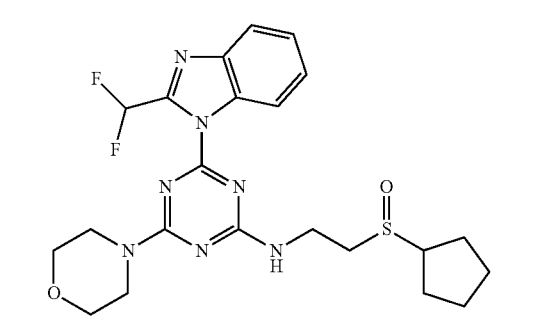 [SMILES: O=S(CCNc1nc(N2CCOCC2)nc(-n2c(C(F)F)nc3ccccc32)n1)C1CCCC1] |
TABLE 62
| Ex | Str |
|---|---|
| 92 | 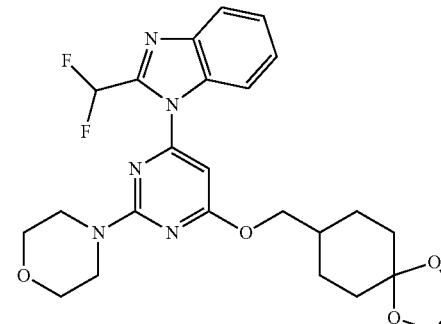 |
| 93 | 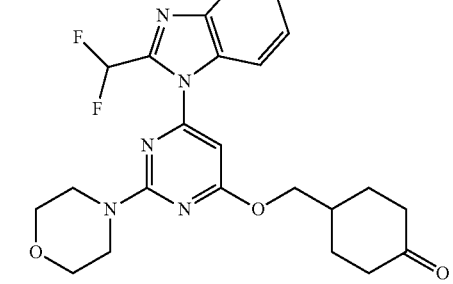 |
| 94 | 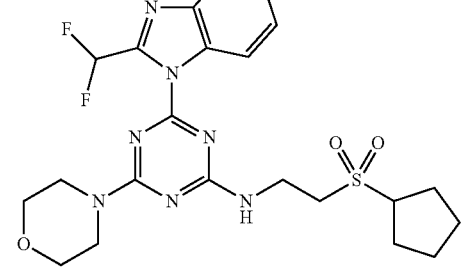 |
| 95 | 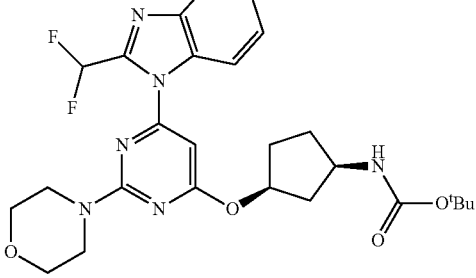 |
| 96 | 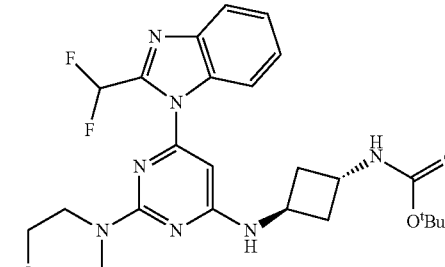 |

TABLE 63
| Ex | Str |
|----|-----|
| 97 | 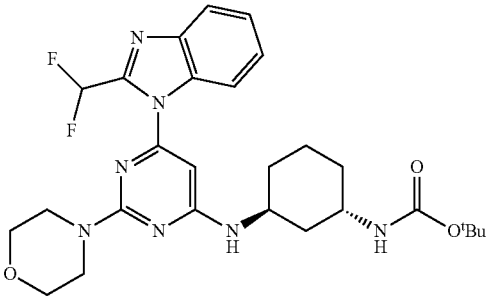 [SMILES: CC(C)(C)OC(=O)N[C@H]1CCC[C@H](Nc2cc(-n3c(C(F)F)nc4ccccc43)nc(N3CCOCC3)n2)C1] |
| 98 | 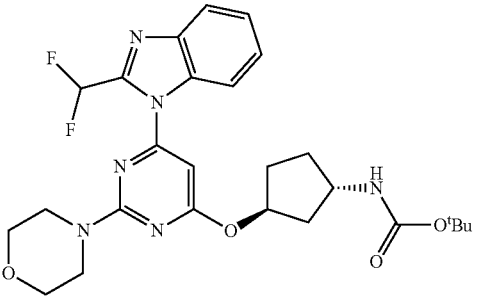 [SMILES: CC(C)(C)OC(=O)N[C@H]1CC[C@H](Oc2cc(-n3c(C(F)F)nc4ccccc43)nc(N3CCOCC3)n2)C1] |
| 99 | 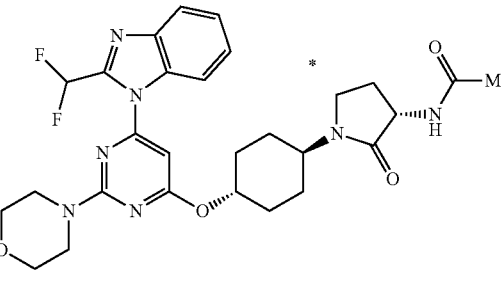 |
| 100 | 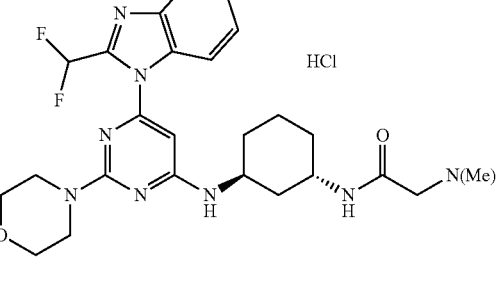 |
| 101 | 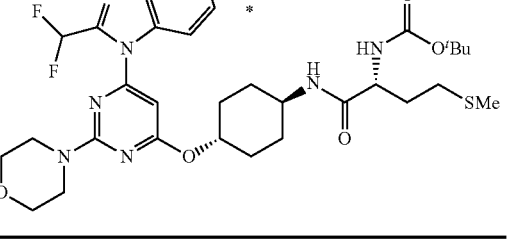 |
TABLE 64
| Ex | Str |
|----|-----|
| 102 | 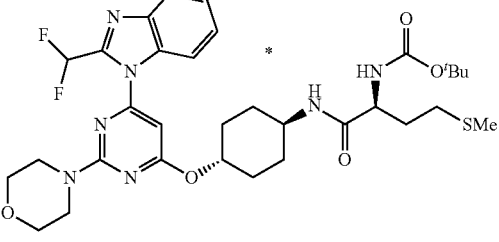 |
| 103 | 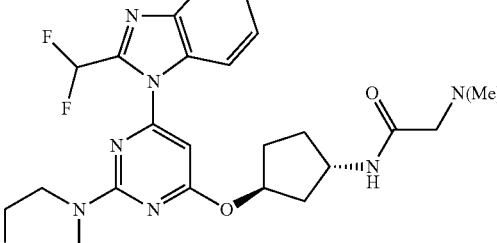 |
| 104 | 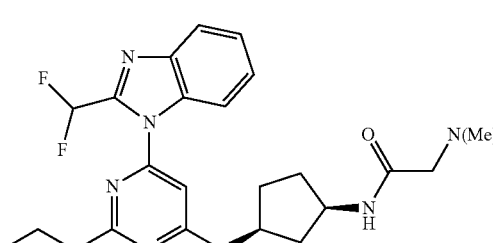 |
| 105 | 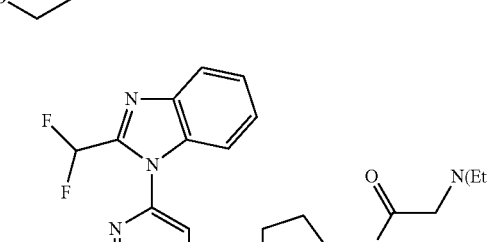 |
| 106 | 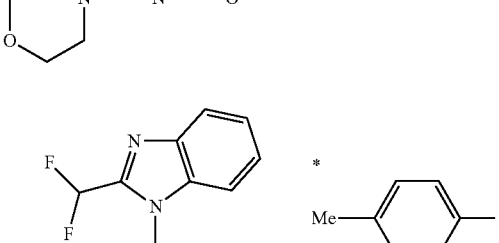 |

TABLE 65

| Ex | Str |
|---|---|
| 107 | |
| 108 | |
| 109 | |
| 110 | |
| 111 | |

TABLE 66

| Ex | Str |
|---|---|
| 112 | |
| 113 | |
| 114 | |
| 115 | |

TABLE 67
| Ex | Str |
|---|---|
| 116 | 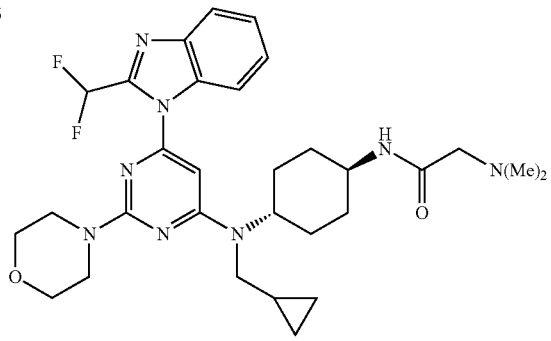 |
| 117 | 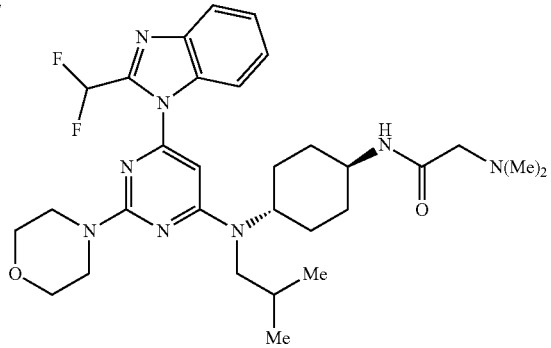 |
| 118 | 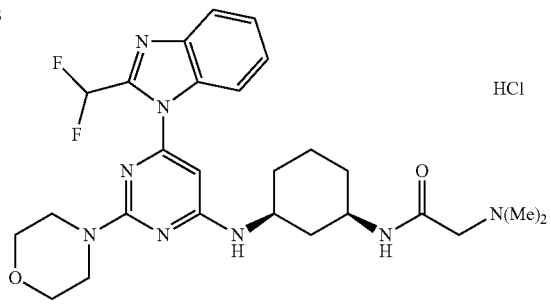 |
| 119 | 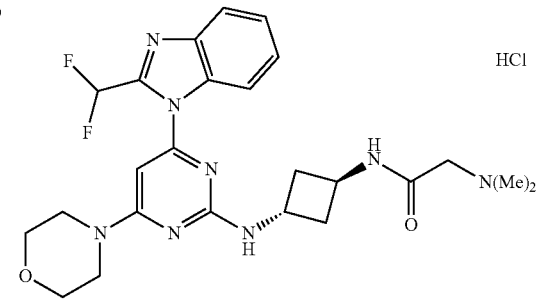 |
TABLE 68
| Ex | Str |
|---|---|
| 120 | 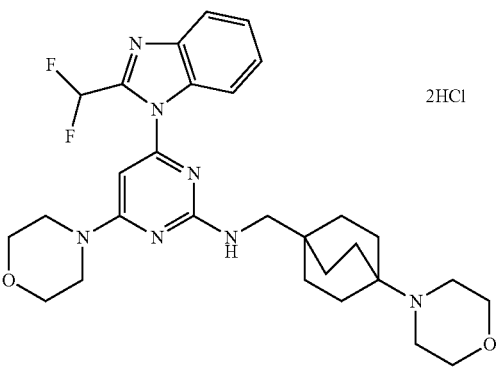 [SMILES: FC(F)c1nc2ccccc2n1-c1cc(N2CCOCC2)nc(NCC23CCC(N4CCOCC4)(CC2)CC3)n1] |
| 121 | 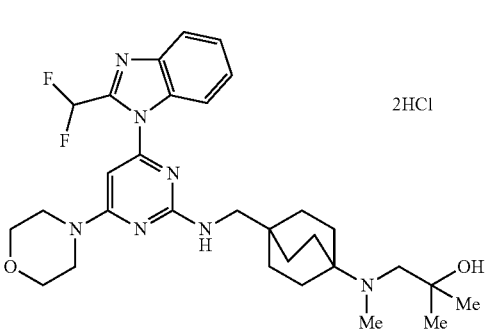 [SMILES: CN(CC(C)(C)O)C12CCC(CNc3nc(N4CCOCC4)cc(-n4c(C(F)F)nc5ccccc54)n3)(CC1)CC2] |
| 122 | 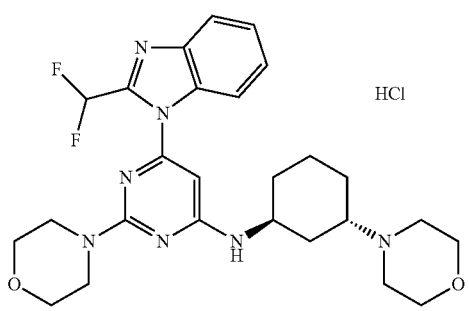 [SMILES: FC(F)c1nc2ccccc2n1-c1cc(N[C@H]2CCC[C@H](N3CCOCC3)C2)nc(N2CCOCC2)n1 ; Cl] |
| 123 | 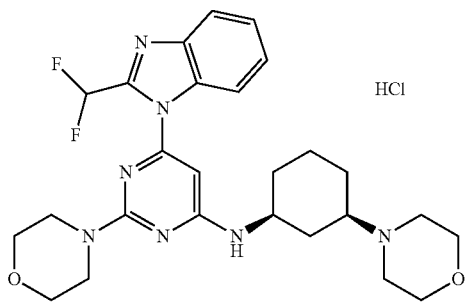 [SMILES: FC(F)c1nc2ccccc2n1-c1cc(N[C@H]2CCC[C@@H](N3CCOCC3)C2)nc(N2CCOCC2)n1 ; Cl] |

TABLE 69
| Ex | Str |
|---|---|
| 124 | 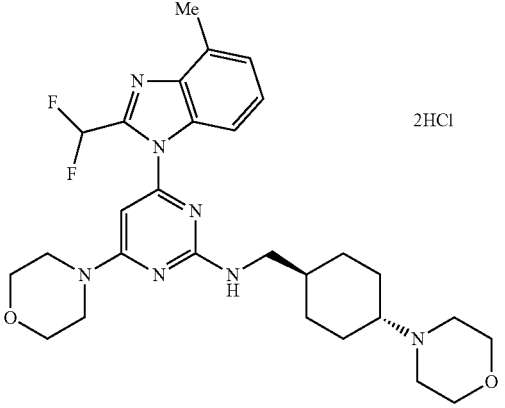 [SMILES: Cc1cccc2c1nc(C(F)F)n2-c1cc(N2CCOCC2)nc(NC[C@H]2CC[C@H](N3CCOCC3)CC2)n1] 2HCl |
| 125 | 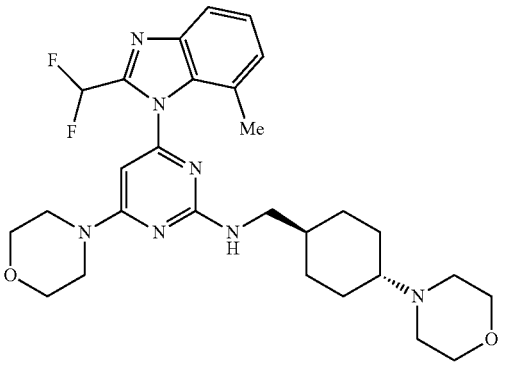 [SMILES: Cc1cccc2nc(C(F)F)n(-c3cc(N4CCOCC4)nc(NC[C@H]4CC[C@H](N5CCOCC5)CC4)n3)c12] |
| 126 | 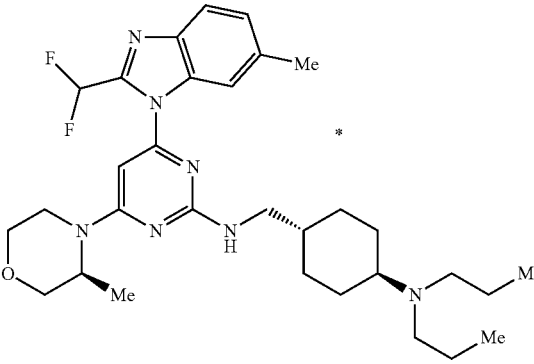 * |
| 127 | 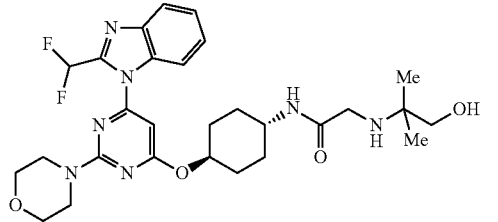 [SMILES: CC(C)(CO)NCC(=O)N[C@H]1CC[C@H](Oc2cc(-n3c(C(F)F)nc4ccccc43)nc(N3CCOCC3)n2)CC1] |
TABLE 70
| Ex | Str |
|---|---|
| 128 | 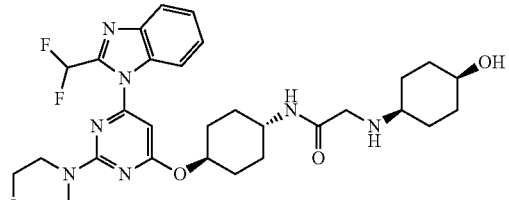 |
| 129 | 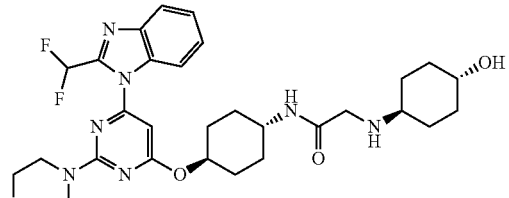 |
| 130 | 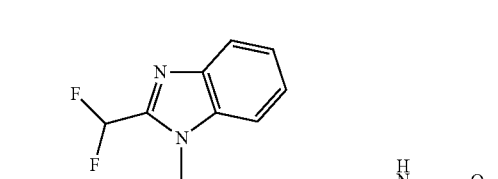 |
| 131 | 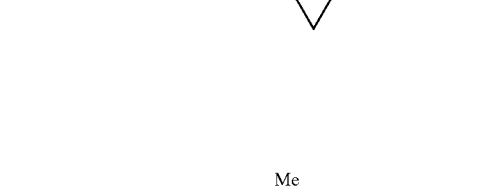 2HCl |

TABLE 71
| Ex | Str |
|---|---|
| 132 | 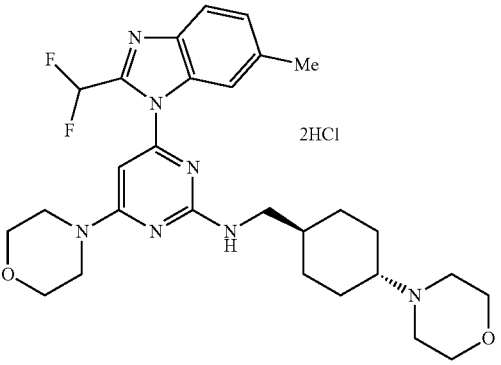 [SMILES: Cc1ccc2nc(C(F)F)n(-c3cc(N4CCOCC4)nc(NC[C@H]4CC[C@H](N5CCOCC5)CC4)n3)c2c1] 2HCl |
| 133 | 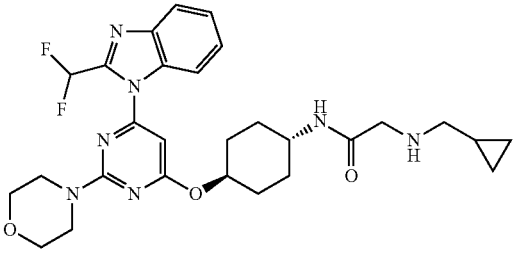 [SMILES: O=C(CNCC1CC1)N[C@H]1CC[C@H](Oc2cc(-n3c(C(F)F)nc4ccccc43)nc(N3CCOCC3)n2)CC1] |
| 134 | 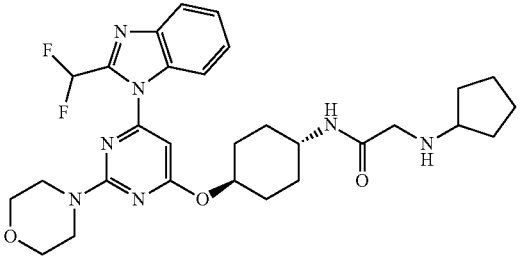 [SMILES: O=C(CNC1CCCC1)N[C@H]1CC[C@H](Oc2cc(-n3c(C(F)F)nc4ccccc43)nc(N3CCOCC3)n2)CC1] |
| 135 | 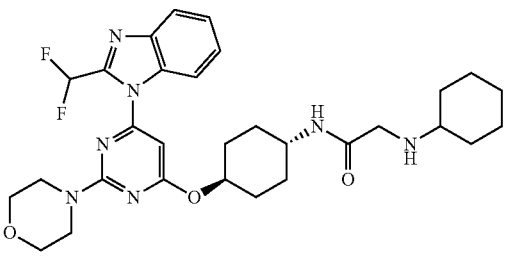 [SMILES: O=C(CNC1CCCCC1)N[C@H]1CC[C@H](Oc2cc(-n3c(C(F)F)nc4ccccc43)nc(N3CCOCC3)n2)CC1] |
| 136 | 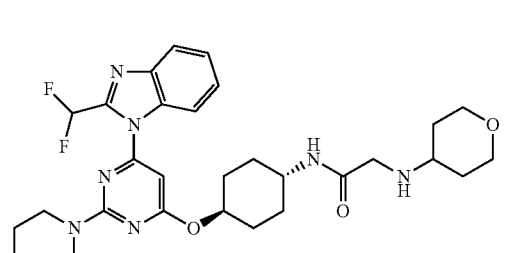 |
TABLE 72
| Ex | Str |
|---|---|
| 137 | 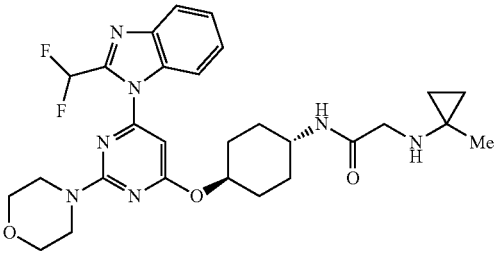 [SMILES: CC1(NCC(=O)N[C@H]2CC[C@H](Oc3cc(-n4c(C(F)F)nc5ccccc54)nc(N4CCOCC4)n3)CC2)CC1] |
| 138 | 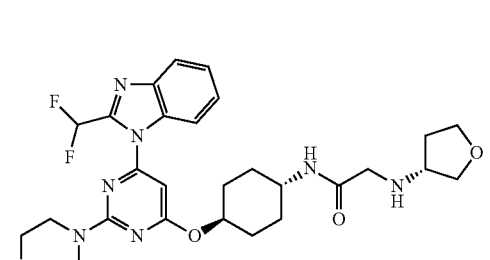 |
| 139 | 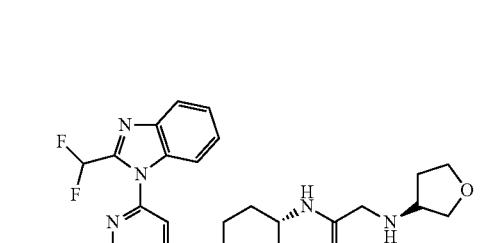 |
| 140 | 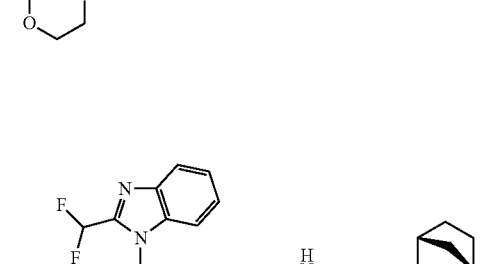 |
| 141 | 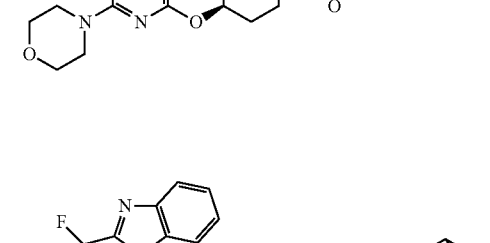 |

TABLE 73
| Ex | Str |
|---|---|
| 142 | 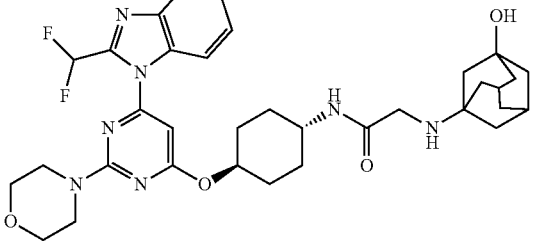 |
| 143 | 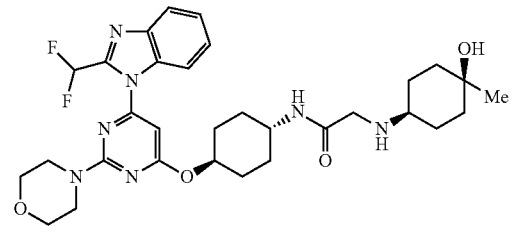 [SMILES: C[C@]1(O)CC[C@@H](NCC(=O)N[C@H]2CC[C@H](Oc3cc(-n4c(C(F)F)nc5ccccc54)nc(N4CCOCC4)n3)CC2)CC1] |
| 144 | 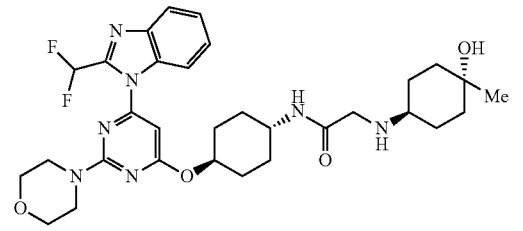 [SMILES: C[C@]1(O)CC[C@H](NCC(=O)N[C@H]2CC[C@H](Oc3cc(-n4c(C(F)F)nc5ccccc54)nc(N4CCOCC4)n3)CC2)CC1] |
| 145 | 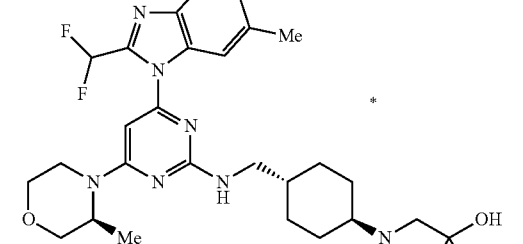 |
| 146 | 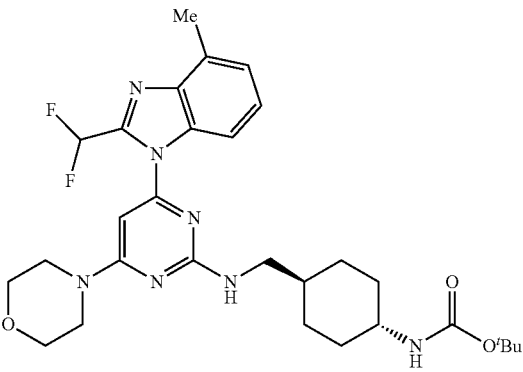 [SMILES: Cc1cccc2c1nc(C(F)F)n2-c1cc(N2CCOCC2)nc(NC[C@H]2CC[C@H](NC(=O)OC(C)(C)C)CC2)n1] |
TABLE 74
| Ex | Str |
|---|---|
| 147 | 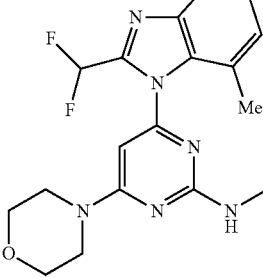 |
| 148 | 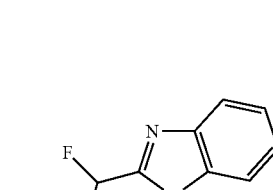 |
| 149 | 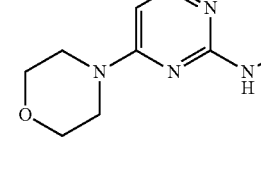 |
| 150 | 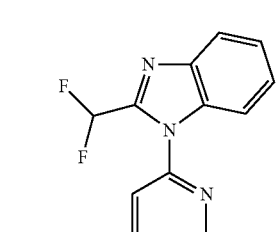 |

TABLE 75
| Ex | Str |
|---|---|
| 151 | 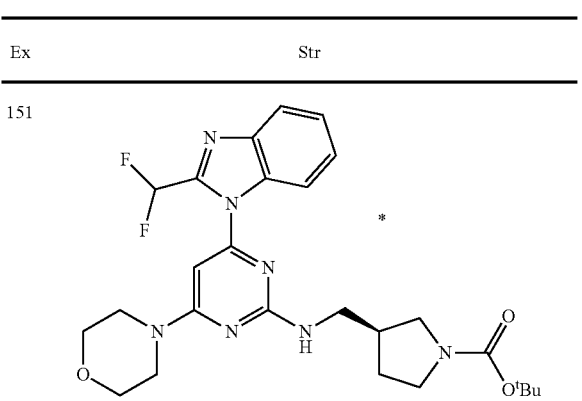 |
| 152 | 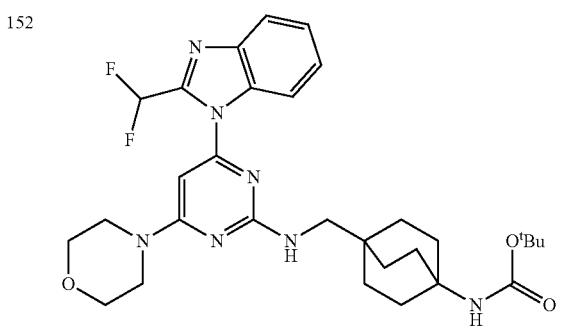 |
| 153 | 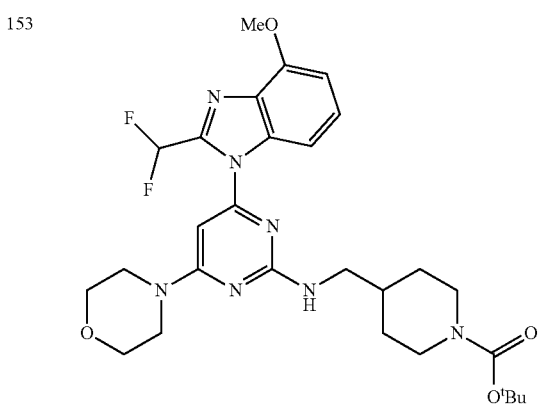 |
| 154 | 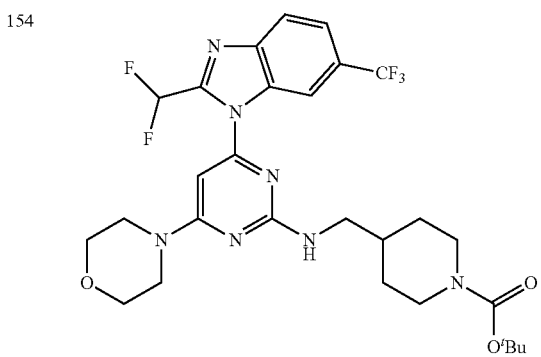 |
TABLE 76
| Ex | Str |
|---|---|
| 155 | 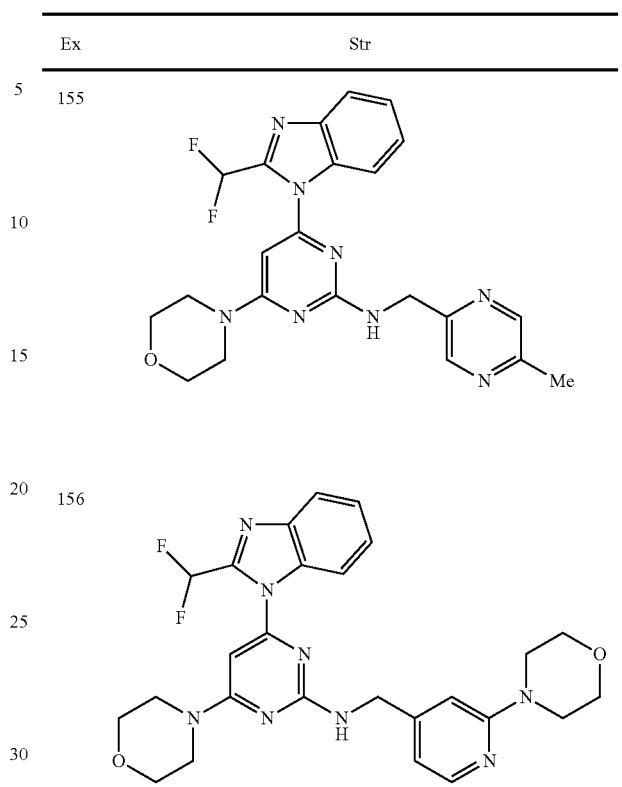 |
| 156 | 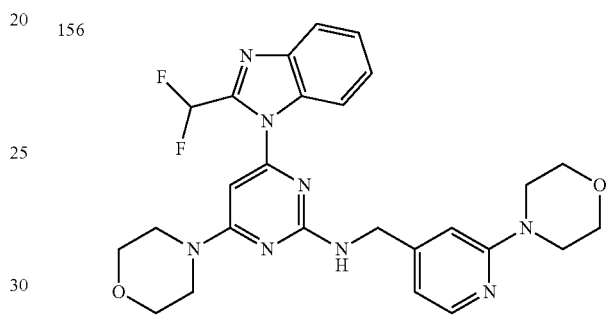 |
| 157 | 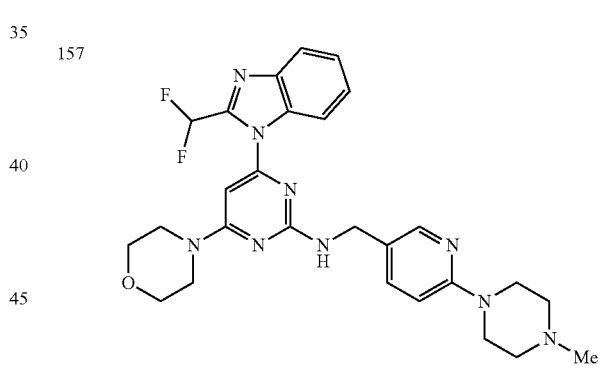 |
| 158 | 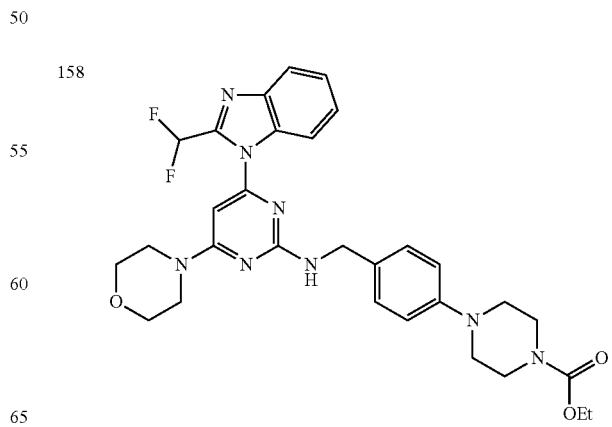 |

TABLE 77

| Ex | Str |
|---|---|
| 159 | |
| 160 | |
| 161 | |
| 162 | |
| 163 | |

TABLE 78

| Ex | Str |
|---|---|
| 164 | |
| 165 | |
| 166 | |
| 167 | |
| 168 | |

TABLE 79

| Ex | Str |
|---|---|
| 169 | (structure) |
| 170 | (structure) |
| 171 | (structure) |
| 172 | (structure) |
| 173 | (structure) |

TABLE 80

| Ex | Str |
|---|---|
| 174 | (structure) |
| 175 | (structure) |
| 176 | (structure) |
| 177 | (structure) |
| 178 | (structure) |

TABLE 81
| Ex | Str |
|---|---|
| 179 | 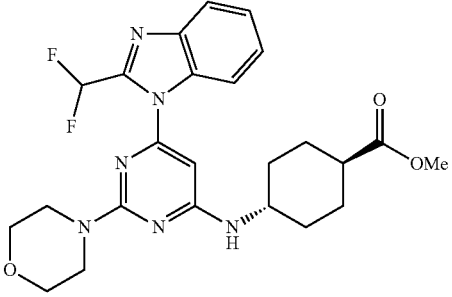 [SMILES: COC(=O)[C@H]1CC[C@H](Nc2cc(-n3c(C(F)F)nc4ccccc43)nc(N3CCOCC3)n2)CC1] |
| 180 | 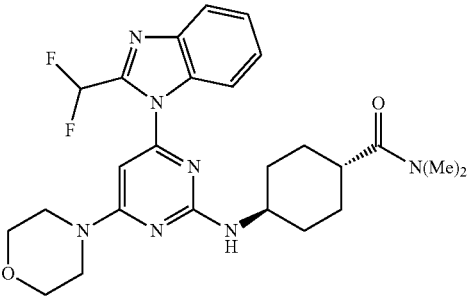 |
| 181 | 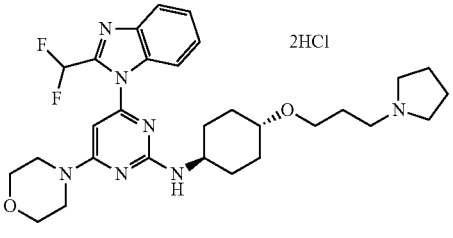 [SMILES: FC(F)c1nc2ccccc2n1-c1cc(N2CCOCC2)nc(N[C@H]2CC[C@H](OCCCN3CCCC3)CC2)n1] |
| 182 | 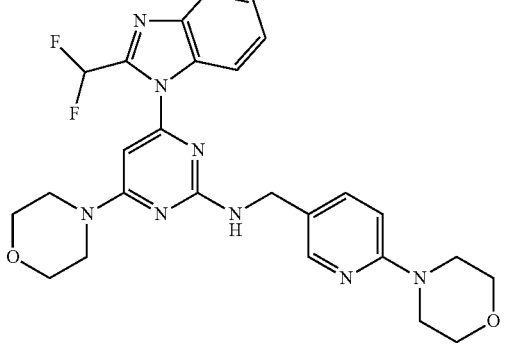 |
| 183 | 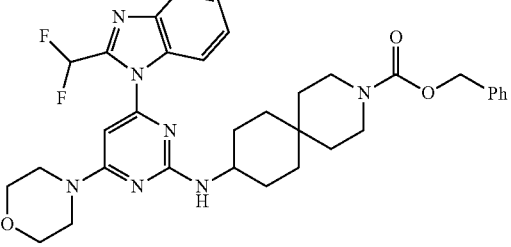 |
TABLE 82
| Ex | Str |
|---|---|
| 184 | 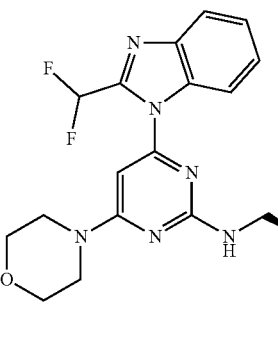 |
| 185 | 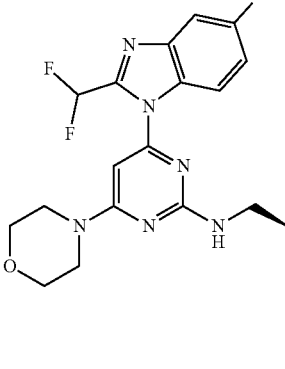 |
| 186 | 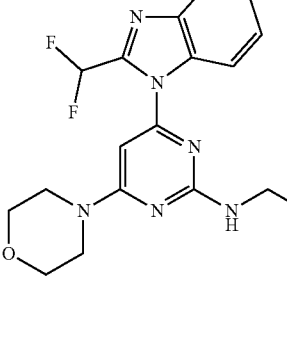 |
| 187 | 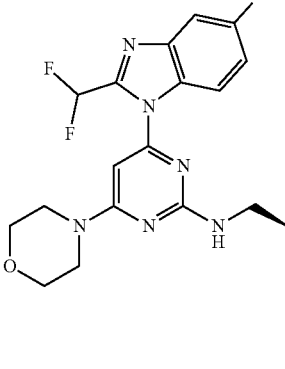 |

TABLE 83
| Ex | Str |
|---|---|
| 188 | |
| 189 | |
| 190 | |
| 191 | |
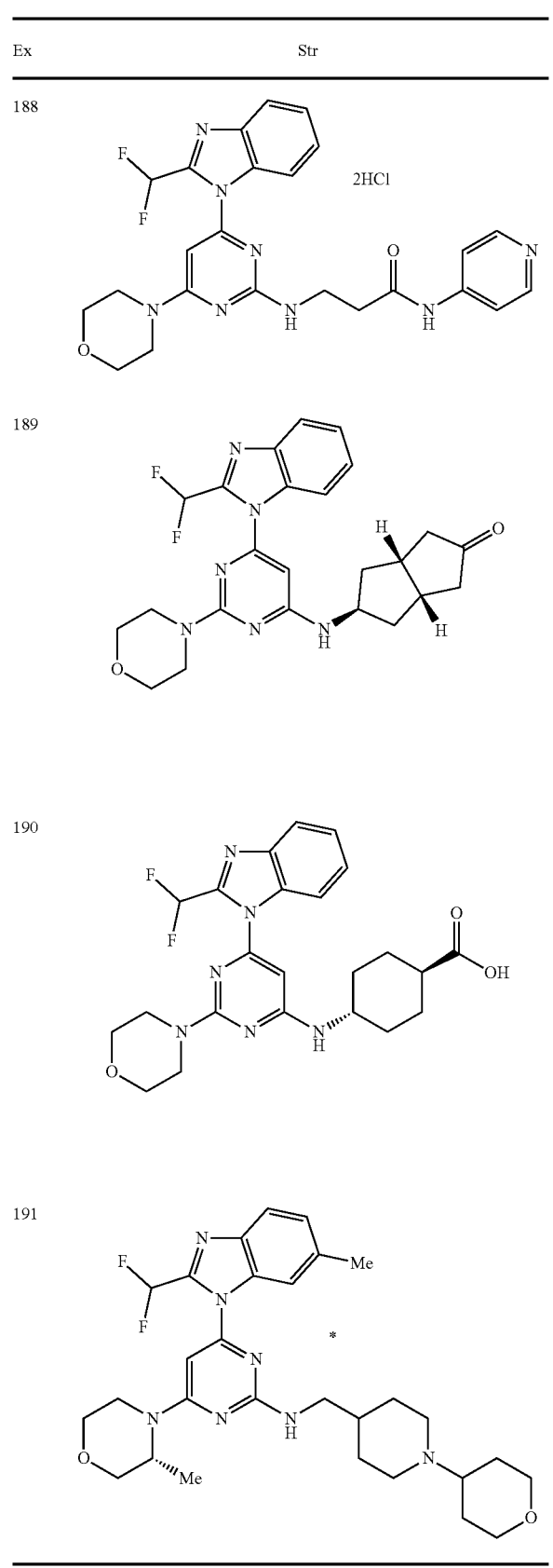
TABLE 84
| Ex | Str |
|---|---|
| 192 | |
| 193 | |
| 194 | |
| 195 | |
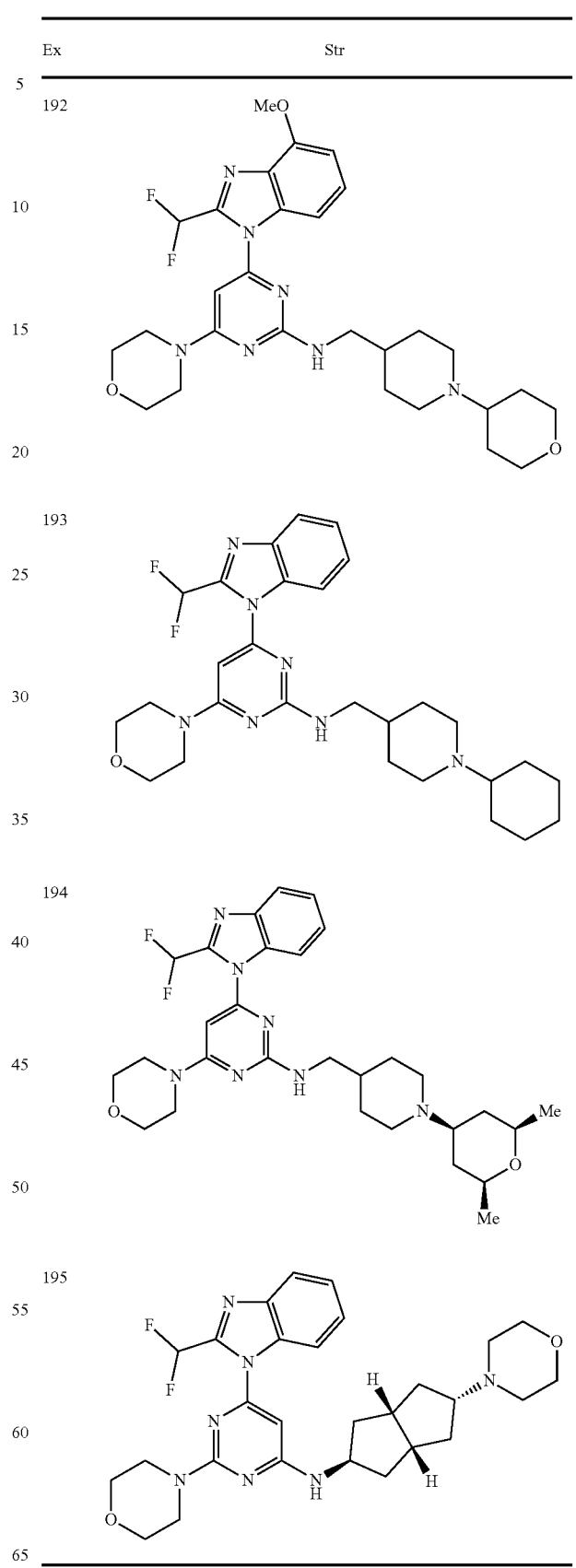

TABLE 85

| Ex | Str |
|---|---|
| 196 | |
| 197 | |
| 198 | |
| 199 | |
| 200 | |

TABLE 86

| Ex | Str |
|---|---|
| 201 | |
| 202 | |
| 203 | |
| 204 | |

165
TABLE 87
| Ex | Str |
|---|---|
| 205 | 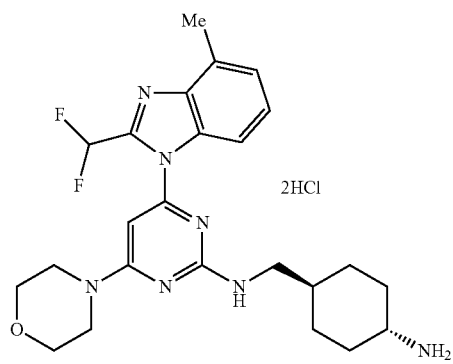 [SMILES: Cc1cccc2c1nc(C(F)F)n2-c1cc(N2CCOCC2)nc(NC[C@H]2CC[C@H](N)CC2)n1 ; "2HCl"] 2HCl |
| 206 | 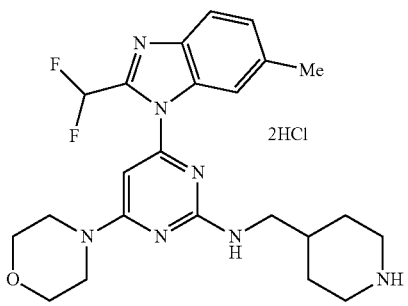 [SMILES: Cc1ccc2nc(C(F)F)n(-c3cc(N4CCOCC4)nc(NCC4CCNCC4)n3)c2c1] 2HCl |
| 207 | 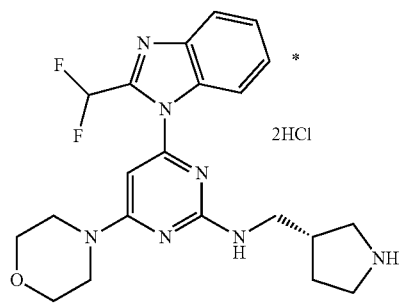 [SMILES: FC(F)c1nc2ccccc2n1-c1cc(N2CCOCC2)nc(NC[C@H]2CCNC2)n1] 2HCl |
| 208 | 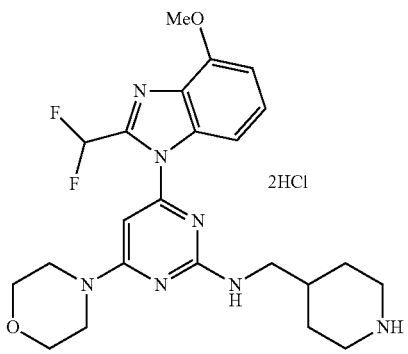 [SMILES: COc1cccc2c1nc(C(F)F)n2-c1cc(N2CCOCC2)nc(NCC2CCNCC2)n1] 2HCl |
166
TABLE 88
| Ex | Str |
|---|---|
| 209 | 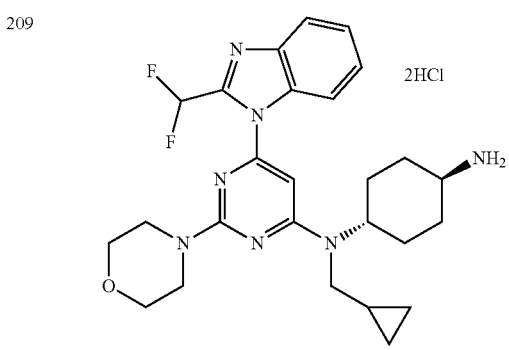 2HCl |
| 210 | 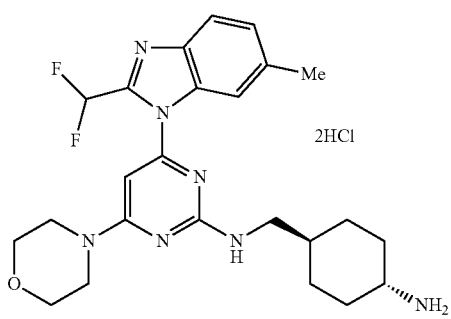 [SMILES: Cc1ccc2nc(C(F)F)n(-c3cc(N4CCOCC4)nc(NC[C@H]4CC[C@H](N)CC4)n3)c2c1] 2HCl |
| 211 | 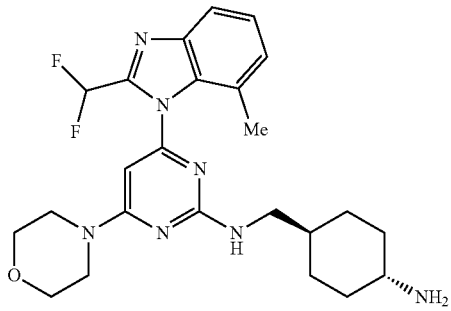 [SMILES: Cc1cccc2nc(C(F)F)n(-c3cc(N4CCOCC4)nc(NC[C@H]4CC[C@H](N)CC4)n3)c12] |
| 212 | 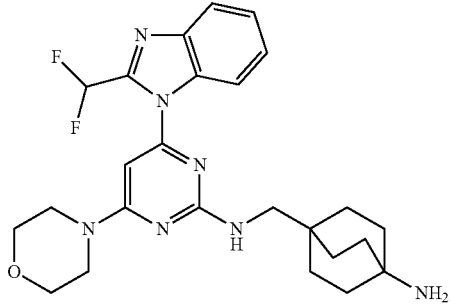 [SMILES: NC12CCC(CNc3nc(N4CCOCC4)cc(-n4c(C(F)F)nc5ccccc54)n3)(CC1)CC2] |

TABLE 89

| Ex | Str |
|---|---|
| 213 | |
| 214 | |
| 215 | |
| 216 | |
| 217 | |

TABLE 90

| Ex | Str |
|---|---|
| 218 | |
| 219 | |
| 220 | |
| 221 | |

169
TABLE 91
| Ex | Str |
|---|---|
| 222 | 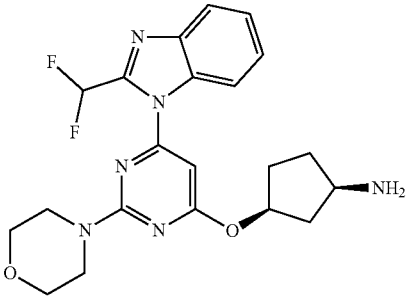 [SMILES: N[C@@H]1CC[C@H](Oc2cc(-n3c(C(F)F)nc4ccccc43)nc(N3CCOCC3)n2)C1] |
| 223 | 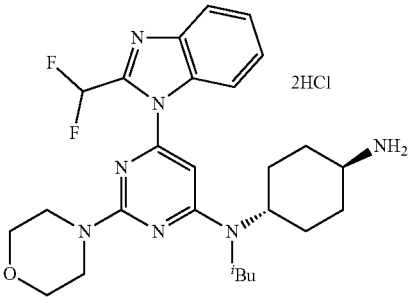 2HCl |
| 224 | 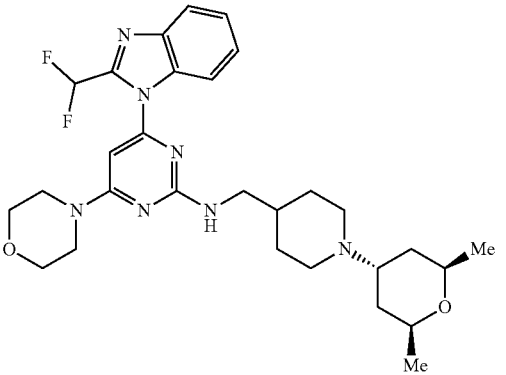 [SMILES: C[C@@H]1C[C@@H](N2CCC(CNc3nc(N4CCOCC4)cc(-n4c(C(F)F)nc5ccccc54)n3)CC2)C[C@H](C)O1] |
| 225 | 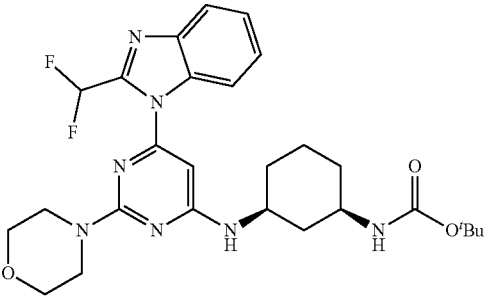 [SMILES: CC(C)(C)OC(=O)N[C@@H]1CCC[C@H](Nc2cc(-n3c(C(F)F)nc4ccccc43)nc(N3CCOCC3)n2)C1] |
170
TABLE 92
| Ex | Str |
|---|---|
| 226 | 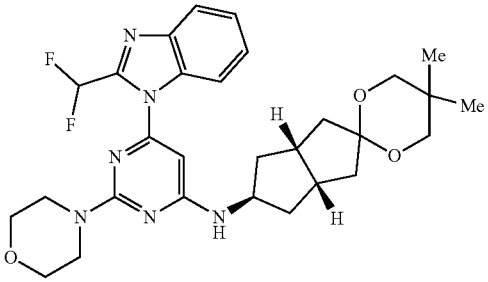 [SMILES: CC1(C)COC2(C[C@H]3C[C@H](Nc4cc(-n5c(C(F)F)nc6ccccc65)nc(N5CCOCC5)n4)C[C@H]3C2)OC1] |
| 227 | 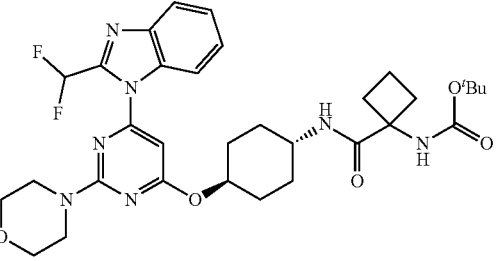 |
| 228 | 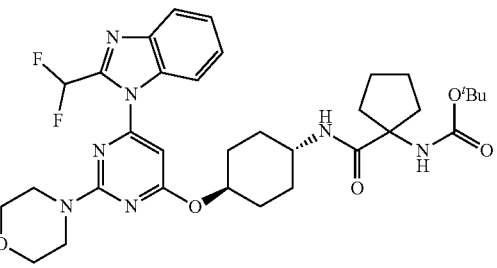 |
| 229 | 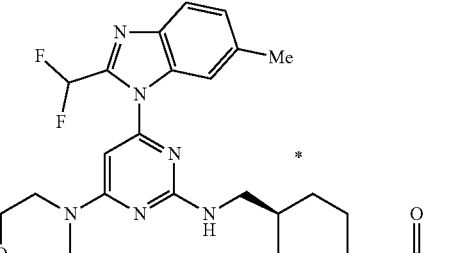 |

TABLE 93
| Ex | Str |
|----|-----|
| 230 | 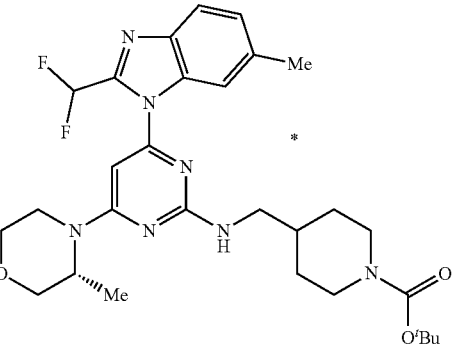 |
| 231 | 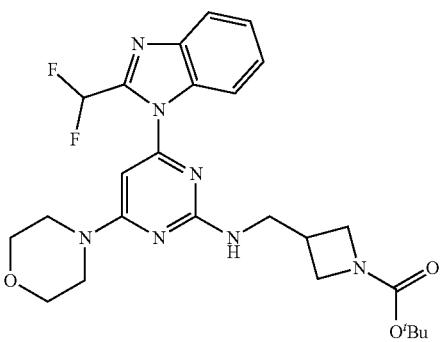 [SMILES: CC(C)(C)OC(=O)N1CC(CNc2nc(N3CCOCC3)cc(-n3c(C(F)F)nc4ccccc43)n2)C1] |
| 232 | 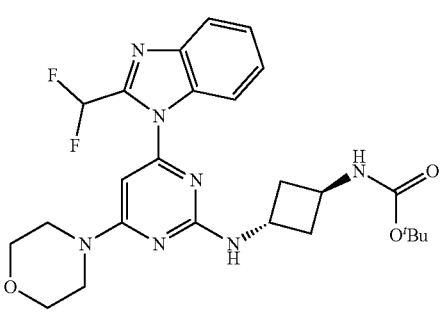 [SMILES: CC(C)(C)OC(=O)N[C@H]1C[C@H](Nc2nc(N3CCOCC3)cc(-n3c(C(F)F)nc4ccccc43)n2)C1] |
| 233 | 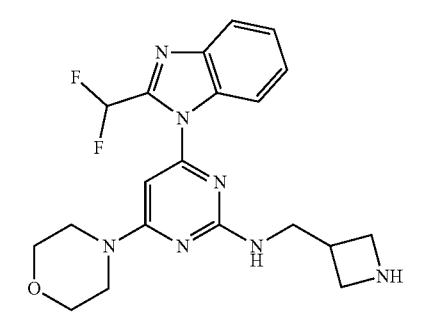 [SMILES: FC(F)c1nc2ccccc2n1-c1cc(N2CCOCC2)nc(NCC2CNC2)n1] |
TABLE 94
| Ex | Str |
|----|-----|
| 234 | 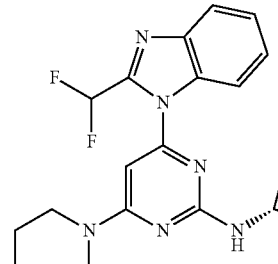 |
| 235 | 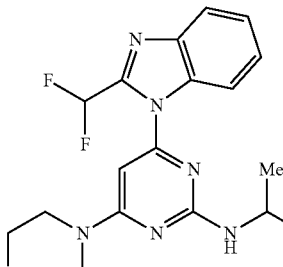 |
| 236 | 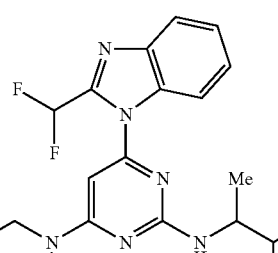 |
| 237 | 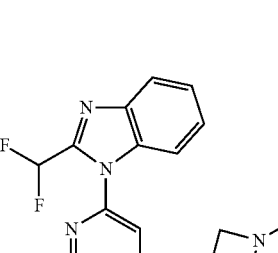 |
| 238 | 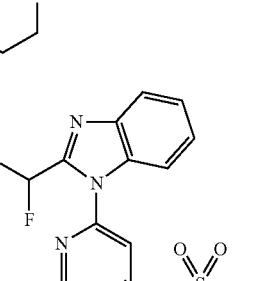 |

TABLE 95

| Ex | Str |
|---|---|
| 239 | (structure) |
| 240 | (structure) 2HCl |
| 241 | (structure) * |
| 242-1 | (structure) 2HCl |
| 242-2 | (structure) 2HCl |

TABLE 96

| Ex | Str |
|---|---|
| 243 | (structure) |
| 244 | (structure) * HCl |
| 245 | (structure) * |
| 246 | (structure) |
| 247 | (structure) |

TABLE 97
| Ex | Str |
|---|---|
| 248 | 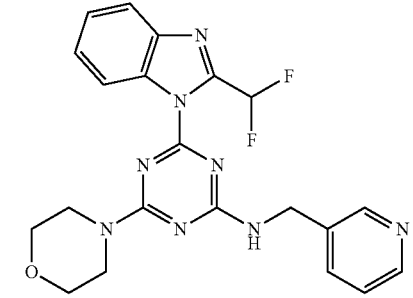 [SMILES: FC(F)c1nc2ccccc2n1-c1nc(NCc2cccnc2)nc(N2CCOCC2)n1] |
| 249-1 | 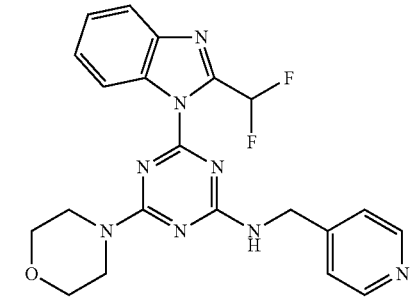 [SMILES: FC(F)c1nc2ccccc2n1-c1nc(NCc2ccncc2)nc(N2CCOCC2)n1] |
| 249-2 | 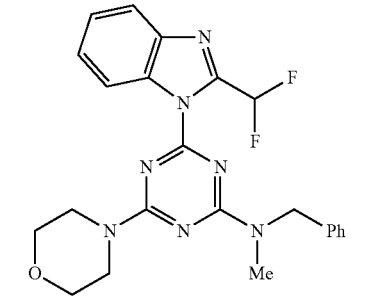 [SMILES: CN(Cc1ccccc1)c1nc(N2CCOCC2)nc(-n2c(C(F)F)nc3ccccc32)n1] |
| 250 | 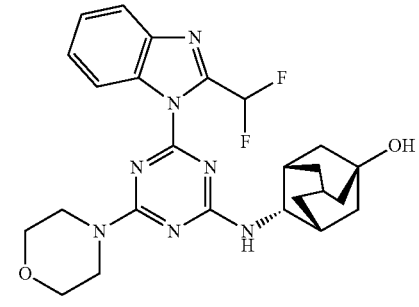 [SMILES: O[C@]12CC3C[C@H](C1)[C@H](Nc1nc(N4CCOCC4)nc(-n4c(C(F)F)nc5ccccc54)n1)[C@@H](C3)C2] |
| 251 | 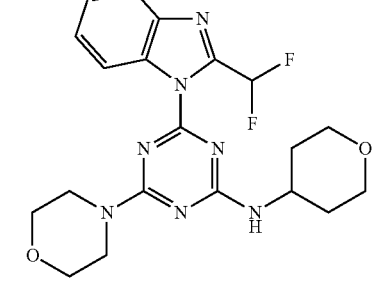 |
TABLE 98
| Ex | Str |
|---|---|
| 252 | |
| 253 | |
| 254 | |
| 255 | |
| 256 | |

TABLE 99

| Ex | Str |
|---|---|
| 257 | (structure) |
| 258 | (structure) |
| 259 | (structure) |
| 260 | (structure) |
| 261 | (structure) |

TABLE 100

| Ex | Str |
|---|---|
| 262 | (structure) |
| 263 | (structure) |
| 264 | (structure) |
| 265 | (structure) |
| 266 | (structure) |

TABLE 101
| Ex | Str |
|---|---|
| 267 | 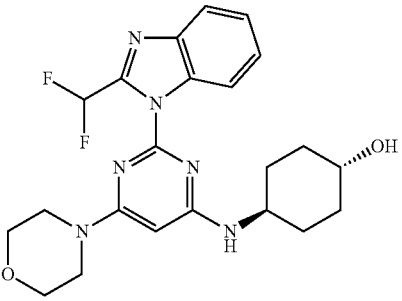 [SMILES: O[C@H]1CC[C@H](Nc2cc(N3CCOCC3)nc(-n3c(C(F)F)nc4ccccc43)n2)CC1] |
| 268 | 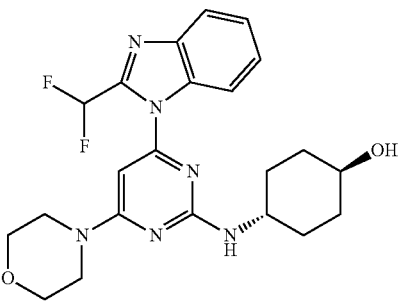 [SMILES: O[C@H]1CC[C@H](Nc2nc(N3CCOCC3)cc(-n3c(C(F)F)nc4ccccc43)n2)CC1] |
| 269 | 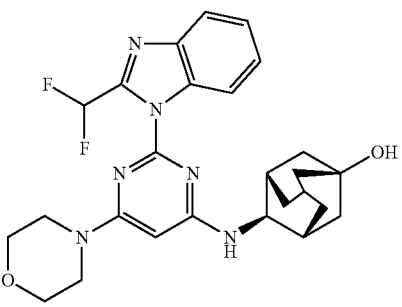 [SMILES: O[C@]12CC3C[C@H](C1)[C@@H](Nc1cc(N4CCOCC4)nc(-n4c(C(F)F)nc5ccccc54)n1)[C@@H](C3)C2] |
| 270 | 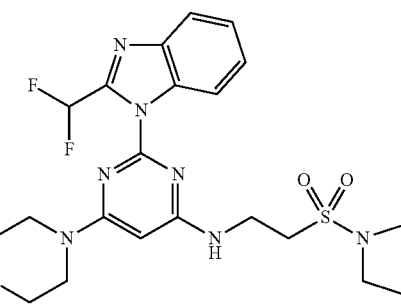 |
| 271 | 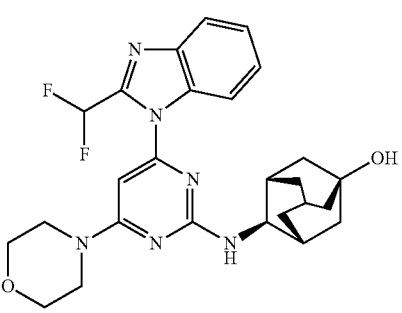 [SMILES: O[C@]12CC3C[C@H](C1)[C@@H](Nc1nc(N4CCOCC4)cc(-n4c(C(F)F)nc5ccccc54)n1)[C@@H](C3)C2] |
TABLE 102
| Ex | Str |
|---|---|
| 272 | 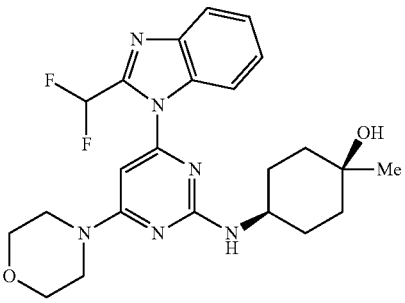 [SMILES: C[C@]1(O)CC[C@@H](Nc2nc(N3CCOCC3)cc(-n3c(C(F)F)nc4ccccc43)n2)CC1] |
| 273 | 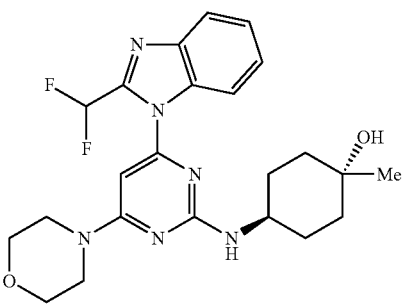 [SMILES: C[C@]1(O)CC[C@H](Nc2nc(N3CCOCC3)cc(-n3c(C(F)F)nc4ccccc43)n2)CC1] |
| 274 | 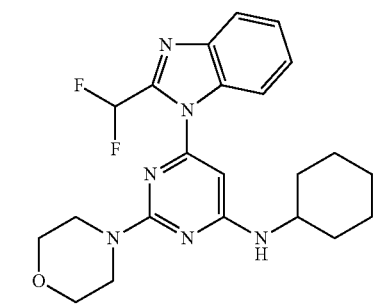 [SMILES: FC(F)c1nc2ccccc2n1-c1cc(NC2CCCCC2)nc(N2CCOCC2)n1] |
| 275 | 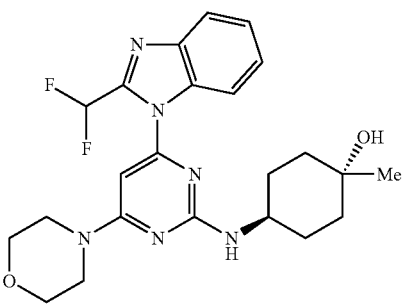 [SMILES: C[C@]1(O)CC[C@H](Nc2nc(N3CCOCC3)cc(-n3c(C(F)F)nc4ccccc43)n2)CC1] |
| 276 | 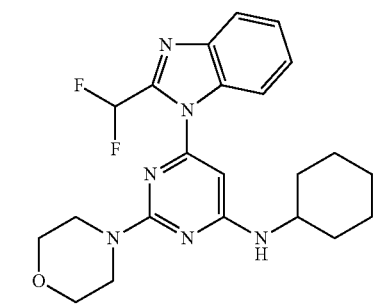 [SMILES: FC(F)c1nc2ccccc2n1-c1cc(NC2CCCCC2)nc(N2CCOCC2)n1] |

TABLE 103
| Ex | Str |
|---|---|
| 277 | 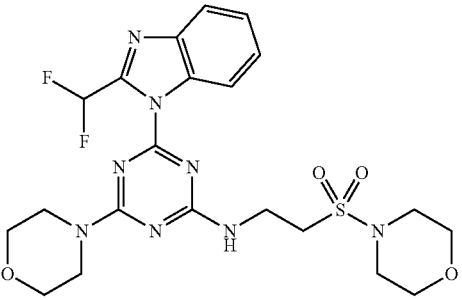 [SMILES: O=S(=O)(CCNc1nc(N2CCOCC2)nc(-n2c(C(F)F)nc3ccccc32)n1)N1CCOCC1] |
| 278 | 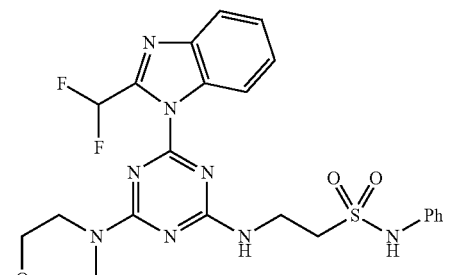 |
| 279 | 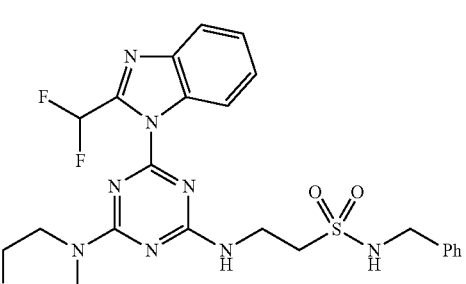 |
| 280 | 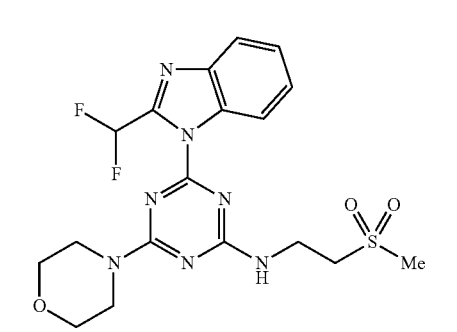 [SMILES: CS(=O)(=O)CCNc1nc(N2CCOCC2)nc(-n2c(C(F)F)nc3ccccc32)n1] |
| 281 | 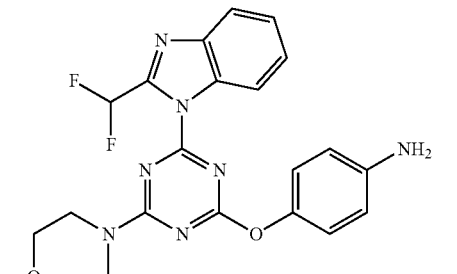 |
TABLE 104
| Ex | Str |
|---|---|
| 282 | 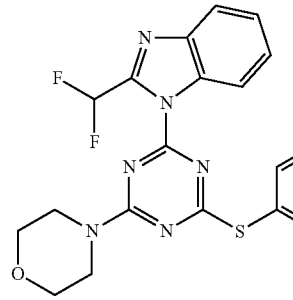 |
| 283 | 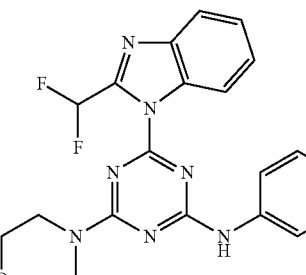 |
| 284 | 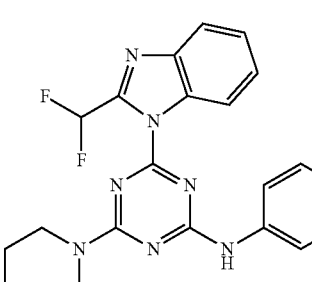 |
| 285 | 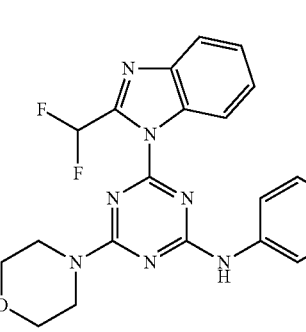 |
| 286 | 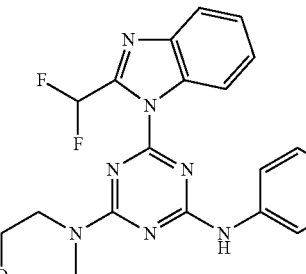 |

TABLE 105

| Ex | Str |
|---|---|
| 287 | (structure) |
| 288 | (structure) |
| 289 | (structure) |
| 290 | (structure) |
| 291 | (structure) |

TABLE 106

| Ex | Str |
|---|---|
| 292 | (structure) |
| 293 | (structure) |
| 294 | (structure) |
| 295 | (structure) |

TABLE 107
| Ex | Str |
|---|---|
| 296 | 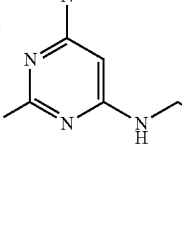 HCl |
| 297 | 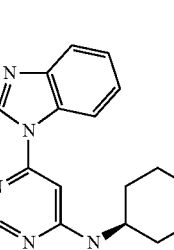 HCl |
| 298 | 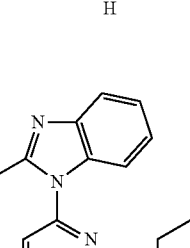 2HCl |
| 299 | 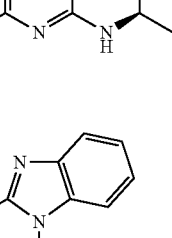 HCl |
| 300 | 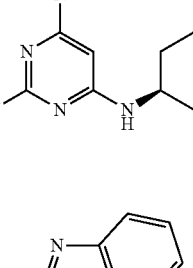 |
TABLE 108
| Ex | Str |
|---|---|
| 301 | 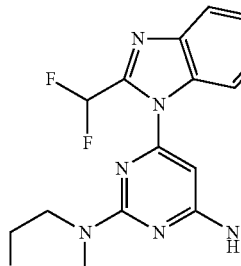 |
| 302 | 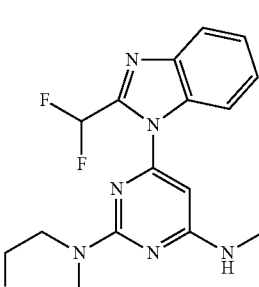 |
| 303 | 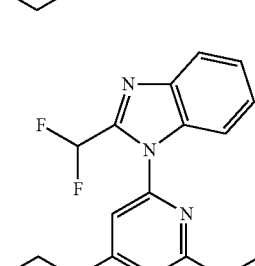 |
| 304 | 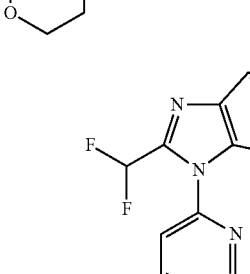 |
| 305 | 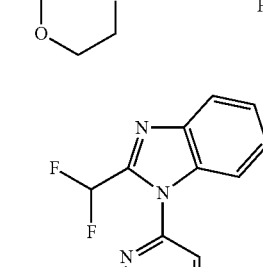 |

TABLE 109

| Ex | Str |
|---|---|
| 306 | |
| 307 | (2HCl) |
| 308 | |
| 309 | |
| 310 | |

TABLE 110

| Ex | Str |
|---|---|
| 311 | |
| 312 | |
| 313 | |
| 314 | |
| 315 | |

TABLE 111
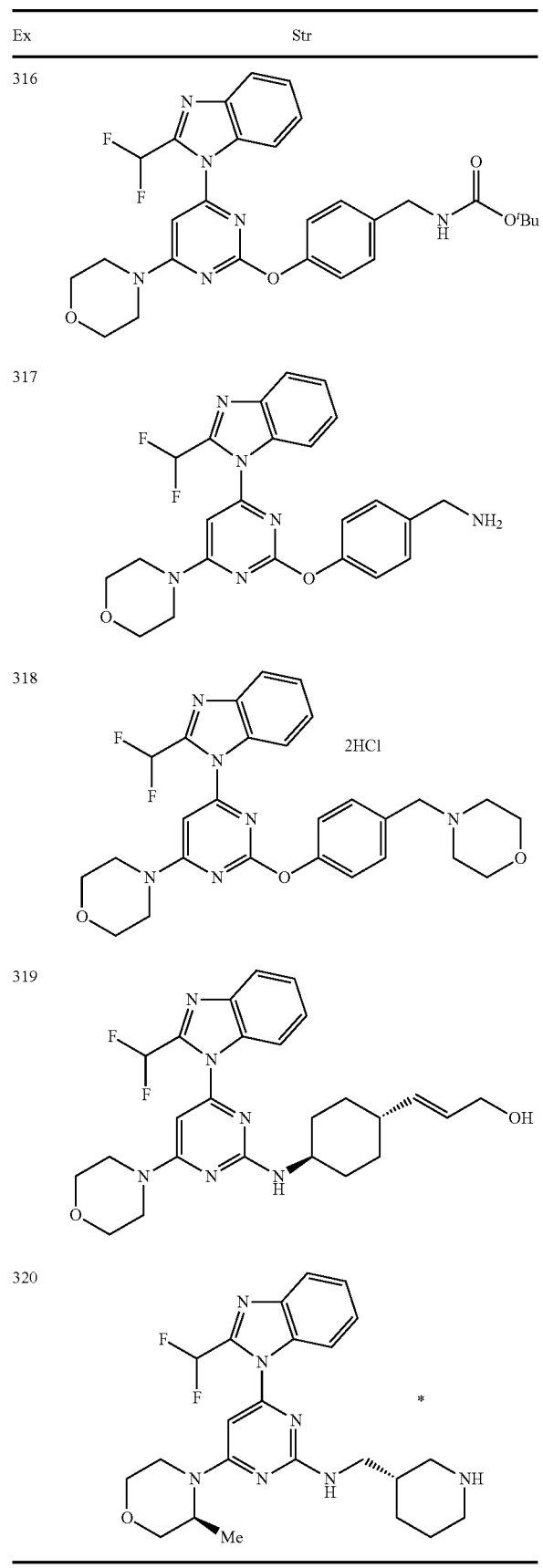
TABLE 112
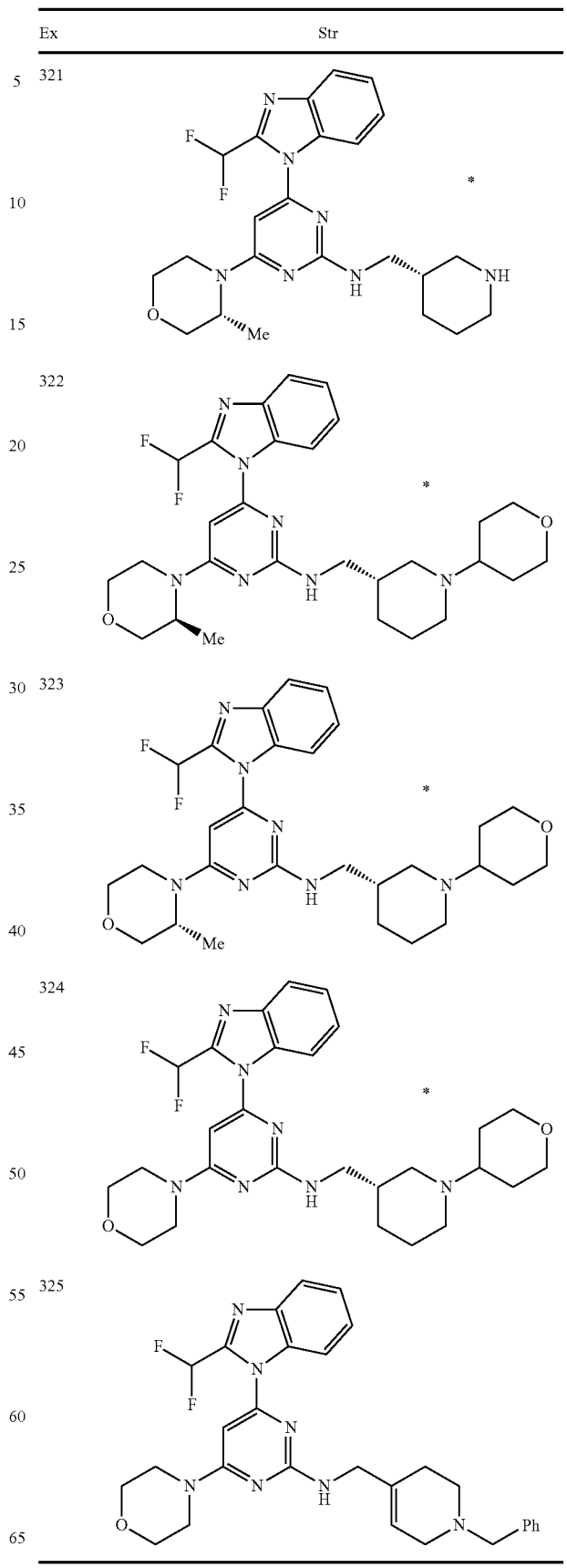

TABLE 113

| Ex | Str |
|---|---|
| 326 | |
| 327 | |
| 328 | |
| 329 | |
| 330 | |

TABLE 114

| Ex | Str |
|---|---|
| 331 | |
| 332 | |
| 333 | |
| 334 | |

TABLE 115

| Ex | Str |
|---|---|
| 335 | (structure) |
| 336 | (structure) |
| 337 | (structure) |
| 338 | (structure) |

TABLE 116

| Ex | Str |
|---|---|
| 339 | (structure) |
| 340 | (structure) |
| 341 | (structure) |
| 342 | (structure) |
| 343 | (structure) |

TABLE 117
| Ex | Str |
|---|---|
| 344 | 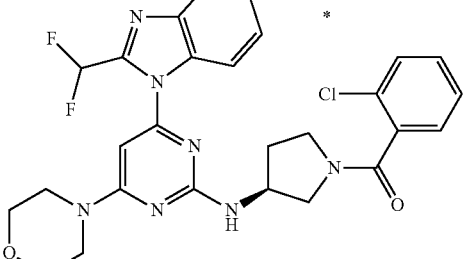 |
| 345 | 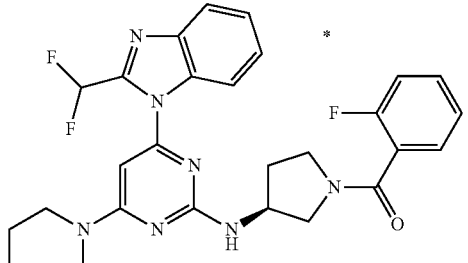 |
| 346 | 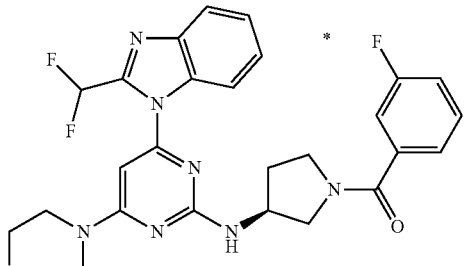 |
| 347 | 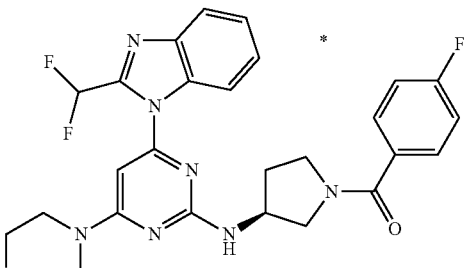 |
| 348 | 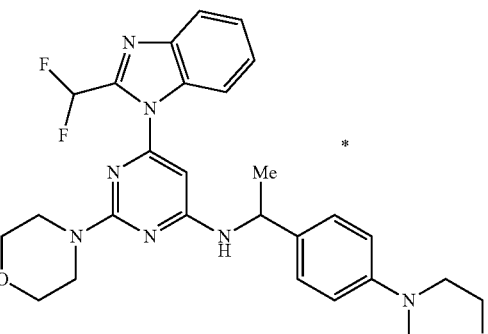 |
TABLE 118
| Ex | Str |
|---|---|
| 349 | 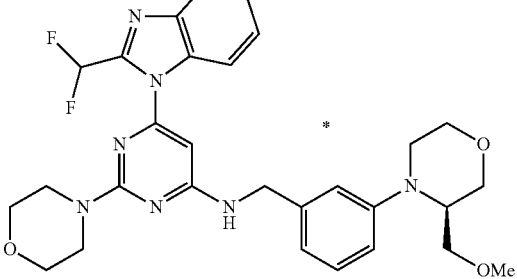 |
| 350 | 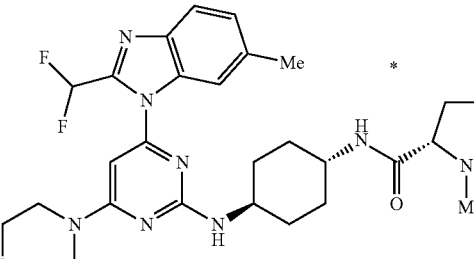 |
| 351 | 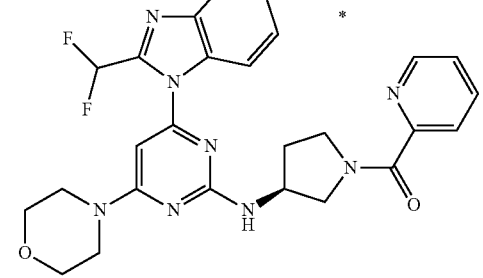 |
| 352 | 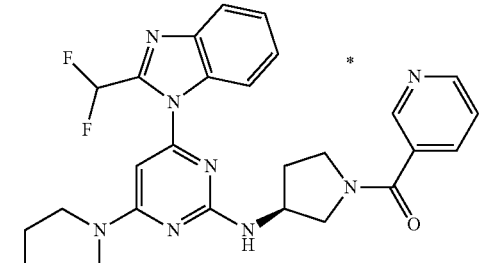 |
| 353 | 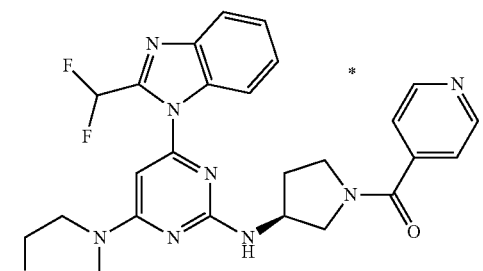 |

TABLE 119
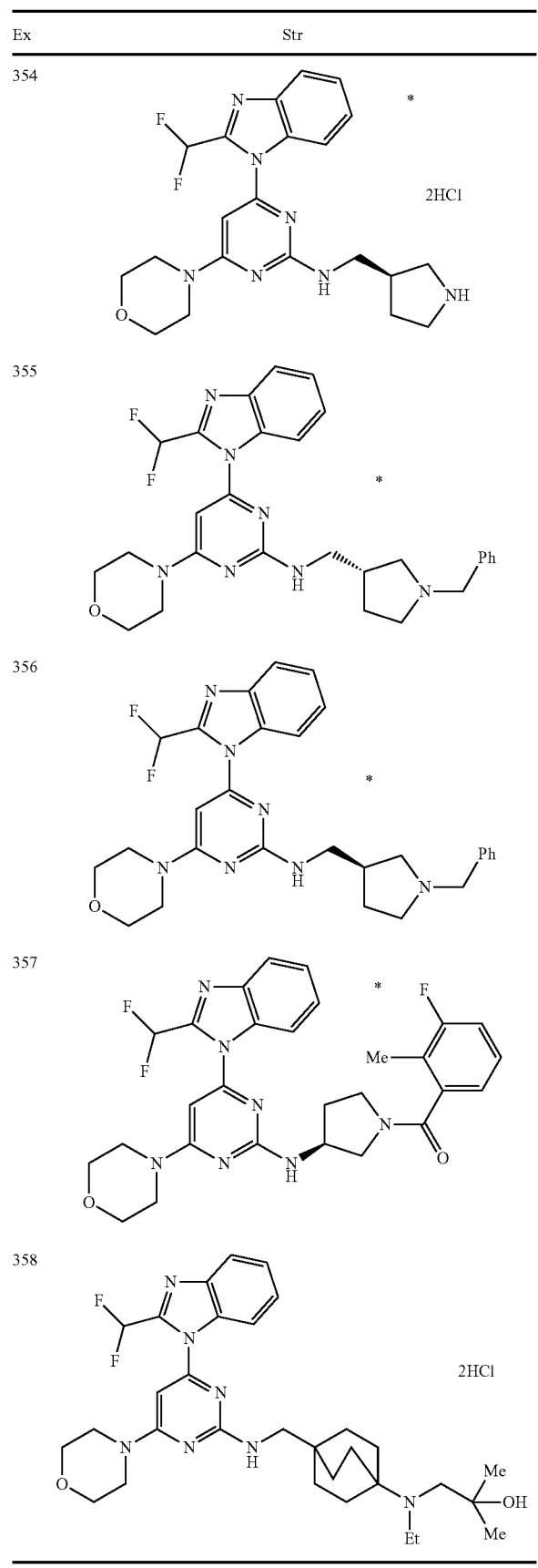
TABLE 120
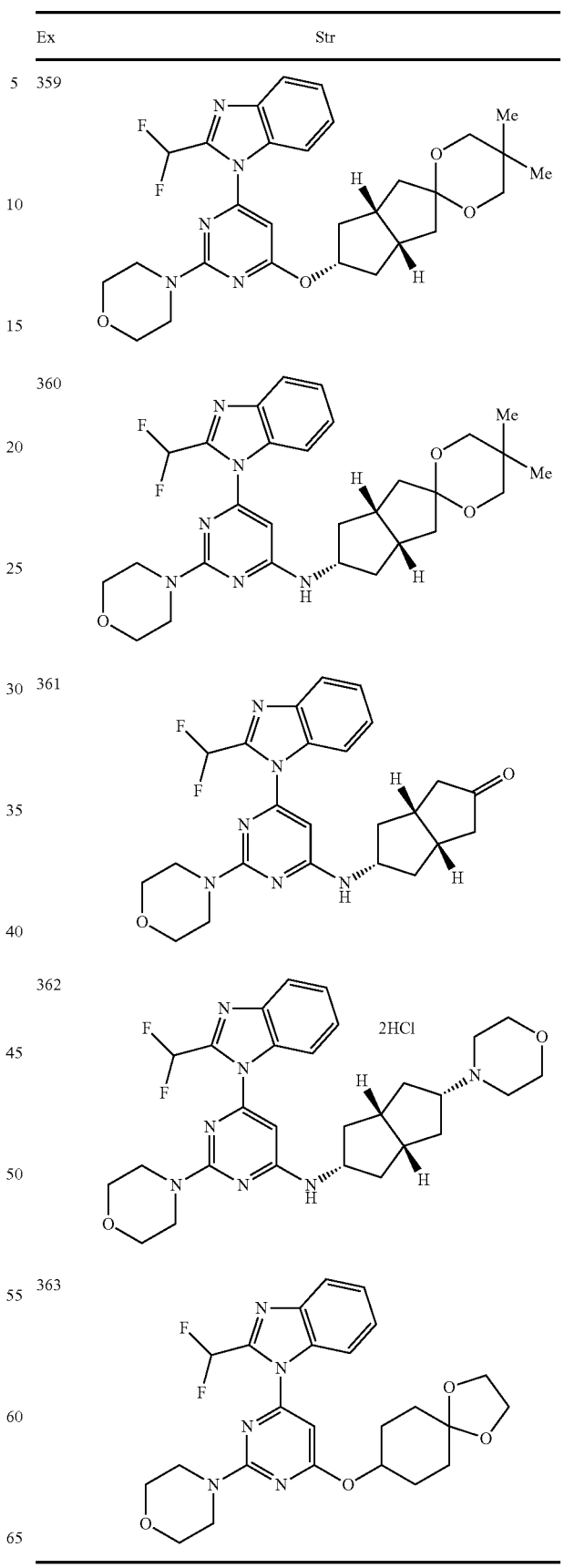

TABLE 121
| Ex | Str |
|----|-----|
| 364 | 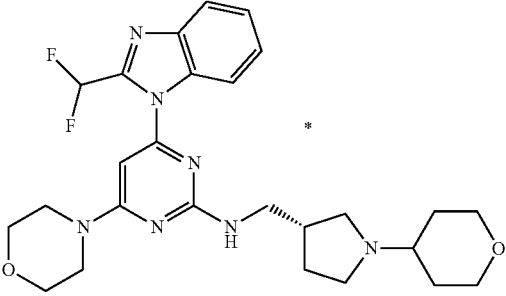 [SMILES: FC(F)c1nc2ccccc2n1-c1cc(N2CCOCC2)nc(NC[C@H]2CCN(C3CCOCC3)C2)n1] |
| 365 | 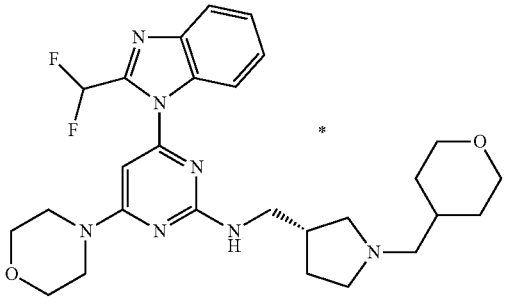 [SMILES: FC(F)c1nc2ccccc2n1-c1cc(N2CCOCC2)nc(NC[C@H]2CCN(CC3CCOCC3)C2)n1] |
| 366 | 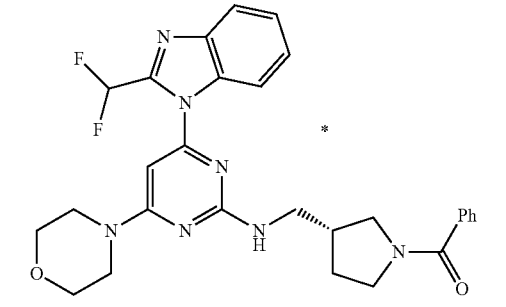 [SMILES: O=C(c1ccccc1)N1CC[C@H](CNc2nc(N3CCOCC3)cc(-n3c(C(F)F)nc4ccccc43)n2)C1] |
| 367 | 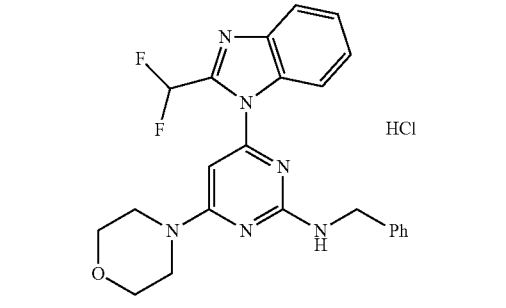 [SMILES: FC(F)c1nc2ccccc2n1-c1cc(N2CCOCC2)nc(NCc2ccccc2)n1 ; Cl] |
| 368 | 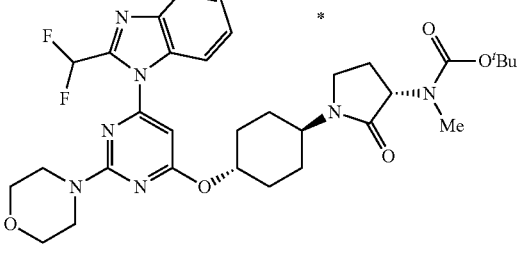 |
TABLE 122
| Ex | Str |
|----|-----|
| 369 | 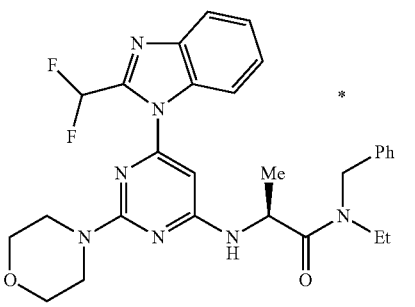 [SMILES: CCN(Cc1ccccc1)C(=O)[C@H](C)Nc1cc(-n2c(C(F)F)nc3ccccc32)nc(N2CCOCC2)n1] |
| 370 | 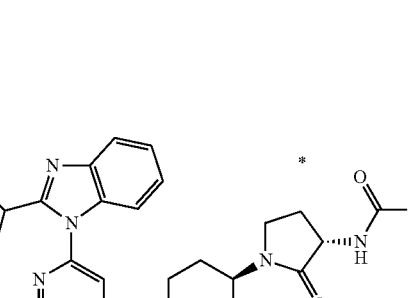 |
| 371 | 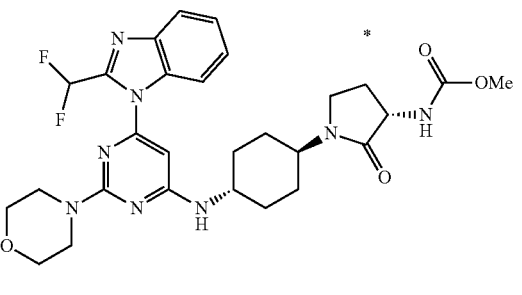 [SMILES: COC(=O)N[C@H]1CCN([C@H]2CC[C@H](Nc3cc(-n4c(C(F)F)nc5ccccc54)nc(N4CCOCC4)n3)CC2)C1=O] |
| 372 | 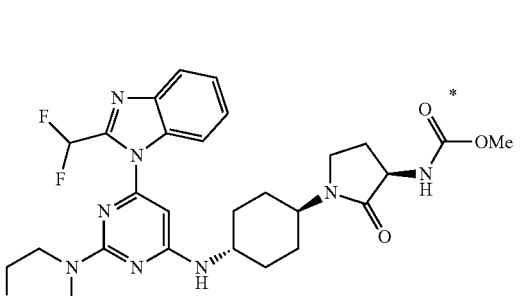 |

TABLE 123

| Ex | Str |
|---|---|
| 373 | |
| 374 | 2HCl |
| 375 | |
| 376 | |

TABLE 124

| Ex | Str |
|---|---|
| 377 | |
| 378 | |
| 379 | |
| 380 | |

TABLE 125
| Ex | Str |
|---|---|
| 381 | 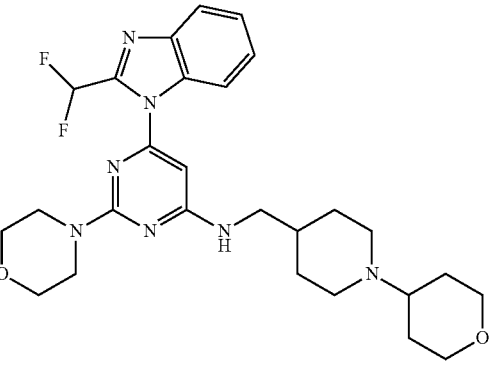 |
| 382 | 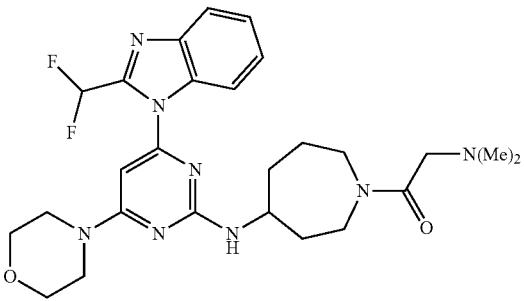 |
| 383 | 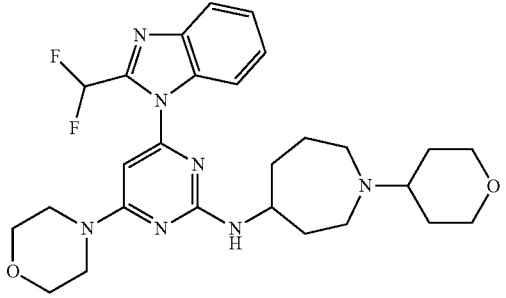 [SMILES: FC(F)c1nc2ccccc2n1-c1cc(N2CCOCC2)nc(NC2CCCN(C3CCOCC3)CC2)n1] |
| 384 | 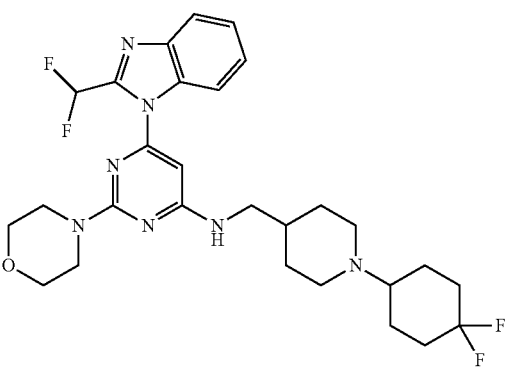 [SMILES: FC(F)c1nc2ccccc2n1-c1cc(NCC2CCN(C3CCC(F)(F)CC3)CC2)nc(N2CCOCC2)n1] |
TABLE 126
| Ex | Str |
|---|---|
| 385 | 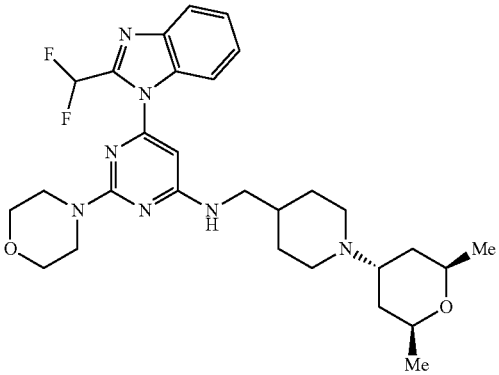 [SMILES: C[C@@H]1C[C@@H](N2CCC(CNc3cc(-n4c(C(F)F)nc5ccccc54)nc(N4CCOCC4)n3)CC2)C[C@H](C)O1] |
| 386 | 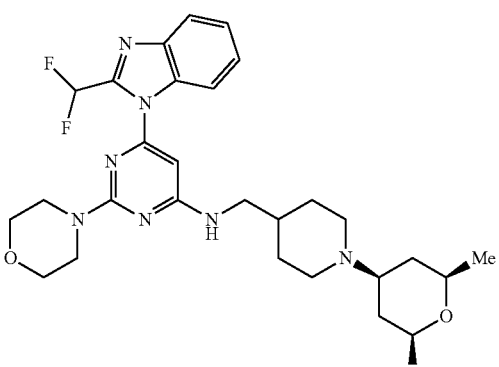 |
| 387 | 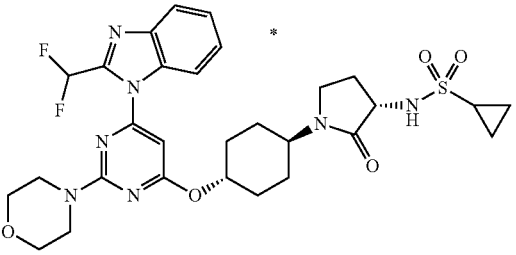 [SMILES: O=C1[C@@H](NS(=O)(=O)C2CC2)CCN1[C@H]1CC[C@H](Oc2cc(-n3c(C(F)F)nc4ccccc43)nc(N3CCOCC3)n2)CC1] |
| 388 | 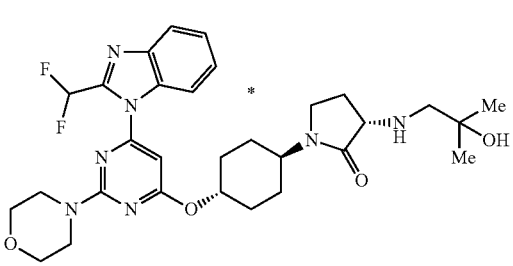 [SMILES: CC(C)(O)CN[C@H]1CCN([C@H]2CC[C@H](Oc3cc(-n4c(C(F)F)nc5ccccc54)nc(N4CCOCC4)n3)CC2)C1=O] |

TABLE 127
| Ex | Str |
|---|---|
| 389 | 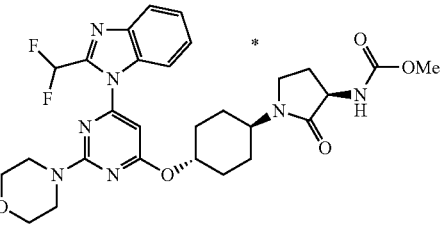 |
| 390 | 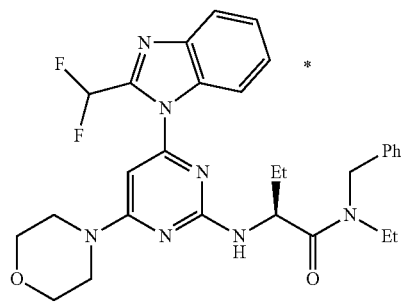 [SMILES: CC[C@H](Nc1nc(N2CCOCC2)cc(-n2c(C(F)F)nc3ccccc32)n1)C(=O)N(CC)Cc1ccccc1] |
| 391 | 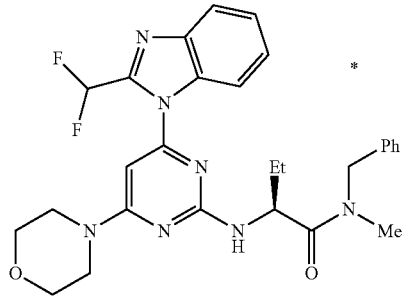 [SMILES: CC[C@H](Nc1nc(N2CCOCC2)cc(-n2c(C(F)F)nc3ccccc32)n1)C(=O)N(C)Cc1ccccc1] |
| 392 | 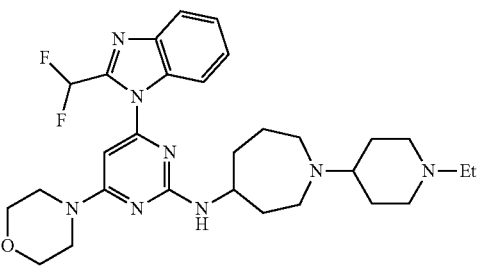 [SMILES: CCN1CCC(N2CCCC(Nc3nc(N4CCOCC4)cc(-n4c(C(F)F)nc5ccccc54)n3)CC2)CC1] |
TABLE 128
| Ex | Str |
|---|---|
| 393 | 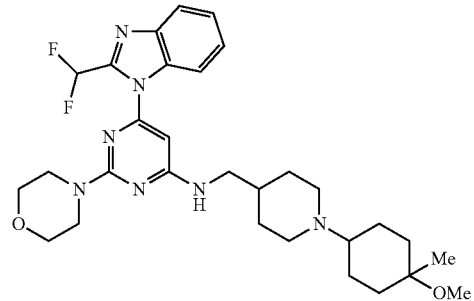 |
TABLE 128-continued
| Ex | Str |
|---|---|
| 394 | 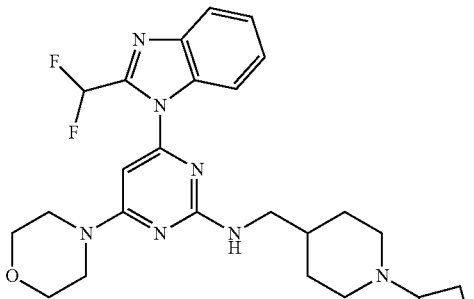 |
| 395 | 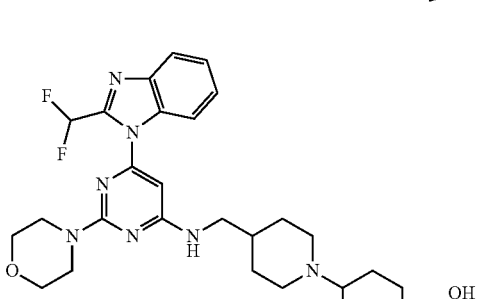 |
| 396 | 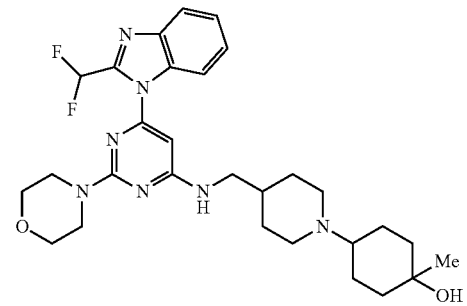 [SMILES: CC1(O)CCC(N2CCC(CNc3cc(-n4c(C(F)F)nc5ccccc54)nc(N4CCOCC4)n3)CC2)CC1] |
TABLE 129
| Ex | Str |
|---|---|
| 397 | 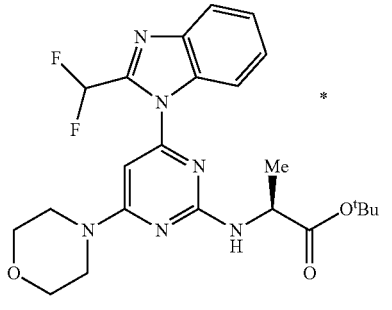 [SMILES: C[C@H](Nc1nc(N2CCOCC2)cc(-n2c(C(F)F)nc3ccccc32)n1)C(=O)OC(C)(C)C] |

TABLE 129-continued

| Ex | Str |
|---|---|
| 398 | (structure) |
| 399 | (structure) |
| 400 | (structure) |

TABLE 130

| Ex | Str |
|---|---|
| 401 | (structure) |
| 402 | (structure) |
| 403 | (structure) |
| 404 | (structure) |

TABLE 131

| Ex | Str |
|---|---|
| 405 | (structure) |

TABLE 131-continued

| Ex | Str |
|---|---|
| 406 | (2-(difluoromethyl)benzimidazol-1-yl)-pyrimidine with morpholine and azepan-4-ylamino substituents |
| 407 | (2-(difluoromethyl)benzimidazol-1-yl)-pyrimidine with morpholine and ((1-acetylpiperidin-4-yl)piperidin-4-yl)methylamino substituents · 2HCl |
| 408 | (2-(difluoromethyl)benzimidazol-1-yl)-pyrimidine with morpholine and (1-(tetrahydropyran-4-yl)azepan-4-yl)amino substituents |

TABLE 132

| Ex | Str |
|---|---|
| 409 | (2-(difluoromethyl)-6-methoxybenzimidazol-1-yl)-pyrimidine with morpholine and ((1-(tetrahydropyran-4-yl)piperidin-4-yl)methyl)amino substituents |

TABLE 132-continued

| Ex | Str |
|---|---|
| 410 | (2-(difluoromethyl)benzimidazol-1-yl)-pyrimidine with morpholine and ((4-(Boc-amino)bicyclo[2.2.2]octan-1-yl)methyl)amino substituents |
| 411 | (2-(difluoromethyl)benzimidazol-1-yl)-pyrimidine with morpholine and ((4-aminobicyclo[2.2.2]octan-1-yl)methyl)amino substituents |
| 412 | (2-(difluoromethyl)benzimidazol-1-yl)-pyrimidine with morpholine and ((4-((2-hydroxy-2-methylpropyl)amino)bicyclo[2.2.2]octan-1-yl)methyl)amino substituents |

TABLE 133

| Ex | Str |
|---|---|
| 413 | (2-(difluoromethyl)benzimidazol-1-yl)-pyrimidine with morpholine and ((4-((2-hydroxy-2-methylpropyl)(methyl)amino)bicyclo[2.2.2]octan-1-yl)methyl)amino substituents |

TABLE 133-continued
| Ex | Str |
|---|---|
| 414 | 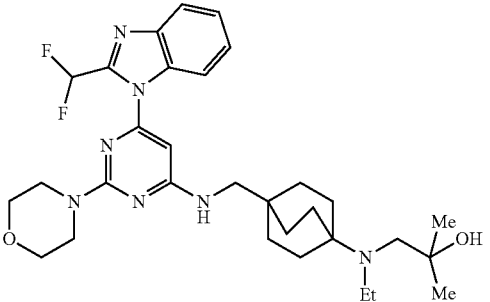 [SMILES: CCN(CC(C)(C)O)C12CCC(CNc3cc(-n4c(C(F)F)nc5ccccc54)nc(N4CCOCC4)n3)(CC1)CC2] |
| 415 | 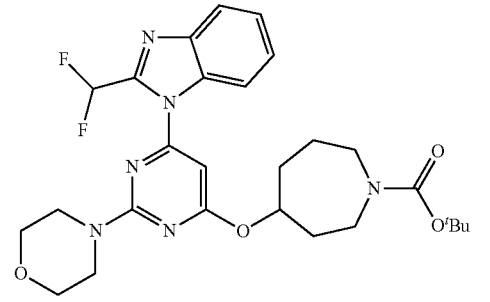 [SMILES: CC(C)(C)OC(=O)N1CCCC(Oc2cc(-n3c(C(F)F)nc4ccccc43)nc(N3CCOCC3)n2)CC1] |
| 416 | 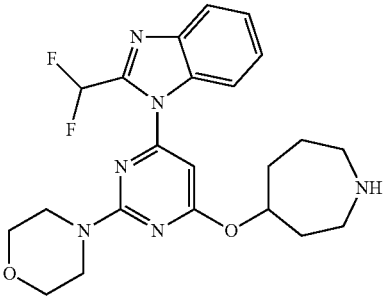 [SMILES: FC(F)c1nc2ccccc2n1-c1cc(OC2CCCNCC2)nc(N2CCOCC2)n1] |
TABLE 134
| Ex | Str |
|---|---|
| 417 | 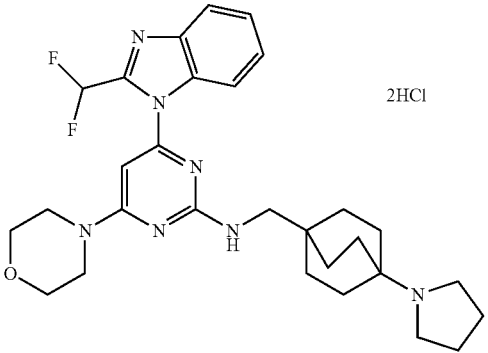 [SMILES: FC(F)c1nc2ccccc2n1-c1cc(N2CCOCC2)nc(NCC23CCC(N4CCCC4)(CC2)CC3)n1] |
TABLE 134-continued
| Ex | Str |
|---|---|
| 418 | 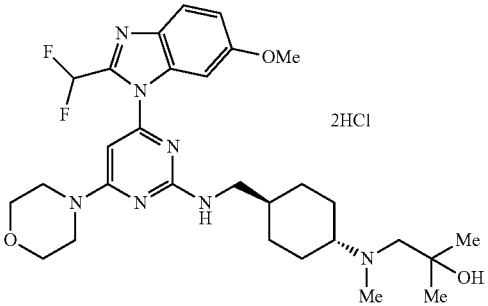 [SMILES: COc1ccc2nc(C(F)F)n(-c3cc(N4CCOCC4)nc(NC[C@H]4CC[C@H](N(C)CC(C)(C)O)CC4)n3)c2c1] 2HCl |
| 419 | 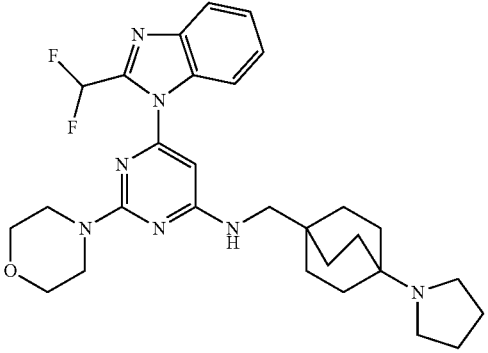 [SMILES: FC(F)c1nc2ccccc2n1-c1cc(NCC23CCC(N4CCCC4)(CC2)CC3)nc(N2CCOCC2)n1] 2HCl |
| 420 | 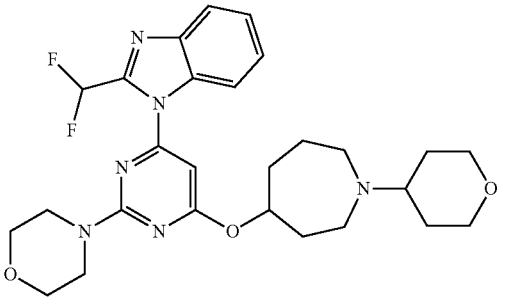 |
TABLE 135
| Ex | Str |
|---|---|
| 421 | 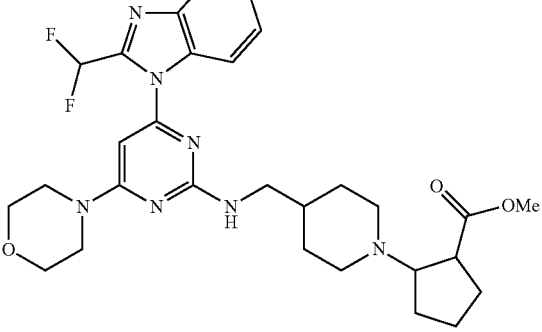 |

TABLE 135-continued
| Ex | Str |
|----|-----|
| 422 | 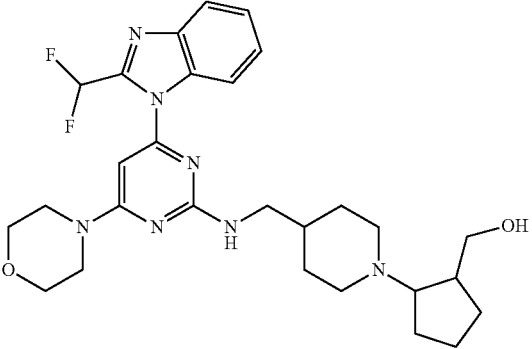 [SMILES: OCC1CCCC1N1CCC(CNc2nc(N3CCOCC3)cc(-n3c(C(F)F)nc4ccccc43)n2)CC1] |
| 423 | 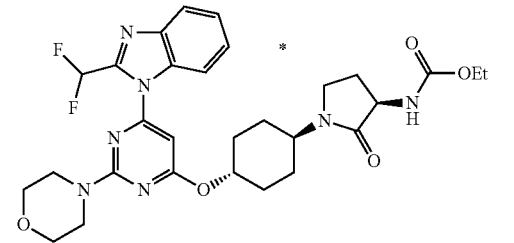 [SMILES: CCOC(=O)N[C@@H]1CCN([C@H]2CC[C@H](Oc3cc(-n4c(C(F)F)nc5ccccc54)nc(N4CCOCC4)n3)CC2)C1=O] |
| 424 | 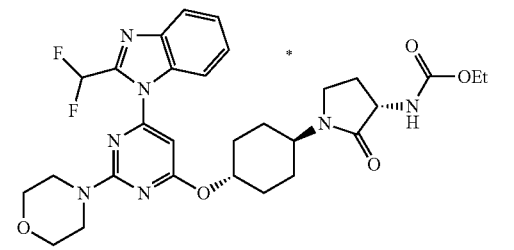 [SMILES: CCOC(=O)N[C@H]1CCN([C@H]2CC[C@H](Oc3cc(-n4c(C(F)F)nc5ccccc54)nc(N4CCOCC4)n3)CC2)C1=O] |
TABLE 136
| Ex | Str |
|----|-----|
| 425 | 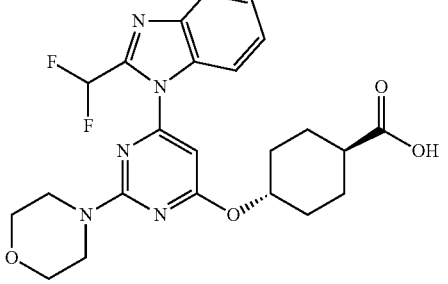 |
| 426 | 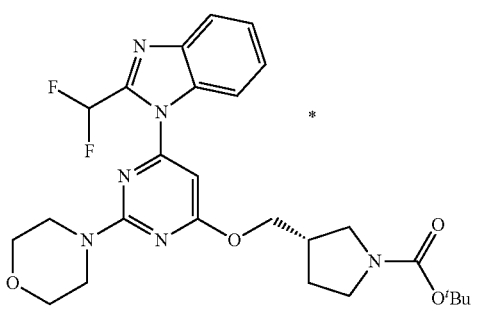 [SMILES: CC(C)(C)OC(=O)N1CC[C@H](COc2cc(-n3c(C(F)F)nc4ccccc43)nc(N3CCOCC3)n2)C1] |
| 427 | 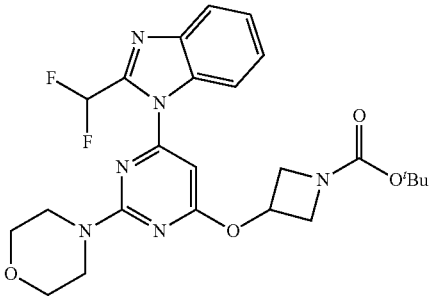 [SMILES: CC(C)(C)OC(=O)N1CC(Oc2cc(-n3c(C(F)F)nc4ccccc43)nc(N3CCOCC3)n2)C1] |
| 428 | 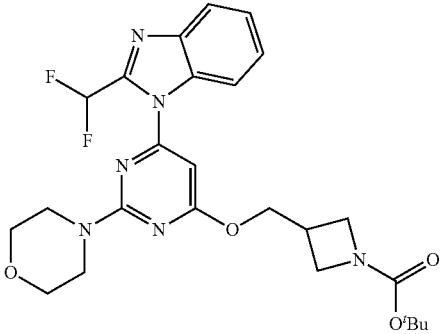 [SMILES: CC(C)(C)OC(=O)N1CC(COc2cc(-n3c(C(F)F)nc4ccccc43)nc(N3CCOCC3)n2)C1] |
| 429 | 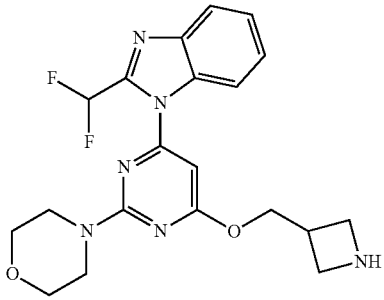 [SMILES: FC(F)c1nc2ccccc2n1-c1cc(OCC2CNC2)nc(N2CCOCC2)n1] |
TABLE 137
| Ex | Str |
|----|-----|
| 430 | 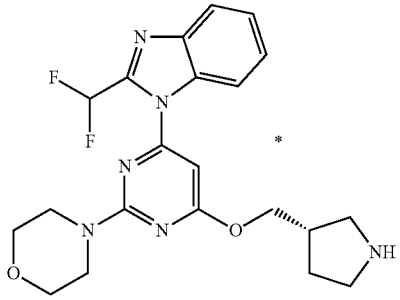 [SMILES: FC(F)c1nc2ccccc2n1-c1cc(OC[C@H]2CCNC2)nc(N2CCOCC2)n1] |

TABLE 137-continued

| Ex | Str |
|---|---|
| 431 | |
| 432-1 | |
| 432-2 | |
| 433 | |

TABLE 138

| Ex | Str |
|---|---|
| 434 | |
| 435 | |
| 436 | |
| 437 | |
| 438 | |

TABLE 139

| Ex | Str |
|---|---|
| 439 | |
| 440 | |
| 441 | |
| 442 | |
| 443 | |

TABLE 140

| Ex | Str |
|---|---|
| 444 | |
| 445 | |
| 446 | |
| 447 | |
| 448 | |

TABLE 141

| Ex | Str |
|---|---|
| 449 | (structure) |
| 450 | (structure) |
| 451 | (structure) |
| 452 | (structure) |
| 453 | (structure) |

TABLE 142

| Ex | Str |
|---|---|
| 454 | (structure) |
| 455 | (structure) |
| 456 | (structure) |
| 457 | (structure) |
| 458 | (structure) |

TABLE 143

| Ex | Str |
|---|---|
| 459 | |
| 460 | |
| 461 | |
| 462 | |
| 463 | |

TABLE 144

| Ex | Str |
|---|---|
| 464 | |
| 465 | |
| 466 | |
| 467 | |

TABLE 145

| Ex | Str |
|---|---|
| 468 | 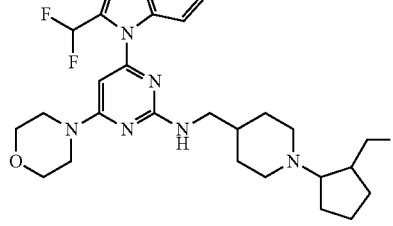 |
| 469 | 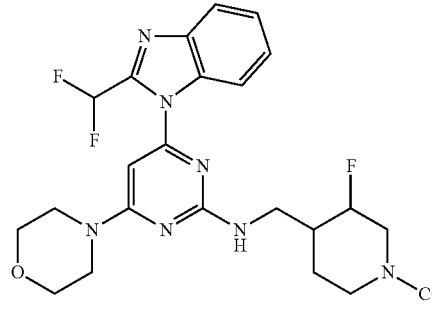 |
| 470 | 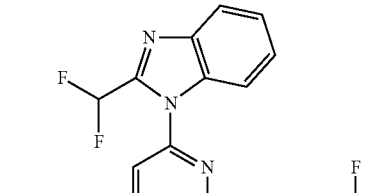 |

TABLE 146

| Ex | Syn | DAT |
|---|---|---|
| 1 | 1 | ESI+: 516<br>NMR1:1.39(9H,s),1.81-1.94(H,m),2.02-2.16(1H,m),3.11-3.87(12H,m),4.27-4.43(1H,m),6.33-6.46(1H,m),7.29-7.87(6H,m) |
| 2 | 1 | ESI+: 458<br>NMR1:1.14-1.27(2H,m),1.46-1.58(1H,m),1.64-1.85(4H,m),2.13(3H,s),2.71-2.80(2H,m),3.06-3.34(2H,m),3.40-3.76(8H,m),5.64(1H,s),7.33-7.49(3H,m),7.79-7.86(1H,m)8.32-8.44(1H,m) |
| 3 | 1 | ESI+: 458<br>NMR1:0.79-1.84(7H,m),2.12(3H,s),2.67-2.71(2H,m),3.01-3.18(2H,m),3.63-3.68(8H,m),6.21-6.38(1H,m),7.13-7.19(1H,m),7.39-7.86(5H,m) |
| 4 | 1 | ESI+: 458<br>NMR1:1.12-1.30(2H,m),1.43-1.60(1H,m),1.63-1.72(2H,m),1.75-1.86(2H,m),2.14(3H,s),2.71-2.80(2H,m),3.21-3.32(2H,m),3.61-3.72(8H,m),6.14(1H,s),7.37-7.89(6H,m) |
| 5 | 1 | ESI+: 567[M+Na]<br>NMR1:0.98-1.13(2H,m),1.36-1.40(9H,m),1.63-1.83(3H,m),2.57-2.80(2H,m),3.22-3.32(2H,m),3.62-3.84(8H,m),3.87-4.01(2H,m),7.39-8.07(5H,m),8.40-8.58(1H,m) |
| 6 | 1 | ESI+: 538[M+Na]<br>NMR1:1.39(9H,s),1.60-2.16(2H,m),3.12-3.45(2H,m),3.59-3.76(9H,m),3.98-4.08(1H,m),4.31-4.40(1H,m),6.02-6.09(1H,m),6.34-6.45(1H,m),7.33-7.90(5H,m) |
| 7 | 1 | ESI+: 552[M+Na]<br>NMR1:1.39(9H,s),1.66-1.98(4H,m),3.57-3.74(10H,m),3.74-3.94(3H,m),6.28-6.41(1H,m),6.99-7.13(1H,m),7.37-7.90(5H,m) |
| 8 | 1 | ESI+: 524[M+Na]<br>NMR1:1.37(9H,s),3.57-4.17(12H,m),4.48-4.57(1H,m),6.37-6.47(1H,m),7.20-7.97(6H,m) |
| 9 | 1 | ESI+: 524[M+Na]<br>NMR1:1.37-1.41(9H,m),3.60-3.72(8H,m),3.74-3.84(2H,m),4.13-4.26(2H,m),4.55-4.70(1H,m),6.11(1H,s),7.36-7.66(3H,m),7.70-7.89(2H,m),8.10-8.22(1H,m) |
| 10 | 1 | ESI+: 528<br>NMR1:0.79(9H,m),1.95-2.10(2H,m),2.26-2.45(1H,m),2.78-2.91(2H,m),3.03-3.42(4H,m),3.54-3.71(8H,m),3.79-3.92(2H,m),6.26-6.37(1H,m),7.13-7.18(1H,m),7.39-7.86(5H,m) |
| 11 | 1 | ESI+: 544<br>NMR1:0.90-1.12(2H,m)1.32-1.45(9H,m),1.58-1.81(3H,m),2.53-2.80(2H,m),3.06-3.26(2H,m),3.55-3.75(8H,m),3.83-4.00(2H,m),6.23-6.40(1H,m),7.18(1H,br-s),7.36-7.89(5H,m) |

TABLE 147

| Ex | Syn | DAT |
|---|---|---|
| 12 | 1 | ESI+: 558<br>NMR1:0.91-1.12(2H,m),1.23(3H,d,J=6.8Hz),1.38(9H,s),1.60-1.82(3H,m),2.53-2.78(2H,m),3.06-3.29(3H,m),3.39-3.52(1H,m),3.57-3.66(1H,m),3.68-3.77(1H,m),3.85-4.16(4H,m),4.41(1H,br-s),6.20-6.35(1H,m),7.18(1H,br-s),7.40-7.90(5H,m) |
| 13 | 1 | ESI+: 558<br>NMR1:0.91-1.12(2H,m),1.23(3H,d,J=6.8Hz),1.38(9H,s),1.60-1.82(3H,m),2.53-2.78(2H,m),3.06-3.29(3H,m),3.39-3.52(1H,m),3.57-3.66(1H,m),3.68-3.77(1H,m),3.85-4.16(4H,m),4.41(1H,br-s),6.20-6.35(1H,m),7.18(1H,br-s),7.40-7.900(5H,m) |
| 14 | 1 | ESI+: 572<br>NMR1:0.90(3H,t,J=7.5Hz),0.92-1.11(2H,m),1.38(9H,s),1.60-1.87(5H,m),2.56-2.78(2H,m),3.06-4.44(11H,m),6.18-6.35(1H,m),7.34-7.89(5H,m) |
| 15 | 1 | ESI+: 574<br>NMR1:0.91-1.11(2H,m),1.20-1.31(1H,m),1.32-1.41(9H,m),1.57-1.81(3H,m),2.59-2.80(2H,m),3.02-3.25(3H,m),3.37-3.62(3H,m),3.66-3.77(1H,m),3.81-4.44(5H,m),4.84-4.92(1H,m),6.20-6.36(1H,m),7.15(1H,br-s),7.35-7.89(5H,m) |
| 16 | 1 | ESI+: 576<br>NMR1:0.92-1.11(2H,m),1.20-1.30(1H,m),1.33-1.42(9H,m),1.54-1.80(3H,m),2.54-2.81(2H,m),3.06-4.30(10H,m),4.55-4.83(2H,m),6.29-6.40(1H,m),7.25(1H,br-s),7.36-7.90(5H,m) |
| 17 | 1 | ESI+: 548<br>NMR1:1.40(9H,s),1.56-1.82(2H,m),2.71-3.80(10H,m),3.91-4.31(3H,m),4.66-5.00(1H,m),6.31-6.48(1H,m),7.00-7.94(6H,m) |

TABLE 147-continued

| Ex | Syn | DAT |
|---|---|---|
| 18 | 1 | ESI+: 544<br>NMR1:0.99-1.43(11H,m),1.54-1.80(3H,m),2.69-2.85(1H,m),3.02-4.00(13H,m),6.25-6.42(1H,m),7.12-7.29(1H,m),7.35-7.89(5H,m) |
| 19 | 1 | ESI+: 544<br>NMR1:0.99-1.43(11H,m),1.54-1.80(3H,m),2.69-2.85(1H,m),3.02-4.00(13H,m),6.25-6.42(1H,m),7.12-7.29(1H,m),7.35-7.89(5H,m) |
| 20 | 1 | ESI+: 558<br>NMR1:1.00-1.42(14H,m),1.54-1.80(3H,m),2.69-2.85(1H,m),3.02-4.00(13H,m),6.25-6.42(1H,m),7.12-7.29(1H,m),7.35-7.89(5H,m) |
| 21 | 1 | ESI+: 558<br>NMR1:1.00-1.41(14H,m),1.54-1.82(3H,m),2.68-2.85(1H,m),3.00-4.17,(11H,m),4.42(1H,br-s),6.19-6.36(1H,m),7.10-7.27(1H,m),7.35-7.89(5H,m) |
| 22 | 22 | ESI+: 520<br>NMR1:2.06-2.27(3H,m),2.79-3.85(14H,m),4.27-4.48(2H,m),5.46-5.70(1H,m),7.35-7.89(11H,m) |

TABLE 148

| Ex | Syn | DAT |
|---|---|---|
| 23 | 22 | ESI+: 506<br>NMR1:2.98-3.84(14H,m),4.36-4.63(3H,m),6.39-6.52(1H,m),7.21-7.88(11H,m) |
| 24 | 22 | ESI+: 506<br>NMR1:1.87-2.54(2H,m),2.96-3.85(12H,m),4.23-4.67(3H,m),6.32-6.53(1H,m),7.28-7.88(11H,m) |
| 25 | 22 | ESI+: 548<br>NMR1:1.33-1.96(8H,m),2.76-3.85(12H,m),4.23-4.67(3H,m),6.32-6.53(1H,m),7.28-7.88(11H,m) |
| 26 | 26 | ESI+: 520<br>NMR1:1.22-3.08(10H,m),3.57-3.71(8H,m),4.24-4.38(1H,m),6.30-6.42(1H,m),7.11-7.88(11H,m) |
| 27 | 26 | ESI+: 502<br>NMR1:0.79-0.89(1H,m),1.21-1.38(2H,m),2.62-2.71(2H,m),2.78-2.86(1H,m),3.45-3.61(4H,m),3.61-3.72(8H,m),4.32-4.45(1H,m),6.29-6.44(1H,m),7.36-7.93(6H,m) |
| 28 | 26 | ESI+: 542<br>NMR1:0.96-3.38(21H,m),3.56-3.78(8H,m),4.18-4.45(1H,m),6.23-6.37(1H,m),7.08-7.18(1H,m),7.36-7.89(5H,m) |
| 29 | 26 | ESI+: 556<br>NMR1:0.74-3.36(23H,m),3.55-3.75(8H,m),4.28-4.37(1H,m),6.24-6.37(1H,m),7.09-7.17(1H,m),7.36-7.90(5H,m) |
| 30 | 26 | ESI+: 627<br>NMR1:1.01-3.74(35H,m),3.85-4.01(2H,m),6.24-6.37(1H,m),7.11-7.19(1H,m),7.36-7.89(5H,m) |
| 31 | 26+44 | ESI+: 541<br>NMR1:1.44-3.76(31H,m),6.29-6.44(1H,m),7.28-7.89(6H,m) |
| 32 | 26+44 | ESI+: 567<br>NMR1:0.70-3.75(33H,m),6.29-6.44(1H,m),7.26-7.89(6H,m) |
| 33 | 26+44 | ESI+: 569<br>NMR1:1.35-4.70(31H,m),6.29-6.45(1H,m),7.28-7.89(6H,m) |
| 34 | 26+44 | ESI+: 605<br>NMR1:1.45-3.77(31H,m),6.30-6.44(1H,m),7.27-7.89(6H,m) |
| 35 | 26+44 | ESI+: 522<br>NMR1:1.49-2.11(5H,m),3.04-3.53(6H,m),3.59-3.75(8H,m),3.83-4.05(1H,m),4.80-5.15(4H,m),6.29-6.44(1H,m),7.25-7.89(6H,m) |
| 36 | 26+44 | ESI+: 562<br>NMR1:1.37-2.23(13H,m),2.83-3.49(7H,m),3.57-3.78(8H,m),6.28-6.43(1H,m),7.25-7.35(1H,m),7.37-7.89(5H,m) |

TABLE 149

| Ex | Syn | DAT |
|---|---|---|
| 37 | 26+44 | ESI+: 542<br>NMR1:1.00-1.27(5H,m),1.30-1.74(7H,m),1.95-2.10(2H,m),2.30-2.42(1H,m),2.80-2.91(2H,m),3.05-3.34(5H,m),3.39-3.52(1H,m),3.56-3.65(1H,m),3.67-3.97(4H,m),4.00-4.14(1H,m),4.33-4.49(1H,m),6.18-6.32(1H,m),7.13(1H,br-s),7.35-7.89(5H,m) |

TABLE 149-continued

| Ex | Syn | DAT |
|---|---|---|
| 38 | 26+44 | ESI+: 542<br>NMR1:1.24(3H,d,J=6.7Hz),1.43-2.08(9H,m),2.71-2.97(2H,m),3.06-3.39(7H,m),<br>3.40-3.82(5H,m),3.89-3.99(3H,m),4.34-4.49(1H,m),6.24-6.39(1H,m),7.24-7.89(6H,m) |
| 39 | 26+44 | ESI+: 542<br>NMR1:1.02-3.36(17H,m),3.42-3.54(2H,m),3.59-3.74(8H,m),3.77-3.89(3H,m),6.39<br>(1H,br-s),7.25-7.89(6H,m) |
| 40 | 26+44 | ESI+: 529<br>NMR:1.64-2.17(9H,m),2.90-3.03(2H,m),3.23-3.81(13H,m),3.93-4.01(2H,m),<br>4.31(2H,d,J=6.3Hz),6.43(1H,s),7.39-7.68(3H,m),7.74-7.79(1H,m),7.85-7.90(1H,m) |
| 41 | 26+44 | ESI+: 528<br>NMR1:1.43-2.08(9H,m),2.74-2.94(2H,m),3.07-3.38(5H,m),3.40-3.52(2H,m),<br>3.58-3.75(8H,m),3.88-4.01(2H,m),6.28-6.45(1H,m),7.24-7.90(6H,m) |
| 42 | 26+44 | ESI+: 528<br>NMR:1.06-4.30(28H,m),6.30-6.45(1H,m),7.29(1H,br-s),7.37-7.88(5H,m) |
| 43-1 | 43 | ESI+: 544<br>NMR1:1.19-2.25(13H,m),2.79-3.43(7H,m),3.58-3.75(8H,m),4.39-4.62(1H,m),<br>6.30-6.46(1H,m),7.25-7.90(6H,m) |
| 43-2 | 43 | ESI+: 544<br>NMR1:1.20-2.18(13H,m),2.82-3.46(7H,m),3.59-3.75(8H,m),4.72-4.91(1H,m),<br>6.26-6.47(1H,m),7.19-7.89(6H,m) |
| 44 | 44 | ESI+: 520<br>NMR1:1.68-2.10(5H,m),3.18-3.95(14H,m),6.29-6.45(1H,m),7.31-7.96(11H,m) |
| 45 | 45 | ESI+: 487<br>NMR1:1.96-2.57(4H,m),2.75-4.07(20H,m),4.45-4.65(1H,m),6.41-6.59(1H,m),<br>7.37-7.90(6H,m) |
| 46 | 45 | ESI+: 530<br>NMR1:1.07-1.30(5H,m),1.43-1.73(3H,m),2.03-2.18(2H,m),2.75-2.86(2H,m),<br>3.07-3.23(4H,m),3.58-3.74(8H,m),4.02-4.11(2H,m),6.23-6.38(1H,m),<br>7.09-7.18(1H,m),7.28-7.87(5H,m) |
| 47 | 45+44 | ESI+: 501<br>NMR1:1.36-2.01(5H,m),2.84-4.51(16H,m),6.27-6.45(1H,m),7.20-8.06(8H,m) |

TABLE 150

| Ex | Syn | DAT |
|---|---|---|
| 48 | 45+44 | ESI+: 528<br>NMR1:1.42-2.03(5H,m),2.49-3.44(7H,m),3.56-4.60(12H,m),6.37(1H,br-s),7.23-7.88(6H,m) |
| 49 | 45+44 | ESI+: 515<br>NMR1:1.37-1.92(5H,m),2.55-2.95(4H,m),3.10-3.48(6H,m),3.60-3.75(8H,m),6.38(1H,br-s),<br>6.98-7.89(8H,m) |
| 50 | 45+44 | ESI+: 504<br>NMR1:1.36-1.93(5H,m),2.01-2.20(2H,m),2.76-2.94(2H,m),3.03-3.54(6H,m),3.60-3.74(8H,m),<br>4.42-4.63(2H,m),6.29-6.45(1H,m),7.24-7.90(6H,m) |
| 51 | 45+44 | ESI+: 518<br>NMR1:1.35-1.92(9H,m),2.74-3.53(8H,m),3.57-3.73(8H,m),4.36-4.57(2H,m),6.29-6.44(1H,m),)<br>7.23-7.34(1H,m),7.37-7.88(5H,m |
| 52 | 52 | ESI+: 520<br>NMR1:1.09-1.31(2H,m),1.46-1.72(2H,m),1.87-1.98(2H,m),2.20-2.34(2H,m),2.77-2.91(2H,m),<br>3.09-3.21(2H,m),3.60-3.73(8H,m),3.73-3.83(2H,m),4.17-4.47(2H,m),4.81-4.87(1H,m),6.26-6.37<br>(1H,m),7.12-7.20(1H,m),7.38-7.90(5H,m) |
| 53 | 53 | ESI+: 416<br>NMR1:1.93-2.02(1H,m),2.11-2.23(1H,m),3.07-3.92(12H,m),4.42-4.53(1H,m),6.46(1H,br-s),<br>7.39-7.87(7H,m),9.35(2H,br-s) |
| 54 | 54 | ESI+: 430<br>NMR1:1.27-1.38(2H,m),1.70-1.88(2H,m),2.86-2.98(2H,m),3.57-3.78(11H,m),<br>6.28-6.38(1H,m),6.94-7.06(1H,m),7.36-7.87(6H,m) |
| 55 | 54 | ESI+: 445<br>NMR1:0.97-1.13(2H,m),1.57-1.73(3H,m),2.31-2.48(2H,m),2.86-2.96(2H,m),3.16-3.32(2H,m),<br>3.62-3.86(8H,m),7.38-7.52(2H,m),7.63-8.08(3H,m),8.42-8.59(1H,m) |
| 56 | 54 | ESI+: 416<br>NMR1:1.57-1.65(1H,m),1.86-2.04(1H,m),2.59-2.78(2H,m),2.83-3.07(2H,m),3.58-3.72(8H,m),<br>4.17-4.27(1H,m),6.28-6.43(1H,m),7.00-7.18(1H,m),7.37-7.87(5H,m) |
| 57 | 54 | ESI+: 402<br>NMR1:3.44-3.60(4H,m),3.62-3.75(8H,m),4.56-4.69(1H,m),6.30-6.42(1H,m),6.83(1H,s),<br>7.37-7.93(5H,m),8.31(1H,s) |
| 58 | 54 | ESI+: 402<br>NMR1:3.41-3.49(2H,m),3.59-3.71(10H,m),4.70-4.81(1H,m),6.10(1H,s),7.36-7.65(3H,m),<br>7.69-7.88(2H,m),7.98-8.06(1H,m) |
| 59 | 54 | ESI+: 499<br>NMR1:1.52-1.66(4H,m),2.62-2.69(1H,m),2.85-2.94(1H,m),3.39-3.53(4H,m),<br>3.62-3.72(8H,m),4.52-4.63(2H,m),6.37-6.49(1H,m),7.37-7.97(6H,m) |

TABLE 151

| Ex | Syn | DAT |
|---|---|---|
| 60 | 54 | ESI+: 444<br>NMR1:0.91-3.28(11H,m),3.55-3.76(8H,m),6.23-6.39(1H,m),<br>7.07-7.19(1H,m),7.36-7.89(5H,m) |
| 61 | 54 | ESI+: 458<br>NMR1:1.0.91-1.11(2H,m),1.23(3H,d,J=6.7Hz),1.54-1.70(3H,m),<br>2.31-2.44(2H,m),2.84-2.95(2H,m),3.03-3.52(5H,m),3.56-3.77(2H,m),<br>3.88-3.98(1H,m),4.00-4.16(1H,m),4.33-4.50(1H,m),6.18-6.32(1H,m),<br>7.05-7.19(1H,m),7.58-7.88(5H,m) |
| 62 | 54 | ESI+: 458<br>NMR1:0.91-1.11(2H,m),1.23(3H,d,J=6.7Hz),1.54-1.70(3H,m),2.31-2.45(2H,m),<br>2.84-2.97(2H,m),3.03-3.53(5H,m),3.57-3.77(2H,m),3.88-3.98(1H,m),<br>4.00-4.16(1H,m),4.33-4.50(1H,m),6.18-6.32(1H,m),7.05-7.19(1H,m),7.58-7.88(5H,m) |
| 63 | 54 | ESI+: 445<br>NMR1:1.09-1.23(2H,m),1.62-1.72(2H,m),1.78-1.91(1H,m),2.40-2.50(2H,m),<br>2.91-2.98(2H,m),3.64-3.79(8H,m)4.22(2H,d,J=6.4Hz),6.42(1H,s),7.39-7.50(2H,m),<br>7.54(1H,t,J=52.5Hz),7.74-7.89(2H,m) |
| 64 | 54 | ESI+: 444<br>NMR1:0.93-1.13(1H,m),1.19-1.37(2H,m),1.44-1.80(3H,m),2.07-2.45(2H,m),2.72-2.99<br>(2H,m),3.02-3.20(2H,m),3.56-3.74(8H,m),6.22-6.39(1H,m),7.13(1H,br-s),7.36-7.89(5H,m) |
| 65 | 54 | ESI+: 444<br>NMR1:0.93-1.13(1H,m),1.19-1.37(2H,m),1.44-1.80(3H,m),2.07-2.45(2H,m),<br>2.72-2.99(2H,m),3.02-3.20(2H,m),3.56-3.74(8H,m),6.22-6.39(1H,m),7.13(1H,br-s),<br>7.36-7.89(5H,m) |
| 66 | 66 | ESI+: 515<br>NMR1:1.22-1.51(2H,m),1.77-2.00(2H,m),2.17(6H,s),2.63-2.83(1H,m),2.96-3.18(3H,m),<br>3.56-3.75(8H,m),3.90-4.05(2H,m),4.18-4.31(1H,m),6.28-6.43(1H,m),7.04-7.17(1H,m),<br>7.37-7.89(5H,m) |
| 67 | 66 | ESI+: 530<br>NMR1:0.95-1.31(2H,m),1.67-1.91(3H,m),2.11-2.21(6H,m),2.86-3.15(3H,m),3.22-3.33<br>(2H,m),3.63-3.85(8H,m),3.99-4.09(1H,m),4.30-4.39(1H,m),7.39-7.53(2H,m),7.64-8.09<br>(3H,m),8.41-8.59(1H,m) |
| 68 | 66 | ESI+: 501<br>NMR1:1.80-2.25(10H,m),2.92-3.01(2H,m),3.45-3.75(10H,m),4.32-4.45(1H,m),6.33-6.47<br>(1H,m),7.31-7.88(6H,m) |
| 69 | 66 | ESI+: 487<br>NMR1:2.17(6H,s),2.83-2.96(2H,m),3.55-3.74(8H,m),3.79-3.85(1H,m),4.01-4.19(2H,m),<br>4.39-4.61(2H,m),6.37-6.48(1H,m),7.37-7.89(6H,m) |
| 70 | 66 | ESI+: 599 |

TABLE 152

| Ex | Syn | DAT |
|---|---|---|
| 71 | 71 | ESI+: 509[M+Na]<br>NMR1:0.96-1.21(4H,m),1.66-1.90(3H,m),1.95-1.99(3H,m),2.91-3.04<br>(1H,m),3.23-3.32(2H,m),3.63-3.87(8H,m),4.32-4.41(1H,m),7.39-7.54<br>(2H,m),7.63-8.09(3H,m),8.41-8.59(1H,m) |
| 72 | 66+44 | ESI+: 529<br>NMR1:0.92-1.28(2H,m),1.67-1.93(3H,m),2.59-2.86(7H,m),2.91-3.30<br>(3H,m),3.54-4.41(12H,m),6.26-6.44(1H,m),7.27(1H,br-s),7.37-7.90(5H,m) |
| 73 | 66+44 | ESI+: 543<br>NMR1:0.89-1.28(2H,m),1.64-1.91(3H,m),2.45-3.28(15H,m),3.76-3.97<br>(8H,m),4.31-4.41(1H,m),6.38(1H,br-s),7.25-7.99(6H,m) |
| 74 | 74 | ESI+: 520 |
| 75 | 74+44 | ESI+: 538<br>NMR1:1.60-2.07(5H,m),3.17-3.95(14H,m),6.29-6.45(1H,m),<br>7.29-7.97(10H,m) |
| 76 | 74+44 | ESI+: 538<br>NMR1:1.41-1.72(2H,m),1.79-1.95(3H,m),2.95-3.35(4H,m),3.59-3.76(10H,m),<br>6.38(1H,br-s),6.80-7.91(10H,m) |
| 77 | 74+44 | ESI+: 538<br>NMR1:1.33-1.53(2H,m),1.68-1.88(3H,m),2.68-2.83(2H,m),3.18-3.32(2H,m),<br>3.34-3.44(2H,m),3.61-3.73(8H,m),6.36(1H,br-s),6.97-7.90(10H,m) |
| 78 | 74+44 | ESI+: 550<br>NMR1:1.74-2.08(5H,m),3.18-3.78(17H,m),6.36(1H,br-s),7.02-7.13(2H,m),<br>7.26-7.90(8H,m) |
| 79 | 74+44 | ESI+: 534<br>NMR1:1.67-2.08(5H,m),2.33(3H,s),3.16-3.77(14H,m),6.36(1H,br-s),7.25-7.89<br>(10H,m) |
| 80 | 80 | ESI+: 545<br>NMR1:1.11-1.26(2H,m),1.40(9H,s),1.70-1.79(2H,m),1.89-2.03(1H,m),2.64-2.85<br>(2H,m),3.63-3.80(8H,m),3.91-4.05(2H,m),4.27(2H,d,J=6.4Hz),6.43(1H,s),<br>7.38-7.50(2H,m),7.54(1H,t,J=52.5Hz),7.73-7.89(2H,m) |

TABLE 152-continued

| Ex | Syn | DAT |
|---|---|---|
| 81 | 80 | ESI+: 559<br>NMR1:1.10-1.27(5H,m),1.40(9H,s),1.70-1.79(2H,m),1.91-2.03(1H,m),2.68-2.84(2H,m),3.17-3.29(1H,m),3.40-3.49(1H,m),3.55-3.62(1H,m),3.68-3.75(1H,m),3.89-4.04(3H,m),4.19-4.33(3H,m),4.56-4.64(1H,m),6.43(1H,s),7.39-7.50(2H,m),7.54(1H,t,J=52.5Hz),7.74-7.90(2H,m) |
| 82 | 82 | ESI+: 422[M+Na] |
| 83 | 83 | ESI+: 487 |
| 84 | 84 | ESI+: 628 |

TABLE 153

| Ex | Syn | DAT |
|---|---|---|
| 85 | 52 | ESI+: 556<br>NMR1:1.03(6H, s), 1.43(12H, brs), 2.28(2H, brs), 3.01-3.14(2H, m), 3.57-3.72(8H, m), 4.01(1H, brs), 6.21-6.37(1H, m), 6.76-7.02(1H, m), 7.34-7.96(5H, m) |
| 86 | 86 | ESI+: 584 |
| 87 | 87 | ESI+: 586<br>NMR1:1.50-1.81(7H, m), 2.23(3H, br), 3.16-3.25(1H, m), 3.28-3.36(1H, m), 3.54(3H, s), 3.70(4H, br), 3.74(4H, br), 3.81(1H, br), 4.08-4.18(1H, m), 4.99-5.08(1H, m), 6.40(1H, m), 6.40(1H, s), 7.38-7.50(3H, m), 7.53(1H, t, J = 52.5 Hz), 7.75(1H, d, J = 7.8 Hz), 7.86(1H, d, J = 7.8 Hz) |
| 88 | 88 | ESI+: 606 |
| 89 | 89 | ESI+: 556<br>NMR1:1.36-1.73(8H, m), 1.81-1.91(2H, m), 1.97-2.21(4H, m), 2.97(2H, s), 3.05-3.16(1H, m), 3.60-3.80(9H, m), 5.00-5.10(1H, m), 6.40(1H, s), 7.38-7.68(4H, m), 7.72-7.78(1H, m), 7.83-7.89(1H, m) |
| 90 | 54 | ESI+: 472 |
| 91 | 91 | ESI+: 514[M + Na]<br>NMR:1.44-1.67(5H, m), 1.76-2.03(3H, m), 2.76-2.87(1H, m), 2.95-3.09(1H, m), 3.12-3.23(1H, m), 3.62-3.94(10H, m), 7.39-7.52(2H, m), 7.70-8.28(3H, m), 8.43-8.58(1H, m) |
| 92 | 92 | ESI+: 502 |
| 93 | 93 | ESI+: 458 |
| 94 | 94 | ESI+: 530[M + Na]<br>NMR1:1.47-1.73(4H, m), 1.80-2.00(4H, m), 3.29-3.92(13H, m), 7.38-8.24(5H, m), 8.43-8.56(1H, m) |
| 95 | 92 | ESI+: 531 |
| 96 | 92 | ESI+: 516<br>NMR1:1.39(9H, s), 2.15-2.34(4H, m), 3.61-3.72(8H, m), 3.99-4.13(1H, m), 4.38-4.50(1H, m), 6.09(1H, s), 7.25-7.94(7H, m) |
| 97 | 92 | ESI+: 544 |
| 98 | 92 | ESI+: 531<br>NMR1:1.38(9H, s), 1.42-2.36(6H, m), 3.54-4.12(9H, m), 5.48(1H, m), 6.97(1H, d, J = 8 Hz), 7.18-7.93(5H, m) |
| 99 | 71 | ESI+: 570<br>NMR1:1.51-1.79(7H, m), 1.84(3H, s), 2.17-2.34(3H, m), 3.17-3.26(1H, m), 3.27-3.38(2H, m), 3.70(4H, br), 3.74(4H, br), 3.82(1H, br), 4.98-5.10(1H, s), 6.40(1H, m), 7.38-7.49(2H, m), 7.54(1H, t, J = 52.4 Hz), 7.74(1H, d, J = 7.8 Hz), 7.86(1H, d, J = 7.4 Hz), 8.15(1H, d, J = 8.2 Hz) |
| 100 | 66 + 44 | ESI+: 529<br>NMR1:1.20-1.90(8H, m), 2.72-2.85(6H, m), 3.58-4.38(12H, m), 6.26(1H, s), 7.39-7.69(4H, m), 7.72-7.78(1H, m), 7.84-7.89(1H, m), 8.54-8.63(1H, m) |
| 101 | 66 | ESI+: 676 |

TABLE 154

| Ex | Syn | DAT |
|---|---|---|
| 102 | 66 | ESI+: 676 |
| 103 | 66 | ESI+: 516 |
| 104 | 66 | ESI+: 516 |
| 105 | 66 | ESI+: 544 |
| 106 | 66 | ESI+: 552 |
| 107 | 66 | ESI+: 541 |
| 108 | 66 | ESI+: 541 |
| 109 | 66 | ESI+: 541 |
| 110 | 66 | ESI+: 542 |
| 111 | 66 | ESI+: 515 |
| 112 | 1 | ESI+: 463<br>NMR1:1.23(4H, s), 3.57(8H, s), 6.21-8.09(12H, m) |
| 113 | 66 | ESI+: 529 |
| 114 | 66 | ESI+: 529 |
| 115 | 66 | ESI+: 556 |
| 116 | 66 | ESI+: 583<br>NMR1:0.2-0.6(4H, m), 0.65-2(12H, m), 2.17(6H, s), 2.80(2H, s), 3.0-4.0(9H, m), 6.30(1H, brs), 7.0-8.0(5H, m) |
| 117 | 66 | ESI+: 585 |
| 118 | 66 + 44 | ESI+: 529 |
| 119 | 66 + 44 | ESI+: 501 |
| 120 | 45 + 44 | ESI+: 554 |

TABLE 154-continued

| Ex | Syn | DAT |
|---|---|---|
| | | NMR1:1.54(6H, brs), 1.82(6H, brs), 2.87-3.02(2H, m), 3.07-3.20(2H, m), 3.29-3.39(2H, m), 3.57-3.76(8H, m), 3.81-4.01(4H, m), 6.27-6.46(1H, m), 7.14(1H, brs), 7.35-7.92(5H, m) |
| 121 | 44 + 44 | ESI+: 570<br>NMR1:1.25(6H, brs), 1.44-2.97(15H, m), 3.13(3H, brs), 3.39-3.49(1H, m), 3.58-3.76(8H, m), 6.29-6.46(1H, m), 7.08-7.91(6H, m) |
| 122 | 45 + 44 | ESI+: 514 |
| 123 | 45 + 44 | ESI+: 514 |
| 124 | 45 + 44 | ESI+: 542 |
| 125 | 45 | ESI+: 542<br>NMR1:0.75-2.16(10H, m), 2.22(3H, s), 2.43(4H, brs), 2.95-3.18(2H, m), 3.42-3.72(12H, m), 6.36(1H, brs), 7.02-7.39(4H, m), 7.61-7.71(1H, m) |
| 126 | 45 | ESI+: 570 |
| 127 | 45 | ESI+: 574<br>NMR1:0.80-2.18(15H, m), 3.02(2H, s), 3.14 (2H, d, J = 5.2 Hz), 3.61-3.77(9H, m), 4.48(1H, t, J = 5.2 Hz), 5.01-5.10(1H, m), 6.39(1H, s), 7.39-7.66(4H, m), 7.70-7.77(1H, m), 7.84-7.88(1H, m) |

TABLE 155

| Ex | Syn | DAT |
|---|---|---|
| 128 | 45 | ESI+: 600<br>NMR1:1.34-2.40(19H, m), 3.05(2H, s), 3.58-3.78(9H, m), 4.29(1H, d, J = 4.0 Hz), 5.0-5.15(1H, s), 7.39-7.66(4H, m), 7.72-7.76(1H, m), 7.84-7.88(1H, m) |
| 129 | 45 | ESI+: 600<br>NMR1:0.81-2.28(19H, m), 3.05(2H, s), 3.61-3.77(9H, m), 4.45(1H, d, J = 4.4 Hz), 5.05-5.15(1H, m), 6.39(1H, s), 7.39-7.66(4H, m), 7.72-7.76(1H, m), 7.84-7.88(1H, m) |
| 130 | 45 | ESI+: 598<br>NMR1:0.17-0.68(4H, m), 0.76-2.13(22H, m), 3.01-3.60 (6H, m), 6.31(1H, brs), 6.73(1H, brs), 7.25-8.03(5H, m) |
| 131 | 45 + 44 | ESI+: 542 |
| 132 | 45 + 44 | ESI+: 542 |
| 133 | 89 | ESI+: 556<br>NMR1:0.05-1.11(2H, m), 0.36-0.44(2H, m), 0.80-0.90 (2H, m), 1.37-1.63(4H, m), 1.81-1.92(2H, m), 2.09-2.19 (2H, m), 2.27-2.37(2H, m), 3.06(2H, s), 3.60-3.78(9H, m), 5.00-5.10(1H, m), 6.40(1H, s), 7.38-7.68(4H, m), 7.72-7.78(1H, m), 7.83-7.88(1H, m) |
| 134 | 89 | ESI+: 570<br>NMR1:1.20-1.72(12H, m), 1.82-1.92(2H, m), 2.05-2.18 (3H, m), 2.89-2.98(1H, m), 3.03(2H, s), 3.60-3.80(9H, m), 5.01-5.11(1H, m), 6.40(1H, s), 7.38-7.68(4H, m), 7.72-7.77 (1H, m), 7.84-7.89(1H, m) |
| 135 | 89 | ESI+: 584<br>NMR1:0.79-2.35(20H, m), 3.06(2H, m), 3.60-3.77(9H, m), 5.01-5.11(1H, m), 6.40(1H, s), 7.39-7.68(4H, m), 7.72-7.78(1H, m), 7.84-7.89(1H ,m) |
| 136 | 89 | ESI+: 586<br>NMR1:1.18-1.31(2H, m), 1.36-1.63(4H, m), 1.65-1.75 (2H, m), 1.81-1.91(2H, m), 2.08-2.18(2H, m), 3.08 (2H, s), 3.21-3.34(4H, m), 3.60-3.86(11H, m), 5.01-5.11 (1H, m), 6.40(1H, s), 7.38-7.68(4H, m), 7.72-7.77(1H, m), 7.84-7.89(1H, m) |
| 137 | 89 | ESI+: 556<br>NMR1:0.26-0.31(2H, m), 0.46-0.52(2H, m), 1.15(3H, s), 1.37-1.62(4H, m), 1.80-1.90(2H, m), 2.07-2.18(2H, m), 2.33-2.44(1H, m), 3.06-3.11(2H, m), 3.59-3.78(9H, m), 5.00-5.11(1H, m), 6.40(1H, s), 7.38-7.68(4H, m), 7.72-7.78(1H, m), 7.83-7.89(1H, m) |
| 138 | 89 | ESI+: 572<br>NMR1:1.35-3.80(27H, m), 5.00-5.11(1H, m), 6.40(1H, s), 7.38-7.69(4H, m), 7.71-7.78(1H, m), 7.83-7.90(1H, m) |
| 139 | 89 | ESI+: 572<br>NMR1:1.35-3.80(27H, m), 5.00-5.11(1H, m), 6.40(1H, s), 7.37-7.69(4H, m), 7.71-7.78(1H, m), 7.82-7.89(1H, m) |

TABLE 156

| Ex | Syn | DAT |
|---|---|---|
| 140 | 89 | ESI+: 596<br>NMR1:1.58-2.21(19H, m), 2.81-3.06(3H, m), 3.59-3.80(9H, m), 5.00-5.12(1H, m), 6.40(1H, s), 7.39-7.69(4H, m), 7.72-7.79(1H, m), 7.84-7.89(1H, m) |
| 141 | 89 | ESI+: 636<br>NMR1:1.37-1.65(16H, m), 1.80-1.90(2H, m), 1.94-2.04(4H, m), 2.08-2.18(2H, m), 3.03(2H, s), 3.59-3.79(9H, m), 5.02-5.13(1H, m), 6.40(1H, s), 7.39-7.71(4H, m), 7.83-7.89(1H, m) |
| 142 | 89 | ESI+: 652<br>NMR1:1.35-1.62(16H, m), 1.81-1.90(2H, m), 2.05-2.19(5H, m), 3.02(2H, s), 3.59-3.79(9H, m), 4.40(1H, s), 5.02-5.12(1H, m), 6.40(1H, s), 7.38-7.70(4H, m), 7.72-7.78(1H, m), 7.83-7.89(1H, m) |
| 143 | 89 | ESI+: 614<br>NMR1:1.07(3H, s), 1.15-2.22(18H, m), 3.06(2H, s), 3.59-3.80(9H, m), 3.93(1H, s), 5.01-5.12(1H, m), 6.40(1H, s), 7.38-7.69(4H, m), 7.72-7.78(1H, m), 7.83-7.89(1H, m) |
| 144 | 89 | ESI+: 614<br>NMR1:1.11-2.46(21H, m), 3.10(2H, s), 3.65-3.87(9H, m), 4.17(1H, s), 5.05-5.17(1H, m), 6.46(1H, s), 7.43-7.75(4H, m), 7.77-7.84(1H, m), 7.88-7.95(1H, m) |
| 145 | 52 | ESI+: 558 |
| 146 | 1 | ESI+: 572 |
| 147 | 1 | ESI+: 572 |
| 148 | 1 | ESI+: 558 |
| 149 | 1 | ESI+: 530 |
| 150 | 1 | ESI+: 474[M + Na]<br>NMR:3.63-3.93(8H, m), 7.41-8.76(10H, m) |
| 151 | 1 | ESI+: 530 |
| 152 | 1 | ESI+: 584 |
| 153 | 1 | ESI+: 574<br>NMR1:0.85-1.13(2H, m), 1.38(9H, s), 1.56-1.80(3H, m), 2.57-2.76(2H, m), 3.06-3.24(2H, m), 3.51-3.75(8H, m), 3.83-4.03(5H, m), 6.20-6.35(1H, m), 6.91(1H, d, J = 8.0 Hz), 7.09-7.80(4H, m) |
| 154 | 1 | ESI+: 612 |
| 155 | 1 | ESI+: 453<br>NMR1:2.45(3H, s), 3.37-3.75(8H, m), 4.53-4.61(2H, m), 6.25-6.49(1H, m), 7.10-7.91(6H, m), 8.38-8.56(2H, m) |
| 156 | 1 | ESI+: 523 |
| 157 | 1 | ESI+: 536 |
| 158 | 1 | ESI+: 593<br>NMR1:1.19(3H, t, J = 8.0 Hz), 3.01-3.13(4H, m), 3.44-3.54(4H, m), 3.56-3.94(8H, m), 4.06(2H, q, J = 8.0 Hz), 4.31-4.45(2H, m), 6.25-6.40(1H, m), 6.92(2H, d, J = 12 Hz), 7.10-7.94(8H, m) |

TABLE 157

| Ex | Syn | DAT |
|---|---|---|
| 159 | 1 | ESI+: 494<br>NMR1:1.41(3H, d, J = 8.0 Hz), 3.40-3.78(8H, m), 4.33-4.47(1H, m), 6.29-6.47(1H, m), 6.92-7.96 (11H, m), 9.84-10.17(1H, m) |
| 160 | 1 | ESI+: 511<br>NMR1:0.62-0.84(2H, m), 0.86-1.03(2H, m), 3.47-3.88(10H, m), 6.18-6.42(1H, m), 6.91-7.93 (10H, m) |
| 161 | 1 | ESI+: 508 |
| 162 | 1 | ESI+: 522<br>NMR1:2.73-2.92(4H, m), 3.47-3.82(12H, m), 4.48-4.65(2H, m), 6.21-6.44(1H, m), 6.86-7.98 (10H, m) |
| 163 | 1 | ESI+: 430 |
| 164 | 1 | ESI+: 446<br>NMR1:1.28-1.43(2H, m), 1.50-1.69(4H, m), 1.70-1.79(1H, m), 1.92-2.03(1H, m), 3.69 (4H, d, J = 4.7 Hz), 3.72(4H, d, J = 4.7 Hz), 3.90(1H, br), 4.70(1H, d, J = 4.7 Hz), 5.15-5.22(1H,m), 6.39(1H,s), 7.39-7.52(2H,m), 7.55(1H, t, J = 52.5 Hz), 7.77(1H, d, J = 7.9 Hz), 7.87(1H, d, J = 7.9 Hz) |

TABLE 157-continued

| Ex | Syn | DAT |
|---|---|---|
| 165 | 1 | ESI+: 446<br>NMR1:1.20-1.43(4H, m), 1.67(2H, br), 1.90(1H, br), 2.12(1H, br), 3.53-3.64(1H, m), 3.69(4H, d, J = 4.2 Hz), 3.73(4H, d, J = 3.7 Hz), 4.86-4.95(1H, m), 4.94 (1H, d, J = 4.7 Hz), 6.39(1H, s), 7.40-7.50(2H, m), 7.55(1H, t, J = 52.5 Hz), 7.77(1H, d, J = 7.9 Hz), 7.87(1H, d, J = 7.9 Hz) |
| 166 | 1 | ESI+: 486<br>NMR1:0.94-1.31(14H, m), 1.72(1H, br), 1.82(1H, br), 3.64(4H, br), 3.68(4H, br), 4.19(1H, br), 6.32(1H, br), 6.96(1H, br), 7.33-7.88(5H, br) |
| 167 | 1 | ESI+: 446 |
| 168 | 1 | ESI+: 482[M + Na]<br>NMR1:1.02-1.16(3H, m), 1.33-1.45(2H, m), 1.55-1.79 (6H, m), 3.64-4.09(10H, m), 7.37-8.10(5H, m), 8.39-8.63(1H, m) |
| 169 | 1 | ESI+: 482[M + Na]<br>NMR1:1.00-1.06(3H, m), 1.35-1.92(8H, m), 3.61-3.94 (9H, m), 4.26-4.33(1H, m), 7.38-8.09(5H, m), 8.40-8.63(1H, m) |
| 170 | 1 | ESI+: 498<br>NMR1:1.30-1.42(2H, m), 1.60-1.71(4H, m), 1.72-1.84(2H, m), 1.94-2.08(3H, m), 2.09-2.20(2H, m), 3.63-3.88(8H, m), 3.97-4.12 (1H, m), 4.40-4.50(1H, m), 7.38-7.52(2H, m), 7.62-8.20(3H, m), 8.41-8.66(1H, m) |
| 171 | 1 | ESI+: 454[M + Na] |
| 172 | 1 | ESI+: 430 |
| 173 | 1 | ESI+: 476<br>NMR1:1.34-1.74(6H, m), 1.86-2.03(2H, m), 3.13-3.27(1H, m), 3.48-3.88(10H, m), 7.33-7.53 (2H, m), 7.62-8.18(3H, m), 8.40-8.58(1H, m) |
| 174 | 1 | ESI+: 540 |

TABLE 158

| Ex | Syn | DAT |
|---|---|---|
| 175 | 1 | ESI+: 444<br>NMR1:0.99-1.38(4H, m), 1.38-1.76(4H, m), 1.76-2.10(2H, m), 3.25-3.54(2H, m), 3.54-3.75(8H, m), 6.22-6.39(1H, m), 6.87-7.02(1H, m), 7.35-7.91(5H, m) |
| 176 | 1 | ESI+: 444<br>NMR1:1.13-1.85(10H, m), 2.94-3.11(1H, m), 3.51-3.76(8H, m), 3.76-3.90(1H, m), 6.24-6.44(1H, m), 6.44-6.73(1H, m), 7.35-7.91(5H, m) |
| 177 | 1 | ESI+: 503 |
| 178 | 1 | ESI+: 498<br>NMR1:1.42-1.65(6H, m), 1.92-2.07(6H, m), 2.16-2.24(2H, m), 3.64-3.83(8H, m), 4.55-4.60(1H, m), 7.38-8.15(5H, m), 8.44-8.63(1H, m) |
| 179 | 1 | ESI+: 487 |
| 180 | 1 | ESI+: 522[M + Na] |
| 181 | 1 + 44 | ESI+: 556 |
| 182 | 1 | ESI+: 523 |
| 183 | 1 | ESI+: 654[M + Na]<br>NMR1:1.01-1.82(12H, m), 3.31-3.45(4H, m), 3.59-3.74(9H, m), 5.06(2H, s), 6.25-6.38(1H, m), 6.89-7.04(1H, m), 7.27-7.88(10H, m) |
| 184 | 1 | ESI+: 501 |
| 185 | 1 | ESI+: 572 |
| 186 | 26 | ESI+: 546 |
| 187 | 1 | ESI+: 572 |
| 188 | 22 | ESI+: 495 |
| 189 | 93 | ESI+: 469 |
| 190 | 83 | ESI+: 473<br>NMR1:1.18-1.35(2H, m), 1.39-1.55(2H, m), 1.85-2.10(4H, m), 2.16-2.27(1H, m), 3.60-3.87(9H, m), 6.09(1H, s), 7.35-7.66(4H, m), 7.68-7.74(1H, m), 7.82-7.87(1H, m), 12.08(1H, brs) |
| 191 | 26 | ESI+: 556 |
| 192 | 26 | ESI+: 558 |
| 193 | 26 | ESI+: 526<br>NMR1:0.98-1.13(2H, m), 1.19(6H, br), 1.57(2H, d, J = 11.2 Hz), 1.72(6H, br), 2.13(2H, br), |

TABLE 158-continued

| Ex | Syn | DAT |
|---|---|---|
| | | 2.79(1H, br), 3.16(2H, br), 3.30(1H, br), 3.64(4H, br), 3.68(4H, br), 6.31(1H, br), 7.15(1H, br), 7.37-7.47(2H, m), 7.53(1H, br), 7.76(1H, d, J = 7.9 Hz), 7.85(1H, d, J = 7.7 Hz) |
| 194 | 26 | ESI+: 556<br>NMR1:0.92-1.02(2H, m), 1.08(6H, d, J = 6.1 Hz), 1.12(2H, br), 1.50(1H, br), 1.66(2H, br), 1.68(2H, br), 2.05(2H, br), 2.45(1H, br), 2.82(2H, br), 3.14(1H, s), 3.18(1H, s), 3.28-3.38(2H, m), 3.63(4H, br), 3.68(4H, br), 6.31(1H, br), 7.13(1H, br), 7.36-7.47(2H, m), 7.50-7.72(1H, m), 7.77(1H, d, J = 7.6 Hz), 7.85(1H, d, J = 7.6 Hz) |
| 195 | 26 | ESI+: 540 |

TABLE 159

| Ex | Syn | DAT |
|---|---|---|
| 196 | 26 | ESI+: 570<br>NMR1:1.41-1.65(6H, m), 1.72-2.00(6H, m), 2.07(3H, s), 2.10-2.19(2H, m), 2.76(2H, s), 2.87-2.97(2H, m), 3.60-3.79(9H, m), 5.00-5.10(1H, m), 6.40(1H, s), 7.38-7.68 (4H, m), 7.72-7.78(1H, m), 7.83-7.89(1H, m) |
| 197 | 26 | ESI+: 500 |
| 198 | 26 | ESI+: 584<br>NMR1:1.49-2.30(16H, m), 2.66-2.71(6H, m), 3.64-3.84(9H, m), 4.98-5.11(1H, m), 6.40(1H, s), 7.39-7.69(3H, m), 7.72-7.77(1H, m), 7.84-7.89(1H, m), 8.19-8.29(1H, m), 10.75-1.88(1H, m) |
| 199 | 26 | ESI+: 598<br>NMR1:0.80-2.30(22H, m), 3.08-3.17(1H, m), 3.56-3.79(9H, m), 5.01-5.11(1H, m), 6.40(1H, s), 7.38-7.70(4H, m), 7.72-7.78(1H, m), 7.84-7.89(1H, m) |
| 200 | 34 | ESI+: 542 |
| 201 | 34 | ESI+: 528 |
| 202 | 26 + 44 | ESI+: 596 |
| 203 | 26 + 44 | ESI+: 542 |
| 204 | 26 + 44 | ESI+: 514 |
| 205 | 53 | ESI+: 472 |
| 206 | 53 | ESI+: 458 |
| 207 | 53 | ESI+: 430 |
| 208 | 53 | ESI+: 474 |
| 209 | 53 | ESI+: 498<br>NMR1:0.16-0.73(4H, m), 1.02-2.20(10H, m), 2.80-3.99(11H, m), 6.33(1H, brs), 7.24-8.01(5H, m), 8.21(2H, brs) |
| 210 | 53 | ESI+: 472 |
| 211 | 54 | ESI+: 472 |
| 212 | 54 | ESI+: 484 |
| 213 | 54 | ESI+: 478 |
| 214 | 54 | ESI+: 512 |
| 215 | 54 | ESI+: 542<br>NMR1:1.38-2.42(14H, m), 3.55-3.78(9H, m), 5.00-5.10(1H, m), 6.40(1H, s), 7.38-7.89(6H, m) |
| 216 | 54 | ESI+: 556<br>NMR1:1.35-2.18(16H, m), 3.54-3.78(9H, m), 5.02-5.11(1H, m), 6.40(1H, s), 7.39-7.88(6H, m) |
| 217 | 54 | ESI+: 444 |
| 218 | 54 | ESI+: 444 |
| 219 | 54 | ESI+: 472 |
| 220 | 54 | ESI+: 486 |
| 221 | 54 | ESI+: 431 |
| 222 | 54 | ESI+: 431 |

TABLE 160

| Ex | Syn | DAT |
|---|---|---|
| 223 | 53 | ESI+: 500 |
| 224 | 26 | ESI+: 556<br>NMR1:1.07(6H, d, J = 6.2 Hz), 1.14(2H, br), 1.16(2H, br), 1.52(1H, br), 1.70(2H, br), 1.72-1.79(2H, m), 1.86(2H, br), 2.28(1H, br), 3.02(2H, br), 3.13(1H, br), 3.20(1H, br), 3.63(4H, br), 3.68(4H, br), 3.73(2H, br), 6.31(1H, br), 7.14(1H, t, J = 5.7 Hz), 7.36-7.48(2H, m), 7.49-7.73(1H, m), 7.76(1H, d, J = 7.7 Hz), 7.85(1H, d, J = 7.7 Hz) |
| 225 | 92 | ESI+: 544 |
| 226 | 92 | ESI+: 555 |
| 227 | 66 | ESI+: 642 |
| 228 | 66 | ESI+: 656 |
| 229 | 1 | ESI+: 586 |
| 230 | 1 | ESI+: 572 |
| 231 | 1 | ESI+: 516 |
| 232 | 1 | ESI+: 516 |
| 233 | 54 | ESI+: 416 |
| 234 | 54 | ESI+: 416 |
| 235 | 54 | ESI+: 458 |
| 236 | 1 | ESI+: 558 |
| 237 | 237 | ESI+: 527 |
| 238 | 239 | ESI+: 586 |
| 239 | 239 | ESI+: 472 |
| 240 | 240 | ESI+: 514 |
| 241 | 241 | ESI+: 520 |
| 242-1 | 242 + 44 | ESI+: 472 |
| 242-2 | 242 + 44 | ESI+: 486 |
| 243 | 243 | ESI+: 526 |
| 244 | 244 | ESI+: 419 |
| 245 | 245 | ESI+: 616 |
| 246 | 246 | ESI+: 531 |
| 247 | 247 | ESI+: 531 |
| 248 | 248 | ESI+: 585<br>NMR:1.27-2.31(10H, m), 3.06-3.38(2H, m), 3.53(3H, s), 3.56-3.92(10H, m), 4.06-4.20(1H, m), 6.22-6.43(1H, m), 6.88-7.13(1H, m), 7.34-7.96(6H, m) |
| 249-1 | 249 | ESI+: 542<br>NMR:1.33-1.88(8H, m), 2.21-2.30(1H, m), 3.20(3H, s), 3.60-3.71(8H, m), 3.75-3.81(1H, m), 4.01-4.06(1H, m), 4.15-4.19(1H, m), 4.48-4.50(1H, m), 4.59-4.71(1H, m), 6.12(1H, s), 7.37-7.64(3H, m), 7.12-7.74(1H, m), 7.73 (1H, d, J = 8 Hz), 7.86(1H, d, J = 7.6 Hz), 8.12-8.20(1H, m) |

TABLE 161

| Ex | Syn | DAT |
|---|---|---|
| 249-2 | 249 | ESI+: 542<br>NMR1:1.07-2.21(8H, m), 3.22(3H, s), 3.62-3.71(8H, m), 3.75-3.81(1H, m), 4.02-4.06(1H, m), 4.15-4.19(1H, m), 4.49-4.53(1H, m), 4.59-4.70(1H, m), 6.12(1H, s), 7.33-7.64(5H, m), 7.73 (1H, d, J = 8.0 Hz), 7.86(1H, d, J = 7.5 Hz), 8.13-8.19(1H, m) |
| 250 | 1 | ESI+: 438 |
| 251 | 1 | ESI+: 439 |
| 252 | 1 | ESI+: 439 |
| 253 | 1 | ESI+: 439 |
| 254 | 1 | ESI+: 452 |
| 255 | 1 | ESI+: 498 |
| 256 | 1 | ESI+: 432 |
| 257 | 1 | ESI+: 424 |
| 258 | 1 | ESI+: 454 |
| 259 | 1 | ESI+: 426 |
| 260 | 1 | ESI+: 425 |
| 261 | 1 | ESI+: 433 |
| 262 | 1 | ESI+: 504[M + Na] |
| 263 | 1 | ESI+: 504[M + Na] |
| 264 | 1 | ESI+: 468[M + Na] |
| 265 | 1 | ESI+: 496 |
| 266 | 1 | ESI+: 445 |
| 267 | 1 | ESI+: 445 |
| 268 | 1 | ESI+: 445 |
| 269 | 1 | ESI+: 497 |
| 270 | 1 | ESI+: 508 |
| 271 | 1 | ESI+: 497 |
| 272 | 1 | ESI+: 459 |
| 273 | 1 | ESI+: 481[M + Na] |
| 274 | 1 | ESI+: 429 |
| 275 | 1 | ESI+: 530[M + Na] |
| 276 | 1 | ESI+: 497 |
| 277 | 1 | ESI+: 547[M + Na] |
| 278 | 1 | ESI+: 553[M + Na] |
| 279 | 1 | ESI+: 567[M + Na] |
| 280 | 94 | ESI+: 454 |
| 281 | 1 | ESI+: 440 |
| 282 | 1 | ESI+: 442 |
| 283 | 1 | ESI+: 463 |
| 284 | 1 | ESI+: 464 |
| 285 | 1 | ESI+: 464 |
| 286 | 1 | ESI+: 481 |

TABLE 162

| Ex | Syn | DAT |
|---|---|---|
| 287 | 1 | ESI+: 496 |
| 288 | 1 | ESI−: 479 |
| 289 | 74 | ESI+: 520 |
| 290 | 1 | ESI+: 478 |
| 291 | 1 | ESI+: 520 |
| 292 | 26 + 44 | ESI+: 520 |
| 293 | 74 | ESI+: 570 |
| 294 | 92 | ESI+: 504[M + Na] |
| 295 | PSyn.8 | ESI+: 452 |
| 296 | 240 + 44 | ESI+: 522 |

TABLE 162-continued

| Ex | Syn | DAT |
|---|---|---|
| 297 | 22 | ESI+: 556 |
| 298 | 22 | ESI+: 542 |
| 299 | 22 | ESI+: 542 |
| 300 | 74 | ESI+: 522 |
| 301 | 74 | ESI+: 480 |
| 302 | 1 | ESI+: 520 |
| 303 | 1 | ESI+: 544 |
| 304 | 54 | ESI+: 444 |
| 305 | 1 | ESI+: 573 |
| 306 | 1 | ESI+: 587 |
| 307 | 66 + 44 | ESI+: 529 |
| 308 | PSyn.81 | ESI+: 489 |
| 309 | PSyn.81 | ESI+: 503 |
| 310 | 1 | ESI+: 497 |
| 311 | 74 | ESI+: 453 |
| 312 | 74 | ESI+: 454 |
| 313 | 74 | ESI+: 453 |
| 314 | 74 | ESI+: 521 |
| 315 | 74 | ESI+: 520 |
| 316 | 1 | ESI+: 575[M + Na] |
| 317 | 54 | ESI+: 453 |
| 318 | 240 + 44 | ESI+: 523 |
| 319 | 1 | ESI+: 485 |
| 320 | 54 | ESI+: 458 |
| 321 | 54 | ESI+: 458 |
| 322 | 26 | ESI+: 542 |
| 323 | 26 | ESI+: 542 |
| 324 | 26 | ESI+: 528 |
| 325 | 1 | ESI+: 532 |
| 326 | 66 | ESI+: 529 |
| 327 | 1 | ESI+: 520 |

TABLE 163

| Ex | Syn | DAT |
|---|---|---|
| 328 | 1 | ESI+: 520 |
| 329 | 66 | ESI+: 501 |
| 330 | PSyn.148 | ESI+: 488 |
| 331 | 66 | ESI+: 534 |
| 332 | 66 | ESI+: 534 |
| 333 | 66 | ESI+: 534 |
| 334 | 74 | ESI+: 506 |
| 335 | 74 | ESI+: 538 |
| 336 | 74 | ESI+: 538 |
| 337 | 74 | ESI+: 550 |
| 338 | 74 | ESI+: 566 |
| 339 | 74 | ESI+: 524 |
| 340 | 92 | ESI+: 515 |
| 341 | 84 | ESI+: 628 |
| 342 | 26 | ESI+: 500 |
| 343 | 66 | ESI+: 550 |
| 344 | 66 | ESI+: 554 |
| 345 | 66 | ESI+: 538 |
| 346 | 66 | ESI+: 538 |
| 347 | 66 | ESI+: 538 |
| 348 | 74 | ESI+: 580 |
| 349 | 74 | ESI+: 566 |
| 350 | 66 | ESI+: 569 |
| 351 | 66 | ESI+: 521 |
| 352 | 66 | ESI+: 521 |
| 353 | 66 | ESI+: 521 |
| 354 | 53 | ESI+: 430 |
| 355 | 26 | ESI+: 520 |
| 356 | 26 | ESI+: 520 |
| 357 | 66 | ESI+: 552 |
| 358 | 89 + 44 | ESI+: 584 |
| 359 | 92 | ESI+: 556 |
| 360 | 92 | ESI+: 555 |
| 361 | 93 | ESI+: 469 |
| 362 | 26 + 44 | ESI+: 540 |
| 363 | 92 | ESI+: 488 |
| 364 | 26 | ESI+: 514 |
| 365 | 26 | ESI+: 528 |
| 366 | 241 | ESI+: 534 |

TABLE 163-continued

| Ex | Syn | DAT |
|---|---|---|
| 367 | 22 | ESI+: 437 |
| 368 | 84 | ESI+: 664[M + Na] |

TABLE 164

| Ex | Syn | DAT |
|---|---|---|
| 369 | 1 | ESI+: 536 |
| 370 | 92 | ESI+: 585<br>NMR1:1.33(3H, br), 1.52-1.81(5H, m), 2.10(2H, br), 2.24 (1H, br), 3.15-3.25(1H, m), 3.54(3H, s), 3.67(8H, br), 3.75 (1H, br), 4.06-4.18(1H, m), 6.10(1H, s), 7.35-7.50(5H, m), 7.51(1H, t, J = 52 Hz), 7.71(1H, d, J = 7.9 Hz), 7.85(1H, d, J = 7.9 Hz) |
| 371 | 92 | ESI+: 585<br>NMR1:1.20-1.33(3H, m), 1.50-1.83(5H, m), 2.01-2.18(2H, m), 2.17-2.31(1H, m), 3.13-3.25(1H, m), 3.54(3H, s), 3.59-3.91 (10H, m), 4.05-4.19(1H, m), 6.10(1H, s), 7.34-7.54(5H, m), 7.72(1H, d, J = 8.2 Hz), 7.85(1H, d, J = 7.7 Hz) |
| 372 | 1 | ESI+: 588 |
| 373 | 1 | ESI+: 446 |
| 374 | 53 | ESI+: 488 |
| 375 | 26 | ESI+: 572 |
| 376 | 1 | ESI+: 536 |
| 377 | 1 | ESI+: 544 |
| 378 | 54 | ESI+: 444 |
| 379 | 92 | ESI+: 544 |
| 380 | 54 | ESI+: 444 |
| 381 | 26 | ESI+: 528 |
| 382 | 66 | ESI+: 529 |
| 383 | 26 | ESI+: 528 |
| 384 | 26 | ESI+: 562 |
| 385 | 43 | ESI+: 556 |
| 386 | 43 | ESI+: 556 |
| 387 | 88 | ESI+: 632 |
| 388 | 85 | ESI+: 600 |
| 389 | 87 | ESI+: 586<br>NMR1:1.52-1.82(7H, m), 2.23(3H, br), 3.17-3.24(1H, m), 3.28-3.36(1H, m), 3.54(3H, s), 3.70(4H, br), 3.75(4H, br), 3.81(1H, br), 4.13(1H, q, J = 9.3 Hz), 5.00-5.08(1H, m), 6.40(1H, s), 7.38-7.50(3H, m), 7.53(1H, t, J = 52.2 Hz), 7.75(1H, d, J = 7.7 Hz), 7.86(1H, d, J = 7.7 Hz) |
| 390 | 1 | ESI+: 550 |
| 391 | 1 | ESI+: 536 |
| 392 | 26 | ESI+: 555 |
| 393 | 26 | ESI+: 556 |
| 394 | 26 | ESI+: 570 |
| 395 | 26 | ESI+: 500 |
| 396 | 26 | ESI+: 628 |
| 397 | 1 | ESI+: 475 |

TABLE 165

| Ex | Syn | DAT |
|---|---|---|
| 398 | 1 | ESI+: 522 |
| 399 | 66 | ESI+: 537 |
| 400 | 43 | ESI+: 558 |
| 401 | 43 | ESI+: 558 |
| 402 | 26 | ESI+: 546 |
| 403 | 26 | ESI+: 576 |
| 404 | 89 | ESI+: 544 |
| 405 | 89 | ESI+: 544 |
| 406 | 54 | ESI+: 444 |
| 407 | 26 + 44 | ESI+: 569 |
| 408 | 26 | ESI+: 528 |
| 409 | 1 | ESI+: 558 |
| 410 | 1 | ESI+: 584 |
| 411 | 54 | ESI+: 484 |
| 412 | 52 | ESI+: 556 |
| 413 | 89 | ESI+: 570 |
| 414 | 89 | ESI+: 584 |
| 415 | 1 | ESI+: 545 |

TABLE 165-continued

| Ex | Syn | DAT |
|---|---|---|
| 416 | 54 | ESI+: 445 |
| 417 | 26 | ESI+: 529 |
| 418 | 240 + 44 | ESI+: 538 |
| 419 | 89 + 44 | ESI+: 574 |
| 420 | 240 | ESI+: 538 |
| 421 | 26 | ESI+: 570 |
| 422 | 422 | ESI+: 542 |
| 423 | 87 | ESI+: 600<br>NMR1:1.16(3H, t, J = 7.1 Hz), 1.50-1.83(7H, m), 2.23(3H, br), 3.15-3.25(1H, m), 3.27-3.36(1H, m), 3.70(4H, d, J = 4.7 Hz), 3.74(4H, d, J = 4.6 Hz), 3.77-3.86(1H, m), 3.99(2H, q, J = 7.1 Hz), 4.12 (1H, q, J = 9.1 Hz), 4.98-5.09(1H, m), 6.40(1H, s), 7.34-7.50(3H, m), 7.53(1H, t, J = 52.5 Hz), 7.75 (1H, d, J = 7.6 Hz), 7.86(1H, d, J = 7.6 Hz) |
| 424 | 87 | ESI+: 600 |
| 425 | 83 | ESI+: 474 |
| 426 | 92 | ESI+: 531 |
| 427 | 1 | ESI+: 503 |
| 428 | 1 | ESI+: 517 |
| 429 | 54 | ESI+: 417 |
| 430 | 54 | ESI+: 431 |
| 431 | 54 | ESI+: 403 |
| 432-1 | 432 | ESI+: 528 |
| 432-2 | 432 | ESI+: 528 |
| 433 | 54 | ESI+: 417 |

TABLE 166

| Ex | Syn | DAT |
|---|---|---|
| 434 | 92 | ESI+: 446 |
| 435 | 92 | ESI+: 516 |
| 436 | 54 | ESI+: 416 |
| 437 | 92 | ESI+: 530 |
| 438 | 54 | ESI+: 430 |
| 439 | 92 | ESI+: 516 |
| 440 | 54 | ESI+: 416 |
| 441 | 248 | ESI+: 585<br>NMR1:1.27-2.29(10H, m), 3.07-3.21(2H, m), 3.53(3H, s), 3.57-3.83(10H, m), 4.06-4.18(1H, m), 6.22-6.41(1H, m), 6.87-7.08(1H, m), 7.31-7.92(6H, m) |
| 442 | 66 | ESI+: 529 |
| 443 | 66 | ESI+: 529 |
| 444 | 66 | ESI+: 528 |
| 445 | 66 | ESI+: 528 |
| 446 | 66 | ESI+: 542 |
| 447 | 66 | ESI+: 542 |
| 448 | 52 | ESI+: 560 |
| 449 | 54 | ESI+: 488 |
| 450 | 1 | ESI+: 588 |
| 451 | 249 | ESI+: 543<br>NMR1:1.34-1.45(4H, m), 1.53-1.65(2H, m), 1.78-1.88 (2H, m), 2.25-2.35(1H, m), 3.19(3H, s), 3.66-3.76(8H, m), 3.86-3.91(1H, m), 4.19-4.34(2H, m), 4.60-4.66(1H, m), 5.44-5.50(1H, m), 6.52(1H, s), 7.41-7.67(4H, m), 7.77-7.79(1H, m), 7.86-7.88(1H, m) |
| 452 | 249 | ESI+: 543<br>NMR1:1.03-1.40(4H, m), 1.67-1.75(2H, m), 1.96-2.25(3H, m), 3.00-3.12(1H, m), 3.22(3H, s), 3.66-3.76(8H, m), 3.85-3.92(1H, m), 4.18-4.33(2H, m), 4.60-4.67(1H, m), 5.43-5.51(1H, m), 6.52(1H, s), 7.42-7.67(3H, m), 7.78(1H, d, J = 7.4 Hz), 7.87(1H, d, J = 7.4 Hz) |
| 453 | 66 | ESI+: 556<br>NMR1:1.38-1.66(10H, m), 1.81-2.02(1H, m), 2.05-2.30(1H, m), 3.31-3.40(2H, m), 3.40-3.52(1H, m), 3.56-3.63 (2H, m), 3.84-3.94(1H, m), 3.66(4H, br), 3.70(4H, br), 4.37 (1H, d, t, J = 1.4, 5.2 Hz), 4.43-4.60(1H, m), 6.14(1H, br), 7.36-7.50(2H, m), 7.52(1H, t, J = 52.7 Hz), 7.73(1H, d, J = 7.6 Hz), 7.75-7.88(1H, m), 7.86(1H, d, J = 7.8 Hz) |
| 454 | 66 | ESI+: 556<br>NMR1:0.85-1.01(2H, m), 1.33(4H, br), 1.67-1.80(4H, m), 1.82-2.03(1H, m), 2.09-2.40(1H, m), 3.17-3.23 (2H, m), 3.34-3.50(1H, m), 3.57-3.63(2H, m), 3.66(4H, br), 3.70 |

TABLE 166-continued

| Ex | Syn | DAT |
|---|---|---|
| | | (4H, br), 3.91(1H, br), 4.36(1H, t, J = 5.3 Hz), 4.44-4.60 (1H, br), 6.14(1H, d, J = 4.8 Hz), 7.37-7.49(2H, m), 7.52(1H, t, J = 52.7 Hz), 7.72(1H, d, J = 8.3 Hz), 7.75-7.88 (1H, br), 7.85(1H, d, J = 7.9 Hz) |

TABLE 167

| Ex | Syn | DAT |
|---|---|---|
| 455 | 66 | ESI+: 544 |
| 456 | 1 | ESI+: 458 |
| 457 | 66 + 44 | ESI+: 543 |
| 458 | 71 | ESI+: 500 |
| 459 | 54 | ESI+: 458 |
| 460 | 92 | ESI+: 558 |
| 461 | 66 | ESI+: 543 |
| 462 | 66 | ESI+: 557 |
| 463 | 71 | ESI+: 514 |
| 464 | 1 | ESI+: 589 |
| 465 | 53 | ESI+: 489 |
| 466 | 85 | ESI+: 586 |
| 467 | 66 | ESI+: 574 |
| 468 | 422 | ESI+: 542 |
| 469 | 1 | ESI+: 562 |
| 470 | 54 | ESI+: 462 |

TABLE 168

| Ex | Str | ESI+ | RT |
|---|---|---|---|
| A1 | 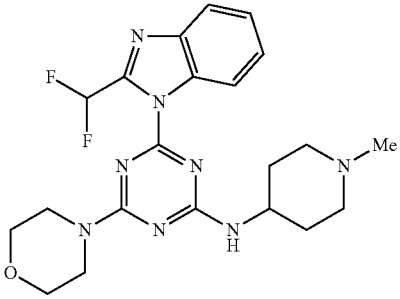 [SMILES: CN1CCC(Nc2nc(N3CCOCC3)nc(-n3c(C(F)F)nc4ccccc43)n2)CC1] | 445 | 2.19 |
| A2 | 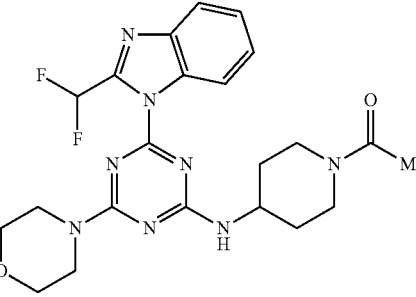 | 473 | 2.81 |

TABLE 168-continued

| Ex | Str | ESI+ | RT |
|---|---|---|---|
| A3 | | 521 | 2.56 |
| A4 | | 459 | 2.28 |
| A5 | | 475 | 2.19 |

TABLE 169

| Ex | Str | ESI+ | RT |
|---|---|---|---|
| A6 | | 459 | 2.33 |

TABLE 169-continued

| Ex | Str | ESI+ | RT |
|---|---|---|---|
| A7 | | 521 | 2.61 |
| A8 | | 392 | 2.58 |
| A9 | | 406 | 2.67 |
| A10 | | 406 | 2.87 |

TABLE 170

| Ex | Str | ESI+ | RT |
|---|---|---|---|
| A11 | | 419 | 2.1 |
| A12 | | 433 | 2.59 |
| A13 | | 422 | 2.37 |
| A14 | | 479 | 2.06 |
| A15 | | 446 | 3.03 |

TABLE 171

| Ex | Str | ESI+ | RT |
|---|---|---|---|
| A16 | | 537 | 2.46 |
| A17 | | 459 | 2.16 |
| A18 | | 473 | 2.95 |
| A19 | | 475 | 2.09 |
| A20 | | 509 | 2.89 |

TABLE 172
| Ex | Str | ESI+ | RT |
|---|---|---|---|
| A21 | 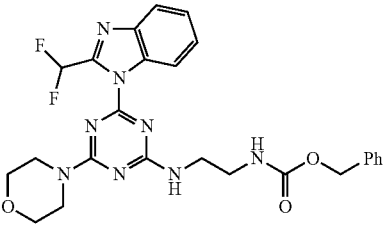 [SMILES: O=C(NCCNc1nc(N2CCOCC2)nc(-n2c(C(F)F)nc3ccccc32)n1)OCc1ccccc1] | 525 | 3.18 |
| A22 | 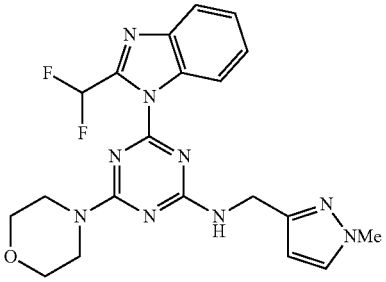 [SMILES: Cn1ccc(CNc2nc(N3CCOCC3)nc(-n3c(C(F)F)nc4ccccc43)n2)n1] | 442 | 2.8 |
| A23 | 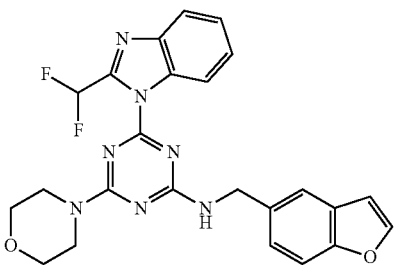 [SMILES: FC(F)c1nc2ccccc2n1-c1nc(NCc2ccc3occc3c2)nc(N2CCOCC2)n1] | 478 | 3.41 |
TABLE 172-continued
| Ex | Str | ESI+ | RT |
|---|---|---|---|
| A24 | 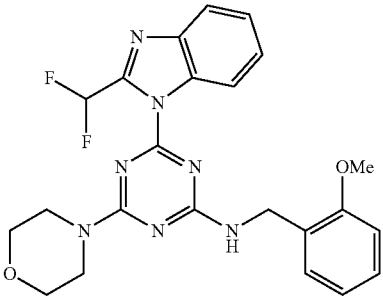 [SMILES: COc1ccccc1CNc1nc(N2CCOCC2)nc(-n2c(C(F)F)nc3ccccc32)n1] | 468 | 3.39 |
| A25 | 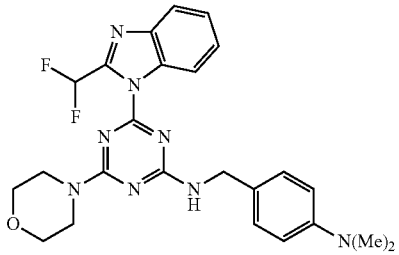 | 481 | 2.51 |
TABLE 173
| Ex | Str | ESI+ | RT |
|---|---|---|---|
| A26 | 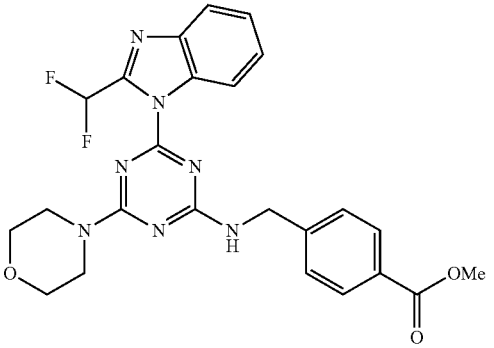 [SMILES: COC(=O)c1ccc(CNc2nc(N3CCOCC3)nc(-n3c(C(F)F)nc4ccccc43)n2)cc1] | 496 | 3.24 |
| A27 | 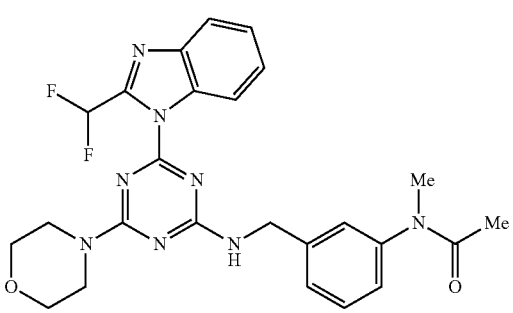 [SMILES: CC(=O)N(C)c1cccc(CNc2nc(N3CCOCC3)nc(-n3c(C(F)F)nc4ccccc43)n2)c1] | 509 | 3.01 |

TABLE 173-continued

| Ex | Str | ESI+ | RT |
|---|---|---|---|
| A28 | | 521 | 2.51 |
| A29 | | 530 | 3.74 |

TABLE 174

| Ex | Str | ESI+ | RT |
|---|---|---|---|
| A30 | | 521 | 2.51 |
| A31 | | 420 | 2.92 |

TABLE 174-continued

| Ex | Str | ESI+ | RT |
|---|---|---|---|
| A32 | | 420 | 3.17 |
| A33 | | 436 | 2.58 |

TABLE 175
| Ex | Str | ESI+ | RT |
|---|---|---|---|
| A34 | 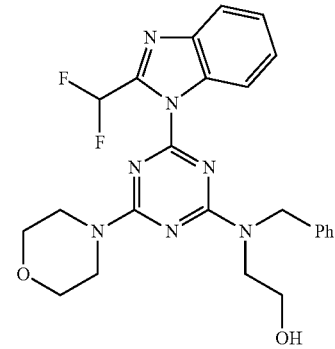 [SMILES: OCCN(Cc1ccccc1)c1nc(N2CCOCC2)nc(-n2c(C(F)F)nc3ccccc32)n1] | 482 | 3.31 |
| A35 | 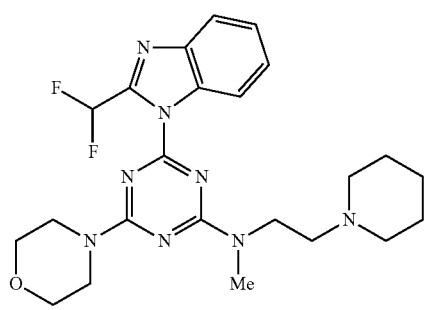 [SMILES: CN(CCN1CCCCC1)c1nc(N2CCOCC2)nc(-n2c(C(F)F)nc3ccccc32)n1] | 473 | 2.29 |
TABLE 175-continued
| Ex | Str | ESI+ | RT |
|---|---|---|---|
| A36 | 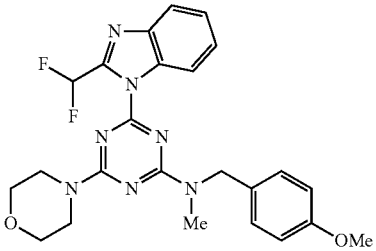 [SMILES: COc1ccc(CN(C)c2nc(N3CCOCC3)nc(-n3c(C(F)F)nc4ccccc43)n2)cc1] | 482 | 3.6 |
| A37 | 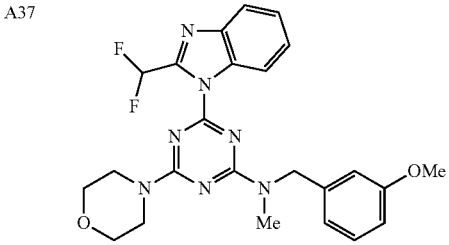 | 482 | 3.59 |
TABLE 176
| Ex | Str | ESI+ | RT |
|---|---|---|---|
| A38 | 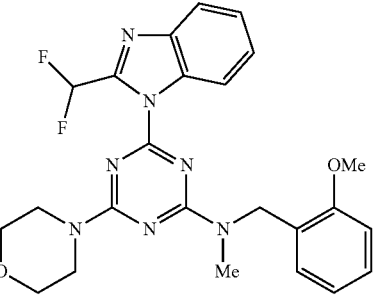 | 482 | 3.68 |
| A39 | 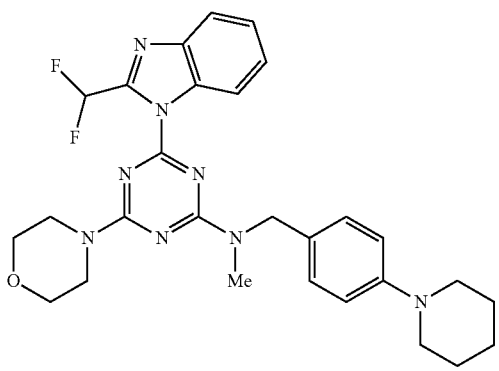 [SMILES: CN(Cc1ccc(N2CCCCC2)cc1)c1nc(N2CCOCC2)nc(-n2c(C(F)F)nc3ccccc32)n1] | 535 | 2.76 |

TABLE 176-continued
| Ex | Str | ESI+ | RT |
|---|---|---|---|
| A40 | 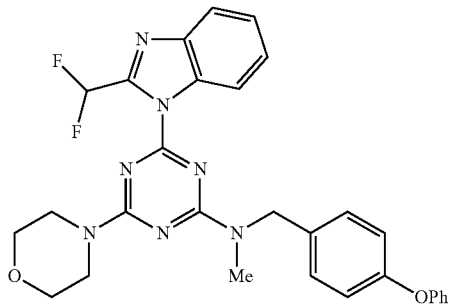 [SMILES: CN(Cc1ccc(Oc2ccccc2)cc1)c1nc(N2CCOCC2)nc(-n2c(C(F)F)nc3ccccc32)n1] | 544 | 3.95 |
| A41 | 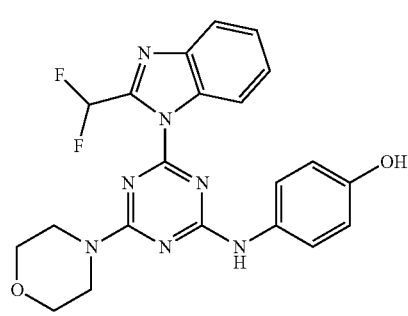 [SMILES: Oc1ccc(Nc2nc(N3CCOCC3)nc(-n3c(C(F)F)nc4ccccc43)n2)cc1] | 440 | 2.94 |
TABLE 177
| Ex | Str | ESI+ | RT |
|---|---|---|---|
| A42 | 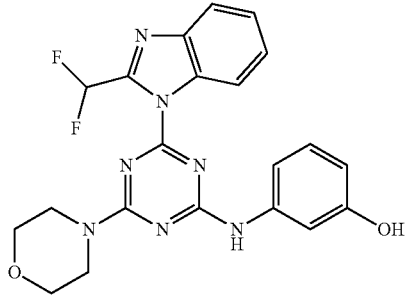 [SMILES: Oc1cccc(Nc2nc(N3CCOCC3)nc(-n3c(C(F)F)nc4ccccc43)n2)c1] | 440 | 3.01 |
| A43 | 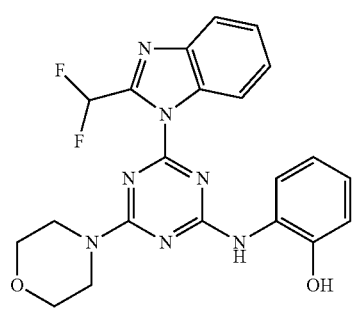 [SMILES: Oc1ccccc1Nc1nc(N2CCOCC2)nc(-n2c(C(F)F)nc3ccccc32)n1] | 440 | 3.16 |
TABLE 177-continued
| Ex | Str | ESI+ | RT |
|---|---|---|---|
| A44 | 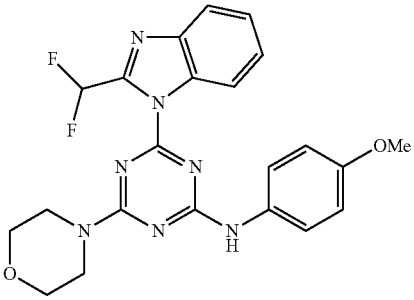 [SMILES: COc1ccc(Nc2nc(N3CCOCC3)nc(-n3c(C(F)F)nc4ccccc43)n2)cc1] | 454 | 3.3 |
| A45 | 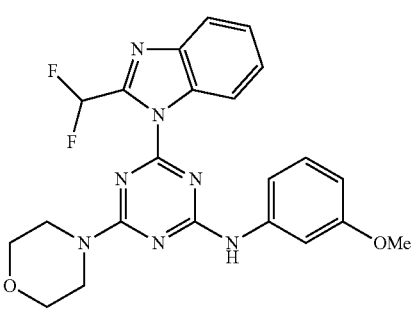 [SMILES: COc1cccc(Nc2nc(N3CCOCC3)nc(-n3c(C(F)F)nc4ccccc43)n2)c1] | 454 | 3.36 |

TABLE 177-continued
| Ex | Str | ESI+ | RT |
|---|---|---|---|
| A46 | 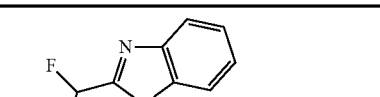 | 467 | 2.54 |
TABLE 178
| Ex | Str | ESI+ | RT |
|---|---|---|---|
| A47 |  | 425 | 2.29 |
| A48 |  | 455 | 3.24 |
TABLE 178-continued
| Ex | Str | ESI+ | RT |
|---|---|---|---|
| A49 |  | 455 | 3.15 |
| A50 |  | 477 | 3.37 |
| A51 |  | 507 | 2.54 |
TABLE 179
| Ex | Str | ESI+ | RT |
|---|---|---|---|
| A52 | 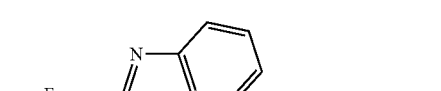 | 489 | 3.63 |

TABLE 179-continued

| Ex | Str | ESI+ | RT |
|---|---|---|---|
| A53 | | 521 | 2.57 |
| A54 | | 521 | 3.16 |
| A55 | | 571 | 3.46 |
| A56 | | 543 | 3.31 |

TABLE 180

| Ex | Str | ESI+ | RT |
|---|---|---|---|
| A57 | | 438 | 3.55 |
| A58 | | 439 | 2.25 |

TABLE 180-continued

| Ex | Str | ESI+ | RT |
|---|---|---|---|
| A59 | | 468 | 3.53 |
| A60 | | 496 | 3.47 |

TABLE 181

| Ex | Str | ESI+ | RT |
|---|---|---|---|
| A61 | | 536 | 2.9 |
| A62 | | 446 | 2.42 |

TABLE 181-continued

| Ex | Str | ESI+ | RT |
| --- | --- | --- | --- |
| A63 | | 474 | 2.67 |
| A64 | | 476 | 2.3 |
| A65 | | 490 | 2.41 |

45

TABLE 182

| Ex | Str | ESI+ | RT |
| --- | --- | --- | --- |
| A66 | | 504 | 2.51 |

TABLE 182-continued
| Ex | Str | ESI+ | RT |
|---|---|---|---|
| A67 | 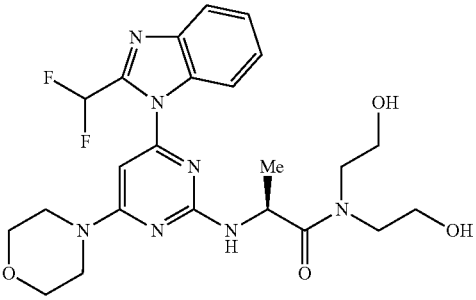 [SMILES: CCN(CCO)C(=O)[C@H](C)Nc1nc(N2CCOCC2)cc(-n2c(C(F)F)nc3ccccc32)n1] | 506 | 2.18 |
| A68 | 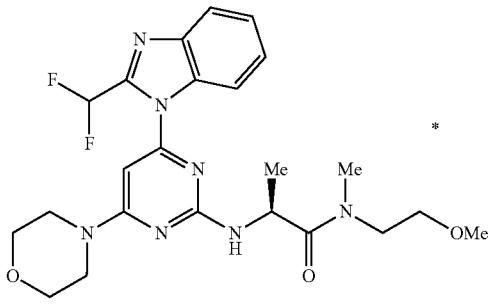 [SMILES: COCCN(C)C(=O)[C@H](C)Nc1nc(N2CCOCC2)cc(-n2c(C(F)F)nc3ccccc32)n1] | 490 | 2.52 |
| A69 | 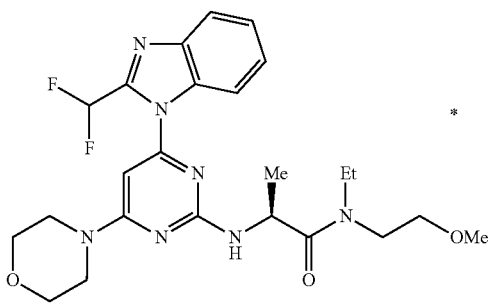 [SMILES: CCN(CCOC)C(=O)[C@H](C)Nc1nc(N2CCOCC2)cc(-n2c(C(F)F)nc3ccccc32)n1] | 504 | 2.64 |
| A70 | 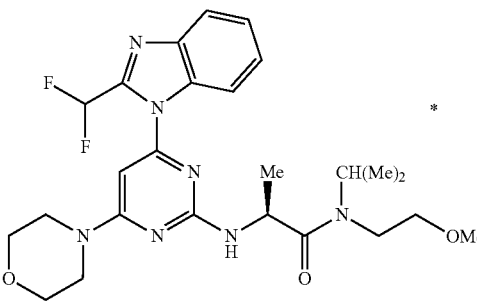 | 518 | 2.74 |

TABLE 183
| Ex | Str | ESI+ | RT |
|---|---|---|---|
| A71 | 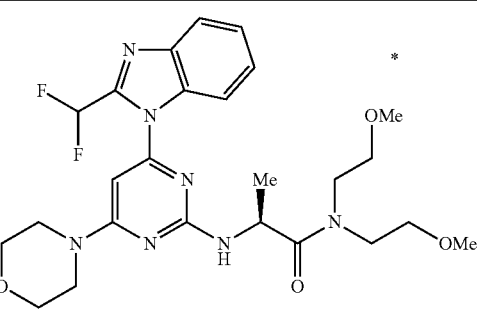 | 534 | 2.62 |
| A72 | 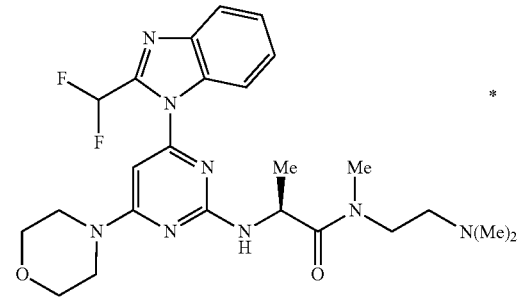 | 503 | 1.87 |
| A73 | 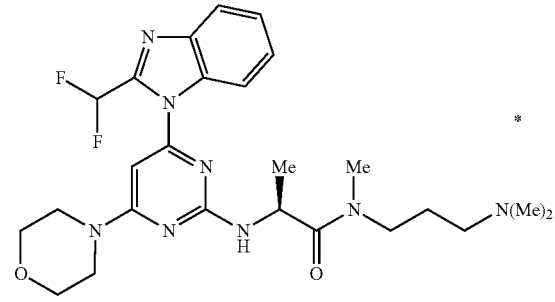 | 517 | 1.88 |
| A74 | 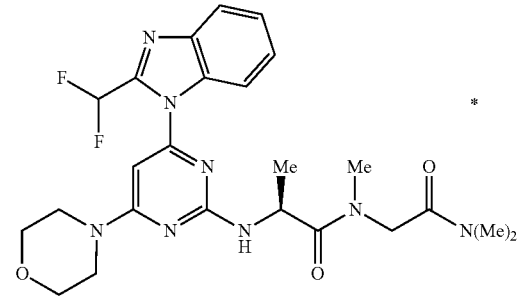 | 517 | 2.35 |
| A75 | 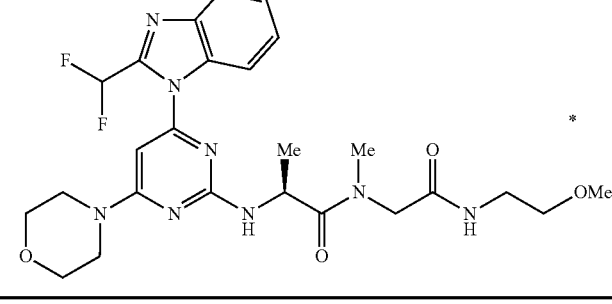 | 547 | 2.36 |

TABLE 184
| Ex | Str | ESI+ | RT |
|---|---|---|---|
| A76 | 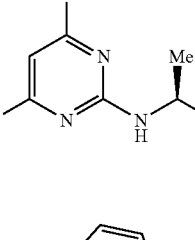 | 511 | 2.53 |
| A77 | 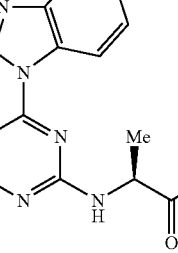 | 514 | 2.94 |
| A78 | 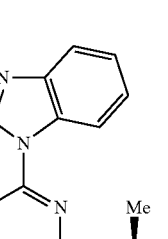 | 528 | 3.06 |
| A79 | 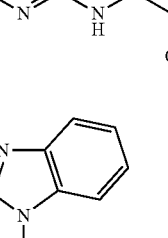 | 544 | 2.79 |
| A80 | 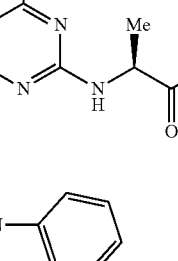 | 601 | 2.07 |

TABLE 185

| Ex | Str | ESI+ | RT |
|---|---|---|---|
| A81 | | 571 | 2.31 |
| A82 | | 593 | 2.73 |
| A83 | | 542 | 2.69 |
| A84 | | 529 | 1.88 |

TABLE 186

| Ex | Str | ESI+ | RT |
|---|---|---|---|
| A85 | | 559 | 1.84 |
| A86 | | 587 | 1.88 |
| A87 | | 573 | 2.02 |
| A88 | | 587 | 2.05 |
| A89 | | 586 | 1.41 |

TABLE 187

| Ex | Str | ESI+ | RT |
|---|---|---|---|
| A90 | | 600 | 1.41 |
| A91 | | 583 | 2.58 |
| A92 | | 601 | 2.46 |
| A93 | | 587 | 2.69 |

TABLE 188
| Ex | Str | ESI+ | RT |
|---|---|---|---|
| A94 | 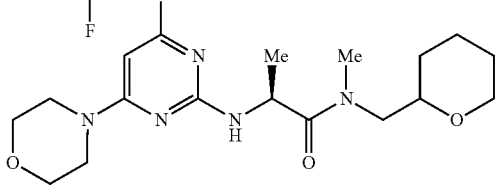 | 530 | 2.78 |
| A95 | 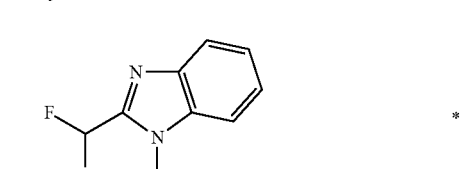 | 530 | 2.52 |
| A96 | 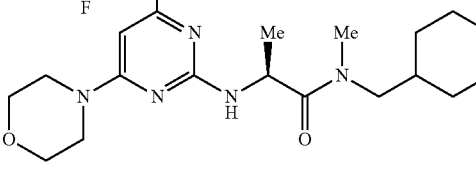 | 543 | 1.93 |
| A97 | 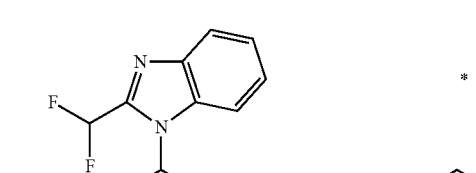 | 543 | 1.93 |
| A98 | 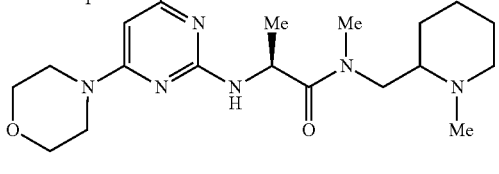 | 543 | 1.91 |

TABLE 189

| Ex | Str | ESI+ | RT |
|---|---|---|---|
| A99 | | 543 | 1.91 |
| A100 | | 573 | 1.93 |
| A101 | | 575 | 1.92 |
| A102 | | 559 | 2.35 |
| A103 | | 588 | 2.91 |

TABLE 190

| Ex | Str | ESI+ | RT |
|---|---|---|---|
| A104 | | 552 | 2.66 |
| A105 | | 566 | 2.69 |
| A106 | | 566 | 2.88 |
| A107 | | 579 | 2.21 |
| A108 | | 552 | 2.86 |

TABLE 191

| Ex | Str | ESI+ | RT |
|---|---|---|---|
| A109 | | 552 | 2.79 |
| A110 | | 552 | 2.78 |
| A111 | | 582 | 2.65 |
| A112 | | 565 | 2.62 |
| A113 | | 556 | 2.89 |

TABLE 192

| Ex | Str | ESI+ | RT |
|---|---|---|---|
| A114 | | 635 | 2.25 |
| A115 | | 523 | 2.39 |
| A116 | | 523 | 2.16 |
| A117 | | 523 | 2.02 |
| A118 | | 528 | 2.31 |

TABLE 193
| Ex | Str | ESI+ | RT |
|---|---|---|---|
| A119 | 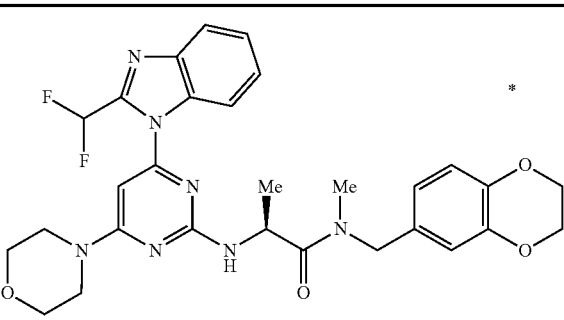 | 580 | 2.74 |
| A120 | 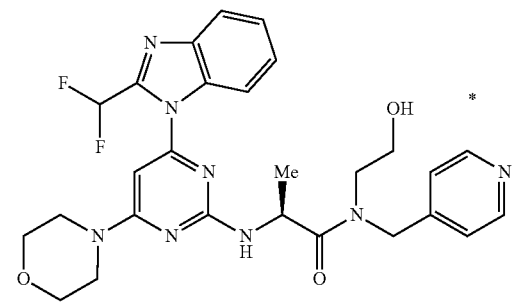 [SMILES: C[C@H](Nc1nc(N2CCOCC2)cc(-n2c(C(F)F)nc3ccccc32)n1)C(=O)N(CCO)Cc1ccncc1] | 553 | 1.93 |
| A121 | 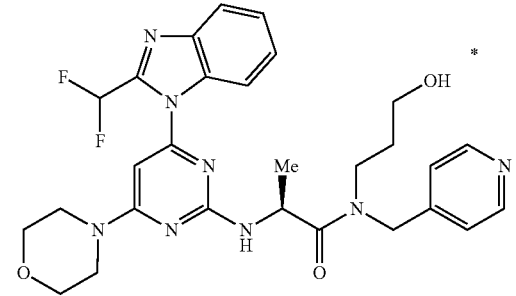 [SMILES: C[C@H](Nc1nc(N2CCOCC2)cc(-n2c(C(F)F)nc3ccccc32)n1)C(=O)N(CCCO)Cc1ccncc1] | 567 | 1.96 |
| A122 | 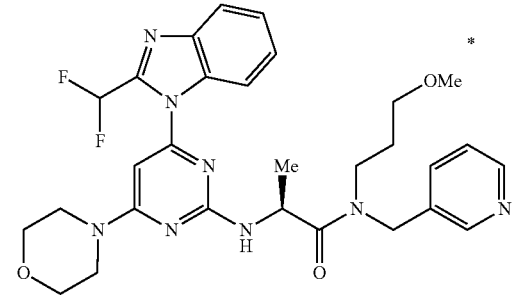 [SMILES: COCCCN(Cc1cccnc1)C(=O)[C@H](C)Nc1nc(N2CCOCC2)cc(-n2c(C(F)F)nc3ccccc32)n1] | 581 | 2.34 |
| A123 | 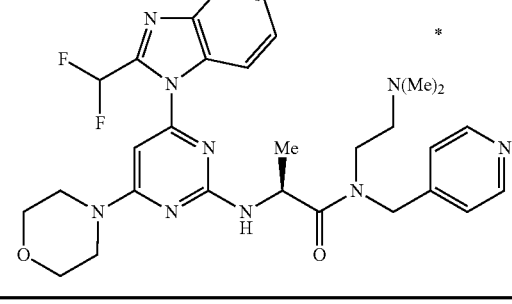 | 580 | 1.66 |

TABLE 194

| Ex | Str | ESI+ | RT |
|---|---|---|---|
| A124 | | 594 | 1.62 |
| A125 | | 622 | 1.69 |
| A126 | | 536 | 2.88 |
| A127 | | 596 | 2.72 |
| A128 | | 566 | 2.75 |

TABLE 195
| Ex | Str | ESI+ | RT |
|---|---|---|---|
| A129 | 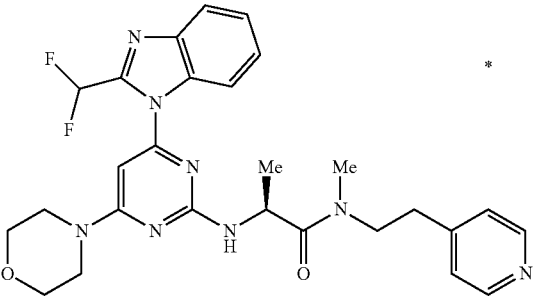 [SMILES: C[C@H](Nc1nc(N2CCOCC2)cc(-n2c(C(F)F)nc3ccccc32)n1)C(=O)N(C)CCc1ccncc1] | 537 | 1.99 |
| A130 | 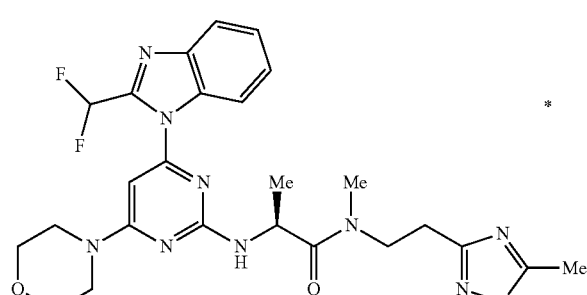 | 542 | 2.5 |
| A131 | 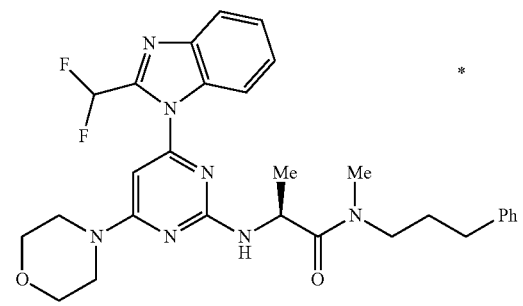 [SMILES: C[C@H](Nc1nc(N2CCOCC2)cc(-n2c(C(F)F)nc3ccccc32)n1)C(=O)N(C)CCCc1ccccc1] | 550 | 2.95 |
| A132 | 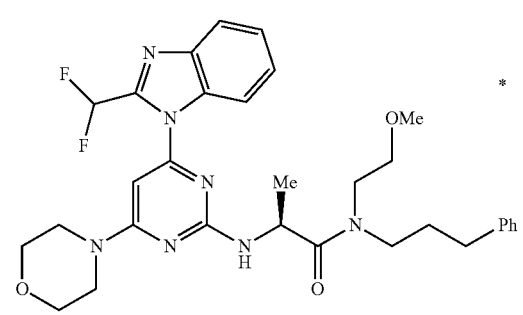 [SMILES: COCCN(CCCc1ccccc1)C(=O)[C@H](C)Nc1nc(N2CCOCC2)cc(-n2c(C(F)F)nc3ccccc32)n1] | 594 | 3.01 |

TABLE 196
| Ex | Str | ESI+ | RT |
|---|---|---|---|
| A133 | 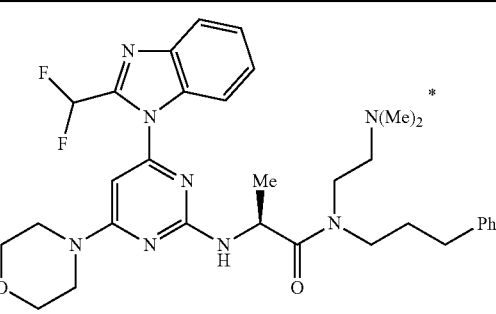 | 607 | 2.37 |
| A134 | 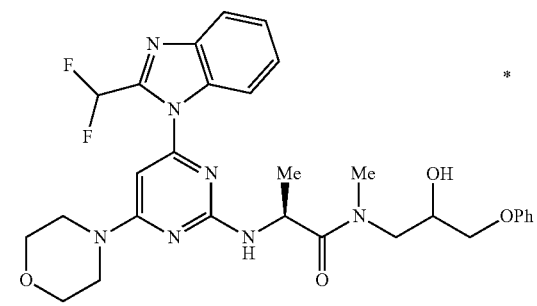 [SMILES: C[C@H](Nc1nc(N2CCOCC2)cc(-n2c(C(F)F)nc3ccccc32)n1)C(=O)N(C)CC(O)COc1ccccc1] | 582 | 2.73 |
| A135 | 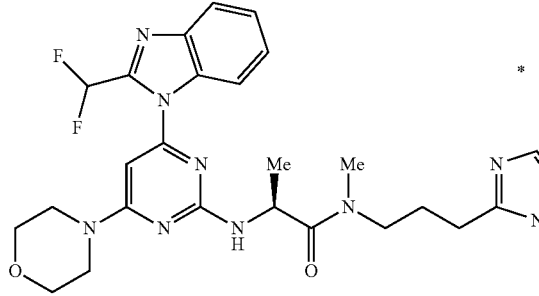 | 554 | 1.88 |
| A136 | 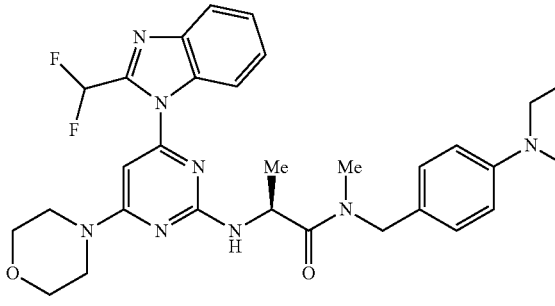 | 607 | 2.72 |
| A137 | 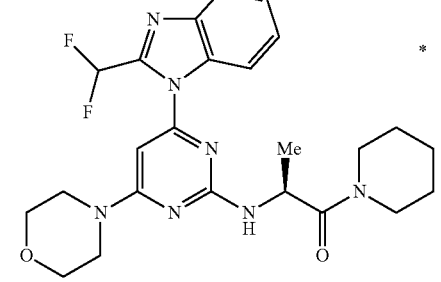 | 486 | 2.72 |

TABLE 197

| Ex | Str | ESI+ | RT |
|---|---|---|---|
| A138 | | 488 | 2.38 |
| A139 | | 501 | 1.77 |
| A140 | | 502 | 2.41 |

TABLE 197-continued

| Ex | Str | ESI+ | RT |
|---|---|---|---|
| A141 | | 502 | 2.34 |
| A142 | | 516 | 2.56 |

TABLE 198

| Ex | Str | ESI+ | RT |
|---|---|---|---|
| A143 | | 518 | 2.26 |
| A144 | | 559 | 1.85 |

TABLE 198-continued

| Ex | Str | ESI+ | RT |
|---|---|---|---|
| A145 | | 529 | 1.83 |
| A146 | | 529 | 2.25 |
| A147 | | 573 | 2.28 |

TABLE 199

| Ex | Str | ESI+ | RT |
|---|---|---|---|
| A148 | | 571 | 1.83 |

TABLE 199-continued
| Ex | Str | ESI+ | RT |
|---|---|---|---|
| A149 | 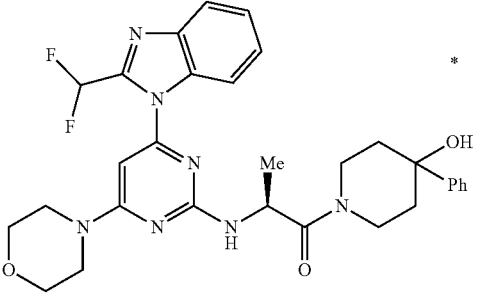 [SMILES: C[C@H](Nc1nc(N2CCOCC2)cc(-n2c(C(F)F)nc3ccccc32)n1)C(=O)N1CCC(O)(c2ccccc2)CC1] | 578 | 2.71 |
| A150 | 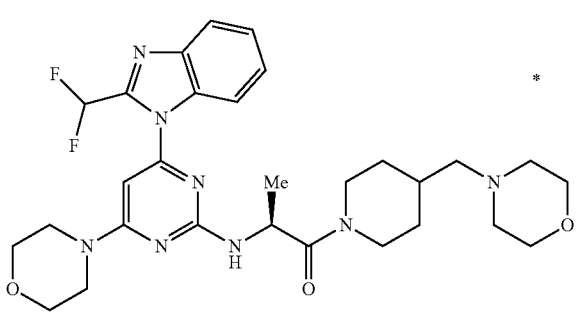 [SMILES: C[C@H](Nc1nc(N2CCOCC2)cc(-n2c(C(F)F)nc3ccccc32)n1)C(=O)N1CCC(CN2CCOCC2)CC1] | 585 | 1.87 |
| A151 | 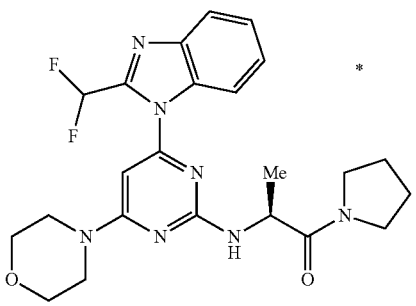 [SMILES: C[C@H](Nc1nc(N2CCOCC2)cc(-n2c(C(F)F)nc3ccccc32)n1)C(=O)N1CCCC1] | 472 | 2.55 |
| A152 | 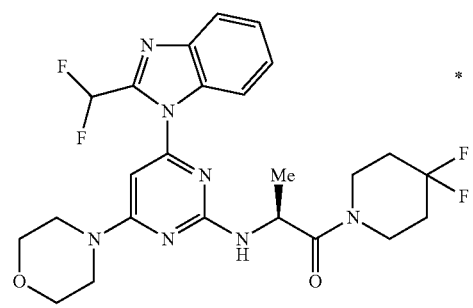 [SMILES: C[C@H](Nc1nc(N2CCOCC2)cc(-n2c(C(F)F)nc3ccccc32)n1)C(=O)N1CCC(F)(F)CC1] | 522 | 2.62 |

TABLE 200
| Ex | Str | ESI+ | RT |
|---|---|---|---|
| A153 | 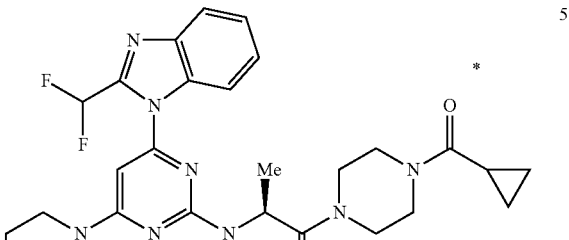 | 516 | 2.61 |
| A154 | | 515 | 1.76 |
| A155 | | 515 | 1.8 |
TABLE 200-continued
| Ex | Str | ESI+ | RT |
|---|---|---|---|
| A156 | 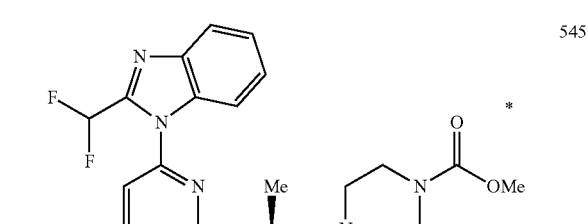 | 501 | 2.13 |
| A157 | | 515 | 2.19 |
TABLE 201
| Ex | Str | ESI+ | RT |
|---|---|---|---|
| A158 | | 555 | 2.42 |
| A159 | | 545 | 2.45 |

TABLE 201-continued

| Ex | Str | ESI+ | RT |
|---|---|---|---|
| A160 | | 565 | 2.3 |
| A161 | | 594 | 2.45 |
| A162 | | 536 | 2.21 |

TABLE 202

| Ex | Str | ESI+ | RT |
|---|---|---|---|
| A163 | | 488 | 2.3 |

TABLE 202-continued

| Ex | Str | ESI+ | RT |
|---|---|---|---|
| A164 | | 488 | 2.29 |
| A165 | | 502 | 2.49 |
| A166 | | 556 | 2.84 |
| A167 | | 502 | 2.44 |

TABLE 203

| Ex | Str | ESI+ | RT |
|---|---|---|---|
| A168 | | 502 | 2.44 |
| A169 | | 502 | 2.33 |
| A170 | | 516 | 2.54 |
| A171 | | 516 | 2.46 |
| A172 | | 516 | 2.41 |

TABLE 204

| Ex | Str | ESI+ | RT |
|---|---|---|---|
| A173 | | 518 | 2.29 |
| A174 | | 518 | 2.3 |
| A175 | | 516 | 2.64 |
| A176 | | 516 | 2.66 |
| A177 | | 516 | 2.57 |

TABLE 205

| Ex | Str | ESI+ | RT |
|---|---|---|---|
| A178 | | 530 | 2.76 |
| A179 | | 530 | 2.72 |
| A180 | | 530 | 2.66 |
| A181 | | 530 | 2.6 |
| A182 | | 530 | 2.54 |

TABLE 206

| Ex | Str | ESI+ | RT |
|---|---|---|---|
| A183 | | 530 | 2.48 |
| A184 | | 544 | 2.78 |
| A185 | | 545 | 1.81 |
| A186 | | 544 | 2.58 |
| A187 | | 545 | 1.74 |

TABLE 207
| Ex | Str | ESI+ | RT |
|---|---|---|---|
| A188 | 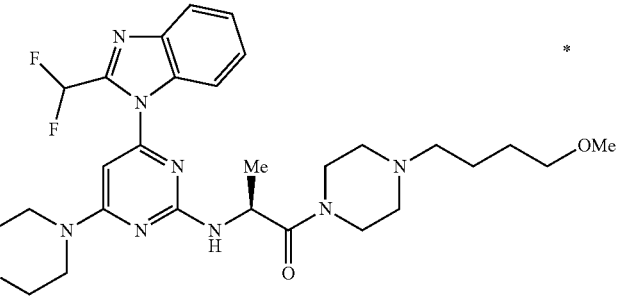 | 573 | 1.85 |
| A189 | 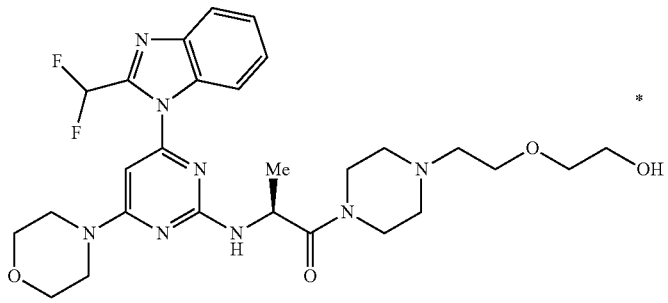 [SMILES: C[C@H](Nc1nc(N2CCOCC2)cc(-n2c(C(F)F)nc3ccccc32)n1)C(=O)N1CCN(CCOCCO)CC1] | 575 | 1.76 |
| A190 | 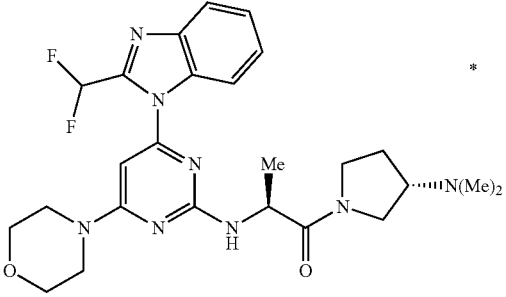 | 515 | 1.77 |
| A191 | 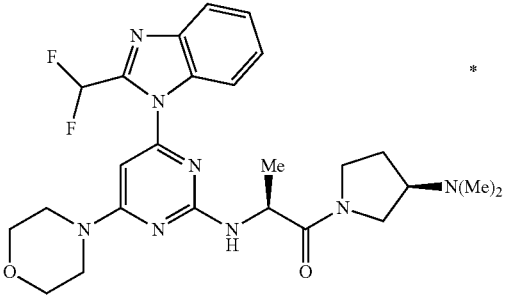 | 515 | 1.76 |
| A192 | 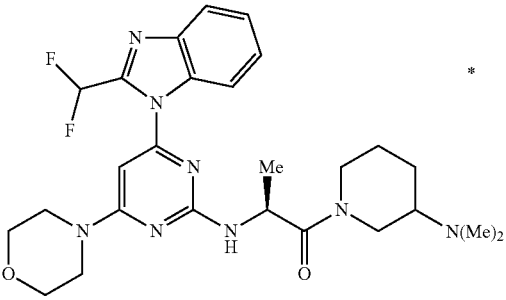 | 529 | 1.87 |

TABLE 208

| Ex | Str | ESI+ | RT |
|---|---|---|---|
| A193 | | 557 | 1.85 |
| A194 | | 543 | 1.95 |
| A195 | | 543 | 1.85 |
| A196 | | 545 | 1.81 |
| A197 | | 557 | 1.91 |

TABLE 209

| Ex | Str | ESI+ | RT |
|---|---|---|---|
| A198 | * | 558 | 1.82 |
| A199 | * | 543 | 2.37 |
| A200 | * | 543 | 2.35 |
| A201 | * | 529 | 2.26 |
| A202 | * | 572 | 1.83 |

TABLE 210

| Ex | Str | ESI+ | RT |
|---|---|---|---|
| A203 | | 593 | 2.08 |
| A204 | | 534 | 2.84 |
| A205 | | 564 | 2.83 |
| A206 | | 568 | 2.95 |
| A207 | | 564 | 2.71 |

TABLE 211
| Ex | Str | ESI+ | RT |
|---|---|---|---|
| A208 | 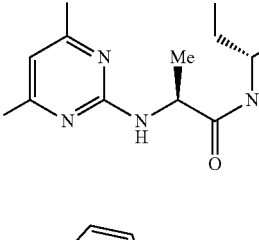 | 564 | 2.71 |
| A209 | 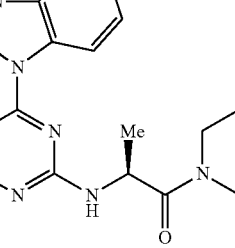 | 569 | 1.89 |
| A210 | 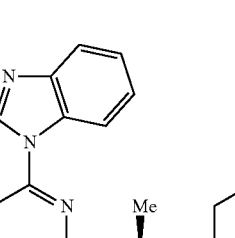 | 555 | 1.84 |
| A211 | 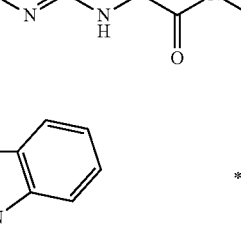 | 585 | 1.81 |
| A212 | 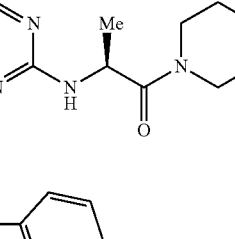 | 584 | 1.56 |

TABLE 212

| Ex | Str | ESI+ | RT |
|---|---|---|---|
| A213 | | 571 | 1.81 |
| A214 | | 600 | 1.86 |
| A215 | | 626 | 1.49 |
| A216 | | 626 | 1.48 |
| A217 | | 562 | 3.02 |

TABLE 213

| Ex | Str | ESI+ | RT |
|---|---|---|---|
| A218 | | 562 | 3 |
| A219 | | 562 | 2.98 |
| A220 | | 578 | 2.83 |
| A221 | | 612 | 2.86 |
| A222 | | 563 | 2.02 |

TABLE 214
| Ex | Str | ESI+ | RT |
|---|---|---|---|
| A223 | 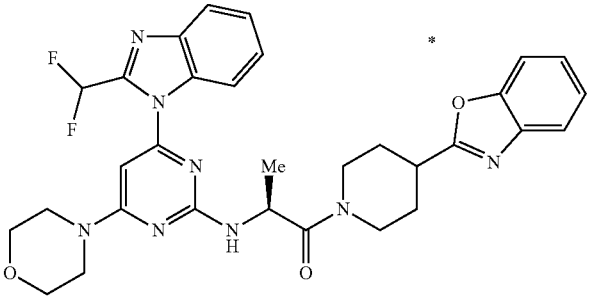 [SMILES: C[C@H](Nc1nc(N2CCOCC2)cc(-n2c(C(F)F)nc3ccccc32)n1)C(=O)N1CCC(c2nc3ccccc3o2)CC1] | 603 | 2.87 |
| A224 | 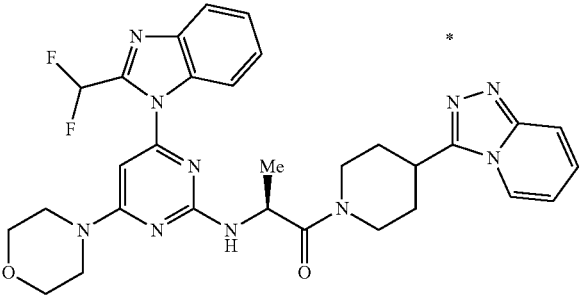 [SMILES: C[C@H](Nc1nc(N2CCOCC2)cc(-n2c(C(F)F)nc3ccccc32)n1)C(=O)N1CCC(c2nnc3ccccn23)CC1] | 603 | 2.34 |
| A225 | 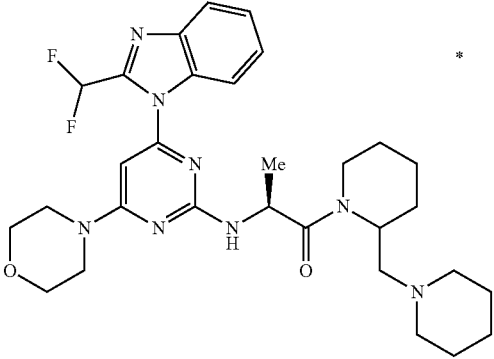 [SMILES: C[C@H](Nc1nc(N2CCOCC2)cc(-n2c(C(F)F)nc3ccccc32)n1)C(=O)N1CCCCC1CN1CCCCC1] | 583 | 2.08 |
| A226 | 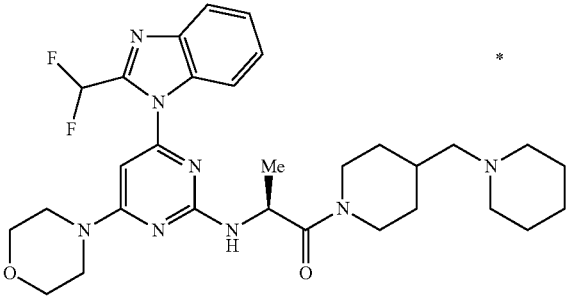 [SMILES: C[C@H](Nc1nc(N2CCOCC2)cc(-n2c(C(F)F)nc3ccccc32)n1)C(=O)N1CCC(CN2CCCCC2)CC1] | 583 | 1.91 |

TABLE 214-continued
| Ex | Str | ESI+ | RT |
|---|---|---|---|
| A227 | 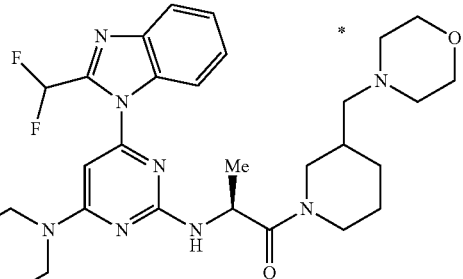 | 585 | 2.08 |
TABLE 215
| Ex | Str | ESI+ | RT |
|---|---|---|---|
| A228 | 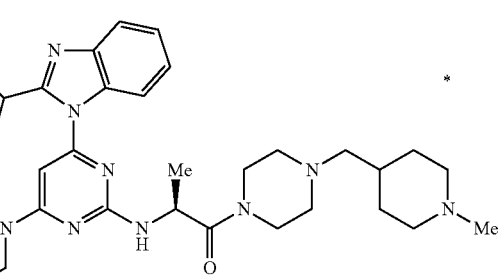 | 585 | 1.98 |
| A229 | 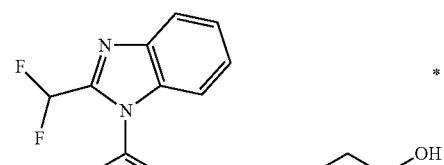 | 598 | 1.46 |
| A230 | | 599 | 1.92 |

TABLE 215-continued

| Ex | Str | ESI+ | RT |
|---|---|---|---|
| A231 | | 617 | 3.14 |
| A232 | | 576 | 3.08 |

TABLE 216

| Ex | Str | ESI+ | RT |
|---|---|---|---|
| A233 | | 576 | 3.09 |
| A234 | | 592 | 2.79 |

TABLE 216-continued

| Ex | Str | ESI+ | RT |
|---|---|---|---|
| A235 | | 578 | 2.97 |
| A236 | | 577 | 2.09 |
| A237 | | 598 | 1.94 |

TABLE 217

| Ex | Str | ESI+ | RT |
|---|---|---|---|
| A238 | | 590 | 3.17 |

TABLE 217-continued
| Ex | Str | ESI+ | RT |
|---|---|---|---|
| A239 | 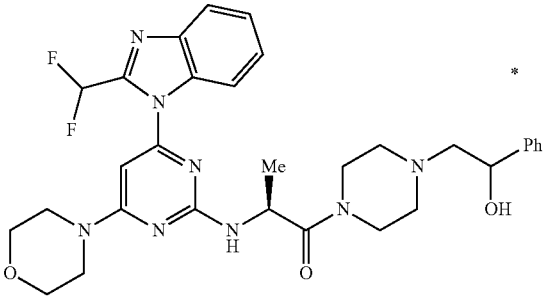 [SMILES: C[C@H](Nc1nc(N2CCOCC2)cc(-n2c(C(F)F)nc3ccccc32)n1)C(=O)N1CCN(CC(O)c2ccccc2)CC1] | 607 | 2.03 |
| A240 | 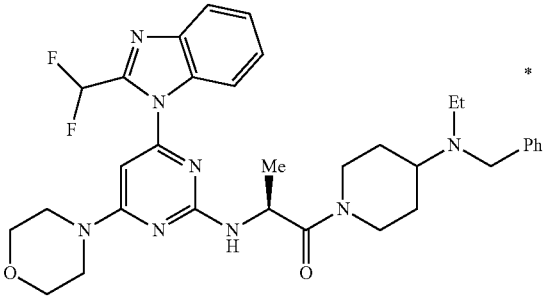 [SMILES: CCN(Cc1ccccc1)C1CCN(C(=O)[C@H](C)Nc2nc(N3CCOCC3)cc(-n3c(C(F)F)nc4ccccc43)n2)CC1] | 619 | 2.24 |
| A241 | 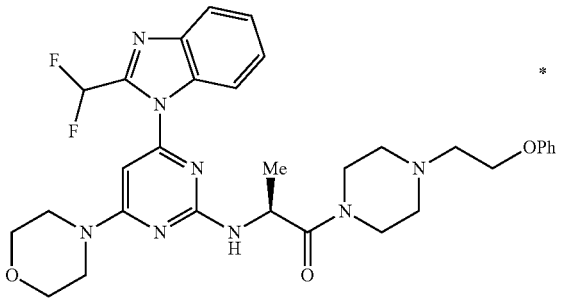 [SMILES: C[C@H](Nc1nc(N2CCOCC2)cc(-n2c(C(F)F)nc3ccccc32)n1)C(=O)N1CCN(CCOc2ccccc2)CC1] | 607 | 2.2 |
| A242 | 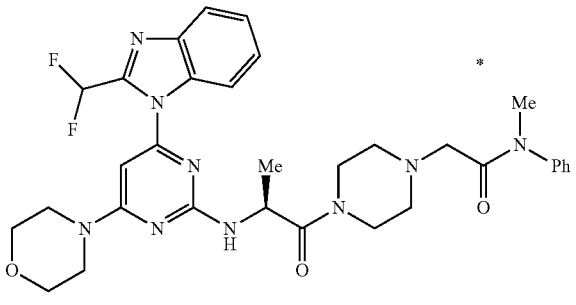 [SMILES: C[C@H](Nc1nc(N2CCOCC2)cc(-n2c(C(F)F)nc3ccccc32)n1)C(=O)N1CCN(CC(=O)N(C)c2ccccc2)CC1] | 634 | 2.23 |

TABLE 218

| Ex | Str | ESI+ | RT |
|---|---|---|---|
| A243 | | 655 | 2.46 |
| A244 | | 621 | 2.19 |
| A245 | | 489 | 2.66 |
| A246 | | 503 | 2.66 |
| A247 | | 503 | 2.8 |

TABLE 219

| Ex | Str | ESI+ | RT |
|---|---|---|---|
| A248 | | 517 | 2.78 |
| A249 | | 546 | 2.69 |
| A250 | | 530 | 2.72 |
| A251 | | 558 | 2.75 |
| A252 | | 529 | 2.88 |

TABLE 220

| Ex | Str | ESI+ | RT |
|---|---|---|---|
| A253 | | 529 | 2.88 |
| A254 | | 543 | 2.88 |
| A255 | | 543 | 2.81 |
| A256 | | 557 | 2.79 |
| A257 | | 571 | 2.97 |

TABLE 221
| Ex | Str | ESI+ | RT |
|----|-----|------|-----|
| A258 | 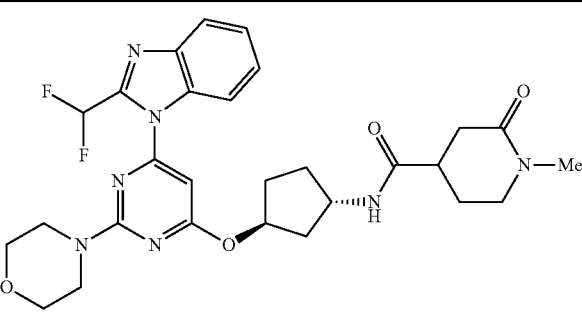 | 570 | 2.7 |
| A259 | 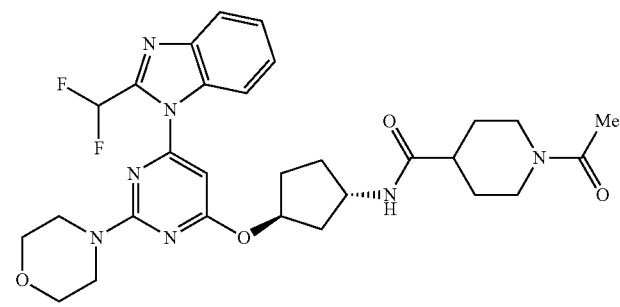 [SMILES: CC(=O)N1CCC(C(=O)N[C@H]2CC[C@H](Oc3cc(-n4c(C(F)F)nc5ccccc54)nc(N4CCOCC4)n3)C2)CC1] | 584 | 2.74 |
| A260 | 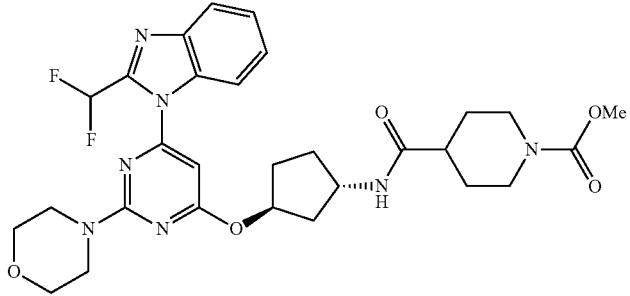 [SMILES: COC(=O)N1CCC(C(=O)N[C@H]2CC[C@H](Oc3cc(-n4c(C(F)F)nc5ccccc54)nc(N4CCOCC4)n3)C2)CC1] | 600 | 2.88 |
| A261 | 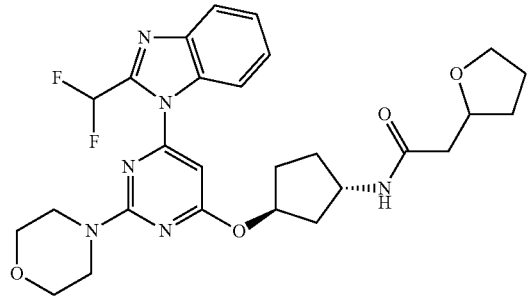 [SMILES: O=C(CC1CCCO1)N[C@H]1CC[C@H](Oc2cc(-n3c(C(F)F)nc4ccccc43)nc(N3CCOCC3)n2)C1] | 543 | 2.87 |
| A262 | 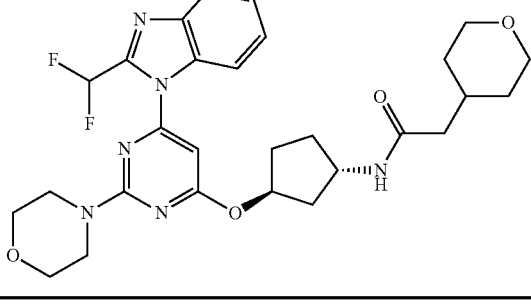 | 557 | 2.86 |

TABLE 222
| Ex | Str | ESI+ | RT |
|---|---|---|---|
| A263 | 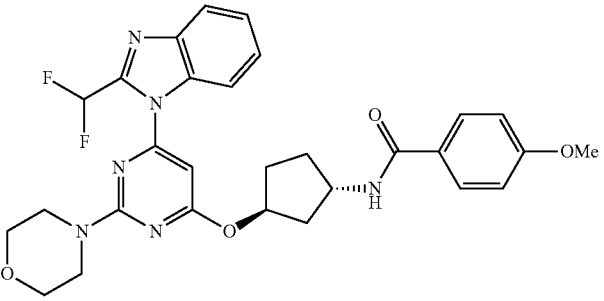 | 565 | 3.02 |
| A264 | 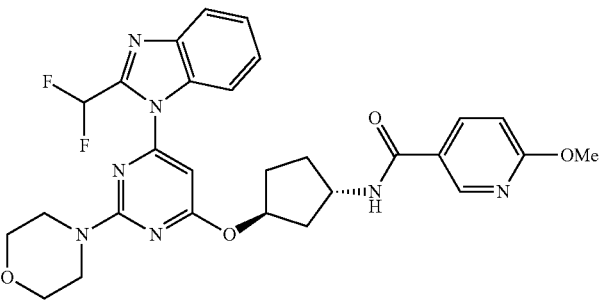 [SMILES: COc1ccc(C(=O)N[C@H]2CC[C@H](Oc3cc(-n4c(C(F)F)nc5ccccc54)nc(N4CCOCC4)n3)C2)cn1] | 566 | 3 |
| A265 | 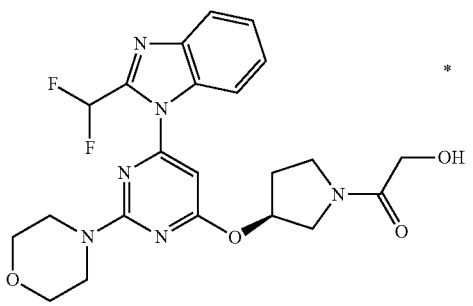 [SMILES: O=C(CO)N1CC[C@H](Oc2cc(-n3c(C(F)F)nc4ccccc43)nc(N3CCOCC3)n2)C1] | 475 | 2.46 |
| A266 | 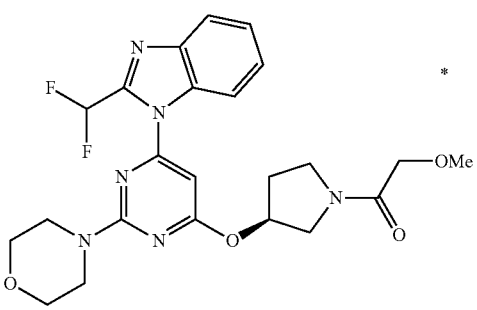 [SMILES: COCC(=O)N1CC[C@H](Oc2cc(-n3c(C(F)F)nc4ccccc43)nc(N3CCOCC3)n2)C1] | 489 | 2.57 |
| A267 | 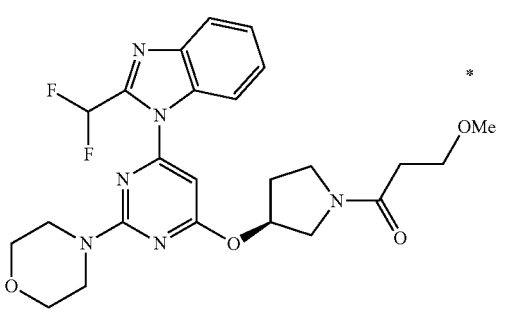 [SMILES: COCCC(=O)N1CC[C@H](Oc2cc(-n3c(C(F)F)nc4ccccc43)nc(N3CCOCC3)n2)C1] | 503 | 2.65 |

TABLE 223

| Ex | Str | ESI+ | RT |
|---|---|---|---|
| A268 | | 532 | 2.54 |
| A269 | | 516 | 2.49 |
| A270 | | 544 | 2.6 |
| A271 | | 515 | 2.68 |
| A272 | | 515 | 2.69 |

TABLE 224
| Ex | Str | ESI+ | RT |
|---|---|---|---|
| A273 | 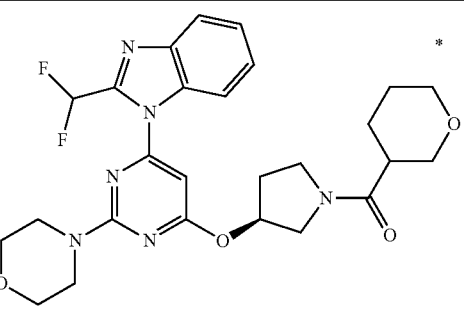 | 529 | 2.72 |
| A274 | 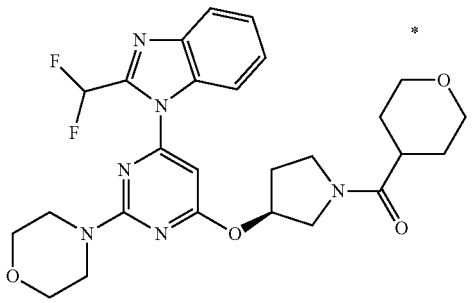 [SMILES: O=C(C1CCOCC1)N1CC[C@H](Oc2cc(-n3c(C(F)F)nc4ccccc43)nc(N3CCOCC3)n2)C1] | 529 | 2.64 |
| A275 | 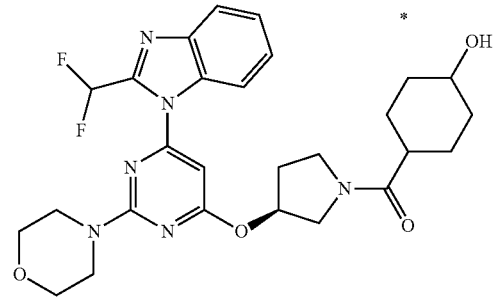 [SMILES: O=C(C1CCC(O)CC1)N1CC[C@H](Oc2cc(-n3c(C(F)F)nc4ccccc43)nc(N3CCOCC3)n2)C1] | 543 | 2.7 |
| A276 | 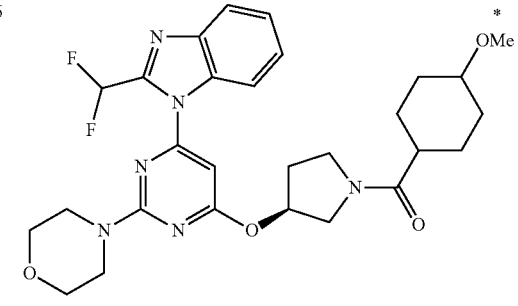 | 557 | 2.88 |
| A277 | 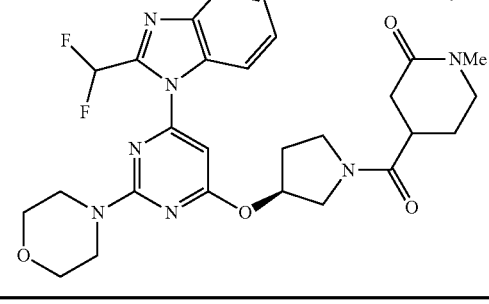 | 556 | 2.5 |

TABLE 225
| Ex | Str | ESI+ | RT |
|---|---|---|---|
| A278 | 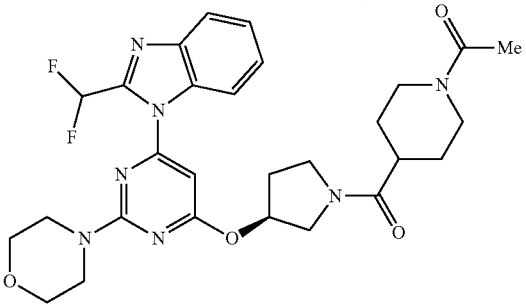 | 570 | 2.55 |
| A279 | 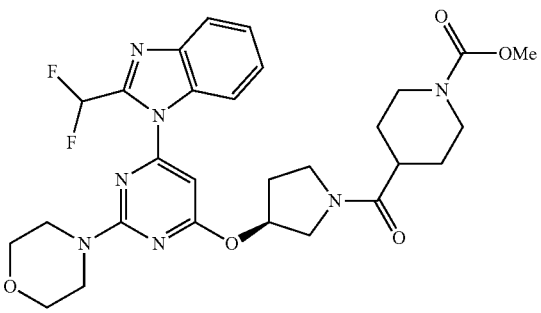 | 586 | 2.72 |
| A280 | 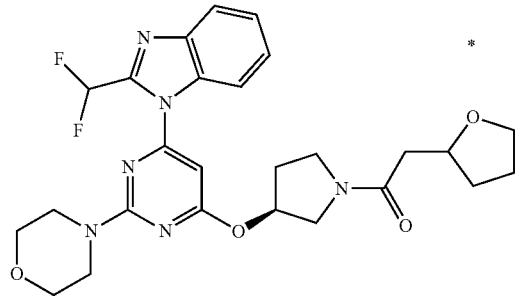 [SMILES: O=C(CC1CCCO1)N1CC[C@H](Oc2cc(-n3c(C(F)F)nc4ccccc43)nc(N3CCOCC3)n2)C1] | 529 | 2.74 |
| A281 | 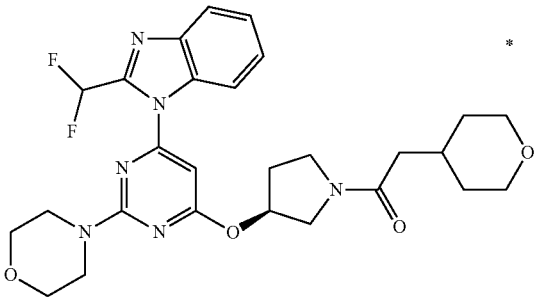 [SMILES: O=C(CC1CCOCC1)N1CC[C@H](Oc2cc(-n3c(C(F)F)nc4ccccc43)nc(N3CCOCC3)n2)C1] | 543 | 2.72 |
| A282 | 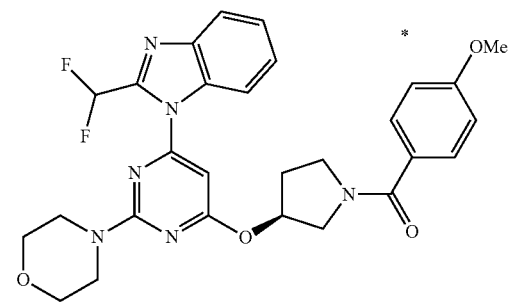 [SMILES: COc1ccc(C(=O)N2CC[C@H](Oc3cc(-n4c(C(F)F)nc5ccccc54)nc(N4CCOCC4)n3)C2)cc1] | 551 | 2.9 |

TABLE 226
| Ex | Str | ESI+ | RT |
|---|---|---|---|
| A283 | 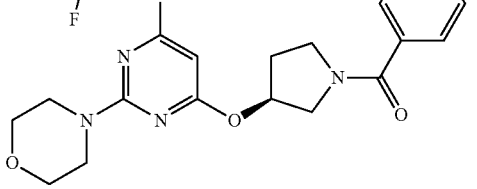 | 552 | 2.83 |
| A284 | 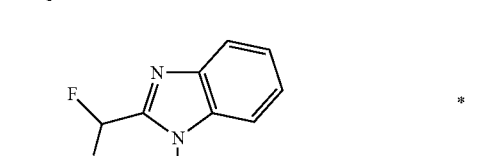 | 474 | 2.4 |
| A285 | 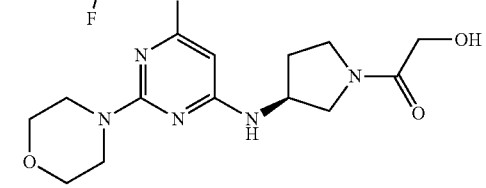 | 488 | 2.51 |
| A286 | 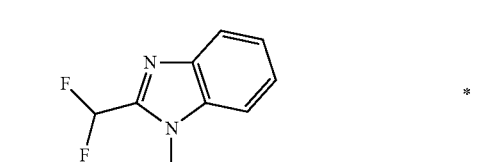 | 502 | 2.59 |
| A287 |  | 531 | 2.49 |

TABLE 227

| Ex | Str | ESI+ | RT |
|---|---|---|---|
| A288 | | 515 | 2.43 |
| A289 | | 543 | 2.56 |
| A290 | | 514 | 2.62 |
| A291 | | 514 | 2.62 |
| A292 | | 528 | 2.66 |

TABLE 228
| Ex | Str | ESI+ | RT |
|---|---|---|---|
| A293 | 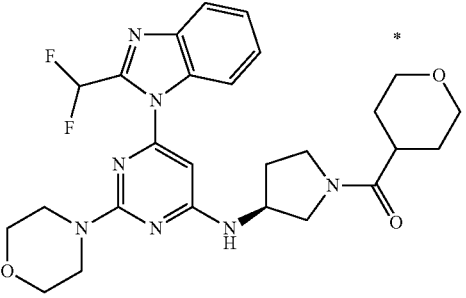 [SMILES: O=C(C1CCOCC1)N1CC[C@H](Nc2cc(-n3c(C(F)F)nc4ccccc43)nc(N3CCOCC3)n2)C1] | 528 | 2.59 |
| A294 | 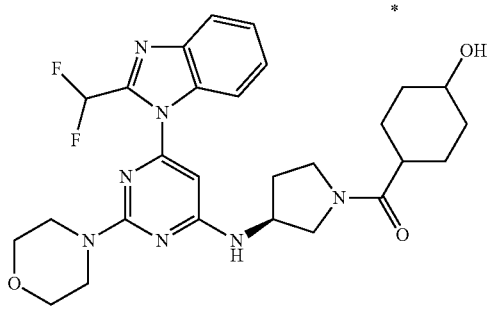 [SMILES: O=C(C1CCC(O)CC1)N1CC[C@H](Nc2cc(-n3c(C(F)F)nc4ccccc43)nc(N3CCOCC3)n2)C1] | 542 | 2.65 |
| A295 | 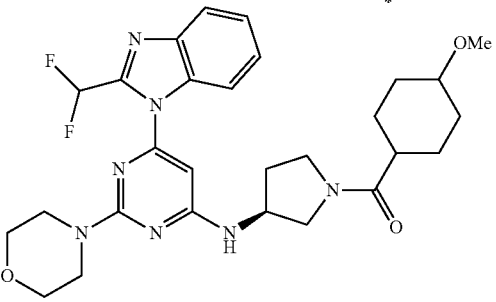 | 556 | 2.83 |
| A296 | 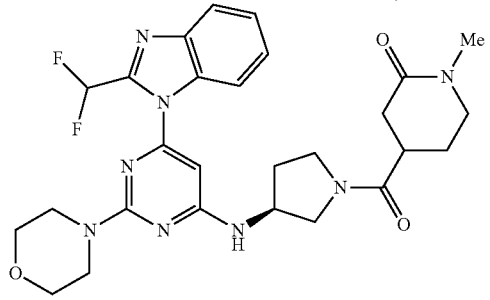 | 555 | 2.46 |
| A297 | 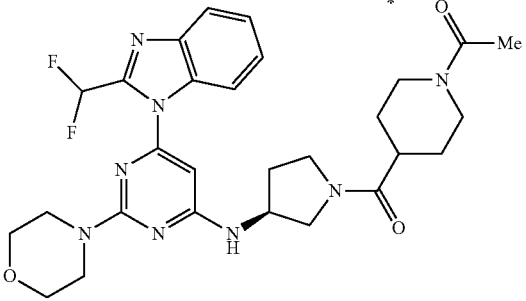 | 569 | 2.5 |

TABLE 229

| Ex | Str | ESI+ | RT |
|---|---|---|---|
| A298 | | 585 | 2.68 |
| A299 | | 528 | 2.68 |
| A300 | | 542 | 2.66 |
| A301 | | 550 | 2.83 |
| A302 | | 551 | 2.76 |

TABLE 230

| Ex | Str | ESI+ | RT |
|---|---|---|---|
| A303 | | 489 | 2.57 |
| A304 | | 503 | 2.68 |
| A305 | | 517 | 2.76 |
| A306 | | 546 | 2.64 |
| A307 | | 530 | 2.57 |

TABLE 231

| Ex | Str | ESI+ | RT |
|---|---|---|---|
| A308 | | 558 | 2.7 |
| A309 | | 529 | 2.78 |
| A310 | | 529 | 2.78 |
| A311 | | 543 | 2.82 |
| A312 | | 543 | 2.75 |

TABLE 232
| Ex | Str | ESI+ | RT |
|---|---|---|---|
| A313 | 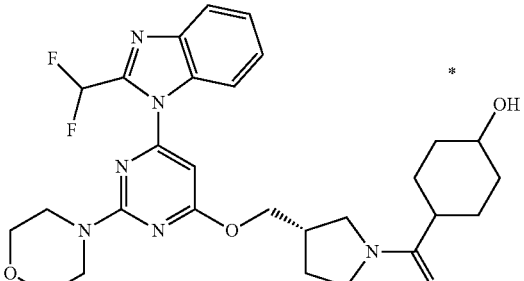 | 557 | 2.8 |
| A314 | 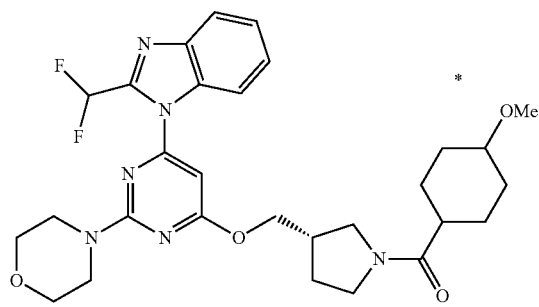 [SMILES: COC1CCC(C(=O)N2CC[C@H](COc3cc(-n4c(C(F)F)nc5ccccc54)nc(N4CCOCC4)n3)C2)CC1] | 571 | 2.97 |
| A315 | 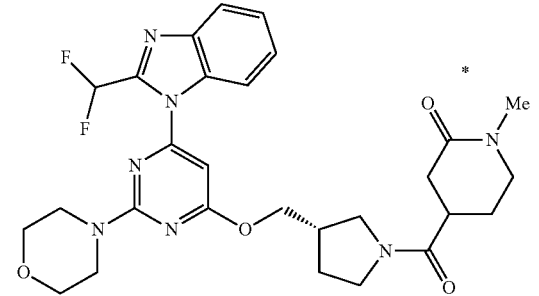 [SMILES: CN1CCC(C(=O)N2CC[C@H](COc3cc(-n4c(C(F)F)nc5ccccc54)nc(N4CCOCC4)n3)C2)CC1=O] | 570 | 2.61 |
| A316 | 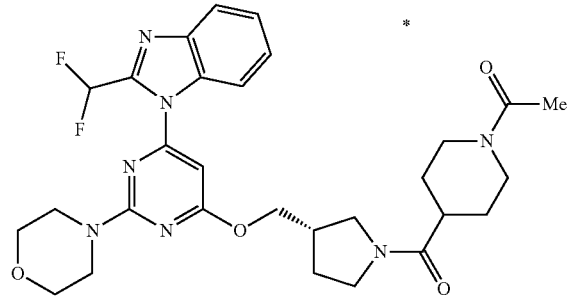 [SMILES: CC(=O)N1CCC(C(=O)N2CC[C@H](COc3cc(-n4c(C(F)F)nc5ccccc54)nc(N4CCOCC4)n3)C2)CC1] | 584 | 2.65 |
| A317 | 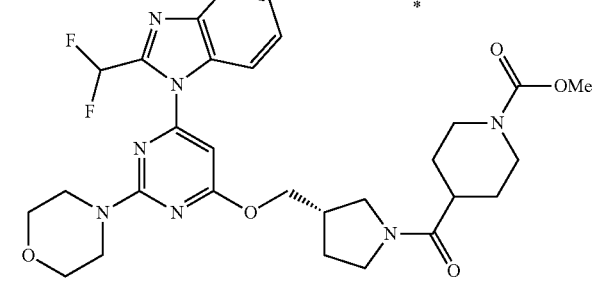 | 600 | 2.82 |

TABLE 233

| Ex | Str | ESI+ | RT |
|---|---|---|---|
| A318 | | 543 | 2.84 |
| A319 | | 557 | 2.83 |
| A320 | | 565 | 2.97 |
| A321 | | 566 | 2.9 |
| A322 | | 488 | 2.44 |

TABLE 234

| Ex | Str | ESI+ | RT |
|---|---|---|---|
| A323 | | 502 | 2.54 |
| A324 | | 516 | 2.62 |
| A325 | | 545 | 2.52 |
| A326 | | 529 | 2.45 |
| A327 | | 557 | 2.58 |

TABLE 235
| Ex | Str | ESI+ | RT |
|---|---|---|---|
| A328 | 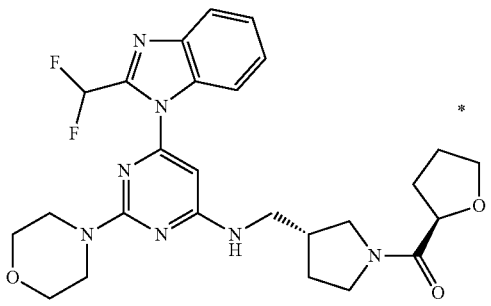 [SMILES: O=C([C@H]1CCCO1)N1CC[C@H](CNc2cc(-n3c(C(F)F)nc4ccccc43)nc(N3CCOCC3)n2)C1] | 528 | 2.65 |
| A329 | 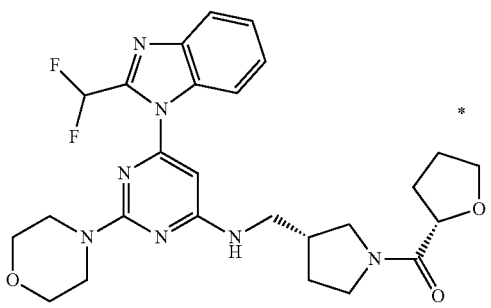 [SMILES: O=C([C@@H]1CCCO1)N1CC[C@H](CNc2cc(-n3c(C(F)F)nc4ccccc43)nc(N3CCOCC3)n2)C1] | 528 | 2.65 |
| A330 | 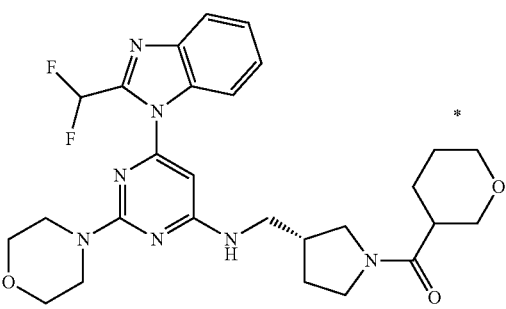 [SMILES: O=C(C1CCCOC1)N1CC[C@H](CNc2cc(-n3c(C(F)F)nc4ccccc43)nc(N3CCOCC3)n2)C1] | 542 | 2.69 |
| A331 | 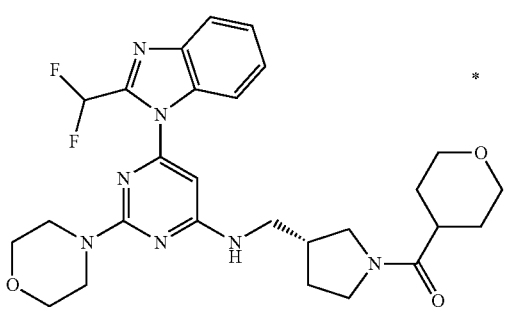 [SMILES: O=C(C1CCOCC1)N1CC[C@H](CNc2cc(-n3c(C(F)F)nc4ccccc43)nc(N3CCOCC3)n2)C1] | 542 | 2.62 |
| A332 | 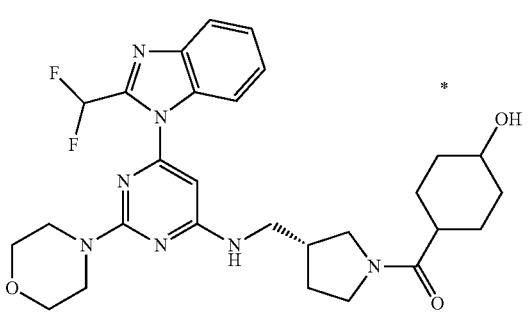 [SMILES: O=C(C1CCC(O)CC1)N1CC[C@H](CNc2cc(-n3c(C(F)F)nc4ccccc43)nc(N3CCOCC3)n2)C1] | 556 | 2.66 |

TABLE 236

| Ex | Str | ESI+ | RT |
|---|---|---|---|
| A333 | | 570 | 2.85 |
| A334 | | 569 | 2.48 |
| A335 | | 583 | 2.53 |
| A336 | | 599 | 2.7 |
| A337 | | 542 | 2.71 |

TABLE 237

| Ex | Str | ESI+ | RT |
|---|---|---|---|
| A338 | | 556 | 2.69 |
| A339 | | 564 | 2.83 |
| A340 | | 565 | 2.76 |
| A341 | | 474 | 2.42 |
| A342 | | 488 | 2.6 |

TABLE 238

| Ex | Str | ESI+ | RT |
|---|---|---|---|
| A343 | | 502 | 2.58 |
| A344 | | 531 | 2.47 |
| A345 | | 515 | 2.49 |
| A346 | | 543 | 2.53 |
| A347 | | 514 | 2.68 |

TABLE 239

| Ex | Str | ESI+ | RT |
|---|---|---|---|
| A348 | | 514 | 2.68 |
| A349 | | 528 | 2.69 |
| A350 | | 528 | 2.61 |
| A351 | | 542 | 2.61 |
| A352 | | 556 | 2.82 |

TABLE 240
| Ex | Str | ESI+ | RT |
|---|---|---|---|
| A353 | 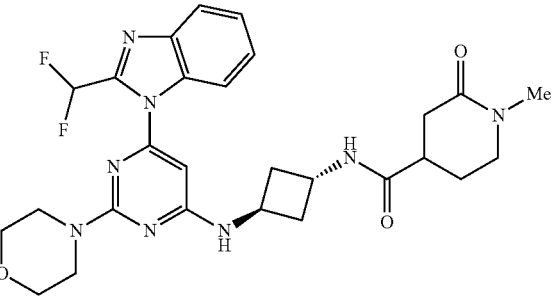 [SMILES: O=C(N[C@H]1C[C@H](Nc2cc(-n3c(C(F)F)nc4ccccc43)nc(N3CCOCC3)n2)C1)C1CCC(O)CC1] | 555 | 2.49 |
| A354 | 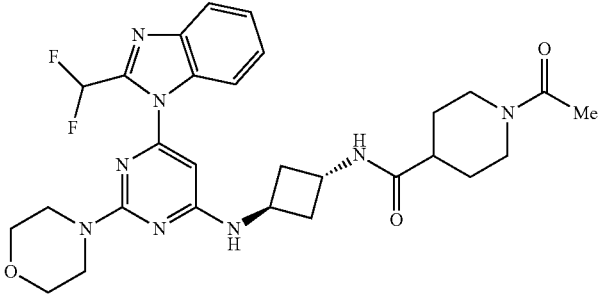 [SMILES: CC(=O)N1CCC(C(=O)N[C@H]2C[C@H](Nc3cc(-n4c(C(F)F)nc5ccccc54)nc(N4CCOCC4)n3)C2)CC1] | 569 | 2.53 |
| A355 | 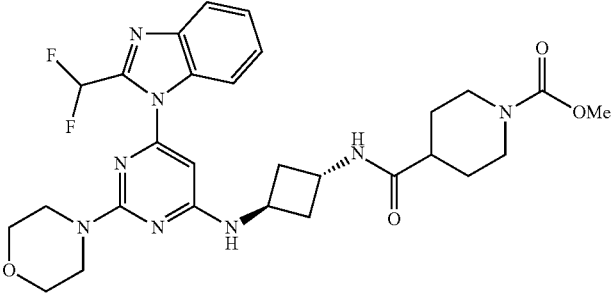 [SMILES: COC(=O)N1CCC(C(=O)N[C@H]2C[C@H](Nc3cc(-n4c(C(F)F)nc5ccccc54)nc(N4CCOCC4)n3)C2)CC1] | 585 | 2.71 |
| A356 | 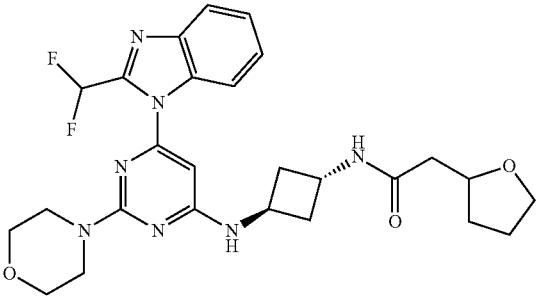 [SMILES: O=C(CC1CCCO1)N[C@H]1C[C@H](Nc2cc(-n3c(C(F)F)nc4ccccc43)nc(N3CCOCC3)n2)C1] | 528 | 2.68 |
| A357 | 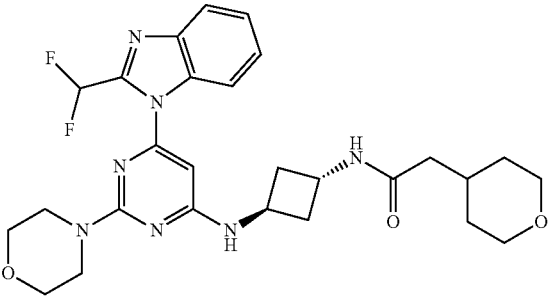 [SMILES: O=C(CC1CCOCC1)N[C@H]1C[C@H](Nc2cc(-n3c(C(F)F)nc4ccccc43)nc(N3CCOCC3)n2)C1] | 542 | 2.66 |

TABLE 241

| Ex | Str | ESI+ | RT |
|---|---|---|---|
| A358 | | 550 | 2.87 |
| A359 | | 551 | 2.84 |
| A360 | | 461 | 2.4 |
| A361 | | 475 | 2.58 |
| A362 | | 489 | 2.61 |

TABLE 242

| Ex | Str | ESI+ | RT |
|---|---|---|---|
| A363 | | 518 | 2.49 |
| A364 | | 502 | 2.49 |
| A365 | | 530 | 2.56 |
| A366 | | 501 | 2.7 |
| A367 | | 501 | 2.7 |

TABLE 243
| Ex | Str | ESI+ | RT |
|---|---|---|---|
| A368 | 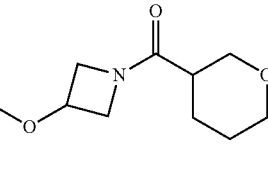 | 515 | 2.69 |
| A369 | 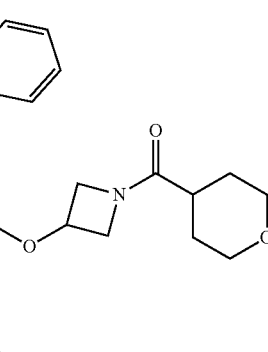 | 515 | 2.61 |
| A370 | 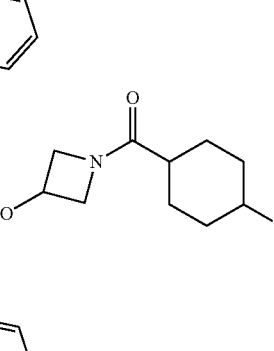 | 529 | 2.66 |
| A371 | 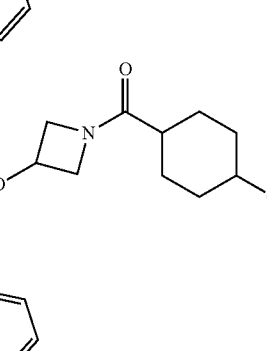 | 543 | 2.86 |
| A372 | 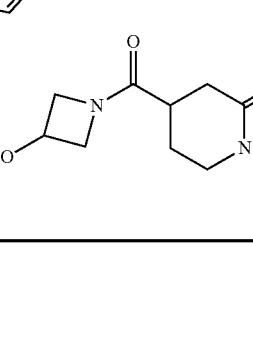 | 542 | 2.46 |

TABLE 244
| Ex | Str | ESI+ | RT |
|---|---|---|---|
| A373 | 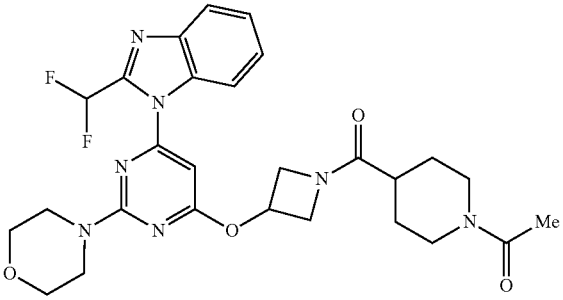 [SMILES: CC(=O)N1CCC(C(=O)N2CC(Oc3cc(-n4c(C(F)F)nc5ccccc54)nc(N4CCOCC4)n3)C2)CC1] | 556 | 2.51 |
| A374 | 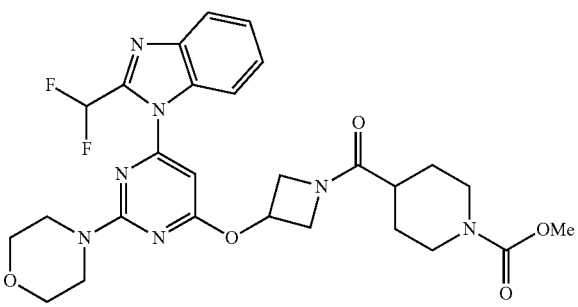 [SMILES: COC(=O)N1CCC(C(=O)N2CC(Oc3cc(-n4c(C(F)F)nc5ccccc54)nc(N4CCOCC4)n3)C2)CC1] | 572 | 2.7 |
| A375 | 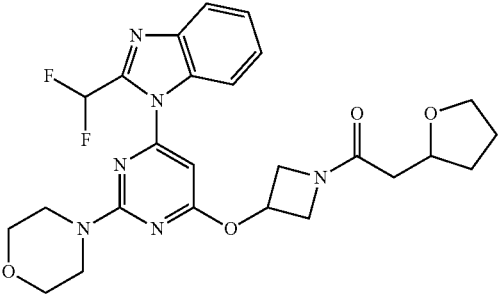 [SMILES: O=C(CC1CCCO1)N1CC(Oc2cc(-n3c(C(F)F)nc4ccccc43)nc(N3CCOCC3)n2)C1] | 515 | 2.7 |
| A376 | 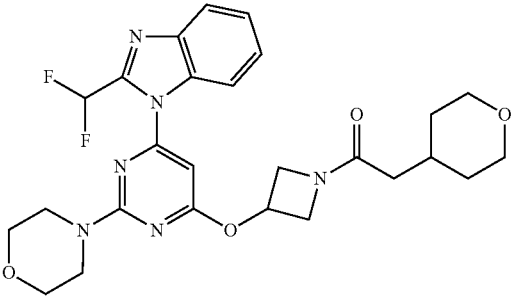 [SMILES: O=C(CC1CCOCC1)N1CC(Oc2cc(-n3c(C(F)F)nc4ccccc43)nc(N3CCOCC3)n2)C1] | 529 | 2.69 |
| A377 | 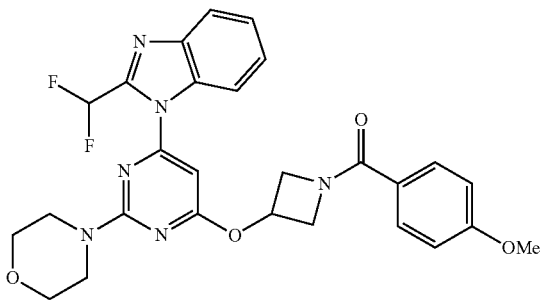 [SMILES: COc1ccc(C(=O)N2CC(Oc3cc(-n4c(C(F)F)nc5ccccc54)nc(N4CCOCC4)n3)C2)cc1] | 537 | 2.92 |

TABLE 245
| Ex | Str | ESI+ | RT |
|---|---|---|---|
| A378 | 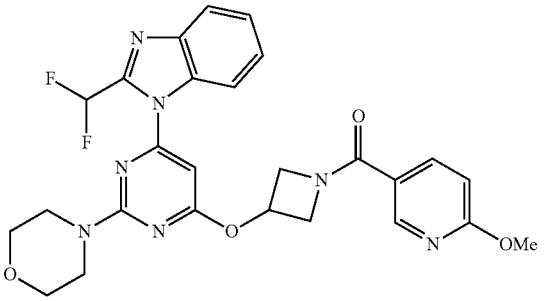 [SMILES: COc1ccc(C(=O)N2CC(Oc3cc(-n4c(C(F)F)nc5ccccc54)nc(N4CCOCC4)n3)C2)cn1] | 538 | 2.85 |
| A379 | 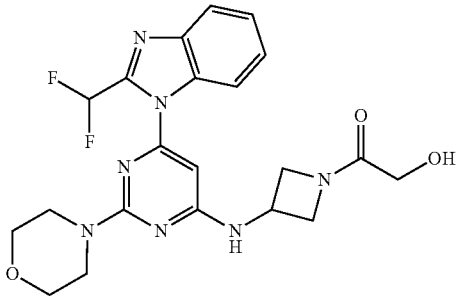 [SMILES: O=C(CO)N1CC(Nc2cc(-n3c(C(F)F)nc4ccccc43)nc(N3CCOCC3)n2)C1] | 460 | 2.32 |
| A380 | 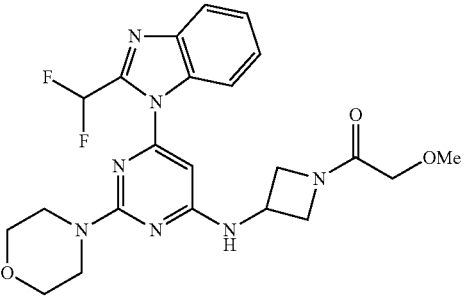 [SMILES: COCC(=O)N1CC(Nc2cc(-n3c(C(F)F)nc4ccccc43)nc(N3CCOCC3)n2)C1] | 474 | 2.49 |
| A381 | 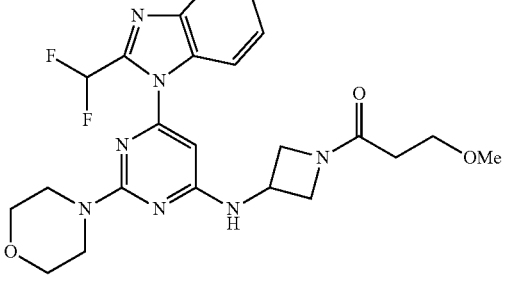 | 488 | 2.54 |
| A382 | 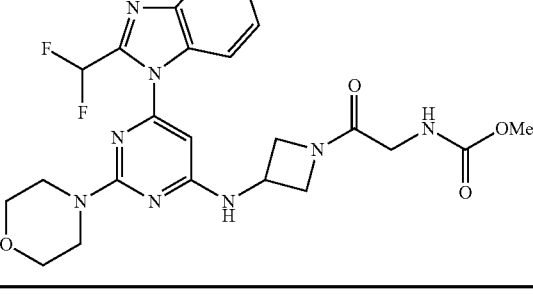 | 517 | 2.43 |

TABLE 246

| Ex | Str | ESI+ | RT |
|---|---|---|---|
| A383 | | 501 | 2.41 |
| A384 | | 529 | 2.5 |
| A385 | | 500 | 2.61 |
| A386 | | 500 | 2.61 |
| A387 | | 514 | 2.62 |

TABLE 247

| Ex | Str | ESI+ | RT |
|---|---|---|---|
| A388 | | 514 | 2.53 |
| A389 | | 528 | 2.6 |
| A390 | | 542 | 2.8 |
| A391 | | 541 | 2.39 |
| A392 | | 555 | 2.44 |

TABLE 248

| Ex | Str | ESI+ | RT |
|---|---|---|---|
| A393 | | 571 | 2.63 |
| A394 | | 514 | 2.64 |
| A395 | | 528 | 2.62 |
| A396 | | 536 | 2.83 |
| A397 | | 537 | 2.77 |

TABLE 249

| Ex | Str | ESI+ | RT |
|---|---|---|---|
| A398 | | 475 | 2.45 |
| A399 | | 489 | 2.61 |
| A400 | | 503 | 2.64 |
| A401 | | 532 | 2.53 |

TABLE 250
| Ex | Str | ESI+ | RT |
|---|---|---|---|
| A402 | 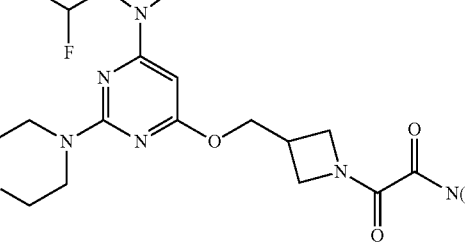 | 516 | 2.5 |
| A403 | 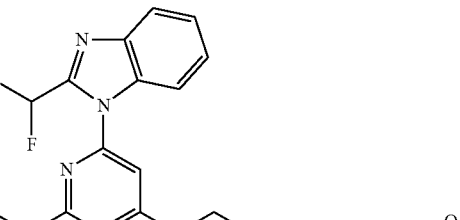 | 544 | 2.59 |
| A404 | 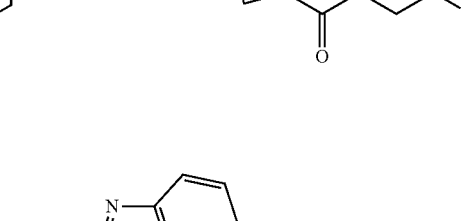 | 515 | 2.71 |
| A405 | 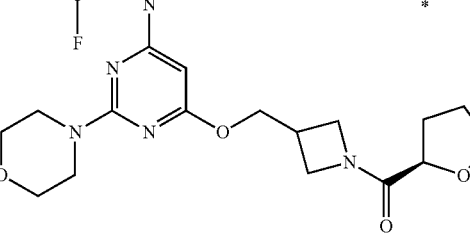 | 515 | 2.71 |

TABLE 251

| Ex | Str | ESI+ | RT |
|---|---|---|---|
| A406 | | 529 | 2.71 |
| A407 | | 529 | 2.64 |
| A408 | | 543 | 2.69 |
| A409 | | 557 | 2.88 |

TABLE 252
| Ex | Str | ESI+ | RT |
|---|---|---|---|
| A410 | 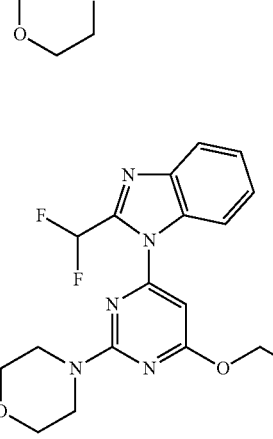 | 556 | 2.49 |
| A411 | 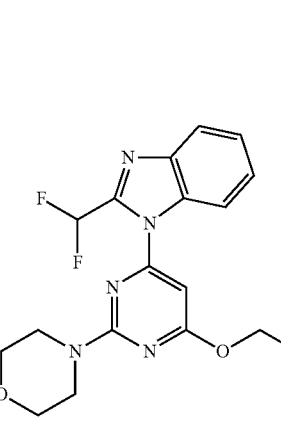 | 570 | 2.54 |
| A412 | 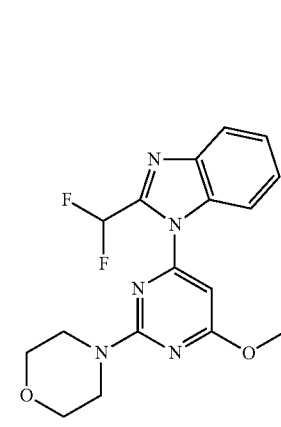 | 586 | 2.72 |
| A413 | 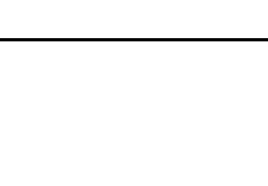 | 529 | 2.73 |

TABLE 253

| Ex | Str | ESI+ | RT |
|---|---|---|---|
| A414 | | 543 | 2.71 |
| A415 | | 551 | 2.92 |
| A416 | | 552 | 2.86 |
| A417 | | 488 | 2.5 |

TABLE 254

| Ex | Str | ESI+ | RT |
|---|---|---|---|
| A418 | | 502 | 2.54 |
| A419 | | 531 | 2.44 |
| A420 | | 528 | 2.61 |
| A421 | | 528 | 2.53 |

TABLE 255

| Ex | Str | ESI+ | RT |
|---|---|---|---|
| A422 | | 556 | 2.78 |
| A423 | | 555 | 2.41 |
| A424 | | 569 | 2.44 |
| A425 | | 585 | 2.62 |

TABLE 256

| Ex | Str | ESI+ | RT |
|---|---|---|---|
| A426 | | 542 | 2.6 |
| A427 | | 550 | 2.8 |
| A428 | | 551 | 2.75 |
| A429 | | 542 | 2.65 |

TABLE 257
| Ex | Str | ESI+ | RT |
|---|---|---|---|
| A430 | 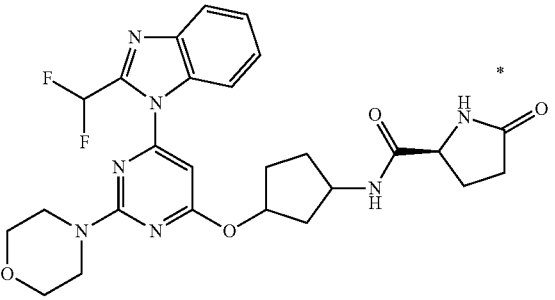 [SMILES: O=C1CC[C@@H](C(=O)NC2CCC(Oc3cc(-n4c(C(F)F)nc5ccccc54)nc(N4CCOCC4)n3)C2)N1] | 542 | 2.65 |
| A431 | 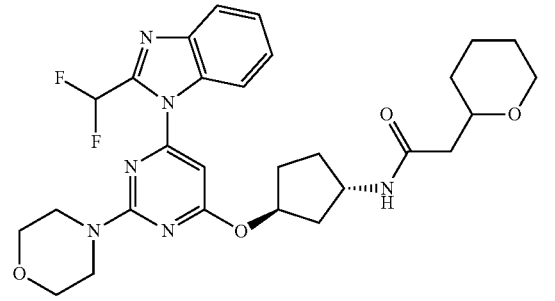 | 557 | 3 |
| A432 | 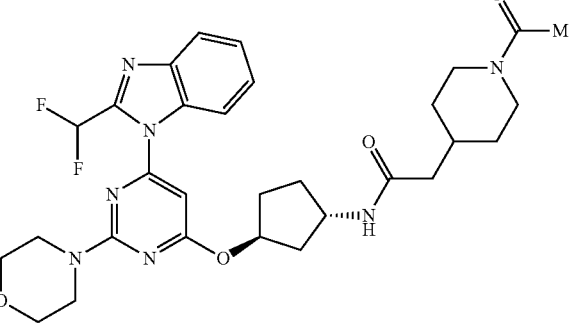 | 598 | 2.79 |
| A433 | 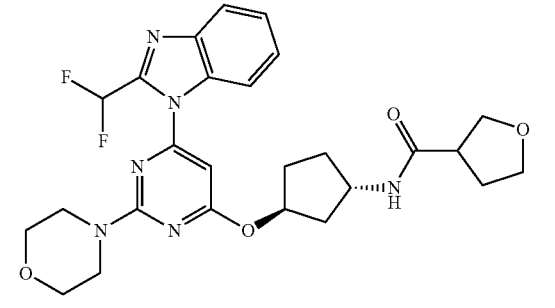 [SMILES: O=C(N[C@H]1CC[C@H](Oc2cc(-n3c(C(F)F)nc4ccccc43)nc(N3CCOCC3)n2)C1)C1CCOC1] | 529 | 2.79 |
| A434 | 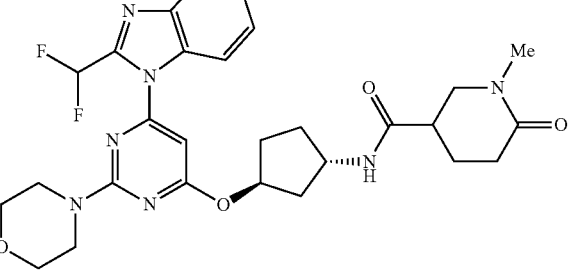 | 570 | 2.74 |

TABLE 258
| Ex | Str | ESI+ | RT |
|---|---|---|---|
| A435 | 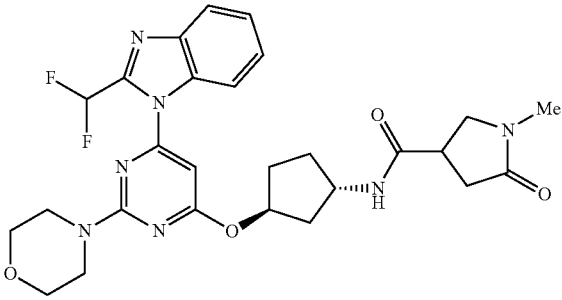 [SMILES: CN1CC(C(=O)N[C@H]2CC[C@H](Oc3cc(-n4c(C(F)F)nc5ccccc54)nc(N4CCOCC4)n3)C2)CC1=O] | 556 | 2.69 |
| A436 | 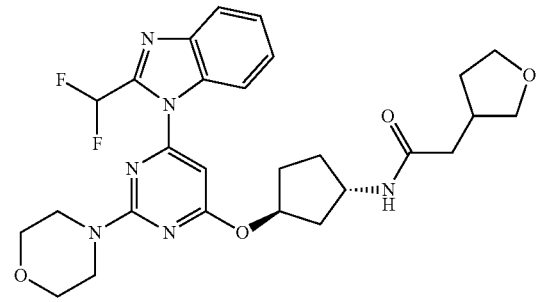 [SMILES: O=C(CC1CCOC1)N[C@H]1CC[C@H](Oc2cc(-n3c(C(F)F)nc4ccccc43)nc(N3CCOCC3)n2)C1] | 543 | 2.82 |
| A437 | 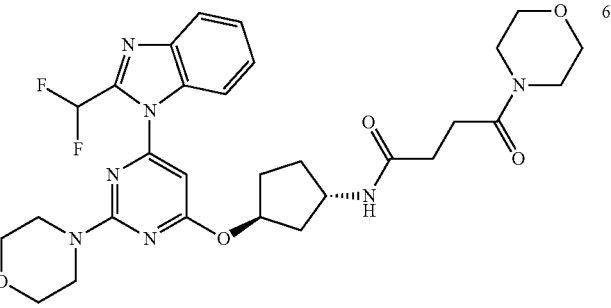 | 600 | 2.75 |
| A438 | 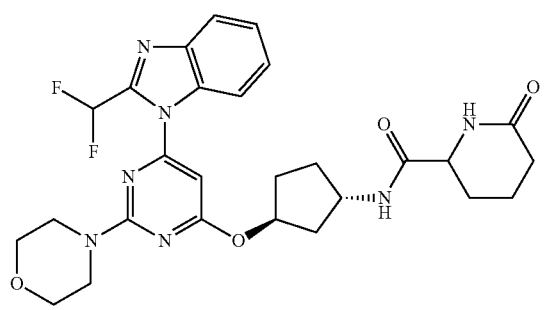 [SMILES: O=C1CCCC(C(=O)N[C@H]2CC[C@H](Oc3cc(-n4c(C(F)F)nc5ccccc54)nc(N4CCOCC4)n3)C2)N1] | 556 | 2.71 |
| A439 | 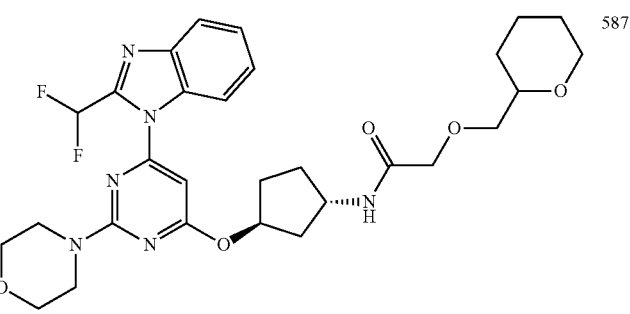 | 587 | 3.1 |

TABLE 259

| Ex | Str | ESI+ | RT |
|---|---|---|---|
| A440 | | 536 | 3.03 |
| A441 | | 536 | 2.84 |
| A442 | | 550 | 2.67 |
| A443 | | 570 | 2.23 |
| A444 | | 584 | 2.26 |

TABLE 260
| Ex | Str | | ESI+ | RT |
|---|---|---|---|---|
| A445 | 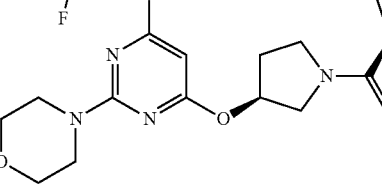 | * | 528 | 2.44 |
| A446 | 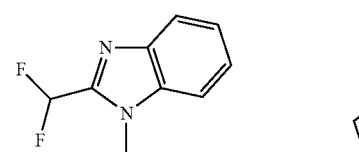 | * | 528 | 2.43 |
| A447 | 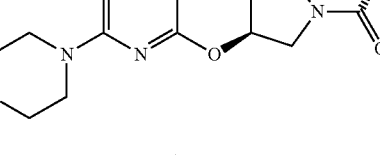 | * | 543 | 2.9 |
| A448 | 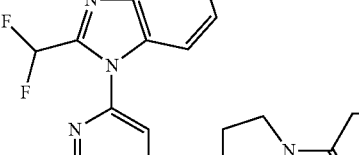 | * | 584 | 2.63 |
| A449 | 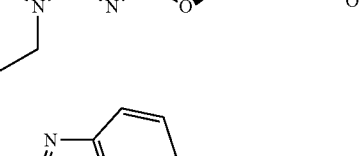 | * | 515 | 2.62 |

TABLE 261
| Ex | Str | ESI+ | RT |
|---|---|---|---|
| A450 | 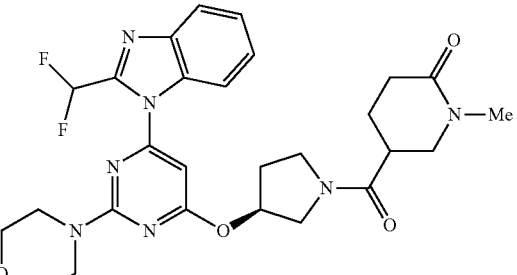 | 556 | 2.52 |
| A451 | 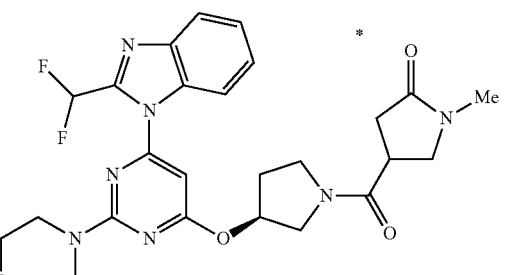 | 542 | 2.48 |
| A452 | 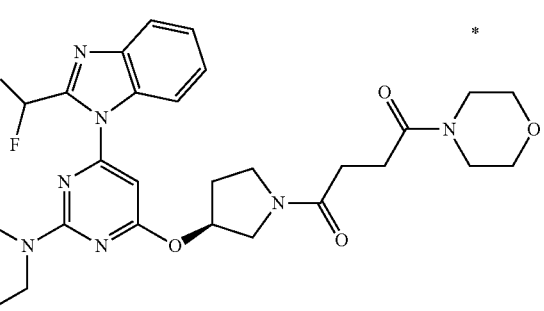 | 586 | 2.6 |
| A453 | 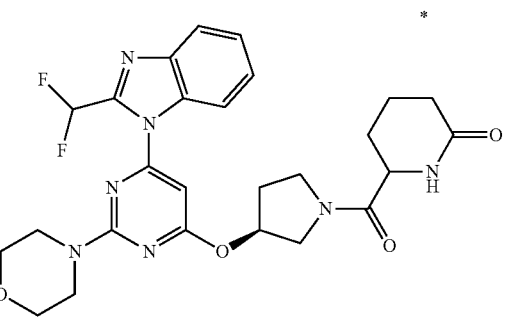 | 542 | 2.5 |
| A454 | 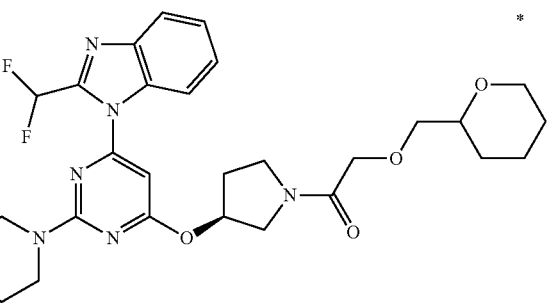 | 573 | 2.85 |

TABLE 262

| Ex | Str | ESI+ | RT |
|---|---|---|---|
| A455 | * | 522 | 2.75 |
| A456 | * | 522 | 2.56 |
| A457 | * | 536 | 2.46 |
| A458 | * | 556 | 2.05 |
| A459 | * | 570 | 2.11 |

TABLE 263

| Ex | Str | ESI+ | RT |
|---|---|---|---|
| A460 | | 527 | 2.39 |
| A461 | | 527 | 2.39 |
| A462 | | 542 | 2.85 |
| A463 | | 583 | 2.57 |
| A464 | | 514 | 2.56 |

TABLE 264

| Ex | Str | ESI+ | RT |
|---|---|---|---|
| A465 | | 555 | 2.47 |
| A466 | | 541 | 2.43 |
| A467 | | 585 | 2.56 |
| A468 | | 541 | 2.45 |
| A469 | | 572 | 2.8 |

TABLE 265
| Ex | Str | ESI+ | RT |
|---|---|---|---|
| A470 | 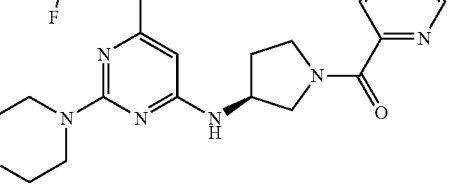 | 521 | 2.67 |
| A471 | 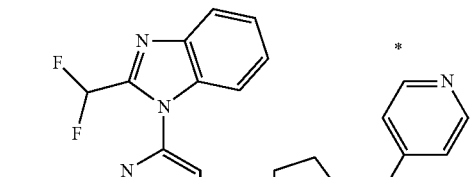 | 521 | 2.49 |
| A472 | 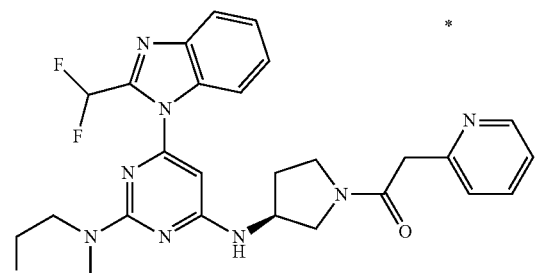 | 535 | 2.41 |
| A473 | 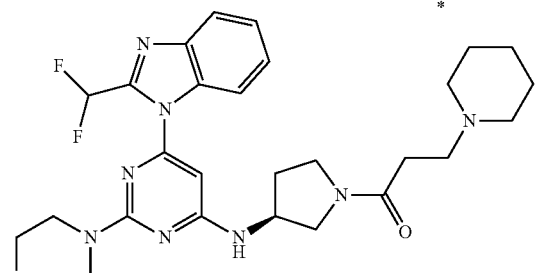 | 555 | 2 |
| A474 | 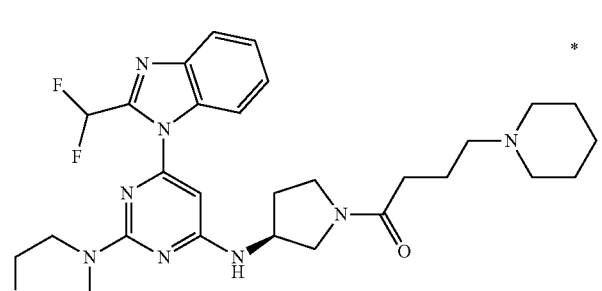 | 569 | 2.05 |

TABLE 266

| Ex | Str | ESI+ | RT |
|---|---|---|---|
| A475 | | 541 | 1.97 |
| A476 | | 543 | 1.94 |
| A477 | | 555 | 2.52 |
| A478 | | 557 | 1.94 |
| A479 | | 571 | 1.98 |

TABLE 267
| Ex | Str | ESI+ | RT |
|---|---|---|---|
| A480 | 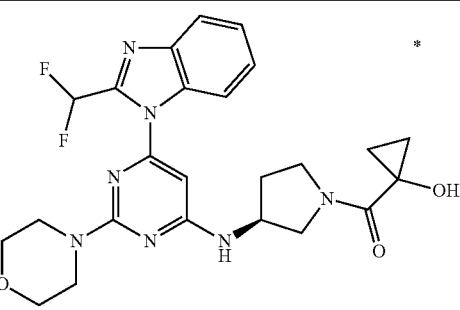 | 500 | 2.58 |
| A481 | 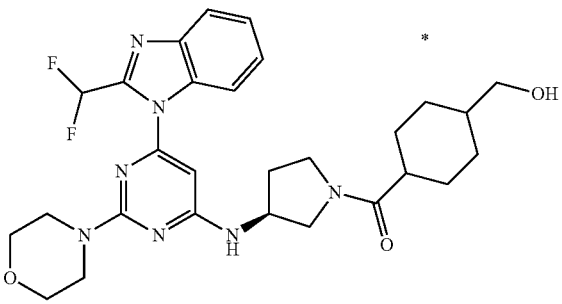 [SMILES: O=C(C1CCC(CO)CC1)N1CC[C@H](Nc2cc(-n3c(C(F)F)nc4ccccc43)nc(N3CCOCC3)n2)C1] | 556 | 2.72 |
| A482 | 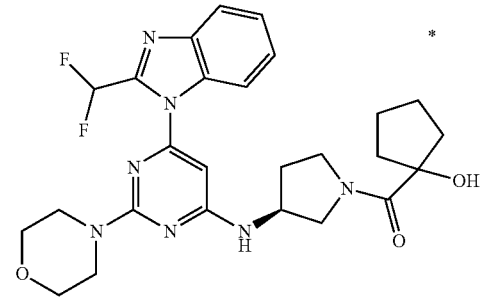 [SMILES: O=C(N1CC[C@H](Nc2cc(-n3c(C(F)F)nc4ccccc43)nc(N3CCOCC3)n2)C1)C1(O)CCCC1] | 528 | 2.76 |
| A483 | 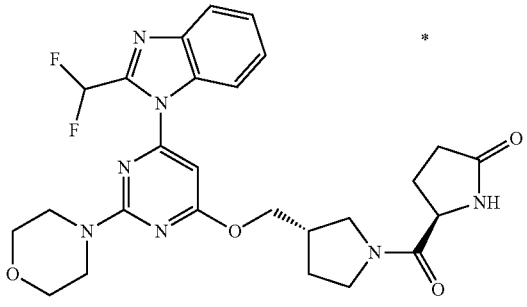 [SMILES: O=C1CC[C@H](C(=O)N2CC[C@H](COc3cc(-n4c(C(F)F)nc5ccccc54)nc(N4CCOCC4)n3)C2)N1] | 542 | 2.54 |
| A484 | 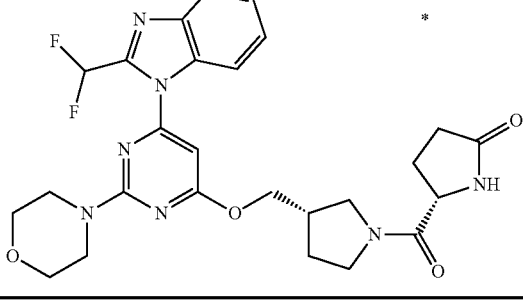 | 542 | 2.54 |

TABLE 268

| Ex | Str | ESI+ | RT |
|---|---|---|---|
| A485 | | 557 | 2.99 |
| A486 | | 598 | 2.73 |
| A487 | | 529 | 2.73 |
| A488 | | 570 | 2.62 |
| A489 | | 556 | 2.58 |

TABLE 269

| Ex | Str | ESI+ | RT |
|---|---|---|---|
| A490 | | 600 | 2.7 |
| A491 | | 556 | 2.6 |
| A492 | | 587 | 2.93 |
| A493 | | 536 | 2.83 |
| A494 | | 536 | 2.65 |

TABLE 270
| Ex | Str | ESI+ | RT |
|---|---|---|---|
| A495 | 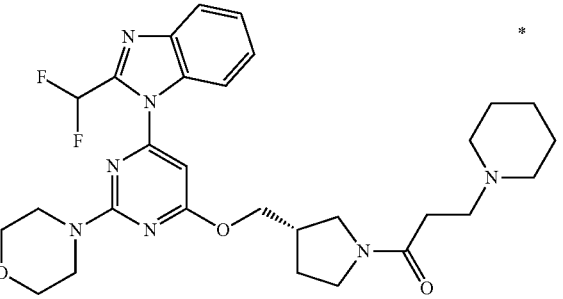 | 570 | 2.14 |
| A496 | 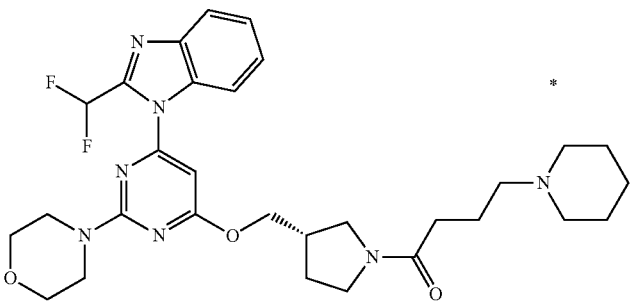 [SMILES: O=C(CCCN1CCCCC1)N1CC[C@H](COc2cc(-n3c(C(F)F)nc4ccccc43)nc(N3CCOCC3)n2)C1] | 584 | 2.2 |
| A497 | 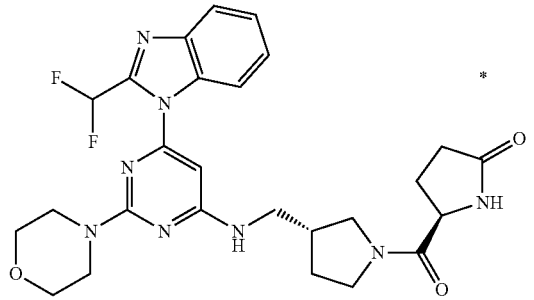 [SMILES: O=C1CC[C@H](C(=O)N2CC[C@H](CNc3cc(-n4c(C(F)F)nc5ccccc54)nc(N4CCOCC4)n3)C2)N1] | 541 | 2.42 |
| A498 | 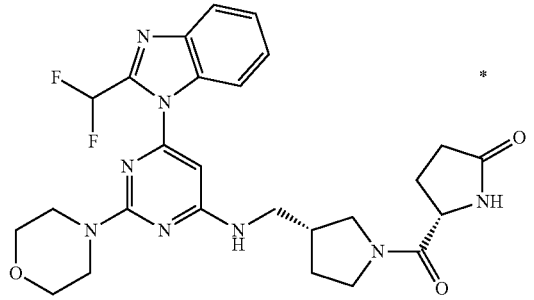 [SMILES: O=C1CC[C@@H](C(=O)N2CC[C@H](CNc3cc(-n4c(C(F)F)nc5ccccc54)nc(N4CCOCC4)n3)C2)N1] | 541 | 2.42 |
| A499 | 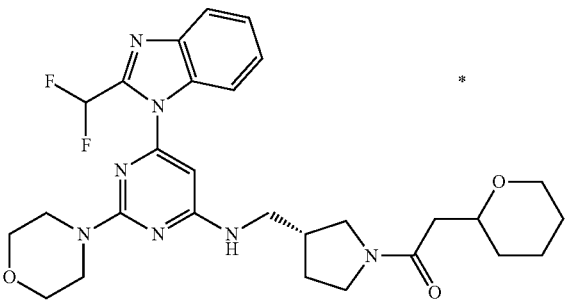 [SMILES: O=C(CC1CCCCO1)N1CC[C@H](CNc2cc(-n3c(C(F)F)nc4ccccc43)nc(N3CCOCC3)n2)C1] | 556 | 2.87 |

TABLE 271
| Ex | Str | ESI+ | RT |
|---|---|---|---|
| A500 | 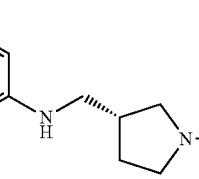 | 597 | 2.6 |
| A501 | 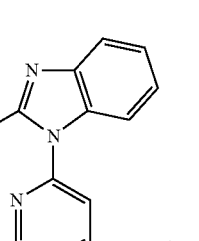 | 528 | 2.6 |
| A502 | 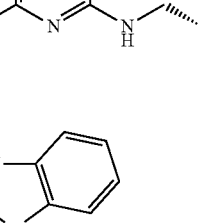 | 569 | 2.5 |
| A503 | 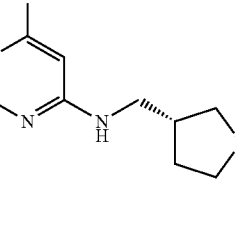 | 555 | 2.46 |
| A504 | 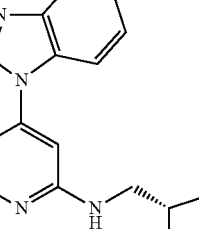 | 599 | 2.58 |

TABLE 272

| Ex | Str | ESI+ | RT |
|---|---|---|---|
| A505 | | 555 | 2.48 |
| A506 | | 586 | 2.82 |
| A507 | | 535 | 2.67 |
| A508 | | 535 | 2.5 |
| A509 | | 549 | 2.42 |

TABLE 273

| Ex | Str | ESI+ | RT |
|---|---|---|---|
| A510 | | 569 | 2.04 |
| A511 | | 583 | 2.08 |
| A512 | | 555 | 2.02 |
| A513 | | 557 | 1.98 |
| A514 | | 569 | 2.55 |

TABLE 274

| Ex | Str | ESI+ | RT |
|---|---|---|---|
| A515 | | 571 | 1.99 |
| A516 | | 585 | 2.02 |
| A517 | | 618 | 2.12 |
| A518 | | 514 | 2.62 |
| A519 | | 570 | 2.74 |

TABLE 275
| Ex | Str | ESI+ | RT |
|---|---|---|---|
| A520 | 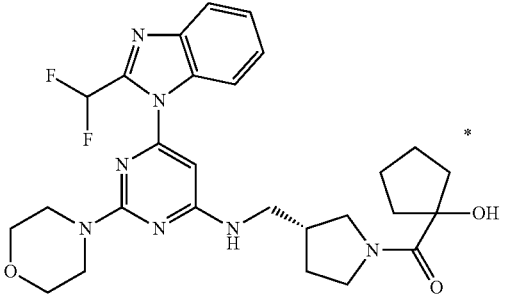 [SMILES: O=C(N1CC[C@H](CNc2cc(-n3c(C(F)F)nc4ccccc43)nc(N3CCOCC3)n2)C1)C1(O)CCCC1] | 542 | 2.79 |
| A521 | 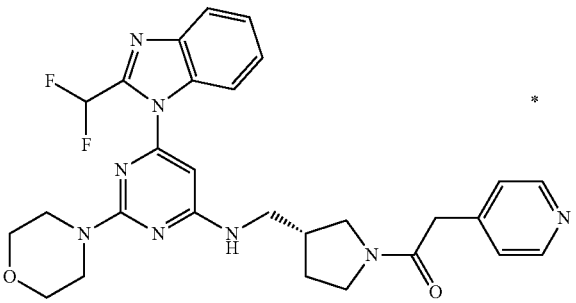 [SMILES: O=C(Cc1ccncc1)N1CC[C@H](CNc2cc(-n3c(C(F)F)nc4ccccc43)nc(N3CCOCC3)n2)C1] | 549 | 2.17 |
| A522 | 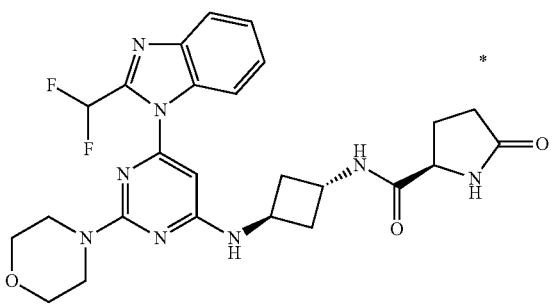 [SMILES: O=C1CC[C@H](C(=O)N[C@H]2C[C@H](Nc3cc(-n4c(C(F)F)nc5ccccc54)nc(N4CCOCC4)n3)C2)N1] | 527 | 2.42 |
| A523 | 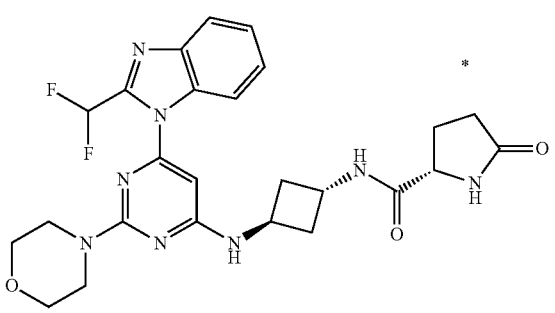 [SMILES: O=C1CC[C@@H](C(=O)N[C@H]2C[C@H](Nc3cc(-n4c(C(F)F)nc5ccccc54)nc(N4CCOCC4)n3)C2)N1] | 527 | 2.42 |
| A524 | 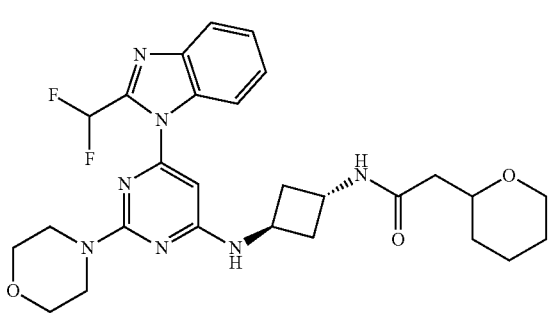 [SMILES: O=C(CC1CCCCO1)N[C@H]1C[C@H](Nc2cc(-n3c(C(F)F)nc4ccccc43)nc(N3CCOCC3)n2)C1] | 542 | 2.83 |

TABLE 276
| Ex | Str | ESI+ | RT |
|---|---|---|---|
| A525 | 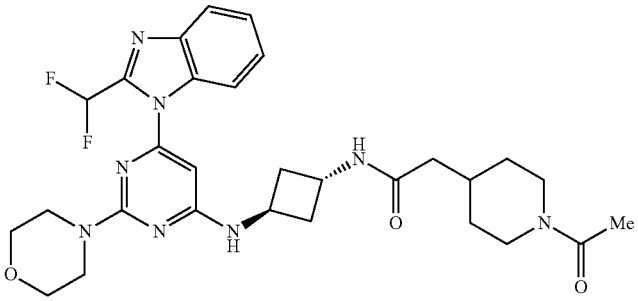 [SMILES: CC(=O)N1CCC(CC(=O)N[C@H]2C[C@H](Nc3cc(-n4c(C(F)F)nc5ccccc54)nc(N4CCOCC4)n3)C2)CC1] | 583 | 2.58 |
| A526 | 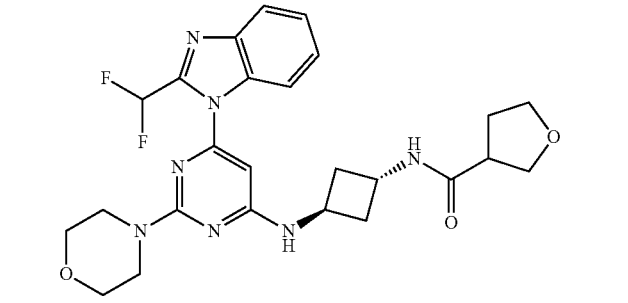 [SMILES: O=C(N[C@H]1C[C@H](Nc2cc(-n3c(C(F)F)nc4ccccc43)nc(N3CCOCC3)n2)C1)C1CCOC1] | 514 | 2.59 |
| A527 | 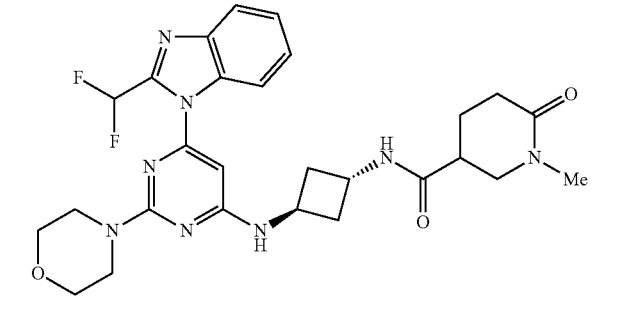 [SMILES: CN1CC(C(=O)N[C@H]2C[C@H](Nc3cc(-n4c(C(F)F)nc5ccccc54)nc(N4CCOCC4)n3)C2)CCC1=O] | 555 | 2.52 |
| A528 | 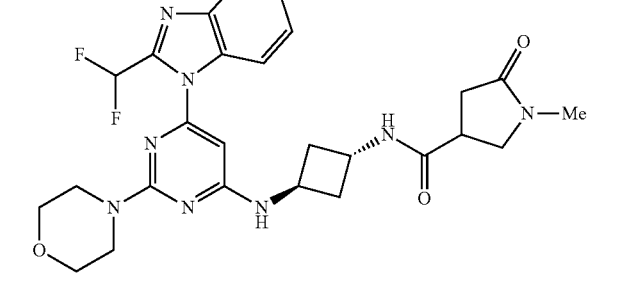 | 541 | 2.47 |
| A529 | 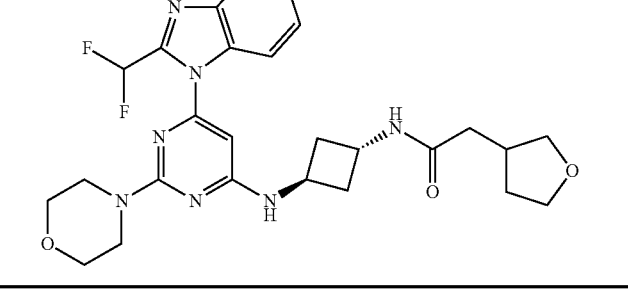 | 528 | 2.62 |

TABLE 277

| Ex | Str | ESI+ | RT |
|---|---|---|---|
| A530 | | 585 | 2.53 |
| A531 | | 541 | 2.49 |
| A532 | | 572 | 2.94 |
| A533 | | 521 | 2.85 |
| A534 | | 521 | 2.62 |

TABLE 278

| Ex | Str | ESI+ | RT |
|---|---|---|---|
| A535 | | 535 | 2.43 |
| A536 | | 555 | 2.01 |
| A537 | | 569 | 2.06 |
| A538 | | 514 | 2.39 |
| A539 | | 514 | 2.39 |

TABLE 279

| Ex | Str | ESI+ | RT |
|---|---|---|---|
| A540 | | 529 | 2.88 |
| A541 | | 570 | 2.59 |
| A542 | | 501 | 2.59 |
| A543 | | 542 | 2.48 |
| A544 | | 528 | 2.44 |

TABLE 280

| Ex | Str | ESI+ | RT |
|---|---|---|---|
| A545 | | 572 | 2.56 |
| A546 | | 528 | 2.46 |
| A547 | | 559 | 2.88 |
| A548 | | 508 | 2.88 |
| A549 | | 508 | 2.58 |

TABLE 281
| Ex | Str | ESI+ | RT |
|---|---|---|---|
| A550 | 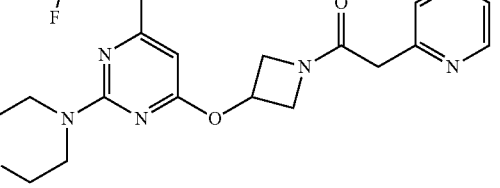 | 522 | 2.48 |
| A551 | 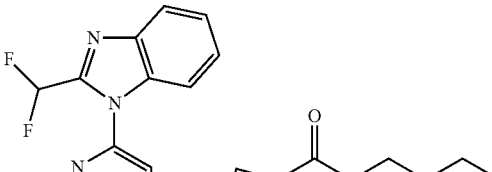 | 542 | 1.99 |
| A552 | 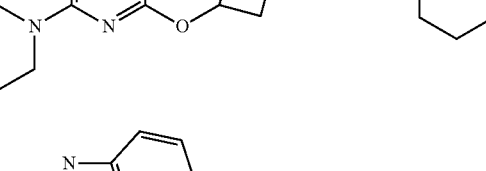 | 556 | 2.04 |
| A553 | 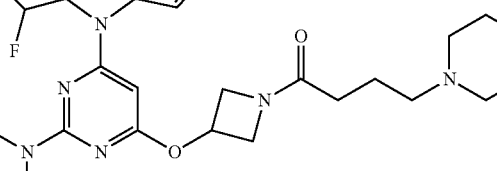 | 528 | 1.96 |
| A554 | 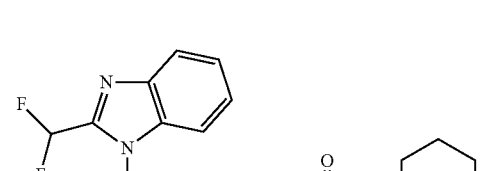 | 530 | 1.98 |

TABLE 282

| Ex | Str | ESI+ | RT |
|---|---|---|---|
| A555 | | 542 | 2.52 |
| A556 | | 544 | 1.93 |
| A557 | | 558 | 1.97 |
| A558 | | 487 | 2.59 |
| A559 | | 543 | 2.75 |

TABLE 283

| Ex | Str | ESI+ | RT |
|---|---|---|---|
| A560 | | 515 | 2.77 |
| A561 | * | 513 | 2.33 |
| A562 | * | 513 | 2.33 |
| A563 | | 528 | 2.81 |
| A564 | | 569 | 2.52 |

TABLE 284
| Ex | Str | ESI+ | RT |
|---|---|---|---|
| A565 | 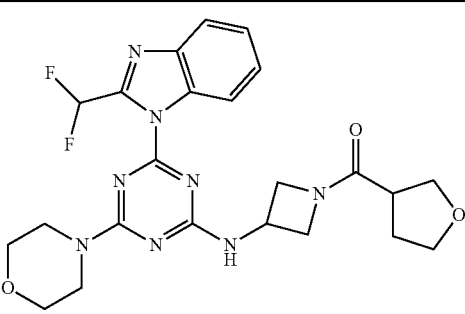 | 500 | 2.51 |
| A566 | 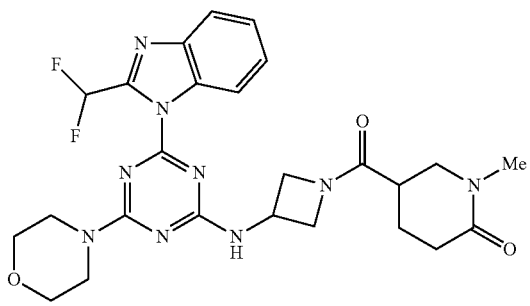 [SMILES: CN1CC(C(=O)N2CC(Nc3nc(N4CCOCC4)nc(-n4c(C(F)F)nc5ccccc54)n3)C2)CCC1=O] | 541 | 2.41 |
| A567 | 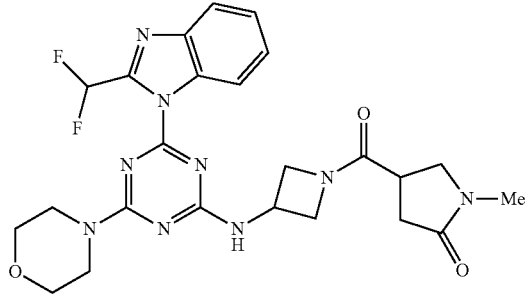 [SMILES: CN1CC(C(=O)N2CC(Nc3nc(N4CCOCC4)nc(-n4c(C(F)F)nc5ccccc54)n3)C2)CC1=O] | 527 | 2.37 |
| A568 | 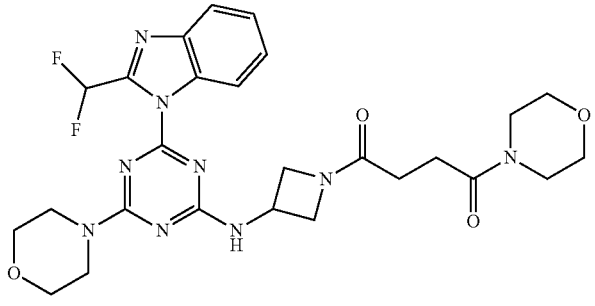 [SMILES: O=C(CCC(=O)N1CC(Nc2nc(N3CCOCC3)nc(-n3c(C(F)F)nc4ccccc43)n2)C1)N1CCOCC1] | 571 | 2.5 |
| A569 | 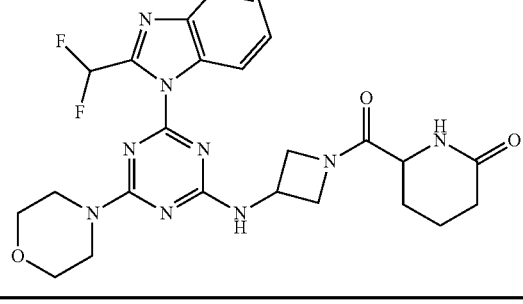 | 527 | 2.4 |

TABLE 285

| Ex | Str | ESI+ | RT |
|---|---|---|---|
| A570 | | 558 | 2.8 |
| A571 | | 507 | 2.75 |
| A572 | | 507 | 2.49 |
| A573 | | 521 | 2.39 |
| A574 | | 541 | 1.96 |

TABLE 286

| Ex | Str | ESI+ | RT |
|---|---|---|---|
| A575 | | 555 | 1.99 |
| A576 | | 527 | 1.94 |
| A577 | | 529 | 1.93 |
| A578 | | 541 | 2.45 |
| A579 | | 543 | 1.9 |

TABLE 287

| Ex | Str | ESI+ | RT |
|---|---|---|---|
| A580 | | 557 | 1.93 |
| A581 | | 590 | 2.04 |
| A582 | | 486 | 2.49 |
| A583 | | 514 | 2.68 |
| A584 | | 521 | 2.09 |

TABLE 288
| Ex | Str | ESI+ | RT |
|---|---|---|---|
| A585 | 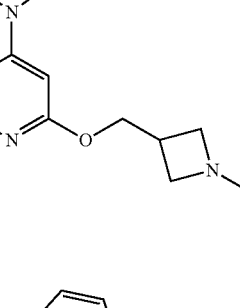 | 528 | 2.43 |
| A586 | 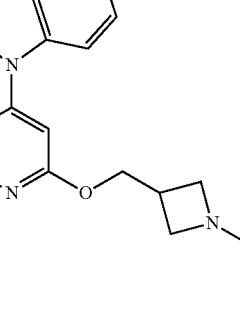 | 528 | 2.43 |
| A587 | 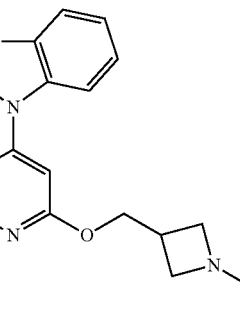 | 543 | 2.89 |
| A588 | 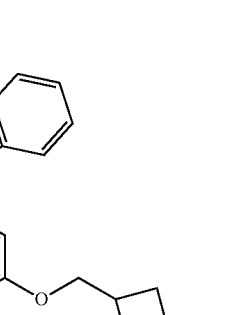 | 584 | 2.61 |

TABLE 289

| Ex | Str | ESI+ | RT |
|---|---|---|---|
| A589 | | 515 | 2.61 |
| A590 | | 556 | 2.51 |
| A591 | | 542 | 2.47 |
| A592 | | 542 | 2.49 |

TABLE 290

| Ex | Str | ESI+ | RT |
|---|---|---|---|
| A593 | | 573 | 2.87 |
| A594 | | 522 | 2.87 |
| A595 | | 522 | 2.6 |
| A596 | | 536 | 2.5 |

TABLE 291

| Ex | Str | ESI+ | RT |
|---|---|---|---|
| A597 | | 556 | 2.04 |
| A598 | | 570 | 2.07 |
| A599 | | 517 | 2.73 |
| A600 | | 543 | 2.85 |

TABLE 292

| Ex | Str | ESI+ | RT |
|---|---|---|---|
| A601 | | 531 | 2.88 |
| A602 | | 545 | 2.93 |
| A603 | | 575 | 2.96 |
| A604 | | 561 | 2.8 |

TABLE 293

| Ex | Str | ESI+ | RT |
|---|---|---|---|
| A605 | | 558 | 2.8 |
| A606 | | 555 | 3.21 |
| A607 | | 571 | 2.87 |
| A608 | | 557 | 2.92 |

TABLE 294

| Ex | Str | ESI+ | RT |
|---|---|---|---|
| A609 | | 587 | 2.83 |
| A610 | | 598 | 2.84 |
| A611 | | 628 | 3.07 |
| A612 | | 632 | 3.14 |
| A613 | | 640 | 2.48 |

TABLE 295
| Ex | Str | ESI+ | RT |
|---|---|---|---|
| A614 | 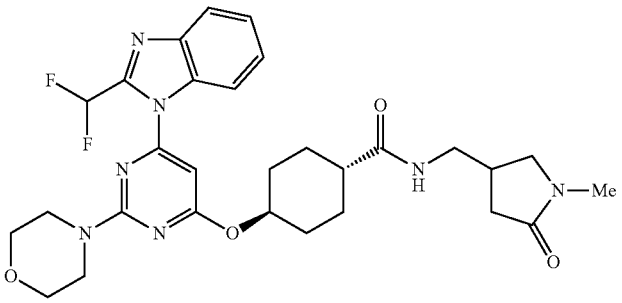 [SMILES: CN1CC(CNC(=O)[C@H]2CC[C@H](Oc3cc(-n4c(C(F)F)nc5ccccc54)nc(N4CCOCC4)n3)CC2)CC1=O] | 584 | 2.78 |
| A615 | 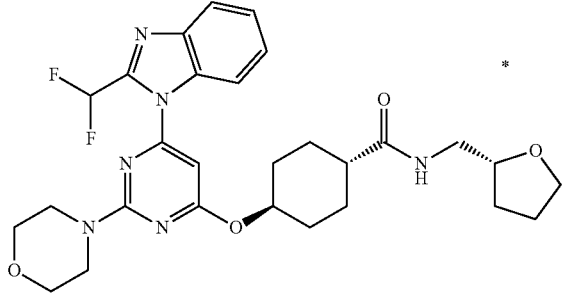 [SMILES: O=C(NC[C@H]1CCCO1)[C@H]1CC[C@H](Oc2cc(-n3c(C(F)F)nc4ccccc43)nc(N3CCOCC3)n2)CC1] | 557 | 2.96 |
| A616 | 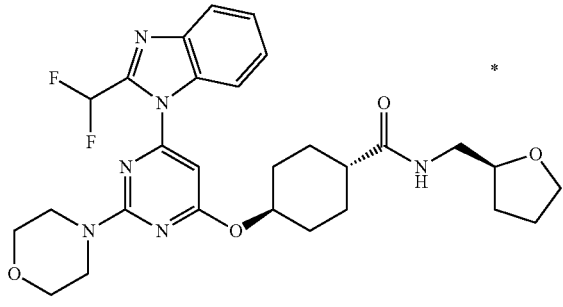 [SMILES: O=C(NC[C@@H]1CCCO1)[C@H]1CC[C@H](Oc2cc(-n3c(C(F)F)nc4ccccc43)nc(N3CCOCC3)n2)CC1] | 557 | 2.97 |
| A617 | 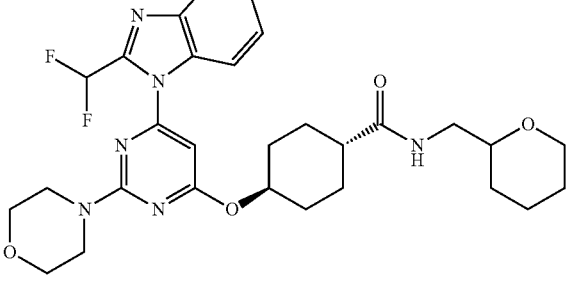 | 571 | 3.08 |
| A618 | 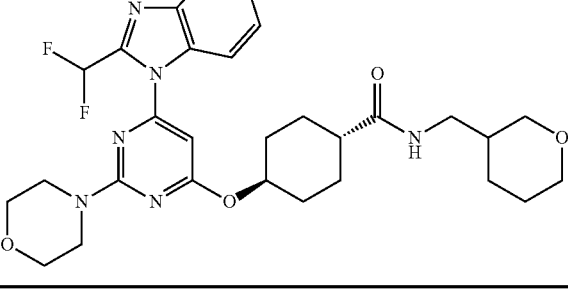 | 571 | 2.98 |

TABLE 296

| Ex | Str | ESI+ | RT |
|---|---|---|---|
| A619 | | 571 | 2.94 |
| A620 | | 585 | 3.01 |
| A621 | | 601 | 2.81 |
| A622 | | 600 | 2.3 |
| A623 | | 586 | 2.31 |

TABLE 297

| Ex | Str | ESI+ | RT |
|---|---|---|---|
| A624 | | 614 | 2.33 |
| A625 | | 600 | 2.79 |
| A626 | | 585 | 3 |
| A627 | | 600 | 2.31 |

TABLE 298

| Ex | Str | ESI+ | RT |
|---|---|---|---|
| A628 | | 616 | 2.32 |
| A629 | | 593 | 3.12 |
| A630 | | 593 | 3.09 |
| A631 | | 593 | 3.08 |
| A632 | | 579 | 2.87 |

TABLE 299
| Ex | Str | ESI+ | RT |
|---|---|---|---|
| A633 | 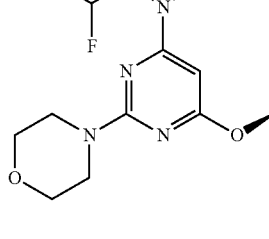 | 564 | 2.8 |
| A634 | 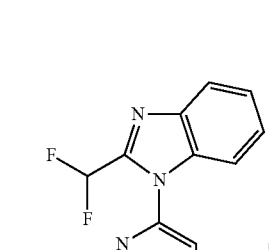 | 564 | 2.64 |
| A635 | 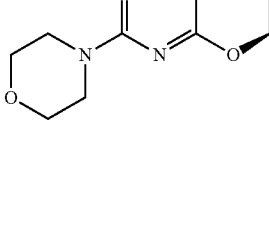 | 564 | 2.5 |
| A636 | 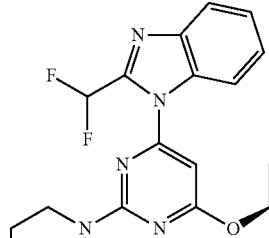 | 569 | 2.75 |

TABLE 300
| Ex | Str | ESI+ | RT |
|---|---|---|---|
| A637 | 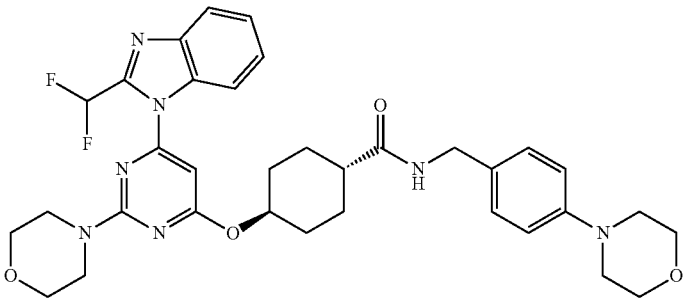 [SMILES: O=C(NCc1ccc(N2CCOCC2)cc1)[C@H]1CC[C@H](Oc2cc(-n3c(C(F)F)nc4ccccc43)nc(N3CCOCC3)n2)CC1] | 648 | 3.03 |
| A638 | 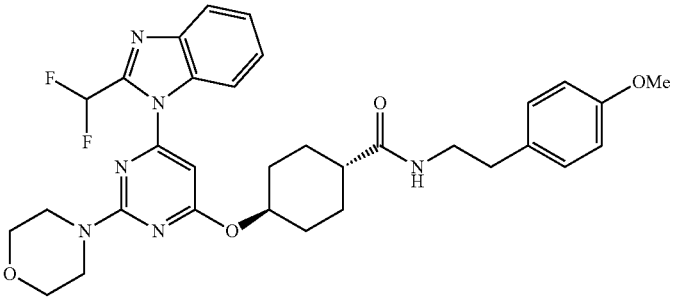 [SMILES: COc1ccc(CCNC(=O)[C@H]2CC[C@H](Oc3cc(-n4c(C(F)F)nc5ccccc54)nc(N4CCOCC4)n3)CC2)cc1] | 607 | 3.14 |
| A639 | 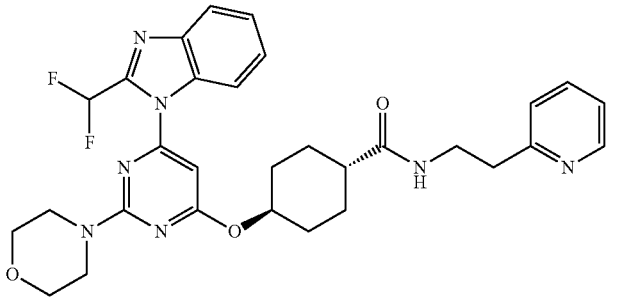 [SMILES: O=C(NCCc1ccccn1)[C@H]1CC[C@H](Oc2cc(-n3c(C(F)F)nc4ccccc43)nc(N3CCOCC3)n2)CC1] | 578 | 2.62 |
| A640 | 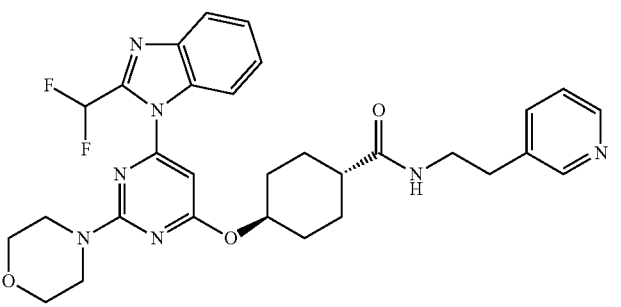 [SMILES: O=C(NCCc1cccnc1)[C@H]1CC[C@H](Oc2cc(-n3c(C(F)F)nc4ccccc43)nc(N3CCOCC3)n2)CC1] | 578 | 2.59 |

TABLE 301

| Ex | Str | ESI+ | RT |
|---|---|---|---|
| A641 | | 578 | 2.47 |
| A642 | | 621 | 3.2 |
| A643 | | 501 | 2.94 |
| A644 | | 545 | 2.99 |

TABLE 302
| Ex | Str | ESI+ | RT |
|---|---|---|---|
| A645 | 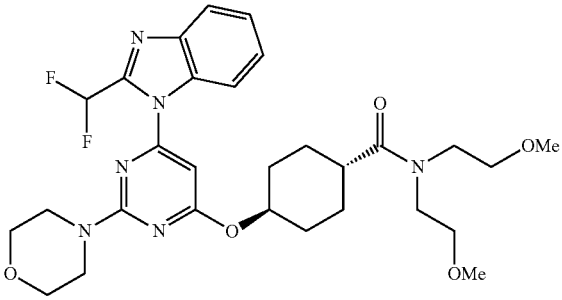 [SMILES: COCCN(CCOC)C(=O)[C@H]1CC[C@H](Oc2cc(-n3c(C(F)F)nc4ccccc43)nc(N3CCOCC3)n2)CC1] | 589 | 3.07 |
| A646 | 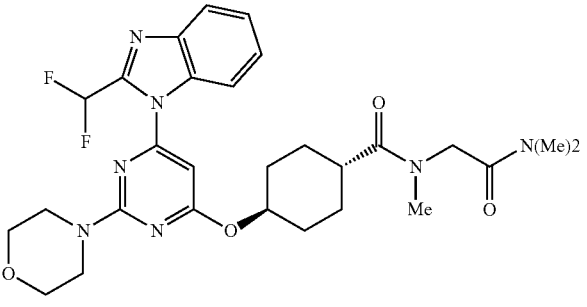 | 572 | 2.81 |
| A647 | 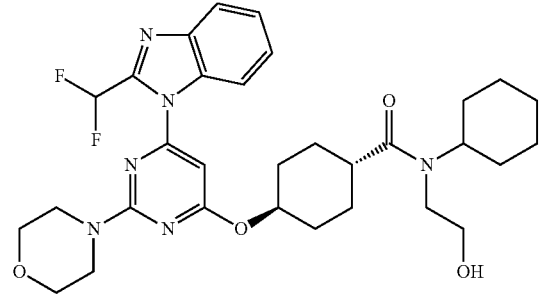 [SMILES: O=C([C@H]1CC[C@H](Oc2cc(-n3c(C(F)F)nc4ccccc43)nc(N3CCOCC3)n2)CC1)N(CCO)C1CCCCC1] | 599 | 3.19 |
| A648 | 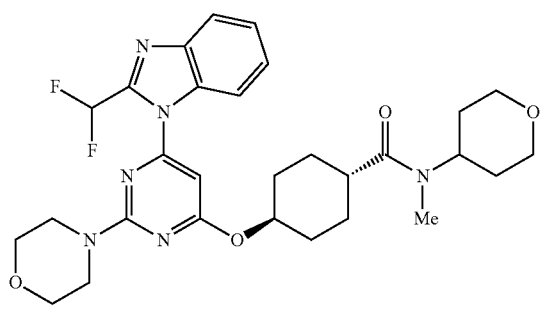 [SMILES: CN(C(=O)[C@H]1CC[C@H](Oc2cc(-n3c(C(F)F)nc4ccccc43)nc(N3CCOCC3)n2)CC1)C1CCOCC1] | 571 | 3 |

TABLE 303

| Ex | Str | ESI+ | RT |
|---|---|---|---|
| A649 | | 642 | 3.12 |
| A650 | | 585 | 3.22 |
| A651 | | 585 | 3.03 |
| A652 | | 598 | 2.37 |

TABLE 304

| Ex | Str | ESI+ | RT |
|---|---|---|---|
| A653 | | 614 | 2.81 |
| A654 | | 607 | 3.2 |
| A655 | | 578 | 2.63 |
| A656 | | 592 | 2.58 |
| A657 | | 541 | 3.18 |

TABLE 305

| Ex | Str | ESI+ | RT |
|---|---|---|---|
| A658 | | 543 | 2.91 |
| A659 | | 543 | 2.8 |
| A660 | | 543 | 2.8 |
| A661 | | 557 | 2.89 |

TABLE 306

| Ex | Str | ESI+ | RT |
|---|---|---|---|
| A662 | | 557 | 2.84 |
| A663 | | 571 | 3.07 |
| A664 | | 571 | 3.04 |
| A665 | | 571 | 3.13 |

TABLE 307

| Ex | Str | ESI+ | RT |
|---|---|---|---|
| A666 | | 571 | 3.13 |
| A667 | | 571 | 2.9 |
| A668 | | 585 | 3.12 |
| A669 | | 573 | 2.79 |

TABLE 308
| Ex | Str | ESI+ | RT |
|---|---|---|---|
| A670 | 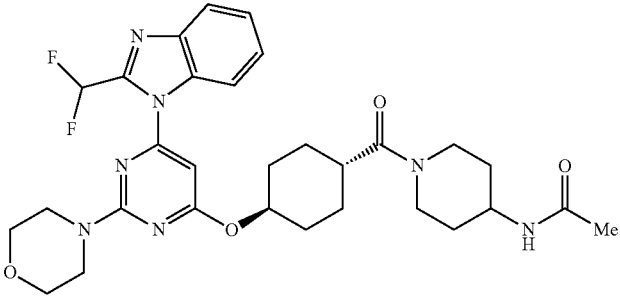 [SMILES: CC(=O)NC1CCN(C(=O)[C@H]2CC[C@H](Oc3cc(-n4c(C(F)F)nc5ccccc54)nc(N4CCOCC4)n3)CC2)CC1] | 598 | 2.81 |
| A671 | 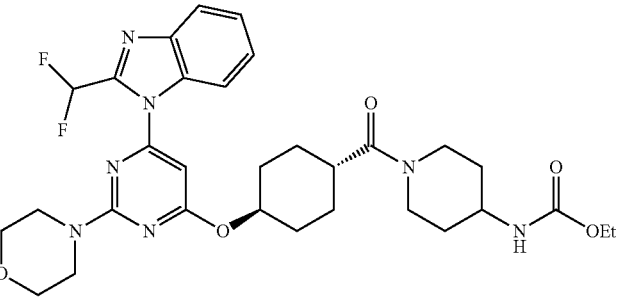 | 628 | 2.99 |
| A672 | 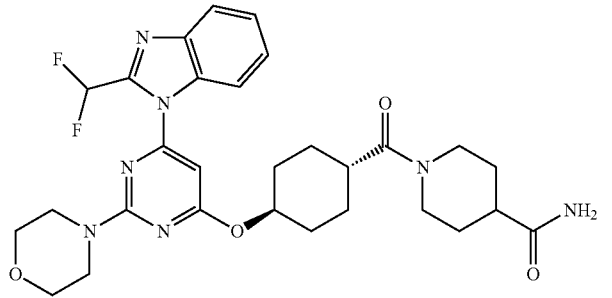 [SMILES: NC(=O)C1CCN(C(=O)[C@H]2CC[C@H](Oc3cc(-n4c(C(F)F)nc5ccccc54)nc(N4CCOCC4)n3)CC2)CC1] | 584 | 2.74 |
| A673 | 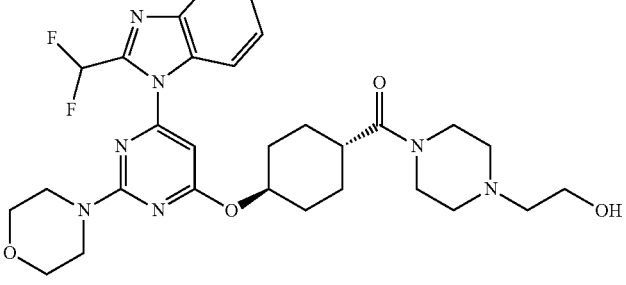 | 586 | 2.27 |
| A674 | 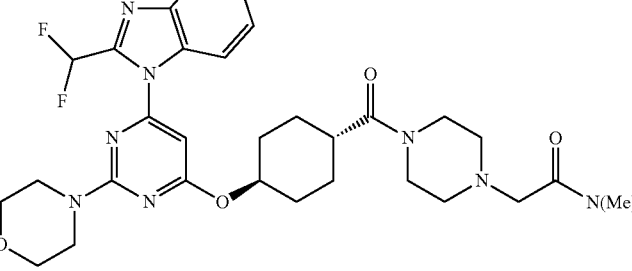 | 627 | 2.33 |

TABLE 309

| Ex | Str | ESI+ | RT |
|---|---|---|---|
| A675 | | 572 | 2.69 |
| A676 | | 570 | 2.76 |
| A677 | | 584 | 2.79 |
| A678 | | 600 | 2.95 |

TABLE 310

| Ex | Str | ESI+ | RT |
|---|---|---|---|
| A679 | | 624 | 2.87 |
| A680 | | 582 | 2.3 |
| A681 | | 619 | 3.28 |
| A682 | | 590 | 2.97 |
| A683 | | 626 | 2.32 |

TABLE 311
| Ex | Str | ESI+ | RT |
|---|---|---|---|
| A684 | 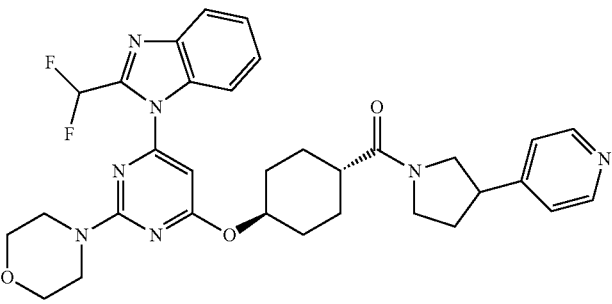 [SMILES: O=C([C@H]1CC[C@H](Oc2cc(-n3c(C(F)F)nc4ccccc43)nc(N3CCOCC3)n2)CC1)N1CCC(c2ccncc2)C1] | 604 | 2.66 |
| A685 | 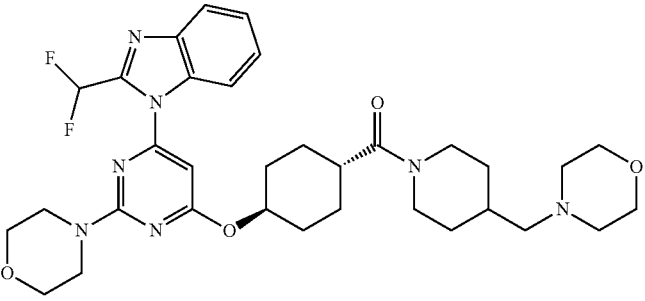 [SMILES: O=C([C@H]1CC[C@H](Oc2cc(-n3c(C(F)F)nc4ccccc43)nc(N3CCOCC3)n2)CC1)N1CCC(CN2CCOCC2)CC1] | 640 | 2.35 |
| A686 | 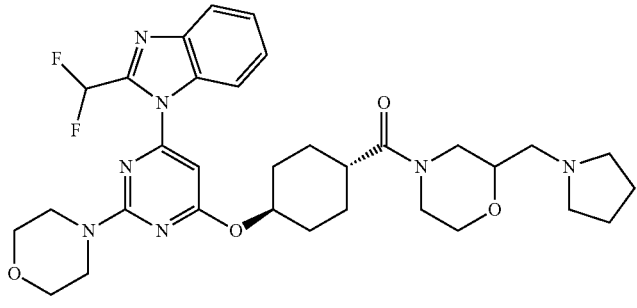 [SMILES: O=C([C@H]1CC[C@H](Oc2cc(-n3c(C(F)F)nc4ccccc43)nc(N3CCOCC3)n2)CC1)N1CCOC(CN2CCCC2)C1] | 626 | 2.35 |
| A687 | 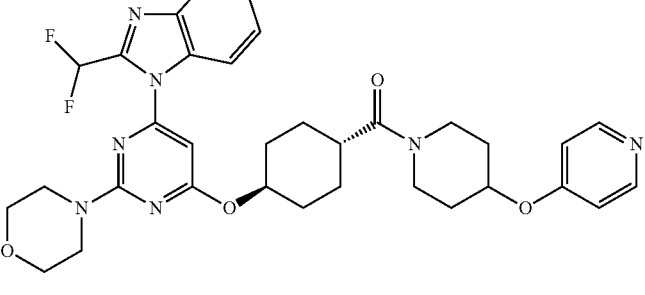 | 634 | 2.44 |
| A688 | 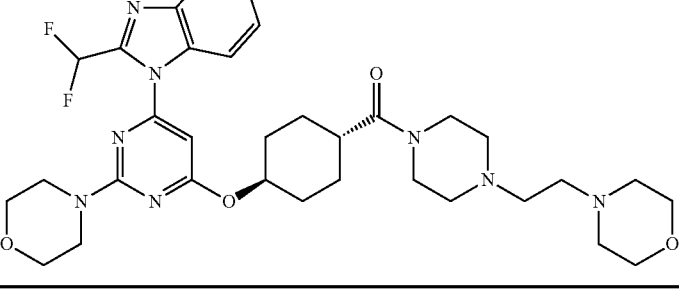 | 655 | 2.33 |

TABLE 312

| Ex | Str | ESI+ | RT |
|---|---|---|---|
| A689 | | 636 | 3.11 |
| A690 | | 580 | 3.09 |
| A691 | | 593 | 3.32 |
| A692 | | 607 | 3.24 |
| A693 | | 621 | 3.27 |

TABLE 313
| Ex | Str | ESI+ | RT |
|---|---|---|---|
| B1 | | 467 | 3.1 |
| B2 | | 425 | 3.32 |
| B3 | | 443 | 3.32 |
| B4 | | 443 | 3.37 |
| B5 | | 443 | 3.35 |
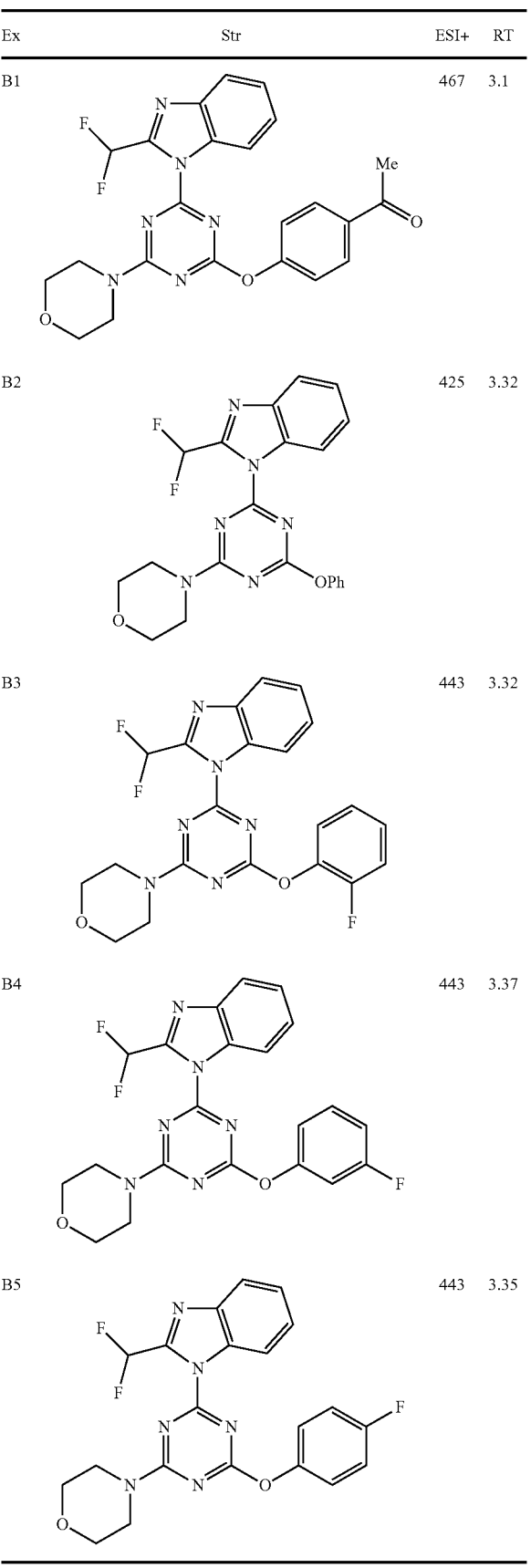
TABLE 314
| Ex | Str | ESI+ | RT |
|---|---|---|---|
| B6 | | 467 | 3.09 |
| B7 | | 483 | 3.14 |
| B8 | | 483 | 3.28 |
| B9 | | 483 | 3.31 |
| B10 | | 450 | 2.96 |
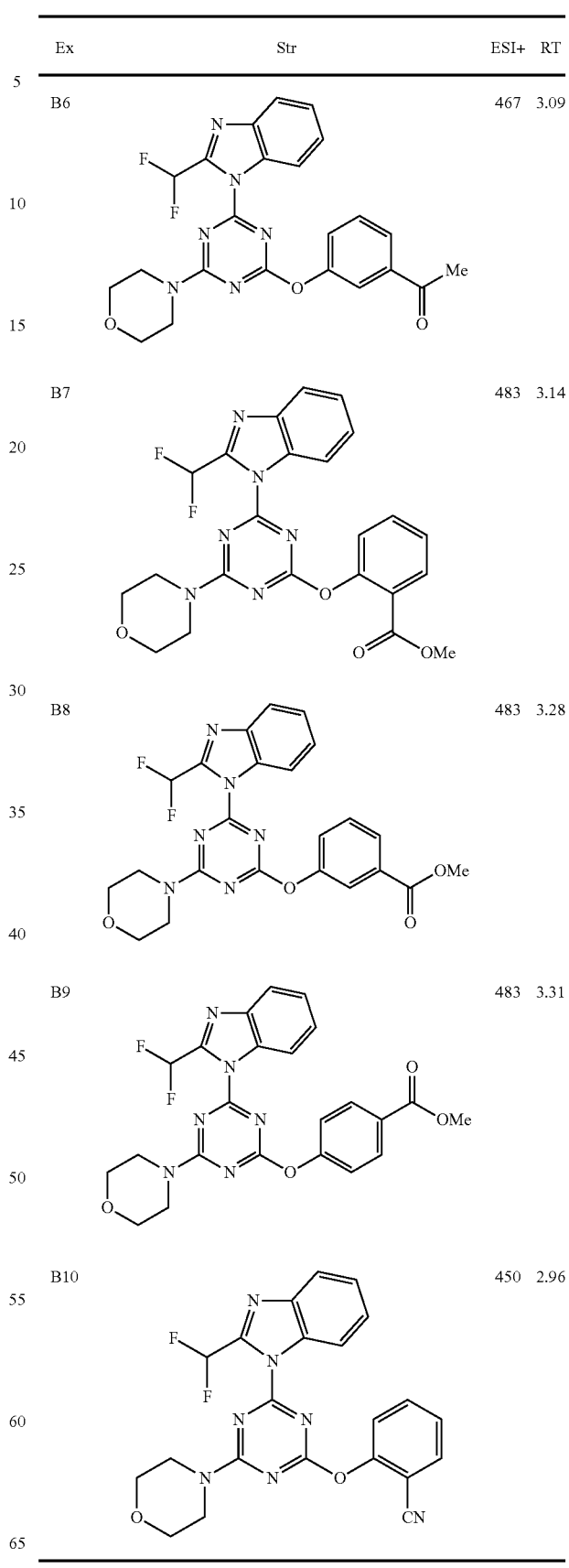

TABLE 315

| Ex | Str | ESI+ | RT |
|---|---|---|---|
| B11 | | 468 | 3.27 |
| B12 | | 496 | 2.86 |
| B13 | | 471 | 3.36 |

TABLE 315-continued

| Ex | Str | ESI+ | RT |
|---|---|---|---|
| B14 | | 471 | 3.51 |
| B15 | | 483 | 3.37 |

TABLE 316

| Ex | Str | ESI+ | RT |
|---|---|---|---|
| B16 | | 455 | 3.34 |
| B17 | | 499 | 2.95 |

TABLE 316-continued
| Ex | Str | ESI+ | RT |
|---|---|---|---|
| B18 | 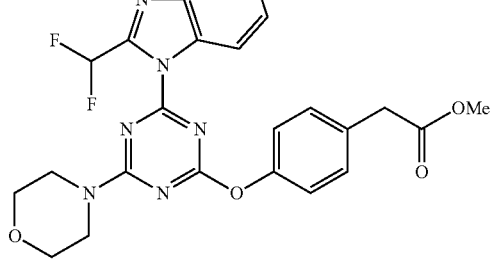 | 497 | 3.24 |
| B19 | 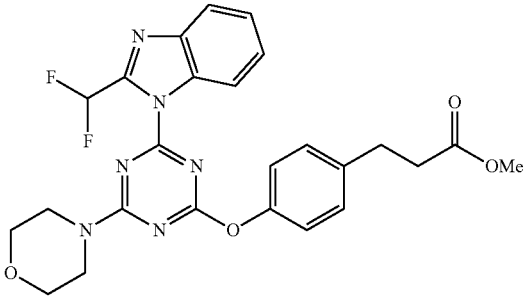 [SMILES: COC(=O)CCc1ccc(Oc2nc(N3CCOCC3)nc(-n3c(C(F)F)nc4ccccc43)n2)cc1] | 511 | 3.37 |
| B20 | 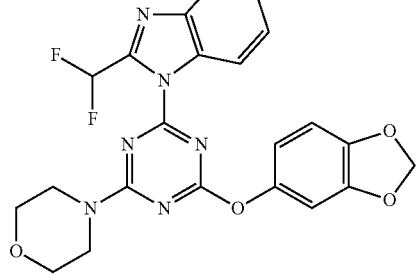 | 469 | 3.28 |
TABLE 317
| Ex | Str | ESI+ | RT |
|---|---|---|---|
| B21 | | 493 | 2.97 |

TABLE 317-continued

| Ex | Str | ESI+ | RT |
|---|---|---|---|
| B22 | | 496 | 3.24 |
| B23 | | 525 | 3.12 |
| B24 | | 526 | 3.17 |
| B25 | | 476 | 2.73 |

TABLE 318
| Ex | Str | ESI+ | RT |
|---|---|---|---|
| B26 | 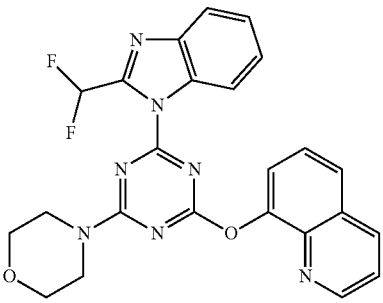 [SMILES: FC(F)c1nc2ccccc2n1-c1nc(Oc2cccc3cccnc23)nc(N2CCOCC2)n1] | 476 | 2.98 |
| B27 | 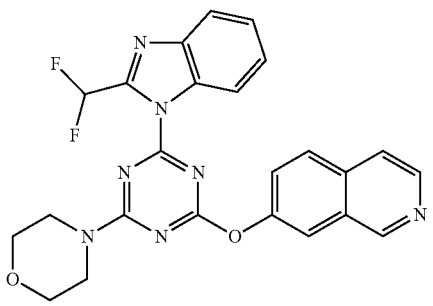 [SMILES: FC(F)c1nc2ccccc2n1-c1nc(Oc2ccc3ccncc3c2)nc(N2CCOCC2)n1] | 476 | 2.46 |
| B28 | 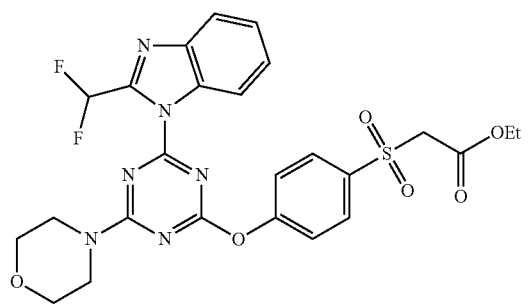 [SMILES: CCOC(=O)CS(=O)(=O)c1ccc(Oc2nc(N3CCOCC3)nc(-n3c(C(F)F)nc4ccccc43)n2)cc1] | 575 | 2.88 |
| B29 | 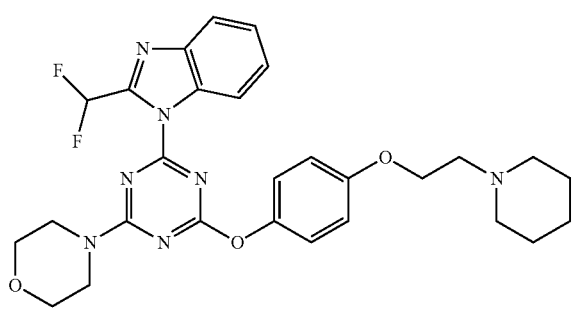 [SMILES: FC(F)c1nc2ccccc2n1-c1nc(Oc2ccc(OCCN3CCCCC3)cc2)nc(N2CCOCC2)n1] | 552 | 2.62 |
| B30 | 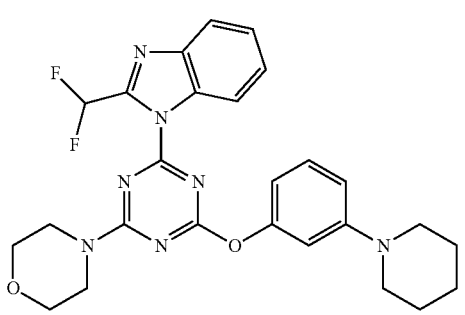 [SMILES: FC(F)c1nc2ccccc2n1-c1nc(Oc2cccc(N3CCCCC3)c2)nc(N2CCOCC2)n1] | 508 | 3 |

TABLE 319

| Ex | Str | ESI+ | RT |
|---|---|---|---|
| B31 | | 510 | 3.25 |
| B32 | | 551 | 3.02 |
| B33 | | 510 | 3.23 |
| B34 | | 531 | 3.84 |
| B35 | | 559 | 3.82 |

TABLE 320
| Ex | Str | ESI+ | RT |
|---|---|---|---|
| B36 | 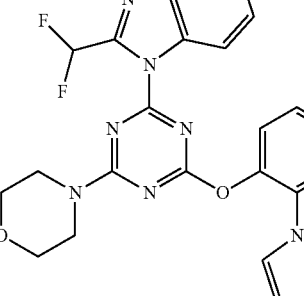 | 490 | 3.43 |
| B37 | 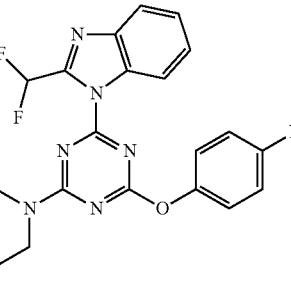 | 490 | 3.62 |
| B38 | 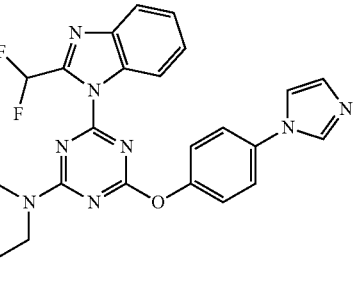 | 491 | 2.35 |
TABLE 320-continued
| Ex | Str | ESI+ | RT |
|---|---|---|---|
| B39 | 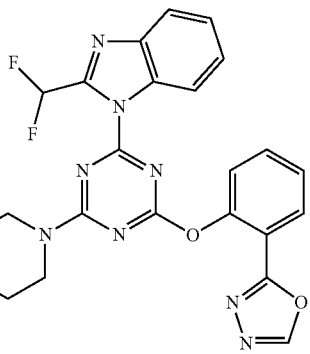 | 493 | 2.88 |
| B40 | 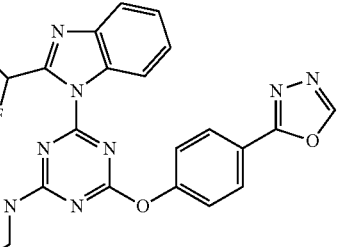 | 493 | 2.95 |
TABLE 321
| Ex | Str | ESI+ | RT |
|---|---|---|---|
| B41 | 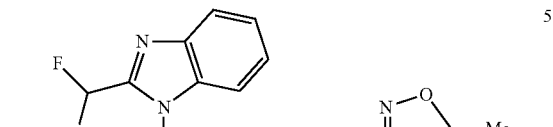 | 507 | 3.36 |
| B42 | 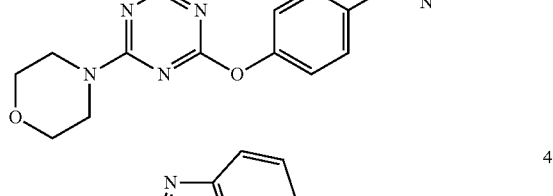 | 492 | 3 |

TABLE 321-continued

| Ex | Str | ESI+ | RT |
|---|---|---|---|
| B43 | | 552 | 3.58 |
| B44 | | 542 | 3.51 |
| B45 | | 541 | 2.54 |

TABLE 322

| Ex | Str | ESI+ | RT |
|---|---|---|---|
| B46 | | 505 | 3.31 |
| B47 | | 523 | 2.73 |

TABLE 322-continued

| Ex | Str | ESI+ | RT |
|---|---|---|---|
| B48 | | 578 | 3.52 |
| B49 | | 536 | 3.57 |

TABLE 322-continued

| Ex | Str | ESI+ | RT |
|---|---|---|---|
| B50 | | 517 | 3.59 |

TABLE 323

| Ex | Str | ESI+ | RT |
|---|---|---|---|
| B51 | | 517 | 3.78 |
| B52 | | 522 | 3.06 |

TABLE 323-continued

| Ex | Str | ESI+ | RT |
|---|---|---|---|
| B53 | | 579 | 2.76 |
| B54 | | 529 | 3.56 |
| B55 | | 529 | 3.54 |

TABLE 324

| Ex | Str | ESI+ | RT |
|---|---|---|---|
| B56 | | 563 | 3.54 |

TABLE 324-continued

| Ex | Str | ESI+ | RT |
|---|---|---|---|
| B57 | | 517 | 2.73 |
| B58 | | 543 | 2.85 |
| B59 | | 531 | 2.88 |
| B60 | | 545 | 2.93 |

TABLE 325

| Ex | Str | ESI+ | RT |
|---|---|---|---|
| B61 | | 575 | 2.96 |
| B62 | | 561 | 2.8 |
| B63 | | 558 | 2.8 |
| B64 | | 555 | 3.21 |
| B65 | | 571 | 2.87 |

TABLE 326

| Ex | Str | ESI+ | RT |
|----|-----|------|-----|
| B66 | | 557 | 2.92 |
| B67 | | 587 | 2.83 |
| B68 | | 598 | 2.84 |
| B69 | | 628 | 3.07 |
| B70 | | 632 | 3.14 |

TABLE 327

| Ex | Str | ESI+ | RT |
|---|---|---|---|
| B71 | | 640 | 2.48 |
| B72 | | 584 | 2.78 |
| B73 | * | 557 | 2.96 |
| B74 | * | 557 | 2.97 |
| B75 | | 571 | 3.08 |

TABLE 328

| Ex | Str | ESI+ | RT |
|---|---|---|---|
| B76 | | 571 | 2.98 |
| B77 | | 571 | 2.94 |
| B78 | | 585 | 3.01 |
| B79 | | 601 | 2.81 |
| B80 | | 600 | 2.3 |

TABLE 329

| Ex | Str | ESI+ | RT |
|---|---|---|---|
| B81 | | 586 | 2.31 |
| B82 | | 614 | 2.33 |
| B83 | | 600 | 2.79 |
| B84 | | 585 | 3 |
| B85 | | 600 | 2.31 |

TABLE 330

| Ex | Str | ESI+ | RT |
|---|---|---|---|
| B86 | | 616 | 2.32 |
| B87 | | 593 | 3.12 |
| B88 | | 593 | 3.09 |
| B89 | | 593 | 3.08 |
| B90 | | 579 | 2.87 |

TABLE 331

| Ex | Str | ESI+ | RT |
|---|---|---|---|
| B91 | | 564 | 2.8 |
| B92 | | 564 | 2.64 |
| B93 | | 564 | 2.5 |
| B94 | | 569 | 2.75 |
| B95 | | 648 | 3.03 |

TABLE 332

| Ex | Str | ESI+ | RT |
|---|---|---|---|
| B96 | | 607 | 3.14 |
| B97 | | 578 | 2.62 |
| B98 | | 578 | 2.59 |
| B99 | | 578 | 2.47 |
| B100 | | 621 | 3.2 |

TABLE 333

| Ex | Str | ESI+ | RT |
|---|---|---|---|
| B101 | | 501 | 2.94 |
| B102 | | 545 | 2.99 |
| B103 | | 589 | 3.07 |
| B104 | | 572 | 2.81 |
| B105 | | 599 | 3.19 |

TABLE 334

| Ex | Str | ESI+ | RT |
|---|---|---|---|
| B106 | | 571 | 3 |
| B107 | | 642 | 3.12 |
| B108 | | 585 | 3.22 |
| B109 | | 585 | 3.03 |
| B110 | | 598 | 2.37 |

TABLE 335

| Ex | Str | ESI+ | RT |
|---|---|---|---|
| B111 | | 614 | 2.81 |
| B112 | | 607 | 3.2 |
| B113 | | 578 | 2.63 |
| B114 | | 592 | 2.58 |
| B115 | | 541 | 3.18 |

TABLE 336
| Ex | Str | ESI+ | RT |
|---|---|---|---|
| B116 | 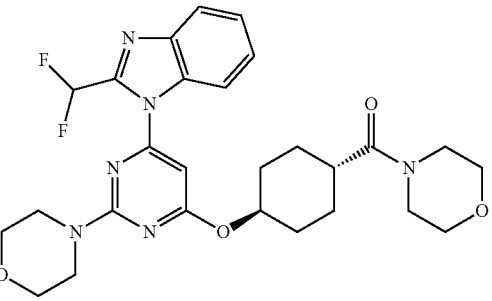 | 543 | 2.91 |
| B117 | 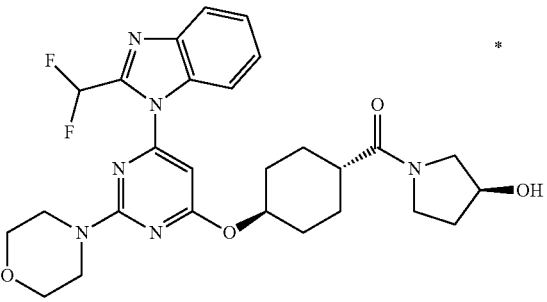 | 543 | 2.8 |
| B118 | 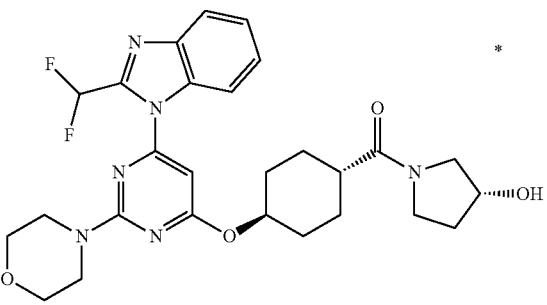 [SMILES: O=C([C@H]1CC[C@H](Oc2cc(-n3c(C(F)F)nc4ccccc43)nc(N3CCOCC3)n2)CC1)N1CC[C@@H](O)C1] | 543 | 2.8 |
| B119 | 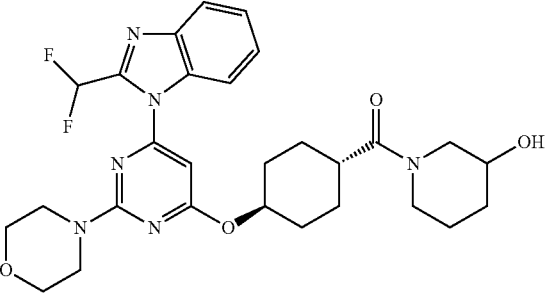 [SMILES: O=C([C@H]1CC[C@H](Oc2cc(-n3c(C(F)F)nc4ccccc43)nc(N3CCOCC3)n2)CC1)N1CCCC(O)C1] | 557 | 2.89 |
| B120 | 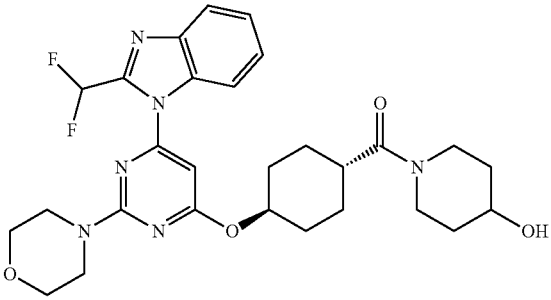 [SMILES: O=C([C@H]1CC[C@H](Oc2cc(-n3c(C(F)F)nc4ccccc43)nc(N3CCOCC3)n2)CC1)N1CCC(O)CC1] | 557 | 2.84 |

TABLE 337

| Ex | Str | ESI+ | RT |
|---|---|---|---|
| B121 | | 571 | 3.07 |
| B122 | | 571 | 3.04 |
| B123 | | 571 | 3.13 |
| B124 | | 571 | 3.13 |
| B125 | | 571 | 2.9 |

TABLE 338

| Ex | Str | ESI+ | RT |
|---|---|---|---|
| B126 | | 585 | 3.12 |
| B127 | | 573 | 2.79 |
| B128 | | 598 | 2.81 |
| B129 | | 628 | 2.99 |
| B130 | | 584 | 2.74 |

TABLE 339

| Ex | Str | ESI+ | RT |
|---|---|---|---|
| B131 | | 586 | 2.27 |
| B132 | | 627 | 2.33 |
| B133 | | 572 | 2.69 |
| B134 | | 570 | 2.76 |
| B135 | | 584 | 2.79 |

TABLE 340

| Ex | Str | ESI+ | RT |
|---|---|---|---|
| B136 | | 600 | 2.95 |
| B137 | | 624 | 2.87 |
| B138 | | 582 | 2.3 |
| B139 | | 619 | 3.28 |
| B140 | | 590 | 2.97 |

TABLE 341

| Ex | Str | ESI+ | RT |
|---|---|---|---|
| B141 | | 626 | 2.32 |
| B142 | | 604 | 2.66 |
| B143 | | 640 | 2.35 |
| B144 | | 626 | 2.35 |
| B145 | | 634 | 2.44 |

TABLE 342

| Ex | Str | ESI+ | RT |
|---|---|---|---|
| B146 | | 655 | 2.33 |
| B147 | | 636 | 3.11 |
| B148 | | 580 | 3.09 |
| B149 | | 593 | 3.32 |
| B150 | | 607 | 3.24 |

TABLE 343

| Ex | Str | ESI+ | RT |
|---|---|---|---|
| B151 | 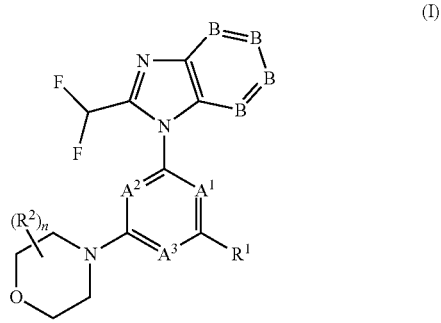 | 621 | 3.27 |

INDUSTRIAL APPLICABILITY

The compound, which is the active ingredient of the drug of the present invention, has a PI3Kδ selective inhibitory action and/or an IL-2 production inhibitory action and/or a B cell proliferation inhibitory action (including an activation inhibitory action), as well as a good pharmacological action based thereon. Thus, the pharmaceutical composition of the present invention can be used as an agent for preventing or treating rejection reactions in various organ transplantations, allergy diseases (asthma, atopic dermatitis, and the like), autoimmune diseases (rheumatoid arthritis, psoriasis, ulcerative colitis, Crohn's disease, systemic lupus erythematosus, and the like), and hematologic tumor (leukemia and the like).

The invention claimed is:

1. A compound of the formula (I) or a salt thereof:

(I)

wherein
$A^2$ and $A^3$ are N and $A^1$ is CH, or $A^1$ and $A^3$ are N and $A^2$ is CH,
B's are CH and n is 0,
$R^1$ is -$L^1$-$L^2$-Y, wherein -$L^1$-$L^2$-is —NH— or —O—,
R2 is halogen, —OH, —O-lower alkyl, —CN, or lower alkyl which may be substituted with one or more substituents selected from the group consisting of halogen, —OH, —O— lower alkyl, and —CN,
Y is a non-aromatic heterocycle which may be substituted with one or more substituents selected from the Group D1, and
the Group D1 consists of:
-$L^{5a}$-non-aromatic heterocycle which may be substituted with one or more substituents selected from the group consisting of lower alkyl, —C(O)O-lower alkyl, —C(O)-lower alkyl, and oxo, wherein $L^{5a}$ represents a bond or —C(O)—.

2. The compound or a salt thereof according to claim 1, wherein $A^2$ and $A^3$ are N and $A^1$ is CH.

3. The compound or a salt thereof according to claim 1, wherein the compound is
[(3 S)-3-({6-[2-(difluoromethyl)-1H-benzimidazol-1-yl]-2-(morpholin-4-yl)pyrimidin-4-yl}amino)pyrrolidin-1-yl][(2R)-tetrahydrofuran-2-yl]methanone,
[(3S)-3-({6-[2-(difluoromethyl)-1H-benzimidazol-1-yl]-2-(morpholin-4-yl)pyrimidin-4-yl}amino)pyrrolidin-1-yl](tetrahydro-2H-pyran-4-yl)methanone,
methyl 4-{[(3S)-3-({6-[2-(difluoromethyl)-1H-benzimidazol-1-yl]-2-(morpholin-4-yl)pyrimidin-4-yl}amino)pyrrolidin-1-yl]carbonyl}piperidine-1-carboxylate,
[(3S)-3-({6-[2-(difluoromethyl)-1H-benzimidazol-1-yl]-2-(morpholin-4-yl)pyrimidin-4-yl}oxy)pyrrolidin-1-yl](tetrahydrofuran-3-yl)methanone,
4-{[(3S)-3-({6-[2-(difluoromethyl)-1H-benzimidazol-1-yl]-2-(morpholin-4-yl)pyrimidin-4-yl }oxy)pyrrolidin-1-yl]carbonyl }-1-methylpyrrolidin-2-one,
[(3S)-3-({6-[2-(difluoromethyl)-1H-benzimidazol-1-yl]-2-(morpholin-4-yl)pyrimidin-4-yl}amino)pyrrolidin-1-yl](tetrahydrofuran-3-yl)methanone,
4-{[(3S)-3-({6-[2-(difluoromethyl)-1H-benzimidazol-1-yl]-2-(morpholin-4-yl)pyrimidin-4-yl}amino)pyrrolidin-1-yl]carbonyl }-1-methylpyrrolidin-2-one,
4-{[3-({6-[2-(difluoromethyl)-1H-benzimidazol-1-yl]-2-(morpholin-4-yl)pyrimidin-4-yl}amino)azetidin-1-yl]carbonyl}-1-methylpyrrolidin-2-one.

4. A pharmaceutical composition comprising the compound or a salt thereof according to claim 1 and a pharmaceutically acceptable excipient.

5. A method for treating systemic lupus erythematosus, comprising administering to a subject in need thereof an effective amount of the compound or a salt thereof according to claim 3.

6. The compound or a salt thereof according to claim 2, wherein -$L^1$-$L^2$- is —NH—.

7. The compound or a salt thereof according to claim 6, wherein Y is a non-aromatic heterocycle which is substituted with —C(O)-non-aromatic heterocycle.

8. The compound or a salt thereof according to claim 3, wherein the compound is [(3S)-3-({6-[2-(difluoromethyl)-1H-benzimidazol-1-yl]-2-(morpholin-4-yl)pyrimidin-4-yl}amino)pyrrolidin-1-yl][(2R)-tetrahydrofuran-2-yl]methanone.

9. The compound or a salt thereof according to claim 3, wherein the compound is [(3S)-3-({6-[2-(difluoromethyl)-1H-benzimidazol-1-yl]-2-(morpholin-4-yl)pyrimidin-4-yl}amino)pyrrolidin-1-yl](tetrahydro-2H-pyran-4-yl)methanone.

* * * * *